(12) United States Patent
Kołaczkowski et al.

(10) Patent No.: US 9,120,767 B2
(45) Date of Patent: Sep. 1, 2015

(54) ARYLOSULFONAMIDES FOR THE TREATMENT OF CNS DISEASES

(71) Applicants: Marcin Kołaczkowski, Wieliczka (PL); Piotr Kowalski, Kraków (PL); Jolanta Jaśkowska, Kraków (PL); Monika Marcinkowska, Kraków (PL); Katarzyna Mitka, Kraków (PL); Adam Bucki, Proszowice (PL); Anna Wesołowska, Kraków (PL); Maciej Pawłowski, Wieliczka (PL)

(72) Inventors: Marcin Kołaczkowski, Wieliczka (PL); Piotr Kowalski, Kraków (PL); Jolanta Jaśkowska, Kraków (PL); Monika Marcinkowska, Kraków (PL); Katarzyna Mitka, Kraków (PL); Adam Bucki, Proszowice (PL); Anna Wesołowska, Kraków (PL); Maciej Pawłowski, Wieliczka (PL)

(73) Assignee: ADAMED SP. Z.O.O., Czosnow k/Warszawy (PL)

( * ) Notice: Subject to any disclaimer, the term of this patent is extended or adjusted under 35 U.S.C. 154(b) by 0 days.

(21) Appl. No.: 14/338,704

(22) Filed: Jul. 23, 2014

(65) Prior Publication Data
US 2014/0336200 A1 Nov. 13, 2014

Related U.S. Application Data

(62) Division of application No. 13/824,066, filed as application No. PCT/EP2011/066054 on Sep. 16, 2011, now Pat. No. 8,822,517.

(30) Foreign Application Priority Data

Sep. 17, 2010 (PL) .......................... 392436

(51) Int. Cl.
| | | |
|---|---|---|
| C07D 261/20 | (2006.01) |
| C07D 401/04 | (2006.01) |
| C07D 209/40 | (2006.01) |
| C07D 235/30 | (2006.01) |
| C07D 275/04 | (2006.01) |
| C07D 319/20 | (2006.01) |
| C07D 413/12 | (2006.01) |
| C07D 401/02 | (2006.01) |
| C07D 403/02 | (2006.01) |
| C07D 409/02 | (2006.01) |
| C07D 413/02 | (2006.01) |
| C07D 417/02 | (2006.01) |
| C07D 417/14 | (2006.01) |
| C07D 471/04 | (2006.01) |
| C07D 263/58 | (2006.01) |
| C07D 277/82 | (2006.01) |
| C07D 405/12 | (2006.01) |
| C07D 409/12 | (2006.01) |
| C07D 409/14 | (2006.01) |
| C07D 413/04 | (2006.01) |
| C07D 417/12 | (2006.01) |

(52) U.S. Cl.
CPC ............ *C07D 401/04* (2013.01); *C07D 209/40* (2013.01); *C07D 235/30* (2013.01); *C07D 263/58* (2013.01); *C07D 275/04* (2013.01); *C07D 277/82* (2013.01); *C07D 319/20* (2013.01); *C07D 401/02* (2013.01); *C07D 403/02* (2013.01); *C07D 405/12* (2013.01); *C07D 409/02* (2013.01); *C07D 409/12* (2013.01); *C07D 409/14* (2013.01); *C07D 413/02* (2013.01); *C07D 413/04* (2013.01); *C07D 413/12* (2013.01); *C07D 417/02* (2013.01); *C07D 417/12* (2013.01); *C07D 417/14* (2013.01); *C07D 471/04* (2013.01)

(58) Field of Classification Search
USPC .................. 514/253.04, 254.02, 25; 544/368; 546/198
See application file for complete search history.

(56) References Cited

U.S. PATENT DOCUMENTS 5,670,511 A 9/1997 Marz et al.
7,799,782 B2 * 9/2010 Munson et al. ............ 514/234.5

FOREIGN PATENT DOCUMENTS

EP 0 976 732 A1 2/2000
WO WO 00/56712 9/2000

OTHER PUBLICATIONS

International Search Report issued by the International Searching Authority (ISA/O.E.P.M.) on Nov. 21, 2011 in connection with International Application No. PCT/EP2011/066054.
Written Opinion of the International Searching Authority issued on Nov. 21, 2011 in connection with International Application No. PCT/EP2011/066054.
U.S. Appl. No. 13/824,066, filed Mar. 15, 2013.
Forbes I T et al., "CCR2B receptor antagonists: conversion of a weak HTS hit to a potent lead compound", Bioorganic & Medicinal Chemistry Letters, Pergamon, Elsevier Science, GB, vol. 10, No. 16, (2000) pp. 1803-1806.

(Continued)

*Primary Examiner* — Rei-Tsang Shiao
(74) *Attorney, Agent, or Firm* — Gary J. Gershik; Cooper & Dunham LLP

(57) ABSTRACT

Arylsulphonamide derivatives of formula (I) and pharmaceutically acceptable salts thereof. The compounds may be useful for the treatment and/or prevention of disorders of the central nervous system.

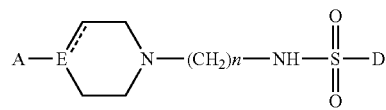

19 Claims, No Drawings

(56) References Cited

OTHER PUBLICATIONS

Ishizumi K. et al., "Succinimide Derivatives. II.1) Synthesis and Antipsychotic Activity of N-not 4-not 4-(1, 2-Benzisothiazol-3-yl)-1-Piperazinyl ¾ Buthl ¾ 1,2-Cis-Cyclohexanedicarboximide (SM-9018) and related Compounds 2.3)", Chemical & Pharmaceutical Bulletin, Pharmaceutical Society of Japan, vol. 12, No. 43, (1995) pp. 2139-2151.

Leopoldo M. et al., "Structure-affinity relationship study on N-[4-(4-arylpiperanzin-1-yl)butyl]arylcarboxamides as potent and selective dopamine D3 receptor ligands", Journal of Medicinal Chemistry, American Chemical Society, US, vol. 45, No. 26, (2006) pp. 5727-5735.

Leopoldo Marcello et al., "Design, synthesis, and binding affinities of potential positron emission tomography (PET) ligands for visualization of brain dopamine D-3 receptors", Journal of Medicinal Chemistry, American Chemical Society, US. vol. 49, No. 1, (2006) pp. 358-365.

Navas at al., "Analogues of the potential antipsychotic agent 1192U90; amide modifications", Bioorganic and Medicinal Chemistry, vol. 6, (1998) pp. 811-823.

Norman et al., "Structure-activity Relationships of a Series of Substitute Benzamides: Potent D2/5-HT2 Antagonists and 5-HT1A Agonists as Neuroleptic Agents", Journal of Medicinal Chemistry, American Chemical Socitey, US, vol. 39, No. 5, (1996) pp. 1172-1178.

\* cited by examiner

ARYLOSULFONAMIDES FOR THE TREATMENT OF CNS DISEASES

This application is a divisional of U.S. Ser. No. 13/824,066, filed Mar. 15, 2013, a §371 national stage of PCT International Application No. PCT/EP2011/066054, filed Sep. 16, 2011, claiming priority of Polish Patent Application No. P.392436, filed Sep. 17, 2010, the contents of all of which are hereby incorporated by reference into this application.

FIELD OF THE INVENTION

The present invention relates to novel arylsulphonamides having affinity to dopaminergic, serotoninergic, adrenergic, sigma and serotonine transporter receptors, pharmaceutical compositions containing the same and to the use thereof. The compounds may be useful for the treatment of diseases of the central nervous system, such as schizophrenia, bipolar affective disorder, depression, anxiety disorders, sleep disorders or Alzheimer disease.

STATE OF THE ART

CNS disorders are considered a global medical problem. A number of people suffering from those diseases constantly grows, particularly in highly developed countries and intensively developing ones. Approximately 20% of population in highly developed societies suffers from CNS disorders. In addition a cost of treatment of such disorders represents nearly 35% of total expenses spent for treatment of all medical diseases in seven countries considered as the biggest pharmaceutical markets.

Among all psychiatric diseases, schizophrenia, bipolar disorder, depression, anxiety, sleep disorders and addictions are the major ones. The main neurologic disorders are Alzheimer's disease, Parkinson's disease, epilepsy and different pain disorders.

Antipsychotic drugs, which are main treatment of schizophrenia, are divided into two main classes on the basis of their liability to induce neurological side effects after long-term treatment. Typical antipsychotic drugs, such as chlorpromazine and haloperidol, induce after repeated administration various extrapyramidal side effects (EPS) including Parkinson-like symptoms and tardive dyskinesia. Repeated treatment with so called atypical antipsychotic drugs, such as clozapine, risperidone, olanzapine, quetiapine, ziprasidone and aripiprazole, is associated with a lower incidence of neurological side effects. Typical antipsychotics reduce positive symptoms but do not reduce negative symptoms and cognitive dysfunctions. Plasma prolactin levels are increased in humans, and there is a gain in bodyweight potentially leading to the development of metabolic syndrome. Atypical antipsychotic drugs effectively reduce positive symptoms and also to some extent negative symptoms and cognitive disturbances producing less serious EPS. Atypical antipsychotic drugs differ in their propensity to elevate plasma prolactin levels in humans. Typical antipsychotic drugs block dopamine D2 receptors in the mesolimbic and nigrostriatal system. This mechanism is responsible for the antipsychotic effect (reduction of positive symptoms) as well as induction of EPS. Clinical support for the dopamine hypothesis of antipsychotic drug action was provided by PET findings of high dopamine D2 receptor occupancy in the striatum of patients responding to different antipsychotic drug treatments. Patients with a good response show dopamine D2 receptor occupancy of more than 65% (Nord and Farde 2010). The occurrence of EPS seems to be related to a higher occupancy of dopamine D2 receptors (above 80%). Atypical antipsychatics, also called second generation antipsychotic drugs, have clinical approvals for the treatment of psychosis and mania. Each drug has a unique pharmacodynamic and pharmacokinetic profile. Some of atypical antipsychotic drugs have additional antidepressant, anxiolytic or hypnotic profile (Schwartz and Stahl 2011). Atypical antipsychotic drugs have in common a potent serotonin 5-HT2A receptor antagonism in relation to a weaker dopamine D2 receptor antagonism. This pharmacodynamic property is the basis of "atypicality" (Meltzer 1989). Antagonism of 5-HT2A receptors likely allows more dopamine activity and neurotransmission to occur in the nigrostriatal system to avoid EPS. The same mechanism may allow small improvement in negative symptoms, and 5-HT2 antagonism in the tuberoinfundibular pathway may help to avoid hyperprolactinemia (Schwartz and Stahl 2011).

The atypical antipsychotics have not fulfilled the initial expectations of improved negative symptoms and cognitive dysfunctions in schizophrenia. Therefore, more molecular targets are presently under investigation for the development of new drugs for the treatment of schizophrenia (Gray and Roth 2007; Schizophrenia Research Forum 2007).

Dopaminergic D3 receptors are Localized in limbic cortex and thus a preferential blockade of these receptors offers locally selective antidopaminergic activity. This results in increased effectiveness in reducing positive symptoms of schizophrenia sparing the blockade of extrapyramidal system and therefore reduces the risk of the main side effect such as pseudoparkinson's syndrome. Moreover, several preclinical data suggests that D3 dopamine receptor antagonism is more efficient in reducing the negative symptoms of schizophrenia and improves working memory.

Agonism or partial agonism of 5-HT1A receptors is considered a possible mechanism associated with the activity of some atypical antipsychotics such as aripiprazole and ziprasidone. It is assumed that stimulation of 5-HT1A receptors takes part in the antipsychotic effect in combination with D2 receptor blockade, especially in the safety profile of drug as well as is beneficial in fighting mood and cognitive symptoms of schizophrenia (Kim D., Building a Better Antipsychotic: Receptor Targets for the Treatment of Multiple Symptom Dimensions of Schizophrenia, Neurotherapeutics, 6(1), 78-85, 2009).

Serotoninergic receptors type 5-HT6 are exclusively localized in the central nervous system (CNS). Both the localization of the 5-HT6 receptors in limbic and cortical brain areas and relatively potent affinity and antagonistic activity of several antipsychotics (clozapine, olanzapine, sertindole) and antidepressants (mianserin, amitryptiline) at 5-HT6 receptors are suggestive of a potential role in pathophysiology and treatment of CNS disorders. Recent data in the literature indicate that blockade of 5-HT6 receptors may be implicated in a pro-cognitive effect due to the increase in cholinergic transmission, in antidepressant activity due to the increase in noradrenergic and dopaminergic one, as well as in an anxiolytic effect. It is evident that the 5-HT6 receptor has emerged as a very interesting molecular target and antagonists of that receptor may serve as potential drugs in treatment of disorders characterized by cognitive impairments, such as Alzheimer's disease, schizophrenia, depression, anxiety so (Liu K. i Robichaud A., 5-HT6 Antagonists as Potential Treatment for Cognitive Dysfunction, 2009; Wesolowska A. i Nikiforuk A., Effects of the brain-penetrant and selective 5-HT6 receptor antagonist SB-399885 in animal models of anxiety and depression, 2007). Moreover, 5-HT6 receptor antagonists have been demonstrated to be active in reduction of food intake and body weight by clinically approved mechanism that is consistent with an enhancement of satiety. Hence, several compounds with 5-HT6 receptor antagonistic activity are currently being clinically evaluated for the treatment of obesity (Heal D. et al., Selective 5-HT6 receptor ligands: progress in the development of a novel pharmacological approach to the treatment of obesity and related metabolic disorders, 2008).

Intensive research conducted since 1993 indicates that serotoninergic 5-HT7 receptors may play some role in the control of circadian rhythms, sleep, thermoregulation, cognitive processes, pain and migraine, as well as in neuronal excitability. Potent affinity and antagonistic activity of several antipsychotic and antidepressant drugs at 5-HT7 receptors suggest a potential role of these receptors in the pathophysiology of many neuropsychiatric disorders. Taking account of the behavioral data presented in the literature, it has been established that selective 5-HT7 receptor antagonists produce antidepressant and anxiolytic activity in rats and mice (Wesolowska A. et al., Effect of the selective 5-HT7 receptor antagonist SB-269970 in animal models of anxiety and depression, 2006). Using mouse models of antipsychotic activity, Galici et al. showed that a selective 5-HT7 receptor antagonist SB-269970 may also evoke antipsychotic-like effects (Galici R. et al., Effects of SB-269970, a 5-HT7 receptor antagonist, in mouse models predictive of antipsychotic-like activity, 2008).

Serotoninergic 5-HTZC and histaminergic H1 receptors localized in hypothalamus play an important role in food intake regulation. Blockade of both types of these receptors produced by antipsychotic drugs is most closely correlated with an increased risk of weight gain and diabetes. On the other hand, blockade of 5-HT2C receptors, mostly localized in cortical areas and in the hippocampus, striatum, septal nuclei, thalamic and midbrain nuclei, may produce profitable antidepressant and pro-cognitive effects. In the substantia nigra, 5-HT2C receptors are co-localised with GABA, indicating that they yield indirect control of dopaminergic transmission. Consequently, the blockade of 5-HT2C receptors, together with the 5-HT2A receptor one, would potentiate the D2 receptor-mediated tonic inhibitory control of dopaminergic projection, with protective effect against extrapyramidal symptoms (Kim D., Building a Better Antipsychotic: Receptor Targets for the Treatment of Multiple Symptom Dimensions of Schizophrenia, 2009). Histaminergic H1 receptor blockade produced by antipsychotic drugs may be implicated in sedative effect that is clinically profitable in controlling arousal accompanies the acute phase of psychosis. It seems that simultaneous reduction in affinity of new molecule for both types of these receptors may be an element that protects against excessive body weight. However, the total elimination of affinity for these receptors may not be necessary because of certain benefits of blockade of 5-HT2C and H1 receptors.

Blockade of alpha1 adrenergic receptors, despite potential peripheral adverse effects involving hypotension, may cause some central nervous system benefits involving decrease in the risk of extrapyramidal side effects caused be antipsychotics. This may be associated with interaction between noradrenergic and serotoninergic neurons (Horacek J. et al., Mechanism of Action of Atypical Antipsychotic Drugs and the Neurobiology of Schizophrenia, CNS Drugs, 20(5), 389-409, 2006).

Blockade of alpha2 adrenergic receptors potentiates antidepressants-induced increase of extracellular monoamines. This may suggest that substances inhibiting monoamine transporters and simultaneously blocking alpha2 adrenergic receptors may be potent and fast acting new antidepressants. Moreover, alpha2 antagonists potentiate acetylcholine secretion in the frontal cortex and may improve cognitive functions, what may provide additional advantages both in antidepressant therapy and antipsychotic therapy (especially improvement in negative symptoms). Blockade of alpha2 adrenergic receptors may also counteract sexual dysfunctions caused by serotonin reuptake inhibitors (Millan M. Dual- and Triple-Acting Agents for Treating Core and Co-morbid Symptoms of Major Depression; Novel Concepts, New Drugs, 2009). Alpha2 antagonists may also be beneficial in reducing extrapyramidal symptoms caused by blockade of D2 receptors in the striatum.

Sigma receptors are a separate group of CNS receptors; however their physiological role is still unknown. It has been shown that some psychotomimetic substances like phencyclidine, metamphetamine, heroin or dextrometorphan are potent sigma receptor agonist. On the other hand, a classic antipsychotic drug, haloperidol, is a strong antagonist of sigma receptors, what may be important for its antipsychotic potential. It has been established that selective sigma receptor agonists may produce antidepressant effect (Cobos E. et al., Pharmacology and Therapeutic Potential of Sigma Receptor Ligands, 2008). The above findings provide evidence that sigma receptors affinity may contribute to the overall beneficial pharmacological profile of a new psychotropic drug.

Because of important role of cholinergic system in the cognitive processes, current is research is focused on substances which can directly or indirectly potentiate the activity of cholinergic system. This includes substances which are agonists of selected subtypes of nicotinic or muscarinic receptors and antagonists of 5-HT6 receptors. On the other hand, potential procognitive effects evoked by interaction with the above receptors may be masked by cholinolytic activity. Thus, in the scope of interest are substances free of antagonistic properties against cholinergic receptors. Moreover this strategy allows elimination of many undesired peripheral autonomic effects like constipations, dry mouth or tachycardia (Miamoto S., Treatments for schizophrenia: a critical review of pharmacology and mechanisms of action of antipsychotic drugs, 2005). In addition, it has been found that M3 muscarinic receptors are engaged in the control of insulin secretion, and their activation stimulates pancreas to secrete insulin. Hence, it can be expected that M3 receptors blockade may be unfavorable in terms of the risk of development of type II diabetes in patients treated with second generation antipsychotics (ex. olanzapine, clozapine, quetiapine). Recent research is focused on substances free of this undesired effect (Silvestre J. i Prous J., Research on adverse drug events. I. Muscarinic M3 receptor binding affinity could predict the risk of antipsychotics to induce type 2 diabetes, 2005).

Another serious side effects caused by antipsychotic drugs, e.g. sertindole, ziprasidone, are cardiac arrhythmias associated with delayed repolarization of cardiomyocytes. This condition appears on electrocardiograms (ECG) as prolonged corrected QT interval (QTc), what is most often evoked by substances which block hERG potassium channels.

To prevent introduction to the developmental pipelines drugs with pro-arrhythmic potential, at a very early stage of research new substances are screened in vitro for their potency to block hERG potassium channels, using electrophysiological methods (Recanatni M., QT Prolongation Through hERG K+ Channel Blockade: Current Knowledge and Strategies for the Early Prediction During Drug Development, 2005).

Despite the advances that have been made in the development of antidepressants, there are clearly still unmet clinical needs with respect to both efficacy and side effects. These needs range from efficacy in treatment resistant patients (about 30% to improved onset, to reductions in side effects such as sexual dysfunction, gastrointestinal events, sedation, weight gain. There are multiple approaches to improve current pharmacological means of modulating biogenic amines neurotransmission by either combining mechanisms or alternatively selectively stimulating/blocking receptor subtypes that may trigger improved efficacy or fewer side effects. One of them is combination therapies that maintain the benefits associated with selective serotonin reuptake inhibitors (SSRIs) (blockers of serotonin transporter) but attempt to either improve efficacy or reduce side effects by adding additional mechanism involving blockade of 5-HT2A or 5-HT2C receptors (Milian M., Dual- and Triple-Acting Agents for Treating Core and Co-morbid Symptoms of Major Depression: Novel Concepts, New Drugs, Neurotherapeutics, 6(1), 53-77, 2009). 5-HT2A receptor antagonists administered atone may produce antidepressant activity and also co-administered with SSRIs augment their antidepressant effects. The mechanism for this interaction may be a further increase in extracellular serotonin levels produced when SSRIs are given with 5-HT2A antagonists. Moreover, blockade of 5-HT2A receptors is part of the pharmacological profile of antidepressant drugs such as mianserin and mirtazapine. Presynaptic 5-HT1A receptors are associated with the risk for depressive behavior and their blockade augments the effects of SSRIs. Postsynaptic 5-HT1A receptors are essential for producing the antidepressant effects of 5-HT1A receptor agonists and possibly SSRIs. Thus partial agonism of 5-HT1A receptors is a preferred feature for new molecules the more that this mechanism occurs in approved anxiolytic buspirone and antidepressant/anxiolytic tandospirone.

Although introduction of new psychotropic drugs (among others narcoleptics, antidepressants, benzodiazepines, acetylocholinesterase inhibitors) since 50-thies of the XX century was an unquestioned breakthrough, therapy of neuropsychiatric disorders is still far from satisfactory both because of limited efficacy and wide spectrum of side effects evoked by available drugs. These disadvantages are a challenge for modern pharmacotherapy and there is a continuous effort to search for new, more effective psychotropic drugs.

Arylsulphonamide derivatives potentially useful for treating cardiovascular diseases, such as angina pectoris, cerebral circulation disorder and thrombosis, were described in the publication of European patent application EP0330065A. Disclosed compounds had aromatic ring, for instance phenyl, naphthyl or pyridil, bound to piperazine ring.

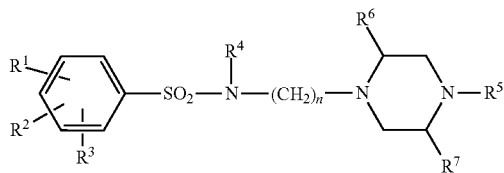

Publication of International patent application WO98/43956 discloses 1,4-disubstituted cyclic amines of the following formula wherein cyclic amine can be linked to bicyclic to system.

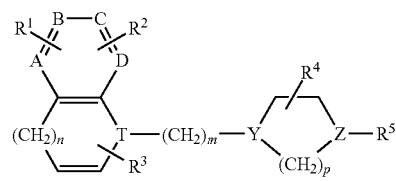

Derivatives mentioned above were described as having antagonistic activity toward serotoninergic receptors and featuring absent or very low affinity toward alpha adrenergic receptors.

In the publication of International patent application WO2004/069794 arylsulphonamide derivatives of the following formula were described as 5-HT1A receptor agonists, having very high activity and selectivity and low or absent cross-reactivity with other receptors.

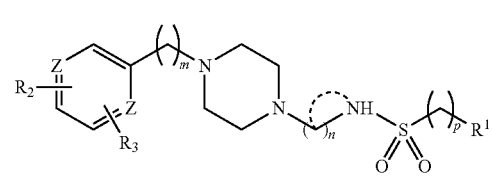

The publication of European patent application EP190472A discloses compounds having antipsychotic activity of the general formula presented below.

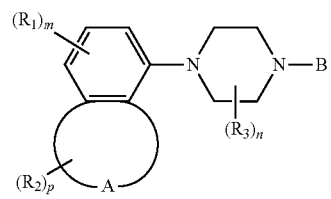

Derivatives of cyclic amines, including derivatives having arylsulphonamide moieties were described in scientific papers as well.

In publication of Ishizumi K. et al. Chem. Pharm. Bull. 43 (12), 2139-2151, 1995, directed to research on structure-activity relationship for succinimide derivatives, a compound of the following structure was disclosed:

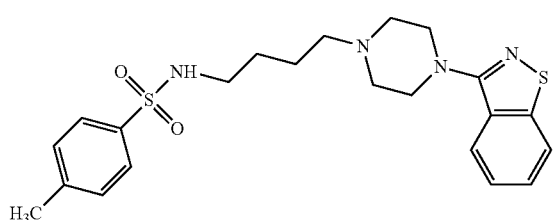

The compound was proposed as a structural modification of another compound, N-[4-[4(1,2-benzoxazol-3-yl)-1-piperazinyl]butyl]-1,2-cis-cyclohexanedicarboxylmide (Perospiron, SM-9018), showing high affinity toward 5-HT2 and D2 receptors. Reportedly, replacement of succinimide with 4-methylbenzenesulphonamide moiety resulted however in decrease of affinity toward receptors mentioned above, in particular toward D2 receptor.

Similarly as in the publication mentioned above, also article of Navas F. et al., Bioorg. Med. Chem. 6 (1998), 811-823 related to structure-activity relationship research, A compound of the following formula was disclosed:

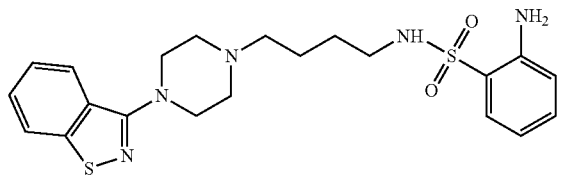 [SMILES: Nc1ccccc1S(=O)(=O)NCCCCN1CCN(c2nsc3ccccc23)CC1]

It was found that replacement of amide group with sulphonamide moiety as in the disclosed compound resulted in considerable decrease of affinity toward serotoninergic 5-HT1A and dopaminergic D2 receptors.

Publication of Forbes I. T. et al., Bioorg. Med. Chem. Lett. 10 (2000) 1803-1806 disclosed indolopiperidine derivatives having antagonistic activity toward chemokine receptor CCR2B, potentially useful for the treatment of diseases of inflammatory origin, such as atherosclerosis and rheumatoid arthritis. Among tested derivatives 3,4-dichloro-N-{[4-(1H-indol-3-yl)piperidin-1-yl]pentyl}benzensulphonamide of the following formula was disclosed:

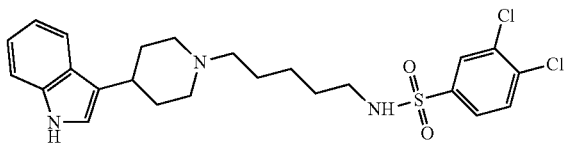 [SMILES: O=S(=O)(NCCCCCN1CCC(c2c[nH]c3ccccc23)CC1)c1ccc(Cl)c(Cl)c1]

However, the above publication did not suggest that this compound could possess activity toward therapeutic targets related to treatment of diseases of central nervous system.

Extended affinity of N-{4-[4-(1,2-benzoxazol-3-yl)piperazin-1-yl]butyl}benzenesulphonamide toward $5\text{-}HT_{1A}$, $5\text{-}HT_{2A}$, $5\text{-}HT_6$, $5\text{-}HT_7$, $\alpha_1$ and dopaminergic $D_2$ receptors was disclosed by R. Bugno et al., in the poster "Examination of $5\text{-}HT_6$ receptor affinity in the group of arylsulfonamide derivatives" published on May 10, 2010 during. The Seventh Multiscipliplinary Conference on Drug Research, May 9-12, 2010, Zakopane, Poland.

AIM OF THE INVENTION

The aim of the present invention is to provide novel compounds potentially useful for is the treatment of diseases of the central nervous system. A further aim of the invention is to provide novel compounds useful for the treatment of diseases of central nervous system having higher effectiveness compared to currently used medicaments. Yet further aim of the present invention is to provide novel compounds useful for the treatment of diseases of the central nervous system, which could allow to eliminate or minimize adverse effects associated with currently used therapies.

DISCLOSURE OF THE INVENTION

The present invention relates to novel arylsulphonamide compounds having the structure represented by the general formula (I)

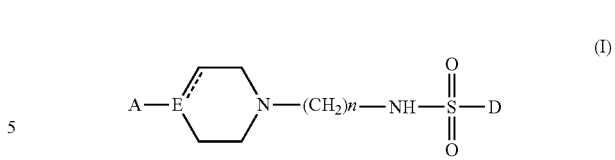

and pharmaceutically acceptable salts thereof,
wherein:
E represents N, C or CH;
----- represents single bond or double bond;
n represents an integer from 2 to 6, inclusive;
A represents a 9- or 10-membered bicyclic group, consisting of benzene ring fused with a 5- or 6-membered heterocyclic ring, which group is linked to E through one of its carbon atoms and has the following formula (A):

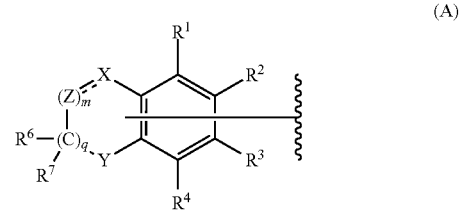

wherein
X represents $CR^5$, $C(R^5)_2$, NH or O;
Z represents $CR^5$, $C(R^5)_2$, or N;
$R^5$ represents hydrogen atom, halogen atom or $C_1$-$C_4$-alkyl;
Y represents NH, 0 or 5;
each of $R^1$, $R^2$, $R^3$, and $R^4$ independently represents hydrogen atom or halogen atom;
each of $R^6$ and $R^7$ independently represents hydrogen atom, halogen atom or $C_1$-$C_4$-alkyl;
or $R^6$ and $R^7$ together form =O;
----- represents single bond or double bond;
m is 0 or 1;
q is 0 or 1;
wherein at least one of q and m is 1;
D is selected from:
unsubstituted phenyl or phenyl substituted with one or more substituents independently selected from the group consisting of branched $C_1$-$C_4$-alkyl, straight $C_1$-$C_4$-alkyl in ortho or meta position with respect to sulphonamide group, $C_1$-$C_3$-alkyloxy, halogeno-$C_1$-$C_3$-alkyl, halogeno-$C_1$-$C_3$-alkyloxy, halogen atom, —CN, —OH, and phenyl;
unsubstituted naphthyl or naphthyl substituted with one or more substituents independently selected from the group consisting of $C_1$-$C_4$-alkyl, $C_1$-$C_3$-alkyloxy, halogeno-$C_1$-$C_3$-alkyl, halogen atom, —CN, —OH, and phenyl;
a 5-membered aromatic heterocyclic group having 1 to 3 heteroatoms independently selected from the group consisting of N, O and S, which is unsubstituted or substituted with one or more substituents independently selected from the group consisting of $C_1$-$C_4$-alkyl, $C_1$-$C_3$-alkyloxy, halogeno-$C_1$-$C_3$-alkyl, halogen atom, —CH, —OH, and phenyl;
a bicyclic group consisting of a ring selected from benzene and pyridine fused with a 5-membered aromatic or non-aromatic heterocyclic ring having 1 to 3 heteroatoms independently selected from the group consisting of N, O, S, said bicyclic group being unsubstituted or substituted with one or more substituent independently selected from the group consisting of $C_1$-$C_4$-alkyl, $C_1$-$C_3$-alkyloxy, halogeno-$C_1$-$C_3$-alkyl, halogen atom, =O, —CN, —OH, and phenyl;

a bicyclic group consisting of a ring selected from benzene and pyridine fused with a 6-membered non-aromatic heterocyclic ring having 1 to 3 heteroatoms independently selected from the group consisting of N, O, and S, said bicyclic group being unsubstituted or substituted with one or more substituents independently selected from the group consisting of $C_1$-$C_4$-alkyl, $C_1$-$C_3$-alkyloxy, halogeno-$C_1$-$C_3$-alkyl, halogen atom, =O, —CN, —OH, and phenyl;

with the proviso that 3,4-dichloro-N-{[4-(1H-indol-3-yl)piperidin-1-yl]pentyl}benzenesulphonamide and N-{4-[4-(1,2-benzoxazol-3-yl)piperazin-1-yl]butyl}benzenesulphonamide are excluded.

In one embodiment of the compounds of the present invention group A is linked to E through carbon atom of benzene ring.

In an alternative embodiment of the compounds of the present invention group A is linked to E through carbon atom of heterocyclic ring.

It will be appreciated by a person skilled in the art that respective substituent $R^1$, $R^2$, $R^3$, $R^4$, $R^5$, $R^6$ or $R^7$ at the carbon atom through which group A is linked to E is absent and is replaced by a bond.

According to one of the variants, compounds of the present invention have the formula (I), wherein in group A ===== represents double bond, q is 0, X represents $C(R^5)$, and Z represents N. In these compounds A corresponds to the following general formula (A1), wherein Y, $R^1$, $R^2$, $R^3$, $R^4$ and $R^5$ have the same meanings as defined above, and which is specific variant of the formula (A):

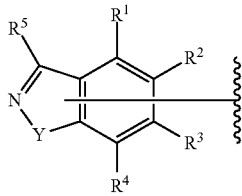

(A1)

Group of formula (A1) may be linked to E through carbon atom of phenyl ring or through carbon atom of 5-membered heterocyclic ring.

Preferably, in the above variant (A1) represents 1,2-benzothiazol-3-yl or 1,2-benzoxazol-3-yl, which may be optionally substituted with halogen atom.

Further variant of the compounds of the present invention are compounds of formula (I), wherein in group A ===== represents double bond, q is 0, X represents $C(R^5)$, and Z represents $C(R^5)$. In these compounds A corresponds to the following general formula (A2), wherein Y, $R^1$, $R^2$, $R^3$, $R^4$ and $R^5$ have meanings as defined above, and which is is specific variant of the formula (A)

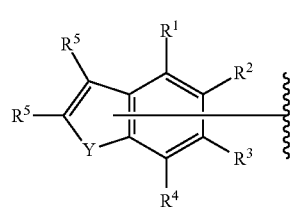

(A2)

Group of formula (A2) may be linked to E through carbon atom of phenyl ring or through carbon atom of 5-membered heteroaromatic ring.

Preferably, in the above variant (A2) represents 1H-indol-3-yl, 2-($C_1$-$C_4$-alkyl)-1H-indol-3-yl or 1H-indol-4-yl, which may be optionally substituted with halogen atom.

Another variant of the compounds of the present invention are compounds of formula (I), wherein in group A ===== represents single bond, and m is 0. In these compounds A corresponds to the following general formula (A3), wherein X, Y, $R^1$, $R^2$, $R^3$, $R^4$, $R^6$ and $R^7$ have the meanings as defined above, and which is specific variant of the formula (A):

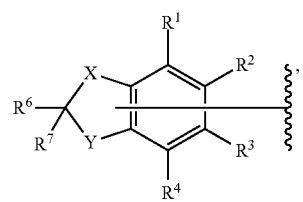

(A3)

Group of formula (A3) may be linked to E through carbon atom of phenyl ring or through carbon atom of heterocyclic ring.

Preferably, in the above variant (A3) represents 2-oxo-2,3-dihydro-1H-benzimidazol-4-yl, 2-oxo-2,3-dihydro-1,3-benzoxazol-4-yl, 2-oxo-2,3-dihydro-1,3-benzoxazol-7-yl, 2-oxo-2,3-dihydro-1H-indol-4-yl, 2,2-dimethyl-2,3-dihydro-1H-indol-4-yl, 2,2-dimethyl-1,3-benzodioxol-4-yl, or 2,2-difluoro-1,3-benzodioxol-4-yl.

Yet another variant of the compounds of the present invention are compounds of formula (I), wherein in group A ===== represents single bond, m is 1, q is 1, and Z represents $CH_2$. In these compounds A corresponds to the following general formula (A4), wherein X, Y, $R^1$, $R^2$, $R^3$, $R^4$, $R^6$ and $R^7$ have the meanings as defined above, and which is specific variant of the formula (A):

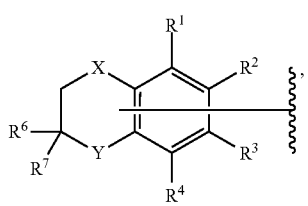

(A4)

Group of formula (A4) may be linked to E through carbon atom of phenyl ring or through carbon atom of 6-membered heterocyclic ring.

Preferably, in the above variant (A4) represents 1,4-benzodioxan-5-yl or 3-okso-3,4-dihydro-2H-1,4-benzoxazin-8-yl.

One of further embodiments of the compounds of the present invention are compounds of formula (I), wherein E represents nitrogen atom. It will be therefore obvious that in such a case ----- in formula (I) will represent single bond.

Another embodiment of compounds of the present invention are compounds of formula (I), wherein E represents CH. It will be therefore obvious that in such a case ----- in formula (I) will represent single bond.

Further embodiment of the compounds of the present invention are compounds (I), wherein E represents C, and thus ----- in formula (I) represents double bond.

Another sub-group of compounds of the invention are compounds of formula (I) wherein D represents phenyl. Phenyl may be unsubstituted or substituted as defined for substituent D above, for example with one or more substituent independently selected the group consisting of straight $C_1$-$C_4$-alkyl in position ortho or meta with respect to sulphonamide group, halogen atom, —CN, —OH, and phenyl;

Yet another sub-group of the compounds of the invention are compounds of formula (I), wherein D represents naphthyl. Naphthyl may be linked to sulphur atom of sulphonamide moiety in position 1 (alpha) or 2 (beta) of naphthyl ring. Naphthyl may be unsubstituted or substituted, as defined for substituent D above, for example with halogen atom.

Yet another group of compounds of the present invention are compounds of formula (I), wherein D represents a 5-membered aromatic heterocyclic group having 1 to 3 heteroatoms independently selected from the group consisting of N, O and S. Preferred aromatic heterocyclic group is thienyl, that is heteroatom represents sulphur atom. 5-Membered aromatic heterocyclic group may be unsubstituted or substituted as defined for substituent D above.

Another sub-group of the compounds of the present invention are compounds of formula (I), wherein D represents a bicyclic group consisting of benzene ring fused with 5-membered aromatic heterocyclic ring having 1 to 3 heteroatoms independently selected from the group consisting of N, O, and S. This bicyclic group may be unsubstituted or substituted as defined above for substituent D, for instance with halogen atom and/or $C_1$-$C_4$-alkyl. Preferably, bicyclic group is selected from the group consisting of 1-benzothiophen-3-yl, 1-benzothiophen-2-yl, 1-benzofuran-2-yl, 1-benzofuran-3-yl, 1H-benzimidazol-2-yl, 1H-indol-2-yl, 1H-indol-5-yl, 1H-indol-6-yl, 1H-indazol-7-yl, 1H-indazol-6-yl, 1,2-benzoxazol-5-yl, 1,3-benzoxazol-4-yl, 1,3-benzothiazol-4-yl, and 1,3-benzothiazol-5-yl.

Further sub-group of the compounds of the present invention are compounds of formula (I), wherein D represents bicyclic group consisting of pyridine ring fused with 5-membered heterocyclic aromatic ring having 1 to 3 heteroatoms independently selected from the group consisting of N, O, and S. This bicyclic group may be unsubstituted or substituted as defined above for substituent D, for instance with halogen atom and/or $C_1$-$C_4$-alkyl. Preferably, bicyclic group is selected from the group consisting of imidazo[1,2-a]-pyridin-3-yl and 1H-pyrrolo[2,3-b]-pyridin-3-yl.

Yet another sub-group of the compounds of the present invention are compounds of formula (I), wherein D represents bicyclic group consisting of benzene ring fused with a 5-membered non-aromatic heterocyclic ring having 1 to 3 heteroatoms independently selected from the group consisting of N, O, and S. This bicyclic group may be unsubstituted or substituted as defined above for substituent D. Preferred bicyclic group is selected from the group consisting of 2,3-dihydro-1-benzofuran-5-yl, 2-oxo-2,3-dihydro-1,3-benzoxazol-6-yl, 2-oxo-1,3-dihydro-2H-indol-5-yl and 1,3-benzodioxol-5-yl.

Yet another sub-group of the compounds of the present invention are compounds of formula (I), wherein D represents bicyclic group consisting of benzene ring, fused with 6-membered non-aromatic heterocyclic ring having from 1 to 3 heteroatoms independently selected from the group consisting of N, O, and S. This bicyclic group may be unsubstituted or substituted as defined above for substituent D. Preferred bicyclic group is 2,3-dihydro-1,4-benzodioxine-6-yl.

Further sub-group of the compounds of the present invention are compounds of formula (I), wherein A represents group of formula (A2) linked to E through carbon atom of heterocyclic ring; E represents CH; and D represents phenyl substituted with one or more halogen atoms.

Another sub-group of the compounds of the present invention are compounds of formula (I), wherein A represents group of formula (A1) wherein Y represents O linked to E through carbon atom of heterocyclic ring; E represents N; and D represents unsubstituted phenyl or phenyl substituted with one or more substituents independently selected from the group as defined for formula (I).

Another sub-group of the compounds of the present invention are compounds of formula (I), wherein n is 2.

Further sub-group of compounds of the present invention are compounds of formula (I), wherein n is 3.

Further sub-group of the compounds of the present invention are compounds of formula (I), wherein n is 4.

The following specific compounds of formula (I) of the invention can be mentioned:

1) N-(4-(4-(1,2-benzothiazol-3-yl)piperazin-1-yl)butyl)naphthalene-1-sulphonamide,
2) N-(4-(4-(1,2-benzothiazol-3-yl)piperazin-1-yl)butyl)naphthalene-2-sulphonamide,
3) N-(4-(4-(1,2-benzothiazol-3-yl)piperazin-1-yl)butyl)-3-methylbenzenesulphonamide,
4) N-(4-(4-(1,2-benzothiazol-3-yl)piperazin-1-yl)butyl)-2-oxo-3H-1,3-benzoxazole-6-sulphonamide,
5) N-(3-(4-(1,2-benzothiazol-3-yl)piperazin-1-yl)propyl)naphthalene-1-sulphonamide,
6) N-(3-(4-(1,2-benzothiazol-3-yl)piperazin-1-yl)propyl)naphthalene-2-sulphonamide,
7) N-(3-(4-(1,2-benzothiazol-3-yl)piperazin-1-yl)propyl)-3-methylbenzenesulphonamide,
8) N-(3-(4-(1,2-benzothiazol-3-yl)piperazin-1-yl)propyl)-2-oxo-3H-1,3-benzoxazole-6-sulphonamide,
9) N-(2-(4-(1,2-benzothiazol-3-yl)piperazin-1-yl)ethyl)naphthalene-1-sulphonamide,
10) N-(2-(4-(1,2-benzothiazol-3-yl)piperazin-1-yl)ethyl)naphthalene-2-sulphonamide,
11) N-(2-(4-(1,2-benzothiazol-3-yl)piperazin-1-yl)ethyl)-3-methylbenzenesulphonamide,
12) N-(2-(4-(1,2-benzothiazol-3-yl)piperazin-1-yl)ethyl)-2-oxo-3H-1,3-benzoxazole-6-sulphonamide,
13) N-(4-(4-(1,2-benzoxazol-3-yl)piperazin-1-yl)butyl)naphthalene-1-sulphonamide,
14) N-(4-(4-(1,2-benzoxazol-3-yl)piperazin-1-yl)butyl)naphthalene-2-sulphonamide,
15) N-(4-(4-(1,2-benzoxazol-3-yl)piperazin-1-yl)butyl)-3-methylbenzenesulphonamide,
16) N-(4-(4-(1,2-benzoxazol-3-yl)piperazin-1-yl)butyl)-2-oxo-3H-1,3-benzoxazole-6-sulphonamide,
17) N-[4-[4 (6-fluoro-1,2-benzoxazol-3-yl)piperidin-1-yl]butyl]naphthalene-1-sulphonamide,
18) N-[4-[4-(6-fluoro-1,2-benzoxazol-3-yl)piperidin-1-yl]butyl]naphthalene-2-sulphonamide, 19) N-[4-[4-(6-fluoro-1,2-benzoxazol-3-yl)piperidin-1-yl]butyl]-3-methylbenzenesulphonamide,
20) N-[3-[4-(6-fluoro-1,2-benzoxazol-3-yl)piperidin-1-yl]propyl]naphthalene-1-sulphonamide,
21) N-[3-[4-(6-fluoro-1,2-benzoxazol-3-yl)piperidin-1-yl]propyl]naphthalene-2-sulphonamide,
22) N-[3-[4-(6-fluoro-1,2-benzoxazol-1-yl)piperidin-1-yl]propyl]-3-methylbenzenesulphonamide,
23) N-[2-[4-(6-fluoro-1,2-benzoxazol-3-yl piperidin-1-yl)ethyl]naphthalene-1-sulphonamide,
24) N-[2-[4-(6-fluoro-1,2-benzoxazol-3-yl)piperidin-1-yl]ethyl]naphthalene-2-sulphonamide,
25) N-[2-[4-(6-fluoro-1,2-benzoxazol-3-yl)piperidin-1-yl]ethyl]-3-methylbenzenesulphonamide,
26) N-{4-[4-(1H-indol-4-yl)piperazin-1-yl]butyl}naphthalene-2-sulphonamide,
27) N-{4-[4-(1H-indol-4-yl)piperazin-1-yl]butyl}benzenesulphonamide,
28) 3-fluoro-N-{4-[4-(1H-indol-4-yl)piperazin-1-yl]butyl}benzenesulphonamide,
29) 3,4-difluoro-N-{4-[4-(1H-indol-4-yl)piperazin-1-yl]butyl}benzenesulphonamide,
30) N-{4-[4-(1H-indol-4-yl)piperazin-1-yl]butyl}-imidazo[1,2-a]pyridine-3-sulphonamide,
31) N-{4-[4-(1H-indol-4-yl)piperazin-1-yl]butyl}-1H-pyrrolo[2,3-b]pyridine-3-sulphonamide,
32) N-{4-[4-(1H-indol-4-yl)piperazin-1-yl]butyl}-1-benzothiophene-3-sulphonamide,
33) N-{4-[4-(1H-indol-4-yl)piperazin-1-yl]butyl}-1-benzothiophene-2-sulphonamide,
34) N-{4-[4-(5-chloro-1H-indol-3-yl)-3,6-dihydropyridin-1(2H)-yl]butyl}naphthalene-1-sulphonamide,
35) N-{4-[4-(5-chloro-1H-indol-3-yl)-3,6-dihydropyridin-1(2H)-yl]butyl}naphthalene-2-sulphonamide,
36) 4-fluoro-N-{4-[4-(5-chloro-1H-indol-3-yl)-3,6-dihydropyridin-1(2H)-yl]butyl}benzenesulphonamide,
37) 3-fluoro-N-{4-[4-(5-chloro-1H-indol-3-yl)-3,6-dihydropyridin-1(2H)-yl]butyl}benzenesulphonamide,
38) 4-chloro-N-{4-[4-(5-chloro-1H-indol-3-yl)-3,6-dihydropyridin-1(2H)-yl]butyl}benzenesulphonamide
39) 3-chloro-N-{4-[4-(5-chloro-1H-indol-3-yl)-3,6-dihydropyridin-1(2H)-yl]butyl}benzenesulphonamide,
40) 3-methyl-N-{4-[4-(5-chloro-1H-indol-3-yl)-3,6-dihydropyridin-(2H)-yl]butyl}benzenesulphonamide,
41) 3-hydroxy-N-{4-[4-(5-chloro-1H-indol-3-yl)-3,6-dihydropyridin-1(2H)-yl]butyl}benzenesulphonamide,
42) 4-methoxy-N-{4-[4-(5-chloro-1H-indol-3-yl)-3,6-dihydropyridin-1(2H)-yl]butyl}benzenesulphonamide
43) N-{3-[4-(5-chloro-1H-indol-3-yl)-3,6-dihydropyridin-1(2H)-yl]propyl}naphthalene-1-sulphonamide,
44) N-{3-[4(5-chloro-1H-indol-3-yl)-3,6-dihydropyridin-1(2H)-yl]propyl}naphthalene-2-sulphonamide,
45) 4-fluoro-N-{3-[4-(5-chloro-1H-indol-3-yl)-3,6-dihydropyridin-1(2H)-yl]propyl}benzenesulphonamide,
46) 3-fluoro-N-{3-[4-(5-chloro-1H-indol-3-yl)-3,6-dihydropyridin-2H)-yl]propyl}benzenesulphonamide,
47) 4-chloro-N-{3-[4-(5-chloro-1H-indol-3-yl)-3,6-dihydropyridin-1(2H)-yl]propyl}benzenesulphonamide,
48) 3-chloro-N-{3-[4-(5-chloro-1H-indol-3-yl)-3,6-dihydropyridin-1(2H)-yl]propyl}benzenesulphonamide,
49) 3-hydroxy-N-{3-[4-(5-chloro-1H-indol-3-yl)-3,6-dihydropyridin-1(2H)-yl]propyl}benzenesulphonamide,
50) N-{2-[4-(5-chloro-1H-indol-3-yl)-3,6-dihydropyridin-1(2H)-yl]ethyl}naphthalene-1-sulphonamide,
51) N-{2-[4-(5-chloro-1H-indol-3-yl)-3,6-dihydropyridin-1(2H)-yl]ethyl}naphthalene-2-sulphonamide,
52) N-{2-[4-(5-chloro-1H-indol-3-yl)-3,6-dihydropyridin-1(2H)-yl]ethyl}-4-fluorobenzenesulphonamide,
53) 3-fluoro-N-{2-[4-(5-chloro-1H-indol-3-yl)-3,6-dihydropyridin-1(2H)-yl]ethyl}benzenesulphonamide,
54) 4-chloro-N-{2-[4-(5-chloro-1H-indo-3-yl)-3,6-dihydropyridin-1(2H)-yl]ethyl}benzenesulphonamide,
55) 3-chloro-N-{2-[4-(5-chloro-1H-indol-3-yl)-3,6-dihydropyridin-1(2H)-yl]ethyl}benzenesulphonamide,
56) 3-methyl-N-{2-[4-(5-chloro-1H-indol-3-yl)-3,6-dihydropyridin-1-(2H)-yl]ethyl}benzenesulphonamide,
57) 3-hydroxy-N-{2-[4-(5-chloro-1H-indol-3-yl)-3,6-dihydropyridin-1(2H) yl]ethyl}benzenesulphonamide,
58) 4-chloro-N-{4-[4-(5-chloro-2-methyl-1H-indol-3-yl)-3,6-dihydropyridin-1(2H)-yl]-butyl}benzenesulphonamide,
59) 7-chloro-N-{4-[4-(1,2-benzothiazol-3-yl)piperazin-1-yl]butyl}naphthalene-2-sulphonamide,
60) 7-chloro-N-{3-[4-(1,2-benzothiazol-3-yl)piperazin-1-yl]propyl}naphthalene-2-sulphonamide,
61) 6-chloro-N-{4-[4-(1,2-benzothiazol-3-yl)piperazin-1-yl]butyl}naphthalene-2-sulphonamide,
62) 6-chloro-N-{3-[4-(1,2-benzothiazol-3-yl)piperazin-1-yl]propyl}naphthalene-2-sulphonamide,
63) 3-chloro-4-fluoro-N-{4-[4-(1,2-benzothiazol-3-yl) piperazin-1-yl]butyl}benzenesulphonamide,
64) 3-chloro-4-fluoro-N-{3-[4-(1,2-benzothiazol-3-yl)piperazin-1-yl]propyl}benzenesulphonamide,
65) 5-fluoro-3-methyl-N-{4-[4-(1,2-benzothiazol-3-yl)piperazin-1-yl]butyl}-1-benzo thiophene-2-sulphonamide,
66) 5-fluoro-3-methyl-N-{3-[4-(1,2-benzothiazol-3-yl)piperazin-1-yl]propyl}-1-benzo-thiophene-2-sulphonamide,
67) 5-chloro-N-{4-[4-(1,2-benzothiazol-3-yl)piperazin-1-yl]butyl}-1-benzothiophene-2-sulphonamide,
68) 5-chloro-N-{3-[4-(1,2-benzothiazol-3-yl)piperazin-1-yl]propyl}-1-benzothiophene-2-sulphonamide,
69) 3-chloro-N-{4-[4-(1,2-benzothiazol-3-yl)piperazin-1-yl]butyl}benzenesulphonamide,
70) 3-chloro-N-{3-[4-(1,2-benzothiazol-3-yl)piperazin-1-yl]propyl}benzenesulphonamide,
71) 3-fluoro-N-{4-[4-(1,2-benzothiazol-3-yl)piperazin-1-yl]butyl}benzenesulphonamide,
72) 3-fluoro-N-{3-[4-(1,2-benzothiazol-3-yl)piperazin-1-yl]propyl}benzenesulphonamide,
73) 3-cyano-N-{4-[4-(1,2-benzothiazol-3-yl)piperazin-1-yl]butyl}benzenesulphonamide,
74) 3-cyano-N-{3-[4-(1,2-benzothiazol-1-yl)piperazin-1-yl]propyl}benzenesulphonamide,
75) N-{4-[4-(1,2-benzothiazol-3-yl)piperazin-1-yl]butyl}-imidazo[1,2-a]-pyridine-3-sulphonamide,
76) N-{3-[4-(1,2-benzothiazol-3-yl)piperazin-1-yl]propyl}-imidazo[1,2-a]pyridine-3-sulphonamide,
77) 7-chloro-N-{4-[4-(1,2-benzoxazol-3-yl)piperazin-1-yl]butyl}naphthalene-2-sulphonamide,
73) 7-chloro-N-{3-[4-(1,2-benzoxazol-3-yl)piperazin-1-yl]propyl}naphthalene-2-sulphonamide,
79) 6-chloro-N-{4-[4-(1,2-benzoxazol-3-yl)piperazin-1-yl]butyl}naphthalene-2-sulphonamide,
80) 6-chloro-N-{3-[4-(1,2-benzoxazol-3-yl)piperazin-1-yl]propyl}naphthalene-2-sulphonamide,
81) 5-fluoro-3-methyl-N-{4-[4-(1,2-benzoxazol-3-yl)piperazin-1-yl]butyl}-1-benzo-thiophene-2-sulphonamide,
82) 5-fluoro-3-methyl-N-{3-[4-(1,2-benzoxazol-3-yl)piperazin-1-yl]propyl}-1-benzo-thiophene-2-sulphonamide,
83) 5-chloro-N-{4-[4-(1,2-benzoxazol-3-yl)piperazin-1-yl]butyl}-1-benzothiophene-2-sulphonamide,
84) 5-chloro-N-{3-[4-(1,2-benzoxazol-3-yl)piperazin-1-yl]propyl}-1-benzothiophene-2-sulphonamide, 85) 3-chloro-N-{4-[4-(1,2-benzoxazol-3-yl)piperazin-1-yl]butyl}benzenesulphonamide,
86) 3-chloro-N-{3-[4-(1,2-benzoxazol-3-yl)piperazin-1-yl]propyl}benzenesulphonamide,
87) 3-fluoro-N-{4-[4-(1,2-benzoxazol-3-yl)piperazin-1-yl]butyl}benzenesulphonamide,
88) 3-fluoro-N-{3-[4-(1,2-benzoxazol-3-yl)piperazin-1-yl]butyl}benzenesulphonamide,
89) N-{4-[4-(1,2-benzoxazol-3-yl)piperazin-1-yl]butyl}-1H-pyrrolo[2,3-b]pyridine-3-sulphonamide,
90) N-{3-[4-(1,2-benzoxazol-3-yl)piperazin-1-yl]propyl}-1H-pyrrolo[2,3-b]pyridine-3-sulphonamide,
91) 3-trifluoromethyl-N-{4-[4-(1,2-benzoxazol-1-yl)piperazin-1-yl]butyl}benzenesulphonamide
92) 3-trifluoromethyl-N-{3-[4-(1,2-benzoxazol-3-yl)piperazin-1-yl]propyl}benzenesulphonamide,
93) 3,4-dichloro-N-{4-[4-(1,2-benzoxazol-3-yl)piperazin-1-yl]butyl}benzenesulphonamide,
94) 3,4-dichloro-N-{3-[4-(1,2-benzoxazol-3-yl)piperazin-1-yl]propyl}benzenesulphonamide,
95) 7-chloro-N-{4-[4-(6-fluoro-1,2-benzoxazol-3-yl)piperidin-1-yl]butyl}naphthalene-2-sulphonamide,
96) 7-chloro-N-{3-[4-(6-fluoro-1,2-benzoxazol-3-yl)piperidin-1-yl]propyl}naphthalene-2-sulphonamide,
is 97) 6-chloro-N-{4-[4-(6-fluoro-1,2-benzoxazol-3-yl)piperidin-1-yl]butyl}naphthalene-2-sulphonamide,
98) 6-chloro-N-{3-[4-(6-fluoro-1,2-benzoxazol-3-yl)piperidin-1-yl]propyl}naphthalene-2-sulphonamide,
99) N-{4-[4-(6-fluoro-1,2-benzoxazol-3-yl)piperidin-1-yl]butyl}-1H-benzimidazole-2-sulphonamide,
100) N-{3-[4-(6-fluoro-1,2-benzoxazol-3-yl)piperidin-1-yl]propyl}-1H-benzimidazole-2-sulphonamide,
101) 5-fluoro-3-methyl-N-{4-[4-(6-fluoro-1,2-benzoxazol-3-yl)piperidin-1-yl]butyl}-1-benzothiophene-2-sulphonamide,
102) 5-fluoro-3-methyl-N-{3-[4-(6-fluoro-1,2-benzoxazol-3-yl)piperidin-1-yl]propyl}-1-benzothiophene-2-sulphonamide,
103) 5-chloro-N-{4-[4-(6-fluoro-1,2-benzoxazol-3-yl)piperidin-1-yl]butyl}-1-benzo-thiophene-2-sulphonamide,
104) 5-chloro-N-{3-[4-(6-fluoro-1,2-benzoxazol-3-yl)piperidin-1-yl]propyl}-1-benzo-thiophene-2-sulphonamide,
105) 3-chloro-N-{4-[4-(6-fluoro-1,2-benzoxazol-3-yl)piperidin-1-yl]butyl}benzenesulphonamide,
106) 3-chloro-N-{3-[4-(6-fluoro-1,2-benzoxazol-3-yl)piperidin-1-yl]propyl}benzenesulphonamide,
107) 3-fluoro-N-{4-[4-(6-fluoro-1,2-benzoxazol-3-yl)piperidin-1-yl]butyl}benzenesulphonamide,
108) 3-fluoro-N-{3-[4-(6-fluoro-1,2-benzoxazol-3-yl)piperidin-1-yl]propyl}benezenesulphonamide,
109) 3-bromo-N-{4-[4-(6-fluoro-1,2-benzoxazol-3-yl)piperidin-1-yl]butyl}benzenesulphonamide,
110) 3-bromo-N-{3-[4-(6-fluoro-1,2-benzoxazol-3-yl)piperidin-1-yl]propyl}benzenesulphonamide,
111) 4-phenyl-N-{4-[4-(6-fluoro-1,2-benzoxazol-3-yl)piperidin-1-yl]butyl}benzenesulphonamide,
112) 4-phenyl-N-{4-[4-(6-fluoro-1,2-benzoxazol-3-yl)piperidin-1-yl]propyl}benzenesulphonamide,
113) 3-chloro-N-{4-[4-(1H-indol-4-yl)piperazin-1-yl]butyl}benzenesulphonamide,
114) 3-chloro-N-{3-[4-(1H-indol-4-yl)piperazin-1-yl]propyl}benzenesulphonamide,
115) N-{4-[4-(1H-indol-4-yl)piperazin-1-yl]butyl}-1,3-benzothiazole-4-sulphonamide,
116) N-{4-[4-(1H-indo-4-yl)piperazin-1-yl]propyl}-1,3-benzothiazote-4-sulphonamide,
117) 7-chloro-N-{4-[4-(5-chloro-1H-indol-3-yl)-3,6-dihydropyridin-1(2H)-yl]butyl}-naphthalene-2-sulphonamide,
118) 7-chloro-N-{3-[4-(5-chloro-1H-indol-3-yl)-3,6-dihydropyridin-1(2H)-yl]propyl}-naphthalene-2-sulphonamide,
119) 6-chloro-N-{4-[4-(5-chloro-1H-indol-3-yl)-3,6-dihydropyridin-1(2H)-yl]butyl}-naphthalene-2-sulphonamide,
120) 6-chloro-N-{3-[4-(5-chloro-1H-indol-3-yl)-3,6-dihydropyridin-1(2H)-yl]propyl}-naphthalene-2-sulphonamide,
121) 5-fluoro-3-methyl-N-{4-[4-(5-chloro-1H-indol-3-yl)-3,6-dihydropyridin-1(2H)-yl]butyl}-1-benzothiophene-2-sulphonamide,
122) 5-fluoro-3-methyl-N-{3-[4-(5-chloro-1H-indo-3-yl)-3,6-dihydropyridin-1(2H)-yl]propyl}-1-benzothiophene-2-sulphonamide,
123) 5-chloro-N-{4-[4-(5-chloro-1H-indol-3-yl)-3,6-dihydropyridin-1(2H)-yl]butyl}-1-benzothiophene-2-sulphonamide,
124) 5-chloro-N-{3-[4-(5-chloro-1H-indol-3-yl)-3,6-dihydropyridin-(2H)-yl]propyl}-benzothiophene-2-sulphonamide,
125) N-{4-[4-(5-chloro-1H-indol-3-yl)-3,6-dihydropyridin-1 (2H)-yl]butyl}-1H-indazole-7-sulphonamide,
126) N-{3-[4-(5-chloro-1H-indol-3-yl)-3,5-dihydropyridin-1(2H)-yl]propyl}-1H-indazole-7-sulphonamide,
127) 7-chloro-N-{4-[4-(5-chloro-2-methyl-1H-indol-3-yl)-3,6-dihydropyridin-1(2H)-yl]-butyl}naphthalene-2-sulphonamide,
128) 7-chloro-N-{3-[4-(5-chloro-2-methyl-1H-indol-3-yl)-3,6-dihydropyridin-1(2H)-yl]-propyl}naphthalene-2-sulphonamide,
129) 6-chloro-N-{4-[4-(5-chloro-2-methyl-1H-indol-3-yl)-3,6-dihydropyridin-1(2H)-yl]-butyl}naphthalene-2-sulphonamide,
130) 6-chloro-N-{3-[4-(5-chloro-2-methyl-1H-indol-3-yl)-3,6-dihydropyridin-1(2H)-yl]-propyl}naphthalene-2-sulphonamide,
131) 5-fluoro-3-methyl-N-{4-[4-(5-chloro-2-methyl-1H-indol-3-yl)-3,6-dihydropyridin-1(2H)-yl]butyl}-1-benzothiophene-2-sulphonamide,
132) 5-fluoro-3-methyl-N-{3-(5-chloro-2-methyl-1H-indol-3-yl)-3,6-dihydropyridin-1(2H)-yl]propyl}-1-benzothiophene-2-sulphonamide,
133) 5-chloro-N-{4-[4-(5-chloro-2-methyl-1H-indol-3-yl)-3,6-dihydropyridin-1(2H)-yl]-butyl}-1-benzothiophene-2-sulphonamide,
134) 5-chloro-N-{3-[4-(5-chloro-2-methyl-1H-indol-3-yl)-3,6-dihydropyridin-1(2H)-yl]-propyl}-1-benzothiophene-2-sulphonamide,
135) N-{4-[4-(5-chloro-2-methyl-1H-indol-3-yl)-3,6-dihydropyridin-1(2H)-yl]butyl}-1H-indazole-7-sulphonamide,
136) N-{3-[4-(5-chloro-2-methyl-1H-indol-3-yl)-3,6-dihydropyridin-1(2H)-yl]propyl}-1H-indazole-7-sulphonamide,
137) 3-chloro-N-{4-[4-(5-chloro-2-methyl-1H-indol-3-yl)-3,6-dihydropyridin-1(2H)-yl]-butyl}benzenesulphonamide,
138) 3-chloro-N-{3-[4-(5-chloro-2-methyl-1H-indol-3-yl)-3,6-dihydropyridin-1(2H)-yl]-propyl}benzenesulphonamide,
139) 3-fluoro-N-{4-[4-(5-chloro-2-methyl-1H-indol-1-yl)-3,6-dihydropyridin-1(2H)-yl]-butyl}benzenesulphonamide, 140) 3-fluoro-N-{3-[4-(5-chloro-2-methyl-1H-indol-3-yl)-3,6-dihydropyridin-1(2H)-yl]-propyl}benzenesulphonamide,
141) 4-tert-butyl-N-{4-[4-(5-chloro-2-methyl-1H-indol-3-yl)-3,6-dihydropyridin-1(2H)-yl]-butyl}benzenesulphonamide,
142) 4-tert-butyl-N-{3-[4-(5-chloro-2-methyl-1H-indol-3-yl)-3,6-dihydropyridin-1(2H)-yl]-propyl}benzenesulphonamide,
143) 7-chloro-N-{4-[4-(2-oxo-2,3-dihydro-1,3-benzoxazol-4-yl)piperazin-1-yl]butyl}-naphthalene-2-sulphonamide,
144) 7-chloro-N-{3-[4-(2-oxo-2,3-dihydro-1,3-benzoxazol-4-yl)piperazin-1-yl]propyl}-naphthalene-2-sulphonamide,
145) 6-chloro-N-{4-[4-(2-oxo-2,3-dihydro-1,3-benzoxazol-4-yl)piperazin-1-yl]butyl}-naphthalene-2-sulphonamide,
146) 6-chloro-N-{3-[4-(2-oxo-2,3-dihydro-1,3-benzoxazol-4-yl)piperazin-1-yl]propyl}-naphthalene-2-sulphonamide,
147) 5-fluoro-3-methyl-N-{4-[4-(2-oxo-2,3-dihydro-1,3-benzoxazol-4-yl)piperazin-1-yl]-butyl}-1-benzothiophene-2-sulphonamide,
148) 5-fluoro-3-methyl-N-{3-[4-(2-oxo-2,3-dihydro-1,3-benzoxazol-4-yl)piperazin-1-yl]propyl}-1-benzothiophene-2-sulphonamide,
149) 5-chloro-N-{4-[4-(2-oxo-2,3-dihydro-1,3-benzoxazol-4-yl)piperazin-1-yl]butyl}-1-benzothiophene-2-sulphonamide,
150) 5-chloro-N-{3-[4-(2-oxo-2,3-dihydro-1,3-benzoxazol-4-yl)piperazin-1-yl]propyl}-1-benzothiophene-2-sulphonamide,
151) N-{4-[4-(2-oxo-2,3-dihydro-1,3-benzoxazol-4-yl)piperazin-1-yl]butyl}-1,2-benzoxazole-5-sulphonamide,
152) N-{3-[4-(2-oxo-2,3-dihydro-1,3-benzoxazol-4-yl)piperazin-1-yl]propyl}-1,2-benzoxazole-5-sulphonamide,
153) 3-chloro-N-{4-[4-(2-oxo-2,3-dihydro-1,3-benzoxazol-4-yl)piperazin-1-yl]butyl}benzenesulphonamide,
154) 3-chloro-N-{3-[4-(2-oxo-2,3-dihydro-1,3-benzoxazol-4-yl)piperazin-1-yl]propyl}benzenesulphonamide,
155) 4-trifluoromethyl-N-{4-[4-(2-oxo-2,3-dihydro-1,3-benzoxazol-4-yl)piperazin-1-yl]-butyl}benzenesulphonamide,
156) 4-trifluoromethyl-N-{3-[4-(2-oxo-2,3-dihydro-1,3-benzoxazol-4-yl)piperazin-1-yl]-propyl}benzenesulphonamide,
157) 3-hydroxy-N-{4-[4-(2-oxo-2,3-dihydro-1,3-benzoxazol-4-yl)piperazin-1-yl]butyl}benzenesulphonamide,
158) 3-hydroxy-N-{3-[4-(2-oxo-2,3-dihydro-1,3-benzoxazol-4-yl)piperazin-1-yl]propyl}benzenesulphonamide,
159) 7-chloro-N-{4-[4-(2-oxo-2,3-dihydro-1H-benzimidazol-4-yl)piperazin-1-yl]butyl}-naphthalene-2-sulphonamide,
160) 7-chloro-N-{3-[4-(2-oxo-2,3-dihydro-1H-benzimidazol-4-yl)piperazin-1-yl]propyl}-naphthalene-2-sulphonamide,
161) 6-chloro-N-{4-[4-(2-oxo-2,3-dihydro-1H-benzimidazol-4-yl)piperazin-1-yl]butyl}-naphthalene-2-sulphonamide,
162) 6-chloro-N-{3-[4-(2-oxo-2,3-dihydro-1H-benzimidazol-4-yl)piperazin-1-yl]propyl}-naphthalene-2-sulphonamide,
163) 5-fluoro-3-methyl-N-{4-[4-(2-oxo-2,3-dihydro-1H-benzimidazol-4-yl)piperazin-1-yl]-butyl}-1-benzothiophene-2-sulphonamide,
164) 5-fluoro-3-methyl-N-{3-[4-(2-oxo-2,3-dihydro-1H-benzimidazol-4-yl)piperazin-1-yl]-propyl}-1-benzothiophene-2-sulphonamide,
165) 5-chloro-3-methyl-N-{4-[4-(2-oxo-2,3-dihydro-1H-benzimidazol-4-yl)piperazin-1-yl]-butyl}-1-benzothiophene-2-sulphonamide,
166) 5-chloro-3-methyl-N-{3-[4-(2-oxo-2,3-dihydro-1H-benzimidazol-4-yl)piperazin-1-yl]-propyl}-1-benzothiophene-2-sulphonamide,
167) 5-chloro-N-{4-[4-(2-oxo-2,3-dihydro-1H-benzimidazol-4-yl)piperazin-1-yl]butyl}-1-benzothiophene-2-sulphonamide,
168) 5-chloro-N-{3-[4-(2-oxo-2,3-dihydro-1H-benzimidazol-4-yl)piperazin-1-yl]propyl}-1-benzothiophene-2-sulphonamide,
169) N-{4-[4-(2-oxo-2,3-dihydro-1H-benzimidazol-4-yl)piperazin-1-yl]butyl}-1,3-benzoxazole-4-sulphonamide,
170) N-{3-[4-(2-oxo-2,3-dihydro-1H-benzimidazol-4-yl)piperazin-1-yl]propyl}-1,3-benzoxazole-4-sulphonamide,
171) 4-cyano-N-{4-[4-(2-oxo-2,3-dihydro-1H-benzimidazol-4-yl)piperazin-1-yl]butyl}benzenesulphonamide,
172) 4-cyano-N-{3-[4-(2-oxo-2,3-dihydro-1H-benzimidazol-4-yl)piperazin-1-yl]propyl}benzenesulphonamide,
173) 3-chloro-N-{4-[4-(2-oxo-2,3-dihydro-1H-benzimidazol-4-yl)piperazin-1-yl]butyl}benzenesulphonamide,
174) 3-chloro-N-{3-[4-(2-oxo-2,3-dihydro-1H-benzimidazol-4-yl)piperazin-1-yl]propyl}benzenesulphonamide,
175) 3-fluoro-N-{4-[4-(2-oxo-2,3-dihydro-1H-benzimidazol-4-yl)piperazin-1-yl]butyl}benzenesulphonamide,
176) 3-fluoro-N-{3-[4-(2-oxo-2,3-dihydro-1H-benzimidazol-4-yl)piperazin-1-yl]propyl}benzenesulphonamide,
177) 7-chloro-N-{4-[4-(2-oxo-2,3-dihydro-1,3-benzoxazol-7-yl)piperazin-1-yl]butyl}-naphthalene-2-sulphonamide,
178) 7-chloro-N-{3-[4-(2-oxo-2,3-dihydro-1,3-benzoxazol-7-yl)piperazin-1-yl]propyl}-naphthalene-2-sulphonamide,
179) 6-chloro-N-{4-[4-(2-oxo-2,3-dihydro-1,3-benzoxazol-7-yl)piperazin-1-yl]butyl}-naphthalene-2-sulphonamide,
180) 6-chloro-N-{3-[4-(2-oxo-2,3-dihydro-1,3-benzoxazol-7-yl)piperazin-1-yl]propyl}-naphthalene-2-sulphonamide,
181) 5-fluoro-3-methyl-N-{4-[4-(2-oxo-2,3-dihydro-1,3-benzoxazol-7-yl)piperazin-1-yl]-butyl}-1-benzothiophene-2-sulphonamide,
182) 5-fluoro-3-methyl-N-{3-[4-(2-oxo-2,3-dihydro-1,3-benzoxazol-7-yl)piperazin-1-yl]-propyl}-1-benzothiophene-2-sulphonamide,
183) 5-chloro-N-{4-[4-(2-oxo-2,3-dihydro-1,3-benzoxazol-7-yl)piperazin-1-yl]butyl}-1-benzothiophene-2-sulphonamide,
184) 5-chloro-N-{3-[4-(2-oxo-2,3-dihydro-1,3-benzoxazol-7-yl)piperazin-1-yl]propyl}-1-benzothiophene-2-sulphonamide,
185) N-{4-[4-(2-oxo-2,3-dihydro-1,3-benzoxazol-7-yl)piperazin-1-yl]butyl}-1-benzothiophene-2-sulphonamide,
186) N-{3-[4-(2-oxo-2,3-dihydro-1,3-benzoxazol-7-yl)piperazin-1-yl]propyl}-1-benzothiophene-2-sulphonamide,
187) N-{4-[4-(2-oxo-2,3-dihydro-1,3-benzoxazole-7-yl)piperazin-1-yl]butyl}-2,3-dihydro-1-benzofurane-5-sulphonamide,
188) N-{3-[4(2-oxo-2,3-dihydro-1,3-benzoxazol-7-yl)piperazin-1-yl]propyl}-2,3-dihydro-1-benzofurane-5-sulphonamide,
189) 4-bromo-N-{4-[4-(2-oxo-2,3-dihydro-1,3-benzoxazol-7-yl)piperazin-1-yl]butyl}benzenesulphonamide,
190) 4-bromo-N-{3-[4-(2-oxo-2,3-dihydro-1,3-benzoxazol-7-yl)piperazin-1-yl]propyl}benzenesulphonamide,
191) 3-chloro-N-{4-[4-(2-oxo-2,3-dihydro-1,3-benzoxazol-7-yl)piperazin-1-yl]butyl}benzenesulphonamide, 192) 3-chloro-N-{3-[4-(2-oxo-2,3-dihydro-1,3-benzoxazol-7-yl)piperazin-1-yl]propyl}benzenesulphonamide,
193) 3-fluoro-N-{4-[4-(2-oxo-2,3-dihydro-1,3-benzoxazol-7-yl)piperazin-1-yl]butyl}benzenesulphonamide,
194) 3-fluoro-N-{3-[4-(2-oxo-2,3-dihydro-1,3-benzoxazol-7-yl)piperazin-1-yl]propyl}benzenesulphonamide,
195) N-{4-[4-(1,2-benzothiazol-3-yl)piperazin-1-yl]butyl}-5-chlorothiophene-2-sulphonamide,
196) N-{3-[4-(1,2-benzothiazol-3-yl)piperazin-1-yl]propyl}-5-chlorothiophene-2-sulphonamide,
197) 7-chloro-N-{4-[4-(3-oxo-3,4-dihydro-2H-1,4-benzoxazin-8-yl)piperazinyl]butyl}-naphthalene-2-sulphonamide,
198) 7-chloro-N-{3-[4(3-oxo-3,4-dihydro-2H-1,4-benzoxazin-8-yl)piperazin-1-yl]propyl}-naphthalene-2-sulphonamide,
199) 6-chloro-N-{1-[4-(3-oxo-3,4-dihydro-2H-1,4-benzoxazin-8-yl)piperazin-1-yl]butyl}-naphthalene-2-sulphonamide,
200) 6-chloro-N-{3-[4-(3-oxo-3,4-dihydro-2H-1,4-benzoxazin-8-yl)piperazin-1-yl]propyl}-naphthalene-2-sulphonamide,
201) 5-fluoro-3-methyl-N-{4-[4-(3-oxo-3,4-dihydro-2H-1,4-benzoxazin-8-yl)piperazin-1-yl]butyl}-1-benzothiophene-2-sulphonamide,
202) 5-fluoro-3-methyl-N-{3-[4-(3-oxo-3,4-dihydro-2H-1,4-benzoxazin-8-yl)piperazin-1-yl]propyl}-1-benzothiophene-2-sulphonamide,
203) 5-chloro-N-{4-[4-(3-oxo-3,4-dihydro-2H-1,4-benzoxazin-8-yl)piperazin-1-yl]butyl}-1-benzothiophene-2-sulphonamide,
204) 5-chloro-N-{3-[4-(3-oxo-3,4-dihydro-2H-1,4-benzoxazin-8-yl)piperazin-1-yl]propyl}-1-benzothiophene-2-sulphonamide,
205) N-{4-[4-(3-oxo-3,4-dihydro-2H-1,4-benzoxazin-8-yl)piperazin-1-yl]butyl}-1-benzothiophene-3-sulphonamide,
206) N-{3-[4-(3-oxo-3,4-dihydro-2H-1,4-benzoxazyn-8-yl)piperazyn-1-yl]propyl}-1-benzothiophene-3-sulphonamide,
207) N-{4-[4-(3-oxo-3,4-dihydro-2H-1,4-benzoxazin-8-yl)piperazin-1-yl]butyl}-1,3-benzodioxole-5-sulphonamide,
208) N-{3-[4-(3-oxo-3,4-dihydro-2H-1,4-benzoxazin-8-yl)piperazin-1-yl]propyl}-1,3-benzodioxole-5-sulphonamide,
209) 3-chloro-N-{4-[4-(3-oxo-3,4-dihydro-2H-1,4-benzoxazin-8-yl)piperazin-1-yl]butyl}benzenesulphonamide,
210) 3-chloro-N-{3-[4-(3-oxo-3,4-dihydro-2H-1,4-benzoxazin-8-yl)piperazin-1-yl]propyl}benzenesulphonamide,
211) 3-fluoro-N-{4-[4-(3-oxo-3,4-dihydro-2H-1,4-benzoxazin-8-yl)piperazin-1-yl]butyl}benzenesulphonamide,
212) 3-fluoro-N-{4-[4-(3-oxo-3,4-dihydro-2H-1,4-benzoxazin-8-yl)piperazin-1-yl]propyl}benzenesulphonamide,
213) 4-isopropyl-N-{4-[4-(3-oxo-3,4-dihydro-2H-1,4-benzoxazin-8-yl)piperazin-1-yl]-butyl}benzenesulphonamide,
214) 4-isopropyl-N-{3-[4-(3-oxo-3,4-dihydro-2H-1,4-benzoxazin-8-yl)piperazin-1-yl]-propyl}benzenesulphonamide,
215) N-{4-[4-(3-oxo-3,4-dihydro-2H-1,4-benzoxazin-8-yl)piperazin-1-yl]butyl}thiophene-2-sulphonamide,
216) N-{3-[4-(3-oxo-3,4-dihydro-2H-1,4-benzoxazin-8-yl)piperazin-1-yl]propyl}thiophene-2-sulphonamide,
217) N-{4-[4-(2,2-difluoro-1,3-benzodioxol-4-yl)piperazin-1-yl]butyl}-naphthalene-2-sulphonamide,
218) N-{3-[4-(2,2-difluoro-1,3-benzodioxol-4-yl)piperazin-1-yl]propyl}-naphthalene-2-sulphonamide,
219) N-{4-[4-(2,2-difluoro-1,3-benzodioxol-4-yl)piperazin-1-yl]butyl}-naphthalene-1-sulphonamide,
220) N-{3-[4-(2,2-difluoro-1,3-benzodioxol-4-yl)piperazin-1-yl]propyl}-naphthalene-1-sulphonamide,
221) 3-fluoro-N-{4-[4-(2,2-difluoro-1,3-benzodioxol-4-yl)piperazin-1-yl]butyl}benzenesulphonamide,
222) 3-fluoro-N-{3-[4-(2,2-difluoro-1,3-benzodioxol-4-yl)piperazyn-1-yl]propyl}-benzenesulphonamide,
223) 3-chloro-N-{4-[4-(2,2-difluoro-1,3-benzodioxol-4-yl)piperazin-1-yl]butyl}benzenesulphonamide,
224) 3-chloro-N-{3-[4-(2,2-difluoro-1,3-benzodioxol-4-yl)piperazin-1-yl]propyl}benzenesulphonamide,
225) N-[4-[4-(1,2-benzothiazol-3-yl)piperazin-1-yl]butyl]-4-fluorobenzenesulphonamide,
226) N-[4-[4-(1,2-benzothiazol-3-yl)piperazin-1-yl]butyl]-3,4-difluorobenzenesulphonamide,
227) N-[4-[4-(1,2-benzothiazol-3-yl)piperazin-1-yl]butyl]-4-chlorobenzenesulphonamide,
228) N-[4-[4-(1,2-benzothiazol-3-yl)piperazin-1-yl]butyl]-3,4-dichlorobenzenesulphonamide,
229) N-[4-[4-(1,2-benzothiazol-3-yl)piperazin-1-yl]butyl]-4-bromobenzenesulphonamide,
230) N-[4-[4-(1,2-benzothiazol-3-yl)piperazin-1-yl]butyl]-3-bromobenzenesulphonamide,
231) N-[4-[4-(1,2-benzothiazol-3-yl)piperazin-1-yl]butyl]-3-hydroxybenzenesulphonamide,
232) N-[4-[4-(1,2-benzothiazol-3-yl)piperazin-1-yl]butyl]-3-methoxybenzenesulphonamide,
233) N-[4-[4-(1,2-benzothiazol-3-yl)piperazin-1-yl]butyl]-4-tert-butylbenzenesulphonamide,
234) N-[4-[4-(1,2-benzothiazol-3-yl)piperazin-1-yl]butyl]-4-(trifluoromethyl)benzenesulphonamide,
235) N-[4-[4-(1,2-benzothiazol-3-yl)piperazin-1-yl]butyl]-3-(trifluoromethyl)benzenesulphonamide,
236) N-[4-[4-(1,2-benzothiazol-3-yl)piperazin-1-yl]butyl]-4-(trifluoromethoxy)benzenesulphonamide,
237) N-[4-[4-(1,2-benzothiazol-3-yl)piperazin-1-yl]butyl]-4-phenylbenzenesulphonamide,
238) N-[4-[4-(1,2-benzothiazol-3-yl)piperazin-1-yl]butyl]thiophene-2-sulphonamide,
239) N-[4-[4-(1,2-benzothiazol-3-yl)piperazin-1-yl]butyl]benzothiophene-2-sulphonamide,
240) N-[4-[4-(1,2-benzothiazol-3-yl)piperazin-1]butyl]benzothiophene-3-sulphonamide,
241) N-[4-[4-(1,2-benzothiazol-3-yl)piperazin-1-yl]butyl]-6-chlorobenzothiophene-2-sulphonamide,
242) N-[4-[4-(1,2-benzothiazol-3-yl)piperazin-1-yl]butyl]-2,3-dihydrobenzofuran-5-sulphonamide,
243) N-[4-[4-(1,2-benzothiazol-3-yl)piperazin-1-yl]buty)]-1,3-benzothiazole-4-sulphonamide,
244) N-[4-[4-(1,2-benzothiazol-3-yl)piperazin-1-yl]butyl]-1H-indazole-6-sulphonamide,
245) N-[4-[4-(1,2-benzothiazol-3-yl)piperazin-1-yl]butyl]-1,3-benzodioxole-5-sulphonamide,
246) N-[4-[4-(1,2-benzothiazol-3-yl)piperazin-1-yl]butyl]imidazo[1,2-a]pyridine-3-sulphonamide,
247) N-[4-[4-(1,2-benzothiazol-3-yl)piperazin-1-yl]butyl]-1H-pyrrolo[2,3-b]pyridine-3-sulphonamide,
248) N-[3-[4-(1,2-benzothiazol-3-yl]propyl]piperazin-fluorobenzenesulphonamide,
249) N-[3-[4-(1,2-benzothiazol-3-yl)piperazin-1-yl]propyl]-3,4-difluorobenzenesulphonamide,
250) N-[3-[4-(1,2-benzothiazol-3-yl)piperazin-1-yl]propyl]-4-chlorobenzenesulphonamide,
251) N-[3-[4-(1,2-benzothiazol-3-yl)piperazin-1-yl]propyl]-4-dichlorobenzenesulphonamide, 252) N-[3-[4-(1,2-benzothiazol-3-yl)piperazin-1-yl]propyl]-4-bromobenzenesulphonamide,
253) N-[3-[4-(1,2-benzothiazol-3-yl)piperazin-1-yl]propyl]-3-bromobenzenesulphonamide,
254) N-[3-[4-(1,2-benzothiazol-3-yl)piperazin-1-yl]propyl]-3-hydroxybenzenesulphonamide,
255) N-[3-[4-(1,2-benzothiazol-3-yl)piperazin-1-yl]propyl]-3-methoxybenzenesulphonamide,
is 256) N-[3-[4-(1,2-benzothiazol-3-yl)piperazin-1-yl]propyl]-4-tert-butylbenzenesulphonamide,
257) N-[3-[4-(1,2-benzothiazol-3-yl)piperazin-1-yl]propyl]-4-(trifluoromethyl)benzenesulphonamide,
258) N-[3-[4-(1,2-benzothiazol-3-yl)piperazin-1-yl]propyl]-3-(trifluoromethyl)benzenesulphonamide,
259) N-[3-[4-(1,2-benzothiazol-3-yl)piperazin-1-yl]propyl]-4-(trifluoromethoxy)benzenesulphonamide,
260) N-[3-[4-(1,2-benzothiazol-3-yl)piperazin-1-yl]propyl]-4-phenylbenzenesulphonamide,
261) N-[3-[4-(1,2-benzothiazol-3-yl)piperazin-1-yl]propyl]thiophene-2-sulphonamide,
262) N-[3-[4-(1,2-benzothiazol-3-yl)piperazin-1-yl]propyl]benzothiophene-2-sulphonamide,
263) N-[3-[4-(1,2-benzothiazol-3-yl)piperazin-1-yl]propyl]benzothiophene-3-sulphonamide,
264) N-[3-[4-(1,2-benzothiazol-3-yl)piperazin-1-yl]propyl]-6-chlorobenzothiophene-2-sulphonamide,
265) N-[3-[4-(1,2-benzothiazol-3-yl)piperazin-1-yl]propyl]-2,3-dihydrobenzofuran-5-sulphonamide,
266) N-[3-[4-(1,2-benzothiazol-3-yl)piperazin-1-yl]propyl]-1,2-benzoxazole-5-sulphonamide,
267) N-[3-[4-(1,2-benzothiazol-3-yl)piperazin-1-yl]propyl]-1,3-benzothiazole-4-sulphonamide,
268) N-[3-[4-(1,2-benzothiazol-3-yl)piperazin-1-yl]propyl]-1H-indazole-6-sulphonamide,
269) N-[3-[4-(1,2-benzothiazol-3-yl)piperazin-1-yl]propyl]-1,3-benzodioxole-5-sulphonamide,
270) N-[3-[4-(1,2-benzothiazol-3-yl)piperazin-1-yl]propyl]-1H-pyrrolo[2,3-b]pyridine-3-sulphonamide,
271) N-[4-[4-(1,2-benzoxazol-3-yl)piperazin-1-yl]butyl]-4-fluorobenzenesulphonamide,
272) N-[4-[4-(1,2-benzoxazol-3-yl)piperazin-1-yl]butyl]-3,4-difluorobenzenesulphonamide,
273) N-[4-[4-(1,2-benzoxazol-3-yl)piperazin-1-yl]butyl]-4-chlorobenzenesulphonamide,
274) N-[4-[4-(1,2-benzoxazol-3-yl)piperazin-1-yl]butyl]-4-bromobenzenesulphonamide,
275) N-[4-[4-(1,2-benzoxazol-3-yl)piperazin-1-yl]butyl]-3-bromobenzenesulphonamide,
276) N-[4-[4-(1,2-benzoxazol-3-yl)piperazin-1-yl]butyl]-3-chloro-4-fluorobenzenesulphonamide,
277) N-[4-[4-(1,2-benzoxazol-3-yl)piperazin-1-yl]butyl]-3-hydroxybenzenesulphonamide,
278) N-[4-[4-(1,2-benzoxazol-1-yl)piperazin-1-yl]butyl]-3-methoxybenzenesulphonamide,
279) N-[4-[4-(1,2-benzoxazol-3-yl)piperazin-1-yl]butyl]-4-tert-butylbenzene-sulphonamide,
280) N-[4-[4-(1,2-benzoxazol-3-yl)piperazin-1-yl]butyl]-4-trifluoromethyl)benzenesulphonamide,
281) N-[4-[4-(1,2-benzoxazol-3-yl)piperazin-1-yl]butyl]-4-(trifluoromethoxy)benzenesulphonamide,
282) N-[4-[4-(1,2-benzoxazol-3-yl)piperazin-1-yl]butyl]-3-cyanobenzenesulphonamide,
283) N-[4-[4-(1,2-benzoxazol-3-yl)piperazin-1-yl]butyl]-4-phenylbenzenesulphonamide,
284) N-[4-[4-(1,2-benzoxazol-3-yl)piperazin-1-yl]butyl]thiophene-2-sulphonamide,
285) N-[4-[4-(1,2-benzoxazol-3-yl)piperazin-1-yl]butyl]-5-chloro-thiophene-2-sulphonamide,
so 286) N-[4-[4-(1,2-benzoxazol-3-yl)piperazin-1-yl]butyl]benzothiophene-2-sulphonamide,
287) N-[4-[4-(1,2-benzoxazol-3-yl)piperazin-1-yl]butyl]benzothiophene-3-sulphonamide,
288) N-[4-[4-(1,2-benzoxazol-3-yl)piperazin-1-yl]butyl]-6-chlorobenzothiophene-2-sulphonamide,
289) N-[4-[4-(1,2-benzoxazol-3-yl)piperazin-1-yl]butyl]-2,3-dihydrobenzofuran-5-sulphonamide,
290) N-[4-[4-(1,2-benzoxazol-3-yl)piperazin-1-yl]butyl]-1,3-benzothiazole-4-sulphonamide,
291) N-[4-[4-(1,2-benzoxazol-3-yl)piperazin-1-yl]butyl]-1H-indazole-6-sulphonamide,
292) N-[4-[4-(1,2-benzoxazol-3-yl)piperazin-1-yl]butyl]-1,3-benzodioxole-5-sulphonamide,
293) N-[4-[4-(1,2-benzoxazol-3-yl)piperazin-1-yl]butyl]imidazo[1,2-a]pyridine-3-sulphonamide,
294) 4-fluoro-N-[4-[4-(6-fluoro-1,2-benzoxazol-3-yl)piperidin-1-yl]butyl]benzenesulphonamide,
295) 3,4-difluoro-N-[4-[4-(6-fluoro-1,2-benzoxazol-3-yl)piperidin-1-yl]butyl]benzenesulphonamide,
296) 4-chloro-N-[4-[4-(6-fluoro-1,2-benzoxazol-3-yl)piperidin-1-yl]butyl]benzenesulphonamide,
297) 3,4-dichloro-N-[4-[4-(6-fluoro-1,2-benzoxazol-3-yl)piperidin-1-yl]butyl]benzenesulphonamide,
298) 4-bromo-N-[4-[4-(6-fluoro-1,2-benzoxazol-3-yl)piperidin-1-yl]butyl]benzenesulphonamide,
299) 3-chloro-4-fluoro-N-[4-[4-(6-fluoro-1,2-benzoxazol-3-yl)piperidin-1-yl]butyl]-benzenesulphonamide,
300) N-[4-[4-(6-fluoro-1,2-benzoxazol-3-yl)piperidin-1-yl]butyl]-3-methoxybenzenesulphonamide,
301) 4-tert-butyl-N-[4-[4-(6-fluoro-1,2-benzoxazol-3-yl)piperidin-1-yl]butyl]benzenesulphonamide,
302) N-[4-[4-(6-fluoro-1,2-benzoxazol-3-yl)piperidin-1-yl]butyl]-4-(trifluoromethyl)-benzenesulphonamide,
303) N-[4-[4-(6-fluoro-1,2-benzoxazol-3-yl)piperidin-1-yl]butyl]-3-(trifluoromethyl)-benzenesulphonamide,
304) N-[4-[4-(6-fluoro-1,2-benzoxazol-3-yl)piperidin-1-yl]butyl]-4-(trifluoromethoxy)-benzenesulphonamide,
305) 4-cyano-N-[4-[4-(6-fluoro-1,2-benzoxazol-3-yl)piperidin-1-yl]butyl]benzenesulphonamide,
306) 3-cyano-N-[4-[4-(6-fluoro-1,2-benzoxazol-3-yl)piperidin-1-yl]butyl]benzenesulphonamide,
307) N-[4-[4-(6-fluoro-1,2-benzoxazol-3-yl)piperidin-1-yl]butyl]thiophene-3-sulphonamide,
308) 5-chloro-N-[4-[4-(6-fluoro-1,2-benzoxazol-3-yl)piperidin-1-yl]butyl]thiophene-2-sulphonamide,
309) N-[4-[4-(6-fluoro-1,2-benzoxazol-3-yl)piperidin-1-yl]butyl]-2,5-dimethyl-thiophene-3-sulphonamide,
310) N-[4-[4-(6-fluoro-1,2-benzoxazol-3-yl)piperidin-1-yl]butyl]-1-methyl-indole-4-sulphonamide,
311) N-[4-[4-(6-fluoro-1,2-benzoxazol-3-yl)piperidin-1-yl]butyl]-1-methyl-indole-6-sulphonamide,
312) N-[4-[4-(6-fluoro-1,2-benzoxazol-3-yl)piperidin-1-yl]butyl]benzothiophene-2-sulphonamide,
313) N-[4-[4-(6-fluoro-1,2-benzoxazol-3-yl)piperidin-1-yl]butyl]benzothiophene-3-sulphonamide,
314) 6-chloro-N-[4-[4-(6-fluoro-1,2-benzoxazol-3-yl)piperidin-1-yl]butyl]benzothiophene-2-sulphonamide,
is 315) 5-chloro-N-[4-[4-(6-fluoro-1,2-benzoxazol-3-yl)piperidin-1-yl]butyl]-3-methylbenzothiophene-2-sulphonamide,
316) N-[4-[4-(6-fluoro-1,2-benzoxazol-3-yl)piperidin-1-yl]butyl]benzofuran-2-sulphonamide,
317) N-[4-[4-(6-fluoro-1,2-benzoxazol-3-yl)piperidin-1-yl]butyl]-2,3-dihydrobenzofuran-5-sulphonamide, 318) N-[4-[4-(6-fluoro-1,2-benzoxazol-3-yl)piperidin-1-yl]butyl]-1,3-benzothiazole-4-sulphonamide,
319) N-[4-[4-(6-fluoro-1,2-benzoxazol-3-yl)piperidin-1-yl]butyl]1H-indazole-6-sulphonamide,
320) N-[4-[4-(6-fluoro-1,2-benzoxazol-3-yl)piperidin-1-yl]butyl]-1,3-benzodioxole-5-sulphonamide,
321) N-[4-[4-(6-fluoro-1,2-benzoxazol-3-yl)piperidin-1-yl]butyl]-2,3-dihydro-1,4-benzodioxine-6-sulphonamide,
322) N-[4-[4-(6-fluoro-1,2-benzoxazol-3-yl)piperidin-1-yl]butyl]imidazo[1,2-a]pyridine-3-sulphonamide,
323) N-[4-[4-(6-fluoro-1,2-benzoxazol-3-yl)piperidin-1-yl]butyl]1H-pyrrolo[2,3-b]-pyridine-3-sulphonamide,
324) N-[4-[4-(6-fluoro-1,2-benzoxazol-3-yl)piperidin-1-yl]butyl]-2-oxo-indoline-5-sulphonamide,
325) N-[4-[4-(6-fluoro-1,2-benzoxazol-3-yl)piperidin-1-yl]butyl]thiophene-2-sulphonamide,
326) 4-fluoro-N-[3-[4-(6-fluoro-1,2-benzoxazol-3-yl)piperidin-1-yl]propyl]benzenesulphonamide,
327) 3,4-difluoro-N-[3-[4-(6-fluoro-1,2-benzoxazol-3-yl)piperidin-1-yl]propyl]benzenesulphonamide,
328) 4-chloro-N-[3-[4-(6-fluoro-1,2-benzoxazol-3-yl)piperidin-1-yl]propyl]benzenesulphonamide,
329) 3,4-dichloro-N-[3-[4-(6-fluoro-1,2-benzoxazol-3-yl)piperidin-1-yl]propyl]benzenesulphonamide,
330) 4-bromo-N-[3-[4-(6-fluoro-1,2-benzoxazol-3-yl)piperidin-1-yl]propyl]benzenesulphonamide,
331) 3-chloro-4-fluoro-N-[3-[4-(6-fluoro-1,2-benzoxazol-3-yl)piperidin-1-yl]propyl]benzenesulphonamide,
332) N-[3-[4-(6-fluoro-1,2-benzoxazol-3-yl)piperidin-1-yl]propyl]-3-methoxybenzenesulphonamide,
333) 4-tert-butyl-N-[3-[4-(6-fluoro-1,2-benzoxazol-3-yl)piperidin-1-yl]propyl]benzenesulphonamide,
334) N-[3-[4-(6-fluoro-1,2-benzoxazol-3-yl)piperidin-1-yl]propyl]-4-(trifluoromethyl)-benzenesulphonamide,
335) N-[3-[4-(6-fluoro-1,2-benzoxazol-3-yl)piperidin-1-yl]propyl]-3-(trifluoromethyl)-benzenesulphonamide,
336) N-[3-[4-(6-fluoro-1,2-benzoxazol-3-yl)piperidin-1-yl]propyl]-4-fluoromethoxy)-benzenesulphonamide,
337) 4-cyano-N-[3-[4-(6-fluoro-1,2-benzoxazol-3-yl)piperidin-1-yl]propyl]benzenesulphonamide,
338) 3-cyano-N-[3-[4-(6-fluoro-1,2-benzoxazol-3-yl)piperidin-1-yl]propyl]benzenesulphonamide,
339) N-[3-[4-(6-fluoro-1,2-benzoxazol-3-yl)piperidin-1-yl]propyl]thiophene-2-sulphonamide,
340) N-[3-[4-(6-fluoro-1,2-benzoxazol-3-yl)piperidin-1-yl]propyl]thiophene-3-sulphonamide,
341) 5-chloro-N-[3-[4-(6-fluoro-1,2-benzoxazol-3-yl)piperidin-1-yl]propyl]thiophene-2-sulphonamide,
342) N-[3-[4-(6-fluoro-1,2-benzoxazol-3-yl)piperidin-1-yl]propyl]-2,5-dimethyl-thiophene-3-sulphonamide,
343) N-[3-[4-(6-fluoro-1,2-benzoxazol-3-yl)piperidin-1-yl]propyl]-1-methyl-indole-4-sulphonamide,
344) N-[3-[4-(6-fluoro-1,2-benzoxazol-3-yl)piperidin-1-yl]propyl]-1-methyl-indole-5-sulphonamide,
345) N-[3-[4-(6-fluoro-1,2-benzoxazol-3-yl)piperidin-1-yl]propyl]benzothiophene-2-sulphonamide,
346) N-[3-[4-(6-fluoro-1,2-benzoxazol-3-yl)piperidin-1-yl]propyl]benzothiophene-3-sulphonamide,
347) 6-chloro-N-[3-[4-(6-fluoro-1,2-benzoxazol-3-yl)piperidin-1-yl]propyl]benzo-thiophene-2-sulphonamide,
348) 5-chloro-N-[3-[4-(6-fluoro-1,2-benzoxazol-3-yl)piperidin-1-yl]propyl]-3-methylbenzothiophene-2-sulphonamide,
349) N-[3-[4-(6-fluoro-1,2-benzoxazol-3-yl)piperidin-1-yl]propyl]benzofuran-2-sulphonamide,
350) N-[3-[4-(6-fluoro-1,2-benzoxazol-piperidin-1-yl]propyl]-2,3-dihydrobenzofuran-5-sulphonamide,
351) N-[3-[4-(6-fluoro-1,2-benzoxazol-3-yl)piperidin-1-yl]propyl]-1,3-benzothiazole-4-sulphonamide,
352) N-[3-[4-(6-fluoro-1,2-benzoxazol-3-yl)piperidin-1-yl]propyl]-1H-indazole-6-sulphonamide,
353) N-[3-[4-(6-fluoro-(1,2-benzoxazol-3-yl)piperidin-1-yl]propyl]-2-oxo-3H-1,3-benzoxazole-6-sulphonamide,
354) N-[3-[4-(6-fluoro-1,2-benzoxazol-3-yl)piperidin-1-yl]propyl]-1,3-benzodioxole-5-sulphonamide,
355) N-[3-[4-(6-fluoro-1,2-benzoxazol-3-yl)piperidin-1-yl]propyl]-2,3-dihydro-1,4-benzodioxine-6-sulphonamide,
356) N-[3-[4-(6-fluoro-1,2-benzoxazol-3-yl)piperidin-1-yl]propyl]imidazo[1,2-a]pyridine-3-sulphonamide,
357) N-[3-[4-(6-fluoro-1,2-benzoxazol-3-yl)piperidin-1-yl]propyl]-1H-pyrrolo[2,3-b]-pyridine-2-sulphonamide,
358) 6-chloro-N-[4-[4-(1H-indol-4-yl)piperazin-1-yl]butyl]naphthalene-2-sulphonamide,
359) 4-fluoro-N-[4-[4-(1H-indol-4-yl)piperazin-1-yl]butyl]benzenesulphonamide,
360) N-[4-[4-(1H-indol-4-yl)piperazin-1-yl]butyl]-4-(trifluoromethyl)benzenesulphonamide,
361) N-[4-[4-(1H-indol-4-yl)piperazin-1-yl]butyl]-3-(trifluoromethyl)benzenesulphonamide,
362) 3-cyano-N-[4-[4-(1H-indol-4-yl)piperazin-1-yl]butyl]benzenesulphonamide,
363) 6-chloro-N-[4-[4-(1H-indo-4-yl)piperazin-1-yl]butyl]benzothiophene-2-sulphonamide,
364) 5-fluoro-N-[4-[4-(1H-indol-4-yl)piperazin-1-yl]butyl]-3-methylbenzothiophene-2-sulphonamide,
365) N-[4-[4-1H-indol-4-yl)piperazin-1-yl]butyl]-1,3-benzodioxole-5-sulphonamide,
366) N-[3-[4-(1,2-benzoxazol-3-yl)piperazin-1-yl]propyl]naphthalene-1-sulphonamide,
367) N-[3-[4-(1,2-benzoxazol-3-yl)piperazin-1-yl]propyl]naphthalene-2-sulphonamide,
368) N-[3-[4-(1,2-benzoxazol-3-yl)piperazin-1-yl]propyl]-4-fluorobenzenesulphonamide,
369) N-[3-[4-(1,2-benzoxazol-3-yl)piperazin-1-yl]propyl]-3,4-difluorobenzenesulphonamide,
370) N-[3-[4-(1,2-benzoxazol-3-yl)piperazin-1-yl]propyl]-4-chlorobenzenesulphonamide,
371) N-[3-[4-(1,2-benzoxazol-3-yl)piperazin-1-yl]propyl]-4-bromobenzenesulphonamide,
372) N-[3-[4-(1,2-benzoxazol-3-yl)piperazin-1-yl]propyl]-3-bromobenzenesulphonamide,
373) N-[3-[4-(1,2-benzoxazol-3-yl)piperazin-1-yl]propyl]-3-chloro-4-fluorobenzenesulphonamide,
374) N-[3-[4-(1,2-benzoxazol-3-yl)piperazin-1-yl]propyl]-4-tert-butyl-benzenesulphonamide,
375) N-[3-[4-(1,2-benzoxazol-3-yl)piperazin-1-yl]propyl]-4-(trifluoromethyl)benzenesulphonamide,
376) N-[3-[4-(1,2-benzoxazol-3-yl)piperazin-1-yl]propyl]-3-cyanobenzenesulphonamide,
377) N-[3-[4-(1,2-benzoxazol-3-yl)piperazin-1-yl]propyl]-4-phenylbenzenesulphonamide,
378) N-[3-[4-(1,2-benzoxazol-3-yl)piperazin-1-yl]propyl]-2,3-dihydrobenzofuran-5-sulphonamide,
379) N-[3-[4-(1,2-benzoxazol-3-yl)piperazin-1-yl]propyl]-1,3-benzothiazole-4-sulphonamide,
380) N-[4-[4-(2,3-dihydro-1,4-benzodioxin-5-yl)piperazin-1-yl]butyl]naphthalene-1-sulphonamide,
381) N-[4-[4-(2,3-dihydro-1,4-benzodioxin-5-yl)piperazin-1-yl]butyl]naphthalene-2-sulphonamide,
382) 6-chloro-N-[4-[4-(2,3-dihydro-1,4-benzodioxin-5-yl)piperazin-1-yl]butyl]-naphthalene-2-sulphonamide,
383) N-[4-[4-(2,3-dihydro-1,4-benzodioxin-5-yl)piperazin-1-yl]butyl]-3-fluorobenzenesulphonamide, 384) N-[4-[4-(2,3-dihydro-1,4-benzodioxin-5-yl)piperazin-1-yl]butyl]-3,4-difluorobenzenesulphonamide,
385) 3-chloro-N-[4-[4-(2,3-dihydro-1,4-benzodioxin-5-yl)piperazin-1-yl]butyl]benzenesulphonamide,
386) 3-bromo-N-[4-[4-(2,3-dihydro-1,4-benzodioxin-5-yl)piperazin-1-yl]butyl]benzenesulphonamide,
387) 3-chloro-N-[4-[4-(2,3-dihydro-1,4-benzodioxin-5-yl)piperazin-1-yl]butyl]-4-fluorobenzenesulphonamide,
388) N-[4-[4-(2,3-dihydro-1,4-benzodioxin-5-yl)piperazin-1-yl]butyl]-3-hydroxybenzenesulphonamide,
389) N-[4-[4-(2,3-dihydro-1,4-benzodioxin-5-yl)piperazin-1-yl]butyl]-3-methoxybenzenesulphonamide,
390) N-[4-[4-(2,3-dihydro-1,4-benzodioxin-5-yl)piperazin-1-yl]butyl]-3-methylbenzenesulphonamide,
391) N-[4-[4-(2,3-dihydro-1,4-benzodioxin-5-yl)piperazin-1-yl]butyl]-4-phenylbenzenesulphonamide,
is 392) N-[4-[4-(2,3-dihydro-1,4-benzodioxin-8-yl)piperazin-1-yl]butyl]thiophene-2-sulphonamide,
393) 5-chloro-N-[4-[4-(2,3-dihydro-1,4-benzodioxin-5-yl)piperazin-1-yl]butyl]thiophene-2-sulphonamide,
394) N-[4-[4-(2,3-dihydro-1,4-benzodioxin-5-yl)piperazin-1-yl]butyl]benzothiophene-2-sulphonamide,
395) N-[4-[4-(2,3-dihydro-1,4-benzodioxin-5-yl)piperazin-1-yl]butyl]benzothiophene-3-sulphonamide,
396) 6-chloro-N-[4-[4-(2,3-dihydro-1,4-benzodioxin-5-yl(piperazin-1-yl]butyl)-benzothiophene-2-sulphonamide,
397) N-[4-[4-(2,3-dihydro-1,4-benzodioxin-5-yl)piperazin-1-yl]butyl]-1H-indazole-6-sulphonamide,
398) N-[4-[4-(2,3-dihydro-1,4-benzodioxin-5-yl)piperazin-1-yl]butyl]-2-oxo-3H-1,3-benzoxazole-6-sulphonamide,
399) N-[4-[4-(2,3-dihydro-1,4-benzodioxin-5-yl)piperazin-1-yl]butyl]-1,3-benzodioxole-5-sulphonamide,
400) N-[3-[4-(2,3-dihydro-1,4-benzodioxin-5-yl)piperazin-1-yl]propyl]naphthalene-1-sulphonamide,
401) N-[3-[4-(2,3-dihydro-1,4-benzodioxin-5-yl)piperazin-1-yl]propyl]naphthalene-2-sulphonamide,
402) 6-chloro-N-[3-[4-(2,3-dihydro-1,4-benzodioxin-5-yl)piperazin-1-yl]propyl]-naphthalene-2-sulphonamide,
403) N-[3-[4-(2,3-dihydro-1,4-benzodioxin-5-yl)piperazin-1-yl]propyl]-4-fluorobenzenesulphonamide,
404) N-[3-[4-(2,3-dihydro-1,4-benzodioxin-5-yl)piperazin-1-yl]propyl]3-fluorobenzenesulphonamide,
405) N-[3-[4-(2,3-dihydro-1,4-benzodioxin-5-yl)piperazin-1-yl]propyl]-3,4-difluorobenzenesulphonamide,
406) 3-chloro-N-[3-[4-(2,3-dihydro-1,4-benzodioxin-5-yl)piperazin-1-yl]propyl]-benzenesulphonamide
407) 4-bromo-N-[3-[4-(2,3-dihydro-1,4-benzodioxin-5-yl)piperazin-1-yl]propyl]-benzenesulphonamide
408) 3-bromo-N-[3-[4-(2,3-dihydro-1,4-benzodioxin-5-yl)piperazin-1-yl]propyl]benzenesulphonamide,
409) N-[3-[4-(2,3-dihydro-1,4-benzodioxin-8-yl)piperazin-1-yl]propyl]-3-methylbenzenesulphonamide,
is 410) N-[3-[4-(2,3-dihydro-1,4-benzodioxin-5-yl)piperazin-1-yl]propyl]-4-phenylbenzenesulphonamide,
411) N-[3-[4-(2,3-dihydro-1,4-benzodioxin-5-yl)piperazin-1-yl]propyl]benzothiophene-3-sulphonamide,
412) N-[3-[4-(2,3-dihydro-1,4-benzodioxin-5-yl)piperazin-1-yl]propyl]-2,3-dihydrobenzofuran-5-sulphonamide,
413) N-[4-[4-(2-oxo-1,3-dihydrobenzimidazol-4-yl)piperazin-1-yl]butyl]naphthalene-1-sulphonamide,
414) N-[4-[4-(2-oxo-1,3-dihydrobenzimidazol-4-yl)piperazin-1-yl]butyl]naphthalene-2-sulphonamide,
415) 4-fluoro-N-[4-[4-(2-oxo-1,3-dihydrobenzimidazol-4-yl)piperazin-1-yl]butyl]benzenesulphonamide,
416) 4-chloro-N-[4-[4-(2-oxo-1,3-dihydrobenzimidazol-4-yl)piperazin-1-yl]butyl]benzenesulphonamide,
417) 3-methyl-N-[4-[4-(2-oxo-1,3-dihydrobenzimidazol-4-yl)piperazin-1-yl]butyl]benzenesulphonamide,
418) N-[3-[4-(2-oxo-1,3-dihydrobenzimidazol-4-yl)piperazin-1-yl]propyl]naphthalene-1-sulphonamide,
419) N-[3-[4-(2-oxo-1,3-dihydrobenzimidazol-4-yl)piperazin-1-yl]propyl]naphthalene-2-sulphonamide,
420) 4-chloro-N-[3-[4-(2-oxo-1,3-dihydrobenzimidazol-4-yl)piperazin-1-yl]propyl]-benzenesulphonamide,
421) 3-methyl-N-[3-[4-(2-oxo-1,3-dihydrobenzimidazol-4-yl)piperazin-1-yl]propyl]-benzenesulphonamide,
422) N-[4-[4-(3-oxo-4H-1,4-benzoxazin-8-yl)piperazin-1-yl]butyl]naphthalene-2-sulphonamide,
423) 4-fluoro-N-[4-[4-(3-oxo-4H-1,4-benzoxazin-8-yl)piperazin-1-yl]butyl]benzenesulphonamide,
424) N-[4-[4-(3-oxo-4H-1,4-benzoxazin-8-yl)piperazin-1-yl]butyl]-4-(trifluoromethyl)-benzenesulphonamide,
425) N-[4-[4-(3-oxo-4H-1,4-benzoxazin-8-yl)piperazin-1-yl]butyl]-3-(trifluoromethyl)-benzenesulphonamide,
426) 5-chloro-N-[4-[4-(3-oxo-4H-1,4-benzoxazin-8-yl)piperazin-1-yl]butyl]thiophene-2-sulphonamide,
427) N-[4-[4-(5-chloro-2-methyl-1H-indol-3-yl)-3,6-dihydro-2H-pyridin-1-yl]butyl]-naphthalene-1-sulphonamide,
428) N-[4-[4-(5-chloro-2-methyl-1H-indol-3-yl)-3,6-dihydro-2H-pyridin-1-yl]butyl]-naphthalene-2-sulphonamide,
429) N-[4-[4-(5-chloro-2-methyl-1H-indol-3-yl)-3,6-dihydro-2H-pyridin-1-yl]butyl]-4-fluorobenzenesulphonamide
430) N-[4-[4-(5-chloro-2-methyl-1H-indol-3-yl)-3,6-dihydro-2H-pyridin-1-yl]butyl]-3-hydroxybenzenesulphonamide,
431) N-[4-[4-(5-chloro-2-methyl-1H-indol-3-yl)-3,6-dihydro-2H-pyridin-1-yl]butyl]-3-methylbenzenesulphonamide,
432) N-[4-[4-(5-fluoro-1H-indol-3-yl)-3,6-dihydro-2H-pyridin-1-yl]butyl]naphthalene-2-sulphonamide,
433) 3-fluoro-N-[4-[4-(5-fluoro-1H-indol-3-yl)-3,6-dihydro-2H-pyridin-1-yl]butyl]-benzenesulphonamide,
434) N-[4-[4-(5-fluoro-1H-indol-3-yl)-3,6-dihydro-2H-pyridin-1-yl]butyl]-3-hydroxy-benzenesulphonamide,
435) N-[4-[4-(5-fluoro-1H-indol-3-yl)-3,6-dihydro-2H-pyridin-1-yl]butyl]-3-methylbenzenesulphonamide,
436) 3-fluoro-N-[3-[4-(5-fluoro-1H-indol-3-yl)-3,6-dihydro-2H-pyridin-1-yl]propyl]-benzenesulphonamide,
437) N-[3-[4-(5-fluoro-1H-indol-3-yl)-3,6-dihydro-2H-pyridin-1-yl]propyl]-3-hydroxy-benzenesulphonamide,
438) N-[2-[4-(5-fluoro-1H-indol-3-yl)-3,6-dihydro-2H-pyridin-1-yl]ethyl]naphthalene-2-sulphonamide,
439) 3-fluoro-N-[2-[4-(5-fluoro-1H-indol-3-yl)-3,6-dihydro-2H-pyridin-1-yl]ethyl]benzenesulphonamide,
440) N-[2-[4-(5-fluoro-1H-indol-3-yl)-3,6-dihydro-2H-pyridin-1-yl]ethyl]-3-methylbenzenesulphonamide,
441) N-[3-[4-(5-chloro-2-methyl-1H-indol-3-yl)-3,6-dihydro-2H-pyridin-1-yl]propyl]-naphthalene-1-sulphonamide,
442) N-[3-[4-(5-chloro-2-methyl-H-indol-3-yl)-3,6-dihydro-2H-pyridin-1-yl]propyl]-naphthalene-2-sulphonamide,
443) N-[3-[4-(5-chloro-2-methyl-1H-indol-3-yl)-3,6-dihydro-2H-pyridin-1-yl]propyl]-4-fluorobenzenesulphonamide,
444) 4-chloro-N-[3-[4-(5-chloro-2-methyl-1H-indol-3-yl)-3,6-dihydro-2H-pyridin-1-yl-propyl]benzenesulphonamide,
445) N-[3-[4-(5-chloro-2-methyl-1H-indol-3-yl)-3,6-dihydro-2H-pyridin-1-yl]propyl]-3-hydroxybenzenesulphonamide, 446) N-[3-[4-(5-chloro-2-methyl-1H-indol-3-yl)-3,6-dihydro-2H-pyridin-1-yl]propyl]-3-methylbenzenesulphonamide,
447) N-[2-[4-(5-chloro-2-methyl-1H-indol-3-yl)-3,6-dihydro-2H-pyridin-1-yl]ethyl]-naphthalene-1-sulphonamide,
448) N-[2-[4-(5-chloro-2-methyl-1H-indol-3-yl)-3,6-dihydro-2H-pyridin-1-yl]ethyl]-naphthalene-2-sulphonamide,
449) N-[2-[4-(5-chloro-2-methyl-1H-indol-1-yl)-3,6-dihydro-2H-pyridin-1-yl]ethyl]-4-fluorobenzenesulphonamide,
450) N-[2-[4-(5-chloro-2-methyl-1H-indol-3-yl)-3,6-dihydro-2H-pyridin-1-yl]ethyl]-3-fluorobenzenesulphonamide,
451) 4-chloro-N-[2-[4-(5-chloro-2-methyl-1H-indol-3-yl)-3,6-dihydro-2H-pyridin-1-yl]-ethyl]benzenesulphonamide,
452) 3-chloro-N-[2-[4-(5-chloro-2-methyl-1H-indol-3-yl)-3,6-dihydro-2H-pyridin-1-yl]-ethyl]benzenesulphonamide,
453) N-[2-[4-(5-chloro-2-methyl-1H-indol-3-yl)-3,6-dihydro-2H-pyridin-1-yl]ethyl]-3-hydroxybenzenesulphonamide,
454) N-[2-[4-(5-chloro-2-methyl-1H-indol-3-yl)-3,6-dihydro-2H-pyridin-1-yl]ethyl]-3-methylbenzenesulphonamide,
and pharmaceutically acceptable salts thereof.

Arylsulphonamide derivatives of the above formula (I) exhibit affinity to receptors which are recognized therapeutical targets in the treatment of CNS disorders, such as dopaminergic, in particular D2 and D3, serotoninergic, in particular 5-HT1A, 5-HT2A, 5-HT6,5-HT7, adrenergic, in particular α1 and α2C, sigma and serotonine transporter receptors and do not exhibit or have low affinity toward biological targets associated with adverse effects, such as potassium channel hERG, muscarinic receptors, histaminergic receptors and serotoninergic receptor 5-HT2C. Due to such a broad pharmacological profile, the compounds of the invention may be useful in medicine as medicaments, for the treatment and/or prevention of the central nervous system disorders such as schizophrenia, schizoaffective disorders, schizophreniform disorders, delusional syndromes and other psychotic conditions related and not related to taking psychoactive substances, affective disorder, bipolar disorder, mania, depression, anxiety disorders of various aetiology, stress reactions, consciousness disorders, coma, delirium of alcoholic or other aetiology, aggression, psychomotor agitation and other conduct disorders, sleep disorders of various aetiology, withdrawal syndromes of various aetiology, addiction, pain syndromes of various aetiology, intoxication with is psychoactive substances, cerebral circulatory disorders of various aetiology, psychosomatic disorders of various aetiology, conversion disorders, dissociative disorders, urination disorders, autism and other developmental disorders, including nocturia, stuttering, tics, cognitive disorders of various types, such as Alzheimer's disease, psychopathological symptoms and neurological disorders in the course of other diseases of the central and peripheral nervous systems.

Thus, the subject of the present invention are the compounds of formula (I) as defined above, for use as a medicament.

In the treatment of central nervous system disorders compound of formula (I) may be administered in the form of a pharmaceutical composition or preparation containing it.

Thus, the subject of the present invention is also the pharmaceutical composition containing a compound or compounds of formula (I) as defined above as an active substance, in combination with pharmaceutically acceptable carrier(s) and/or excipient(s).

The subject of the invention is also a use of arylsulphonamide derivatives of the above formula (I) for the treatment of disorders of central nervous system.

The invention relates also to a method for the treatment of disorders of the central nervous system in mammals, including humans, comprising administration of a therapeutically effective amount of the compound of above formula (I) or the pharmaceutical composition containing the compound of formula (I) as defined above as an active substance.

Terms used in the description of the present invention have the following meanings.

Unless otherwise indicated, the term "$C_1$-$C_4$-alkyl" relates to a saturated, straight or branched hydrocarbon group, having indicated number of carbon atoms. Specific examples of groups encompassed by this term are methyl, ethyl, n-propyl, isopropyl, n-butyl, tert-butyl, and sec-butyl.

The term "$C_1$-$C_3$-alkyloxy" relates to a —O—$C_1$-$C_3$-alkyl group, wherein $C_3$-$C_3$-alkyl represents saturated hydrocarbon group having indicated number of carbon atoms, and which is a straight- or branched-chain. Specific examples of groups encompassed by this term are methoxy, ethoxy, n-propoxy, and iso-propoxy.

The term "halogen atom" relates to a substituent selected from F, Cl, Br and I.

The term "halogeno-$C_1$-$C_3$-alkyl" relates to a saturated, straight or branched hydrocarbon group, having indicated number of carbon atoms and in which one carbon atom may be substituted with from 1-3 halogen atoms, depending on the number of carbon atoms bonded to it. Halogen atom has the meaning as defined above. Particularly preferred example of a group encompassed by this term is trifluoromethyl group —$CF_3$.

The term "halogeno-$C_1$-$C_3$-alkyloxy" relates to a —O—$C_1$-$C_3$-halogenoalkyl group, wherein $C_1$-$C_3$-halogenoalkyl means saturated, straight or branched hydrocarbon group having indicated number of carbon atoms and in which one carbon atom may be substituted with 1-3 halogen atoms, depending on the number of carbon atoms bonded to it. Halogen atom has the meaning as defined above. Particularly preferred example of a group encompassed by his term is trifluoromethoxy group —O—$CF_3$.

The compounds of formula (I) can be prepared in a process presented in the following scheme:

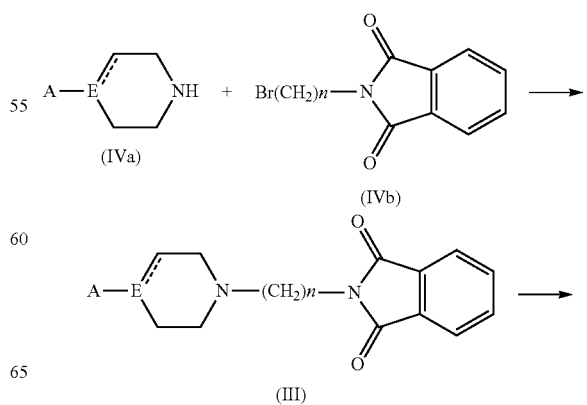

$$A-E\overset{\diagup}{\underset{\diagdown}{\bigcirc}}N-(CH_2)n-NH_2 \;+\; Cl-\overset{O}{\underset{O}{\overset{\|}{\underset{\|}{S}}}}-D \longrightarrow$$

(IIa) \hspace{2cm} (IIb)

$$A-E\overset{\diagup}{\underset{\diagdown}{\bigcirc}}N-(CH_2)n-NH-\overset{O}{\underset{O}{\overset{\|}{\underset{\|}{S}}}}-D$$

(I)

In the first step compound (IVa), for example as hydrochloride, is reacted with appropriate 2-(bromoalkyl)-1H-isoindoline-1,3(2H)-dione (IVb) in a solvent, such as N,N-dimethylformamide or acetonitrile, in the presence of a base at room temperature or at elevated temperature, to give a compound of formula (III). Then imide (III) is hydrolysed using 40% aqueous methylamine solution at room temperature, to obtain amine derivative (IIa). Compound (IIa) is reacted with appropriate arylsulphonyl chloride (IIb), for example in methylene chloride in the presence of triethylamine, at room temperature, to give arylsulphonamide derivative (I) of the invention.

Starting compounds of formulas (IVa) and (IVb) are either well known or commercially available, or can be prepared from commercially available starting materials by adapting and applying known methods, such as described in publication of Hallett D. J. et al., J. Org. Chem. 2000, 65, 4984-4993. Preparation of exemplary starting compounds of formula (III) is described in detail in the experimental part.

Since the compounds of formula (I) have alkaline character (contain at least one tertiary amine group), they can form acid addition salts.

Salts with acids can be pharmaceutically acceptable, especially when they are intended to be an active ingredient in pharmaceutical composition. The present invention relates also to salts of the compounds of formula (I) with acids other than pharmaceutically acceptable ones, which may be useful for example as intermediates suitable for purification of the compounds of the invention. In practice, it is often desirable to isolate first the compound from a reaction mixture in the form of a salt which is not pharmaceutically acceptable to purify the compound, and then convert the salt into free base by treatment with alkaline agent and to isolate, and optionally convert into the salt again.

Acid addition salts can be formed with inorganic (mineral) or organic acids. In particular, hydrochloric, hydrobromic, hydroiodic, phosphoric, sulphuric, nitric, carbonic, succinic, maleic, formic, acetic, propionic, fumaric, citric, tartaric, lactic, benzoic, salicylic, glutamic, aspargic, p-toluenesulphonic, benzenesulphonic, methanesulphonic, ethanesulphonic, naphthalenesulphonic such as 2-naphthalenesulphonic, pamoic, xinafoic or hexanoic acids can be mentioned as examples of acids.

Acid addition salt can be prepared in a simple manner by reaction of the compound of formula (I) with suitable inorganic or organic acid, optionally in suitable solvent, such as organic solvent, to form a salt that is usually isolated, for example by crystallization and filtration. For example, compounds in the form of a free base can be converted into corresponding hydrochloride salts by reaction of a compound in a solution, for example in methanol, with stoichiometric amount of hydrochloric acid or with solution of hydrochloric acid in methanol, ethanol or diethyl ether, followed by evaporation of solvent(s).

The term "disorders of the central nervous system" should be understood as including disorders selected from schizophrenia, schizoaffective disorders, schizophreniform disorders, delusional syndromes and other psychotic conditions related and not related to taking psychoactive substances, affective disorder, bipolar disorder, mania, depression, anxiety disorders of various aetiology, stress reactions, consciousness disorders, coma, delirium of alcoholic and other aetiology, aggression, psychomotor agitation and other conduct disorders, sleep disorders of various aetiology, withdrawal syndromes of various aetiology, addiction, pain syndromes of various aetiology, intoxication with psychoactive substances, cerebral circulatory disorders of various aetiology, psychosomatic disorders of various aetiology, conversion disorders, dissociative disorders, urination disorders, autism and other developmental disorders, including nocturia, stuttering, and tics, cognitive disorders of various types, like Alzheimer's disease, psychopathological symptoms and neurological disorders in the course of other diseases of the central and peripheral nervous systems are.

In the treatment of the disorders mentioned above, compounds of formula (I) of the present invention can be administered as a chemical compound, but usually will be applied in the form of a pharmaceutical compositions containing the compound of the present invention or its pharmaceutically acceptable salt as defined above as an active ingredient in combination with pharmaceutically acceptable carrier(s) and/or excipient(s).

In the treatment of the above mentioned disorders the pharmaceutical compositions of the invention can be delivered by any route of administration, preferably oral or parenteral, and will have the form of a preparation for use in medicine, depending on the intended route of administration.

Compositions for oral administration may have the form of solid or liquid preparations. Solid preparations may be in the form, for example, tablets or capsules prepared in conventional manner using pharmaceutically acceptable inactive ingredients, such as binding agents (e.g. pregelatinized maize starch, polyvinylpyrrolidone or hydroxypropylmethylcellulose); fillers (e.g. lactose, sucrose, carboxymethylcellulose, microcrystalline cellulose or calcium hydrogen phosphate) lubricants (e.g. magnesium stearate, talc or silica); disintegrants (e.g. crospovidone, maize starch or sodium starch glycolate); wetting agents (e.g. sodium (auryl sulfate). The tablets may be coated using methods well known in the art with conventional coatings, delaying/controlling release coatings or enteric coatings. Liquid preparations for oral administration may have the form of e.g. solutions, syrups or suspensions, or may be prepared from a dry product suitable for reconstitution with water or other suitable carrier ex tempore. Such liquid preparations may be prepared by conventional methods with pharmaceutically acceptable inactive ingredients, such as suspending agents (e.g. sorbitol syrup, cellulose derivatives or hydrogenated edible fats), emulsifying agents (e.g. lecithin or acacia gum), non-aqueous matrix components (e.g. almond oil, oils esters, ethyl alcohol or fractionated vegetable oils) and preservatives (e.g. methyl or propyl p-hydroxybenzoates or sorbic acid). The preparations may also contain suitable buffering systems, flavouring and aroma agents, colourants and sweeteners.

Preparations for oral administration can be formulated according to methods well known to those skilled in the art to afford a controlled release of the active compound.

The parenteral route of administration comprises administration by intramuscular and intravenous injections and intravenous continuous infusions. Compositions for parenteral administration may be in the form of a dosage unit, e.g. in ampoules or in multidose containers with the addition of a preservative. The compositions may be in a form of suspensions, solutions or emulsions in oily or aqueous media, and may contain pharmaceutically acceptable excipients, such as suspending agents, stabilizing and/or dispersing agents. Alternatively, the active ingredient may be in the form of a powder for reconstitution ex tempore in a suitable carrier, e.g. sterile pyrogen-free water.

Method of treatment using compounds of this invention will be based on administration of a therapeutically effective amount of the compound of the invention, preferably in the form of a pharmaceutical composition, to a subject in need of such a treatment.

The proposed dose of the compounds of the invention will be comprised in the range from 1 to about 1000 mg per day, in a single dose or in divided doses. It will be so apparent to those skilled in the art that selection of a dose required to achieve the desired biological effect will depend on several factors, such as the type of specific compound, the indication, route of administration, age and condition of a patient and the exact dose will be finally determined at the discretion of attending physician.

EXAMPLE 1

Preparation of Starting Materials of the General Formula (III)

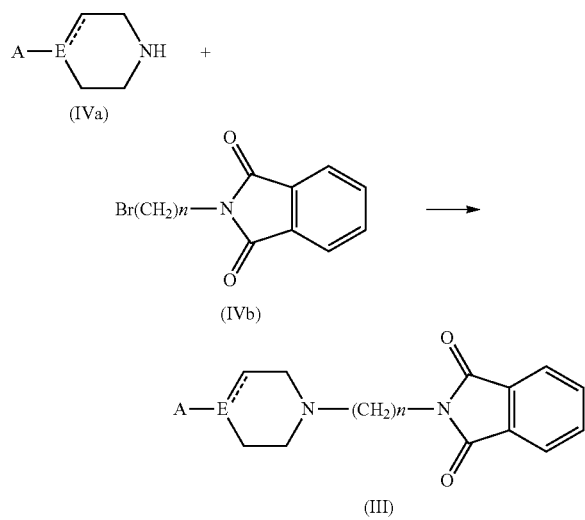

a) General Procedure for Compounds Wherein in Formula (IVa) ----- Represents Single Bond A mixture of 10 mmol of compound (IVa) as hydrochloride and 10 mmol of compound (IVb), 30 mmol of potassium carbonate, small crystal of potassium iodide and 20 ml of N,N-dimethylformamide was stirred at room temperature until disappearance of starting materials (TLC monitoring). Usually, the reaction was carried out for 2 days. The reaction mixture was subsequently poured into 50 ml of water, and precipitate thus formed was isolated by filtration. For purification, crude product was suspended in 20 ml of methanol, then the solid was filtered off and dried to constant weight.

Alternatively (for III-8), the reaction was carried out in acetonitrile, after completion of the reaction the solvent was evaporated and product was purified by column chromatography on silica gel using chloroform/methanol 95:5 as eluent.

Structures of products were confirmed by mass spectrometry.

According to the above procedure the following compounds were prepared:

2-(4-(4-(1,2-benzothiazol-3-yl)piperazin-1-yl)butyl)-1H-isoindole-1,3(2H)-dione (III-1), reaction in N,N-dimethylformamide, MS: 421[M+H$^+$], yield: 87%;

2-(3-(4-(1,2-benzothiazol-3-yl)piperazin-1-yl)propyl)-1H-isoindole-1,3(2H)-dione (III-2), reaction in N,N-dimethylformamide, MS: 407[M+H$^+$], yield: 77%;

2-(2-(4-(1,2-benzothiazol-3-yl)piperazin-1-yl)ethyl)-1H-isoindole-1,3(2H)-dione (III-3), reaction in N,N-dimethylformamide, MS: 393[M+H$^+$], yield: 37%;

2-(4-(4-(1,2-benzoxazol-3-yl)piperazin-1-yl)butyl)-1H-isoindole-1,3(2H)-dione (III-4), reaction in N,N-dimethylformamide, MS: 405[M+H$^+$], yield: 75%;

2-(4-(4-(6-fluoro-1,2-benzoxazol-3-yl)piperidin-1-yl)butyl)-1H-isoindole-1,3(2H)-dione (III-5), reaction in N,N-dimethylformamide, MS: 422[M+H$^+$], yield: 71%;

2-(3-(4-(6-fluoro-1,2-benzoxazol-3-yl)piperidin-1-yl)propyl)-1H-isoindole-1,3(2H)-dione (III-6), reaction in N,N-dimethylformamide, MS: 408[M+H$^+$], yield; 55%;

2-{2-[4-(6-fluoro-1,2-benzoxazol-3-yl)piperydyn-1-yl]ethyl}-1H-isoindole-1,3(2H)-dione (III-7), reaction in N,N-dimethylformamide, MS: 394[M+H$^+$], yield: 47%;

2-[4-[4-(1H-indol-4-yl)piperazin-1-yl]butyl]-1H-isoindole-1,3(2H)-dione (III-8), reaction in acetonitrile, MS: 403 [M+H$^+$], yield: 71%.

2-(3-(4-(1,2-benzoxazol-3-yl)piperazin-1-yl)propyl)-1H-isoindole-1,3(2H)-dione (III-13), reaction in N,N-dimethylformamide, MS: 391[M+H$^+$], yield: 77%;

2-[4-[4-(2,3-dihydro-1,4-benzodioxin-5-yl)piperazin-1-yl]butyl]-1H-isoindole-1,3(2H)-dione (III-14), reaction in N,N-dimethylformamide, MS: 422[M+H$^+$], yield: 73%;

2-[3-[4-(2,3-dihydro-1,4-benzodioxin-5-yl)piperazin-1-yl]propyl]-1H-isoindole-1,3(2H)-dione (III-15), reaction in N,N-dimethylformamide, MS: 408[M+H$^+$], yield: 68%;

2-[4-[4-(2-oxo-2,3-dihydro-1H-benzimidazol-4-yl)piperazin-1-yl]butyl]-1H-isoindole-1,3(2H)-dione (III-16), reaction in N,N-dimethylformamide, MS: 420[M+H$^+$], yield: 70%;

2-[3-[4-(2-oxo-2,3-dihydro-1H-benzimidazol-4-yl)piperazin-1-yl]propyl]-1H-isoindole-1,3(2H)-dione (III-17), reaction in N,N-dimethylformamide, MS: 406[M+H$^+$], yield: 72%;

2-{4-[4-(3-oxo-3,4-dihydro-2H-1,4-benzoxazin-8-yl)piperazin-1-yl]butyl}-1H-isoindole-1,3(2H)-dione (III-18), reaction in N,N-dimethylformamide, MS: 435[M+H$^+$], yield: 79%;

b) General Procedure for Compounds Wherein in Formula (IVa) ----- Represents Double Bond:

b1) General Procedure for Starting Compounds (IVa) Easily Soluble in N,N-dimethylformamide:

A mixture of 5.6 mmol of compound (IVa) and 5.6 mmol of compound (IVb), 12 mmol of N,N-diisopropylethylamine, and 20 ml of N,N-dimethylformamide was stirred at room temperature until disappearance of starting materials (TLC monitoring). Usually, the reaction was carried out for 2.5 days. Then to the mixture 100 ml of water was added and the whole was left for 1 hour. Subsequently, 20 ml of methanol was added to the resulting mixture and after heating, it was refluxed for 20 minutes. Precipitated product was isolated by filtration and dried to the constant weight. Structure of the product was confirmed by mass spectrometry.

The following compounds were prepared according to the above procedure:
2-{4-[4-(5-chloro-1H-indol-3-yl)-3,6-dihydropyridin-1(2H)-yl]butyl}-1H-isoindole-1,3(2H)-dione (III-9) MS: 434[M+H$^+$], yield: 57%;
2-{3-[4-(5-chloro-1H-indol-3-yl)-3,6-dihydropyridin-1(2H)-yl]propyl}-1H-isoindole-1,3(2H)-dione (III-10) MS: 420[M+H$^+$], yield: 45%;
2-{2-[4-(5-chloro-1H-indol-3-yl)-3,6-dihydropyridin-1(2H)-yl]ethyl}-1H-isoindole-1,3(2H)-dione (III-11) MS: 406[M+H$^+$], yield: 30%.
2-{4-[4-(5-fluoro-1H-indol-3-yl)-3,6-dihydropyridin-1(2H)-yl]butyl}-1H-isoindole-1,3(2H)-dione (III-19) MS: 418[M+H$^+$], yield: 79%;
2-{3-[4-(5-fluoro-1H-indol-3-yl)-3,6-dihydropyridin-1(2H)-yl]propyl}-1H-isoindole-1,3(2H)-dione (III-20) MS: 404[M+H$^+$], yield: 84%;
2-{2-[4-(5-fluoro-1H-indol-3-yl)-3,6-dihydropyridin-1(2H)-yl]ethyl}-1H-isoindole-1,3(2H)-dione (III-21) MS: 390[M+H$^+$], yield: 77%.

b2) General Procedure for Starting Compounds (IVa) Poorly Soluble in Acetonitrile:

A mixture of 13 mmol of compound (IVa) and 13 mmol of compound (IVb), 13 mmol N,N-diisopropylethylamine, catalytic amount of potassium iodide and 300 ml of mixture of N,N-dimethylformamide and acetonitrile 1:1 was stirred at 70° C. for 3 days. Then the reaction mixture was concentrated under reduced pressure and the residue was purified using column chromatography on silica gel using methylene chloride:methanol=9:1 as eluent. Structure of the product was confirmed by mass spectrometry.

According to the above procedure, the following compounds were prepared:
2-{4-[4-(5-chloro-2-methyl-1H-indol-3-yl)-3,6-dihydropyridin-1(2H)-yl]butyl}-1H-isoindole-1,3(2H)-dione (III-12) MS: 448[M+H$^+$], yield: 36%.
2-{3-[4-(5-chloro-2-methyl-1H-indol-3-yl)-3,6-dihydropyridin-1(2H)-yl]propyl}-1H-isoindole-1,3(2H)-dione (III-22) MS: 404[M+H$^+$], yield: 40%.
2-{2-[4-(5-chloro-2-methyl-1H-indol-3-yl)-3,6-dihydropyridin-2H)-yl]ethyl}-1H-isoindole-1,3(2H)-dione (III-23) MS: 390[M+H$^+$], yield: 47%.

EXAMPLE 2

General Procedure for the Preparation of Starting Materials of General Formula (IIa) by Hydrolysis of Imide (III)

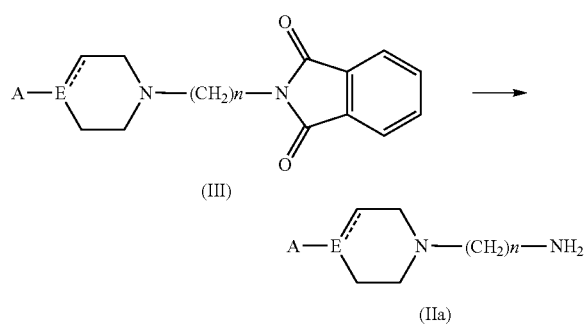

a) General Procedure for Compounds Wherein in Formula (III) ----- Represents Single Bond.

A mixture of 6 mmol of compound (III) and 30 ml of 40% aqueous solution of methylamine was stirred at room temperature for 3 days. To the resulting solution 30 ml of 20% aqueous solution of sodium hydroxide was added and the whole was stirred for 1.5 hours. Then 4 g of sodium chloride was added and the solution was extracted with methylene chloride (2×30 ml). Organic layer was washed with water (2×30 ml), and then dried over anhydrous magnesium sulphate. Product was obtained by evaporation of methylene chloride from dry solution. If necessary, the product was purified using column chromatography on silica gel, with chloroform/methanol 95:5 as eluent. Structure of the product was confirmed by mass spectrometry.

According to the above procedure the following compounds were prepared:
4-[4-(1,2-benzothiazol-3-yl)piperazin-1-yl]butan-1-amine (IIa-1) from compound (III-1) MS: 291[M+H$^+$], yield: 81%;
3-[4-(1,2-benzothiazol-3-yl)piperazin-1-yl]propan-1-amine (IIa-2) from compound (III-2) MS: 277[M+H$^+$], yield: 78%;
2-[4-(1,2-benzothiazol-3-yl)piperazin-1-yl]ethan-1-amine (IIa-3) from compound (III-3) MS: 263[M+H]$^+$, yield: 71%;
4-(4-(1,2-benzoxazol-3-yl)piperazin-1-yl)butan-1-amine (IIa-4) from compound (III-4) MS: 275[M+H$^+$], yield: 88%;
4-(4-(6-fluoro-1,2-benzoxazol-3-yl)piperidin-1-yl)butan-1-amine (IIa-5) from compound (III-5) MS: 292[M+H$^+$], yield: 82%;
3-(4-(6-fluoro-1,2-benzoxazol-3-yl)piperidin-1-yl)propan-1-amine (IIa-6) from compound (III-7) MS: 278[M+H$^+$], yield: 86%;
2-[4-(6-fluoro-1,2-benzoxazol-3-yl)piperidin-1-yl]ethan-1-amine (IIa-7) from compound (III-7) MS: 264[M+H$^+$], yield: 74%;
4-[4-(1H-indol-4-yl)piperazin-1-yl]butan-1-amine (IIa-8) from compound (III-8) MS: 273[M+H$^+$], yield: 67%.
3-[4-(1,2-benzoxazol-3-yl)piperazin-1-yl]propan-1-amine (IIa-13) from compound (III-13) MS: 261[M+H$^+$], yield: 77%.
4-[4-(2,3-dihydro-1,4-benzodioxin-5-yl)piperazin-1-yl]butan-1-amine (IIa-14) from compound (III-14) MS: 292[M+H$^+$], yield: 83%.
3-[4-(2,3-dihydro-1,4-benzodioxin-5-yl)piperazin-1-yl]propan-1-amine (IIa-15) from compound (III-15) MS: 278[M+H$^+$], yield: 85%.
4-[4-(2-oxo-2,3-dihydro-1H-benzimidazol-4-yl)piperazin-1-yl]butan-1-amine (IIa-16) from compound (III-16) MS: 290[M+H$^+$], yield: 70%.
3-[4-(2-oxo-2,3-dihydro-1H-benzimidazol-4-yl)piperazin-1-yl]propan-1-amine (IIa-17) from compound (III-17) MS: 276[M+H$^+$], yield: 74%.
4-[4-(3-oxo-3,4-dihydro-2H-1,4-benzoxazin-8-yl)piperazin-1-yl]butan-1-amine (IIa-18) from compound (III-18) MS: 305[M+H$^+$], yield: 90%.

b) General Procedure for Compounds Wherein in Formula (III) Represents Double Bond.

1.7 Mmol of compound (III) was suspended in 40 ml of 40% aqueous solution of methylamine and stirred at room temperature for 16 hours. Then methylamine was evaporated and resulting precipitate was filtered off. Precipitate was washed with water and dried to the constant weight.

Structure of the product was confirmed by mass spectrometry.

According to the above procedure, the following compounds were prepared:
4-[4-(5-chloro-1H-indol-3-yl)-3,6-dihydropyridin-1(2H)-yl]butan-1-amine (IIa-9) from compound (III-9) MS: 304[M+H⁺], yield: 85%;
3-[4-(5-chloro-1H-indol-3-yl)-3,6-dihydropyridin-1(2H)-yl]propan-1-amine (IIa-10) from compound (III-10) MS: 290 [M+H⁺], yield: 66%;
2-[4-(5-chloro-1H-indol-3-yl)-3,6-dihydropyridin-1(2H)-yl]ethan-1-amine (IIa-11) compound (III-11) MS: 276[M+H⁺], yield: 65%;
4-[4-(5-chloro-2-methyl-1H-indol-3-yl)-3,6-dihydropyridin-1(2H)-yl]butan-1 amine (IIa-12) from compound (III-12) MS: 318[M+H⁺], yield: 80%.
4-[4-(5-fluoro-1H-indol-3-yl)-3,6-dihydropyridin-1(2H)-yl]butyl-1-amine (IIa-19) from compound (III-19) MS: 288 [M+H⁺], yield: 62%;
3-[4-(5-fluoro-1H-indol-3-yl)-3,6-dihydropyridin-1(2H)-yl]propyl-1-amine (IIa-20) from compound (III-20) MS: 274 [M+H⁺], yield: 60%;
2-[4-(5-fluoro-1H-indol-3-yl)-3,6-dihydropyridin-1(2H)-yl]ethyl-1-amine (IIa-21) from compound (III-21) MS: 260 [M+H⁺], yield: 67%.
3-[4-(5-chloro-2-methyl-1H-indol-3-yl)-3,6-dihydropyridin-1(2H)-yl]propyl-1-amine (IIa-22) from compound (III-22) MS: 304[M+H⁺], yield: 66%.
2-[4-(5-chloro-2-methyl-1H-indol-3-yl)-3,6-dihydropyridin-1(2H)-yl]ethyl-1-amine (IIa-23) from compound (III-23) MS: 290[M+H⁺], yield: 60%.

EXAMPLE 3

General Procedure for the Preparation of Compounds (I) of the Invention

Compounds of the invention were prepared according to the following scheme.

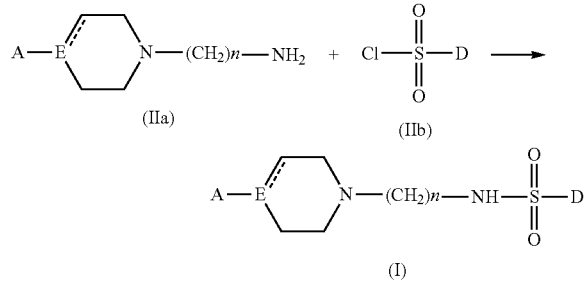

a) General Procedure for Compounds Wherein in Formula (IIa) ----- Represents Single Bond.

0.5 ml Of triethylamine and then 0.5 mmol of suitable arylsulphonyl chloride (IIb) were added to the solution of 0.5 mmol of amine (IIa) in 10 ml of methylene chloride at 10° C. Upon dissolution of chloride (IIb) the reaction mixture was left at room temperature for 3 hours, then the solvent and excess of triethylamine were evaporated. Precipitate thus formed was dissolved in 10 ml of methylene chloride and washed subsequently with 5% solution of sodium hydrogen carbonate (10 ml) and water (10 ml). Organic layer was dried over anhydrous magnesium sulphate, and the solvent was evaporated. Crude sulphonamides were usually purified by crystallization (from methanol), and some of them using column chromatography on silica gel using chloroform:methanol=9:1 as eluent.

Structure of prepared compounds was confirmed by MS data, and purity by HPLC analysis. For selected compounds structure identification was confirmed by ¹H-NMR analysis.
Following the general procedure described above and starting from appropriate amine (IIa) and arylsulphonyl chloride (IIb), the following compounds were obtained.

Compound 1.

N-(4-(4-(1,2-Benzothiazol-3-yl)piperazin-1-yl)butyl)naphthalene-1-sulphonamide

The title compound was prepared starting from amine (IIa-1) and naphthalene-1-sulphonyl chloride. Yield: 62%. ¹H-NMR (300 MHz, DMSO-d₆): δ 8.66 (d, 1H, J=8.5 Hz), 8.21 (d, 1H, J=8.1 Hz), 8.13-7.98 (m, 4H), 7.74-7.64 (m, 3H), 7.55 (t, 1H, J=6.9 Hz), 7.42 (t, 1H, J=8.4 Hz), 3.09-3.00 (m, 2H), 2.85-2.78 (m, 4H), 2.42-2.32 (m, 4H), 2.16-2.05 (m, 2H), 1.21-1.32 (m, 4H). MS: 481[M+H⁺].

Compound 2.

N-(4-(4-(1,2-Benzothiazol-3-yl)piperazin-1-yl)butyl)naphthalene-2-sulphonamide

The title compound was prepared starting from amine (IIa-1) and naphthalene-2-sulphonyl chloride. Yield: 60%. ¹H-NMR (300 MHz, DMSO-d₆): δ 8.42 (s, 1H), 8.16-8.11 (m, 2H), 8.06-7.98 (m, 3H), 7.81 (d, 1H, J=8.7 Hz), 7.74 (t, 1H, J=6.0 Hz), 7.66-7.62 (m, 1H), 7.54 (t, 1H, J=7.2 Hz), 7.42 (t, 1H, J=7.2 Hz), 2.84-2.78 (m, 4H), 2.48-2.4 (m, 6H), 2.26-2.18 (m, 2H), 1.36-1.41 (m, 4H). MS: 481[M+H⁺].

Compound 3.

N-(4-(4-(1,2-Benzothiazol-3-yl)piperazin-1-yl)butyl)-3-methylbenzenesulphonamide The title compound was prepared starting from amine (IIa-1) and 3-methylbenzene-sulphonyl chloride. Yield: 51%. ¹H-NMR (300 MHz, DMSO-d₆): δ 8.05 (d, 2H, J=7.2 Hz), 7.60-7.41 (m, 6H), 3.40-3.35 (m, 4H), 2.72-2.79 (m, 2H), 2.50-2.48 (m, 4H), 2.38 (s, 3H), 2.28-2.26 (m, 2H), 1.36-1.44 (m, 4H). MS: 445[M+H⁺].

Compound 4.

N-(4-(4-(1,2-Benzothiazol-3-yl)piperazin-1-yl)butyl)-2-oxo-3H-1,3-benzoxazole-6-sulphonamide The title compound was prepared starting from amine (IIa-1) and 2-oxo-3H-1,3-benzoxazole-6-sulphonyl chloride. Yield: 47%. MS: 488[M+H⁺].

Compound 5.

N-(3-(4-(1,2-Benzothiazol-3-yl)piperazin-1-yl)propyl)naphthalene-1-sulphonamide

The title compound was prepared starting from amine (IIa-2) and naphthalene-1-sulphonyl chloride. Yield: 53%. ¹H-NMR (300 MHz, DMSO-d₆): δ 8.66 (d, 1H, J=8.4 Hz), 8.21 (d, 1H, J=8.1 Hz), 8.14-7.96 (m, 3H), 7.74-7.61 (m, 3H), 7.53 (t, 1H, J=6.9 Hz), 7.41 (t, 1H, J=7.2) Hz), 3.31-3.25 (m, 4H), 2.81-2.88 (m, 2H), 2.29-2.25 (m, 4H), 2.14 (t, 2H, J=7.2 Hz), 1.44 (quintet, 2H, J=6.9 Hz). MS: 467[M+H⁺].

Compound 6.

N-(3-(4-(1,2-Benzothiazol-3-yl)piperazin-1-yl)propyl)naphthalene-2-sulphonamide

The title compound was prepared starting from amine (IIa-2) and naphthalene-2-sulphonyl chloride. Yield: 56%.

¹H-NMR (300 MHz, CD₃OD): δ 8.44 (s, 1H), 8.10-8.05 (m, 2H), 8.00-7.85 (m, 4H), 7.70-7.61 (m, 2H), 7.53 (t, 1H, J=6.9 Hz), 7.42 (t, 1H, J=7.2 Hz), 3.46-3.43 (m, 4H), 3.00 (t, 2H, J=6.9 Hz), 2.61-2.58 (m, 4H), 2.46 (t, 2H, J=7.2 Hz), 1.69 (quintet, 2H, J=6.9 Hz). MS: 467[M+H⁺].

Compound 7.

N-(3-(4-(1,2-Benzothiazol-3-yl)piperazin-1-yl)propyl)-3-methylbenzenesulphonamide The title compound was prepared starting from amine (IIa-2) and 3-methyl-benzenesulphonyl chloride. Yield: 49%. ¹H-NMR (300 MHz, DMSO-d₆): δ8.03 (t, 2H, J=7.2 Hz), 7.60-7.39 (m, 6H), 3.39-3.35 (m, 4H), 2.76-2.82 (m, 2H), 2.50-2.46 (m, 4H), 2.38 (s, 3H), 2.30 (t, 2H, J=7.2 Hz), 1.54 (quintet, 2H, J=6.9 Hz). MS: 431[M+H⁺].

Compound 8.

N-(3-(4-(1,2-Benzothiazol-3-yl)piperazin-1-yl)propyl)-2-oxo-3H-1,3-benzoxazole-6-sulphonamide The title compound was prepared starting from amine (IIa-2) and 2-oxo-3H-1,3-benzoxazole-6-sulphonyl chloride. Yield: 31%. ¹H-NMR (300 MHz, CDCl₃): δ 7.88-7.79 (m, 1H), 7.62 (s, 1H), 7.47 (t, 1H, J=7.4 Hz), 7.35 (t, 1H, J=7.4 Hz), 7.24 (t, 1H, J=8.2 Hz), 6.75 (t, 1H, J=8.2 Hz), 6.59-6.49 (m, 1H), 5.62-5.55 (m, 2H), 3.57-3.52 (m, 4H), 3.09 (t, 2H, J=5.9 Hz), 2.66-2.61 (m, 4H), 2.51 (t, 2H, J=5.9 Hz), 1.69 (quintet, 2H, J=5.9 Hz). MS: 474[M+H⁺].

Compound 9.

N-(2-(4-(1,2-Benzothiazol-3-yl)piperazin-1-yl)ethyl)naphthalene-1-sulphonamide The title compound was prepared starting from amine (IIa-3) and naphthalene-1-sulphonyl chloride. Yield: 51%. ¹H-NMR (300 MHz, CDCl₃): δ 8.68 (d, 1H, J=8.5 Hz), 8.29 (d, 1H, J=7.4 Hz), 8.08 (d, 1H, J=8.2 Hz), 7.95 (d, 1H, J=8.2 Hz), 7.82-7.68 (m, 3H), 7.62-7.54 (m, 2H), 7.46 (t, 1H, J=6.9 Hz), 7.33 (t, 1H, J=6.9) Hz), 3.33-3.27 (m, 4H), 3.03-2.97 (m, 2H), 2.37-2.30 (m, 6H). MS: 453[M+H⁺].

Compound 10.

N-(2-(4-(1,2-Benzothiazol-3-yl)piperazin-1-yl)ethyl)naphthalene-2-sulphonamide The title compound was prepared starting from amine (IIa-3) and naphthalene-2-sulphonyl chloride. Yield: 51%. ¹H-NMR (300 MHz, CDCl₃): δ 8.47 (s, 1H), 8.00-7.79 (m, 6H), 7.68-7.59 (m, 2H), 7.46 (t, 1H, J=6.9 Hz), 7.33 (t, 1H, J=6.9) Hz), 5.39 (s, 1H), 3.47-3.43 (m, 4H), 3.11-3.04 (m, 2H), 2.52-2.44 (m, 6H). MS: 453[M+H⁺].

Compound 11.

N-(2-(4-(1,2-Benzothiazol-3-yl)piperazin-1-yl)ethyl)-3-methylbenzenesulphonamide The title compound was prepared starting from amine (IIa-3) and 3-methyl-benzenesulphonyl chloride. Yield: 49%. ¹H-NMR (300 MHz, CDCl₃): δ 7.86-7.79 (m, 2H), 7.72-7.66 (m, 2H), 7.49-7.31 (m, 4H), 5.28 (s, 1H), 148-3.43 (m, 4H), 3.08-3.01 (m, 2H), 2.53-2.46 (m, 6H), 2.43 (s, 3H); MS: 417[M+H⁺].

Compound 12.

N-(2-(4-(1,2-Benzothiazol-3-yl)piperazin-1-yl)ethyl)-2-oxo-3H-1,3-benzoxazole-6-sulphonamide The title compound was prepared starting from amine (IIa-3) and 2-oxo-3H-1,3-benzoxazole-6-sulphonyl chloride. Yield: 41%. ¹H-NMR (300 MHz, DMSO-d₆): δ 8.02 (t, 2H, J=8.2 Hz), 7.62-7.51 (m, 3H), 7.45-7.38 (m, 3H), 3.37-3.24 (m, 4H), 2.93-185 (m, 2H), 2.52-2.47 (m, 4H), 2.39 (t, 2H, J=67 Hz). MS: 460[M+H⁺].

Compound 13.

N-(4-(4-(1,2-Benzoxazol-3-yl)piperazin-1-yl)butyl)naphthalene-1-sulphonamide The title compound was prepared starting from amine (IIa-4) and naphthalene-1-sulphonyl chloride. Yield: 64%. MS: 465[M+H⁺].

Compound 14.

N-(4-(4-(1,2-Benzoxazol-3-yl)piperazin-1-yl)butyl)naphthalene-2-sulphonamide The title compound was prepared starting from amine (IIa-4) and naphthalene-2-sulphonyl chloride. Yield: 67%. MS: 465[M+H⁺].

Compound 15.

N-(4-(4-(1,2-Benzoxazol-3-yl)piperazin-1-yl)butyl)-3-methylbenzenesulphonamide The title compound was prepared starting from amine (IIa-4) and 3-methylbenzene-sulphonyl chloride. Yield: 59%. MS: 429[M+H⁺].

Compound 16

N-(4-(4-(1,2-Benzoxazol-3-yl)piperazin-1-yl)butyl)-2-oxo-3H-1,3-benzoxazole-6-sulphonamide The title compound was prepared starting from amine (IIa-4) and 2-oxo-3H-1,3-benzoxazole-6-sulphonyl chloride. Yield: 71%. MS: 472[M+H⁺].

Compound 17.

N-[4-[4-(6-Fluoro-1,2-benzoxazol-3-yl)piperidin-1-yl]butyl]naphthalene-1-sulphonamide The title compound was prepared starting from amine (IIa-5) and naphthalene-1-sulphonyl chloride. Yield: 52%. MS: 483[M+H⁺].

Compound 18.

N-[4-[4-(6-Fluoro-1,2-benzoxazol-3-yl)piperidin-1-yl]butyl]naphthalene-2-sulphonamide The title compound was prepared starting from amine (IIa-5) and naphthalene-2-sulphonyl chloride. Yield: 44%, MS: 483[M+H⁺].

Compound 19.

N-[4-[4-(6-Fluoro-1,2-benzoxazol-3-yl)piperidin-1-yl]butyl]-3-methylbenzenesulphonamide The title compound was prepared starting from amine (IIa-5) and 3-methylbenzene-sulphonyl chloride. Yield: 65%. ¹H-NMR (300 MHz, CDCl₃-d₆): δ 7.96-7.91 (m, 1H), 7.69-7.65 (m, 2H), 7.40-7.35 (m, 2H), 7.24 (d, 1H, J=9.0 Hz), 7.05 (t, 1H, J=9 Hz), 3.13-296 (m, 4H), 2.41-2.34 (m, 5H), 2.31-2.04 (m, 7H), 1.60-1.58 (m, 4H). MS: 446[M+H⁺].

Compound 20.

N-[3-[4-(6-Fluoro-1,2-benzoxazol-3-yl)piperidin-1-yl]propyl]naphthalene-1-sulphonamide The title compound was prepared starting from amine (IIa-6) and naphthalene-1-sulphonyl chloride. Yield: 45%.

¹H-NMR (300 MHz, CDCl₁-d₆): δ 8.75-8.70 (m, 1H), 8.28-8.24 (m, 1H), 8.09-8.03 (m, 1H), 7.89-7.83 (m, 1H), 7.68-7.52 (m, 3H), 7.29-7.24 (m, 2H), 7.13-6.98 (m, 1H), 3.32-114 (m, 5H), 2.66 (t, 2H, J=6.0 Hz), 2.46-2.17 (m, 6H), 1.78 (quintet, 2H, J=6.0 Hz). MS: 468[M+H⁺].
Compound 21.

N-[3-[4-(6-Fluoro-1,2-benzoxazol-3-yl)piperidin-1-yl]propyl]naphthalene-2-sulphonamide The title compound was prepared starting from amine (IIa-6) and naphthalene-2-sulphonyl chloride. Yield: 37%. ¹H-NMR (300 MHz, CDCl₃-d₆): δ 8.44 (s, 1H), 7.99-7.83 (m, 5H), 7.67-7.57 (m, 2H), 7.27-7.23 (m, 1H), 7.11 (t, 1H, J=8.9 Hz), 3.14 (t, 3H, J=5.3 Hz), 3.03-3.02 (m, 2H), 2.47 (t, 2H, J=5.6 Hz), 2.19-2.05 (m, 6H), 1.66 (quintet, 2H, J=5.6 Hz). MS: 468[M+H⁺].
Compound 22.

N-[3-[4-(6-Fluoro-1,2-benzoxazol-3-yl)piperidin-1-yl]propyl]-3-methylbenzenesulphonamide The title compound was prepared starting from amine (IIa-6) and 3-methylbenzene-sulphonyl chloride. Yield: 55%. MS: 432[M+H⁺].
Compound 23.

N-[2-[4-(6-Fluoro-1,2-benzoxazol-3-yl)piperidin-1-yl]ethyl]naphthalene-1-sulphonamide The title compound was prepared starting from amine (IIa-7) and naphthalene-1-sulphonyl chloride. Yield: 58%. ¹H-NMR (300 MHz, CDCl₃-d₆): δ 8.74-8.68 (m, 1H), 832-827 (m, 1H), 8.09-8.04 (m, 1H), 7.95-7.85 (m, 1H), 7.74-7.51 (m, 3H), 7.29-7.24 (m, 2H), 7.09 (t, 1H, J=9.0 Hz), 5.57-5.30 (m, 1H), 2.98-2.85 (m, 3H), 2.48-2.40 (m, 2H), 2.29-2.22 (m, 2H), 2.00 (t, 2H, J=11.5 Hz), 1.84-1.67 (m, 4H). MS: 454[M+H⁺].
Compound 24.

N-[2-[4-(6-Fluoro-1,2-benzoxazol-3-yl)piperidin-1-yl]ethyl]naphthalene-2-sulphonamide The title compound was prepared starting from amine (IIa-7) and naphthalene-2-sulphonyl chloride. Yield: 33%. ¹H-NMR (300 MHz, DMSO-d₆): δ 10.54 (s, 1H), 8.50 (s, 1H), 8.20-8.03 (m, 4H), 7.88 (d, 2H, J=6.6 Hz), 7.75-7.72 (m, 3H), 7.34 (t, 1H, J=9.2 Hz), 3.65-3.57 (m, 2H), 3.46-3.37 (m, 1H), 3.26-3.10 (m, 6H), 2.26-2.17 (m, 4H). MS: 454[M+H⁺].
Compound 25.

N-[2-[4-(6-Fluoro-1,2-benzoxazol-3-yl)piperidin-1-yl]ethyl]-3-methylbenzenesulphonamide The title compound was prepared starting from amine (IIa-7) and 3-methylbenzene-sulphonyl chloride. Yield: 41%. ¹H-NMR (300 MHz, CDCl₃-d₆): δ 7.71-7.66 (m, 3H), 7.64-7.38 (m, 2H), 7.36-7.26 (m, 1H), 7.08 (t, 1H, J=9 Hz), 5.27 (s, 1H), 3.08-2.98 (m, 3H), 2.77-233 (m, 2H), 2.48-2.42 (m, 5H), 2.16-2.07 (m, 2H), 2.03-1.96 (m, 4H). MS: 418[M+H⁺].
Compound 26.

N-{4-[4-(1H-Indol-4-yl)piperazin-1-yl]butyl}naphthalene-2-sulphonamide

The title compound was prepared starting from amine (IIa-8) and naphthalene-2-sulphonyl chloride. Yield: 68%. ¹H-NMR (300 MHz, CDCl₃): δ 8.42 (s, 1H), 8.32 (s, 1H), 7.96-7.82 (m, 4H), 7.64-7.52 (m, 2H), 7.16-7.06 (m, 4H), 6.64-6.58 (m, 1H), 6.58-6.44 (t, 1H, J=2.3 Hz), 3.38-3.26 (m, 4H), 3.06-2.98 (m, 2H), 2.74-2.64 (m, 4H), 2.46-2.38 (m, 2H), 1.68-1.54 (m, 4H). MS: 463[M+H⁺].
Compound 27.

N-[4-[4-(1H-Indol-4-yl)piperazin-1-yl]butyl]benzenesulphonamide

The title compound was prepared starting from amine (IIa-8) and benzenesulphonyl chloride. Yield: 50%. ¹H-NMR (300 MHz, aceton-d₆): δ 10.2 (bs, 1H), 7.91-7.86 (m, 2H), 7.64-7.54 (m, 3H), 7.23 (t, 1H, J=2.8 Hz), 7.10-6.98 (m, 2H), 6.54-6.48 (m, 2H), 3.28-3.20 (m, 4H), 3.00-2.94 (m, 2H), 2.78-2.64 (m, 4H), 2.50-2.42 (m, 2H), 1.66-1.52 (4H). MS: 413 [M+H⁺].
Compound 28.

3-Fluoro-N-{4-[4-(1H-indol-4-yl)piperazin-1-yl]butyl}benzenesulphonamide

The title compound was prepared starting from amine (IIa-8) and 3-fluorobenzenesulphonyl chloride. Yield: 61%. ¹H-NMR (300 MHz, CDCl₃): δ 8.30 (s, 1H), 7.90-7.84 (m, 1H), 7.68-7.62 (m, 1H), 7.58-7.52 (m, 2H), 7.48-7.38 (m, 2H), 7.21-7.18 (m, 2H), 6.66-6.60 (m, 2H), 6.54-6.48 (m, 1H), 3.38-3.30 (m, 4H), 3.06-2.98 (m, 2H), 2.80-2.42 (m, 4H), 2.50-2.48 (m, 2H), 1.68-1.60 (m, 4H). MS: 431 [M+H⁺].
Compound 29.

3,4-Difluoro-N-{4-[4-(1H-indol-4-yl)piperazin-1-yl]butyl}benzenesulphonamide The title compound was prepared starting from amine (IIa-8) and 3,4-difluorobenzene-sulphonyl chloride Yield: 48%. ¹H-NMR (300 MHz, CDCl₃): δ 8.26 (s, 1H), 7.72-7.69 (m, 1H), 7.68-7.60 (m, 1H), 7.29-7.20 (m, 2H), 7.18-7.06 (m, 2H), 6.64-6.60 (dd, 1H, J=1.2 Hz and 6.9 Hz), 6.54-6.50 (m, 1H), 138-3.30 (m, 4H), 3.06-2.98 (m, 2H), 2.82-2.74 (m, 4H), 2.52-2.44 (m, 2H), 1.70-1.60 (m, 4H). MS: 449[M+H⁺].
Compound 30.

N-{4-[4-(1H-Indol-4-yl)piperazin-1-yl]butyl}-imidazo[1,2-a]pyridine-3-sulphonamide The title compound was prepared starting from amine (IIa-8) and imidazo[1,2-a]-pyridine-3-sulphonyl chloride. Yield: 52%. ¹H-NMR (300 MHz, CDCl₃): δ 8.68-8.62 (m, 1H), 8.24 (s, 1H), 8.12 (s, 1H), 7.74-7.70 (m, 1H), 7.40-7.34 (m, 1H), 7.18-7.08 (m, 3H), 6.98-6.90 (m, 1H), 6.68-6.62 (dd, 1H, J=1.2 and 6.9 Hz), 6.56-6.50 (m, 1H), 3.42-3.32 (m, 4H), 3.02-2.98 (m, 2H), 2.82-2.72 (m, 4H), 2.52-2.46 (m, 2H), 1.68-1.58 (m, 4H). MS: 453[M+H⁺].
Compound 31.

N-{4-[4-(1H-Indol-4-yl)piperazin-1-yl]butyl}-1H-pyrrolo[2,3-b]pyridine-3-sulphonamide The title compound was prepared starting from amine (IIa-8) and 1H-pyrrolo-[2,3-b]-pyridine-3-sulphonyl chloride. Yield: 73%. ¹H-NMR (300 MHz, CDCl₃): δ 10.6 (bs, 1H), 8.38 (dd, 1H, J=1.7 and 4 Hz), 8.30 (dd, 1H, J=1.5 and 7.9 Hz), 8.22 (s, 1H), 7.86 (s, 1H), 7.22-7.08 (m, 4H), 6.62-6.60

(dd, 1H, J=1.2 and 6.9 Hz), 6.50 (t, 1H, J=2.3 Hz), 3.32-3.24 (m, 4H), 3.08-2.98 (m, 2H), 2.70-2.64 (m, 4H), 2.46-2.38 (m, 2H), 1.68-1.58 (m, 4H). MS: 453[M+H$^+$].
Compound 32.

N-{4-[4-(1H-Indol-4-yl)piperazin-1-yl]butyl}-1-benzothiophene-3-sulphonamide The title compound was prepared starting from amine (IIa-8) and 1-benzo-thiophene-3-sulphonyl chloride. Yield: 81%. $^1$H-NMR (300 MHz, CDCl$_3$): δ 8.29-8.22 (m, 2H), 8.18 (s, so 1H), 7.90-7.84 (m, 1H), 7.46-7.40 (m, 2H), 7.18-7.06 (m, 3H), 6.68-6.62 (dd, 1H, J=1.2 and 6.9 Hz), 6.52 (m, 1H), 3.38-3.32 (m, 4H), 3.06-3.00 (m, 2H), 2.78-2.68 (m, 4H), 2.46-2.40 (m, 2H), 1.60-1.52 (m, 4H). MS: 469[M+H$^+$].
Compound 33.

N-{4-[4-(1H-Indol-4-yl)piperazin-1-yl]butyl}-1-benzothiophene-2-sulphonamide The title compound was prepared starting from amine (IIa-8) and 1-benzothiophene-2-sulphonyl chloride. Yield: 78%. MS: 469[M+H$^+$].
Compound 61.

N-[4-[4-(1,2-Benzothiazol-3-yl)piperazin-1-yl]butyl]-6-chloro-naphthalene-2-sulphonamide, hydrochloride The title compound was prepared starting from amine (IIa-1) and 6-chloro-naphthalene-2-sulphonyl chloride. Yield: 87%. MS: 515[M+H$^+$].
Compound 62.

N-[3-[4-(1,2-Benzothiazol-3-yl)piperazin-1-yl]propyl]-6-chloro-naphthalene-2-sulphonamide The title compound was prepared starting from amine (IIa-2) and 6-chloro-naphthalene-2-sulphonyl chloride. Yield: 67%, MS: 501[M+H$^+$].
Compound 63.

N-[4-[4-(1,2-Benzothiazol-3-yl)piperazin-1-yl]butyl]-3-chloro-4-fluorobenzenesulphonamide The title compound was prepared starting from amine (IIa-1) and 3-chloro-4-fluorobenzenesulphonyl chloride. Yield: 80%. MS: 483[M+H$^+$].
Compound 64.

N-[3-[4-(1,2-Benzothiazol-3-yl)piperazin-1-yl]propyl]-3-chloro-4-fluorobenzenesulphonamide The title compound was prepared starting from amine (IIa-2) and 3-chloro-4-fluorobenzenesulphonyl chloride. Yield: 76%. MS: 469[M+H$^+$].
Compound 65.

N-[4-[4-(1,2-Benzothiazol-3-yl)piperazin-1-yl]butyl]-5-fluoro-3-methylbenzothiophene-2-sulphonamide The title compound was prepared starting from amine (IIa-1) and 5-fluoro-3-methylbenzothiophene-2-sulphonyl chloride. Yield: 94%. MS: 519[M+H$^+$].
Compound 66.

N-[3-[4-(1,2-Benzothiazol-3-yl)piperazin-1-yl]propyl]-5-fluoro-3-methylbenzothiophene-2-sulphonamide The title compound was prepared starting from amine (IIa-2) and 5-fluoro-3-methylbenzothiophene-2-sulphonyl chloride. Yield: 94%. MS: 505[M+H$^+$].
Compound 69.

N-[4-[4-(1,2-Benzothiazol-3-yl)piperazin-1-yl]butyl]-3-chlorobenzenesulphonamide The title compound was prepared starting from amine (IIa-1) and 3-chloro-benzenesulphonyl chloride. Yield: 79%. MS: 465[M+H$^+$].
Compound 70.

N-[3-[4-(1,2-Benzothiazol-3-yl)piperazin-1-yl]propyl]-3-chlorobenzenesulphonamide The title compound was prepared starting from amine (IIa-2) and 3-chloro-benzenesulphonyl chloride. Yield: 80%. MS: 451[M+H$^+$].
Compound 71.

N-{4-[4-(1,2-Benzothiazol-3-yl)piperazin-1-yl]butyl}-3-fluorobenzenesulphonamide The title compound was prepared starting from amine (IIa-1) and 3-fluorobenzenesulphonyl chloride. Yield: 81%. MS: 449[M+H$^+$].
Compound 72.

N-[3-[4-(1,2-Benzothiazol-3-yl)piperazin-1-yl]propyl]-3-fluorobenzenesulphonamide The title compound was prepared starting from amine (IIa-21 and 3-fluorobenzenesulphonyl chloride. Yield: 79%. MS: 435[M+H$^+$].
Compound 73.

N-[4-[4-(1,2-Benzothiazol-3-yl)piperazin-1-yl]butyl]-3-cyanobenzenesulphonamide The title compound was prepared starting from amine (IIa-1) and 3-cyanobenzene-sulphonyl chloride. Yield: 85%. MS: 456[M+H$^+$].
Compound 74.

N-[3-[4-(1,2-Benzothiazol-3-yl)piperazin-1-yl]propyl]-3-cyanobenzenesulphonamide The title compound was prepared starting from amine (IIa-2) and 3-cyanobenzene-sulphonyl chloride. Yield: 91%. $^1$H-NMR (300 MHz, DMSO-d$_6$): δ 8.03 (dd, 2H, J=8.0 Hz, J=3.6 Hz), 7.79 (d, 2H, J=6.4 Hz), 7.74 (br. s, 1H), 7.26 (d, 2H, J=8.7 Hz), 7.54 (t, 1H, J=72 Hz), 7.41 (t, 1H, J=7.2 Hz), 3.38 (br. s, 4H), 2.84-2.78 (m, 2H), 2.49 (br. s, 4H), 2.31 (br.s, 2H), 1.57 (br. s, 2H). MS: 442[M+H$^+$].
Compound 76.

N-[3-[4-(1,2-Benzothiazol-3-yl)piperazin-1-yl]propyl]imidazo[1,2-a]pyridine-3-sulphonamide The title compound was prepared starting from amine (IIa-2) and imidazo[1,2-a]-pyridine-3-sulphonyl chloride. Yield: 63%. MS: 457[M+H$^+$].

Compound 79.

N-[4-[4-(1,2-Benzoxazol-3-yl)piperazin-1-yl]butyl]-6-chloro-naphthalene-2-sulphonamide The title compound was prepared starting from amine (IIa-4) and 6-chloro-naphthalene-2-sulphonyl chloride. Yield: 78%. MS: 499[M+H$^+$].

Compound 80.

N-[3-[4-(1,2-Benzoxazol-3-yl)piperazin-1-yl]propyl]-6-chloro-naphthalene-2-sulphonamide The title compound was prepared starting from amine (IIa-13) and 6-chloro-naphthalene-2-sulphonyl chloride. Yield: 78%. MS: 485[M+H$^+$].

Compound 81.

N-[4-[4-(1,2-Benzoxazol-3-yl)piperazin-1-yl]butyl]-5-fluoro-3-methylbenzothiophene-2-sulphonamide The title compound was prepared starting from amine (IIa-4) and 5-fluoro-3-methylbenzothiophene-2-sulphonyl chloride. Yield: 92%. MS: 503[M+H$^+$].

Compound 82.

N-[3-[4-(1,2-Benzoxazol-3-yl)piperazin-1-yl]propyl]-5-fluoro-3-methylbenzothiophene-2-sulphonamide The title compound was prepared starting from amine (IIa-13) and 5-fluoro-3-methylbenzothiophene-2-sulphonyl chloride. Yield: 51%. MS: 489[M+H$^+$].

Compound 85.

N-[4-[4-(1,2-Benzoxazol-3-yl)piperazin-1-yl]butyl]-3-chlorobenzenesulphonamide The title compound was prepared starting from amine (IIa-4) and 3-chlorobenzene-sulphonyl chloride. Yield: 76%. MS: 449[M+H$^+$].

Compound 86.

N-[3-[4-(1,2-Benzoxazol-3-yl)piperazin-1-yl]propyl]-3-chlorobenzenesulphonamide The title compound was prepared starting from amine (IIa-13) and 3-chlorobenzene-sulphonyl chloride. Yield: 72%. MS: 435[M+H$^+$], Compound 87.

N-[4-[4-(1,2-Benzoxazol-3-yl)piperazin-1-yl]butyl]-1-fluorobenzenesulphonamide The title compound was prepared starting from amine (IIa-4) and 3-fluorobenzenesulphonyl chloride. Yield: 81%. MS: 433[M+H$^+$].

Compound 89.

N-[4-[4-(1,2-Benzoxazol-3-yl)piperazin-1-yl]butyl]-1H-pyrrolo[2,3-b]pyridine-3-sulphonamide The title compound was prepared starting from amine (IIa-4) and 1H-pyrrolo[2,3-b]-pyridine-3-sulphonyl chloride. Yield: 65%. MS: 455[M+H$^+$].

Compound 91.

N-{4-[4-(1,2-Benzoxazol-3-yl)piperazin-1-yl]butyl}-3-(trifluoromethyl)benzenesulphonamide The title compound was prepared starting from amine (IIa-4) and 3-(trifluoromethyl)-benzenesulphonyl chloride. Yield: 90%. MS: 483[M+H$^+$].

Compound 92.

N-[3-[4-(1,2-Benzoxazol-3-yl)piperazin-1-yl]propyl]-3-(trifluoromethyl)benzenesulphonamide The title compound was prepared starting from amine (IIa-13) and 3-(trifluoromethyl)-benzenesulphonyl chloride. Yield: 58%. MS: 469[M+H$^+$].

Compound 93.

N-[4-[4-(1,2-Benzoxazol-3-yl)piperazin-1-yl]butyl]-3,4-dichlorobenzenesulphonamide The title compound was prepared starting from amine (IIa-4) and 3,4-dichlorobenzenesulphonyl chloride. Yield: 78%. MS: 483[M+H$^+$].

Compound 94.

N-[3-[4-(1,2-Benzoxazol-3-yl)piperazin-1-yl]propyl]-3,4-dichlorobenzenesulphonamide The title compound was prepared starting from amine (IIa-13) and 3,4-dichlorobenzenesulphonyl chloride. Yield: 61%. $^1$H-NMR (300 MHz, DMSO-d$_6$): δ 7.96 (d, 1H, J=2.1 Hz), 7.91-7.87 (m, 1H), 7.85-7.80 (m, 1H), 7.74 (d, 1H, J=8.2 Hz), 7.37 (d, 1H, J=7.4 Hz), 7.26 (d, 1H, J=7.7 Hz), 7.12 (t, 1H, J=7.5 Hz), 7.00 (t, 1H, J=7.7 Hz), 3.55 (br. s, 4H), 2.86-2.78 (m, 2H), 2.38 (br. s, 4H), 2.85 (t, 2H, J=6.9 Hz), 1.60-1.48 (m, 2H). MS: 469[M+H$^+$].

Compound 97.

6-Chloro-N-[4-[4-(6-fluoro-1,2-benzoxazol-3-yl)piperidin-1-yl]butyl]naphthalene-2-sulphonamide The title compound was prepared starting from amine (IIa-5) and 6-chloro-naphthalene-2-sulphonyl chloride. Yield: 67%. MS: 516[M+H$^+$].

Compound 98.

6-Chloro-N-[3-[4-(6-fluoro-1,2-benzoxazol-3-yl)piperidin-1-yl]propyl]naphthalene-2-sulphonamide The title compound was prepared starting from amine (IIa-6) and 6-chloro-naphthalene-2-sulphonyl chloride. Yield: 76%. MS: 503[M+H$^+$].

Compound 101.

5-Fluoro-N-[4-[4-(6-fluoro-1,2-benzoxazol-3-yl)piperidin-1-yl]butyl]-3-methylbenzothiophene-2-sulphonamide The title compound was prepared starting from amine (IIa-5) and 5-fluoro-3-methylbenzothiophene-2-sulphonyl chloride. Yield: 51%. MS: 520[M+H$^+$].

Compound 102.

5-Fluoro-N-[3-[4-(6-fluoro-1,2-benzoxazol-3-yl)piperidin-1-yl]propyl]-3-methylbenzothiophene-2-sulphonamide The title compound was prepared starting from amine (IIa-6) and 5-fluoro-3-methylbenzothiophene-2-sulphonyl chloride. Yield: 91%, $^1$H-NMR (300 MHz, DMSO-d$_6$): δ 8.18 (br. s, 1H), 8.07 (dd, 1H, J=8.7 Hz, J=5.1 Hz), 7.93 (dd, 1H, J=8.7 Hz, j=5.1 Hz), 7.78 (dd, 1H, J=9.7 Hz, J=2.3 Hz), 7.66 (dd, 1H, J=9.2 Hz, J=2.3 Hz), 7.39 (td, 1H, J=9.0 Hz, J=2.6 Hz), 7.25 (td, 1H, J=9.5 Hz, J=2.3 Hz), 3.10-2.98 (m, 1H), 2.95 (t, 2H, J=6.3 Hz), 2.82-2.73 (m, 2H), 2.59 (s, 3H), 2.26 (t, 2H, J=7.2 Hz), 2.00-1.85 (m, 4H), 1.76-1.60 (m, 2H), 1.60-1.50 (m, 2H). MS: 506[M+H$^+$].

Compound 105.

3-Chloro-N-[4-[4-(6-fluoro-1,2-benzoxazol-3-yl)piperidin-1-yl]butyl]benzenesulphonamide The title compound was prepared starting from amine (IIa-5) and 3-chlorobenzene-sulphonyl chloride. Yield: 71%. MS: 466[M+H$^+$].

Compound 106.

3-Chloro-N-[3-[4-(6-fluoro-1,2-benzoxazol-3-yl)piperidin-1-yl]propyl]benzenesulphonamide The title compound was prepared starting from amine (IIa-6) and 3-chlorobenzene-sulphonyl chloride. Yield: 66%. MS: 453[M+H$^+$].

Compound 107.

3-Fluoro-N-[4-[4-(6-fluoro-1,2-benzoxazol-3-yl)piperidin-1-yl]butyl]benzenesulphonamide The title compound was prepared starting from amine (IIa-5) and 3-fluorobenzenesulphonyl chloride. Yield: 68%. MS: 450[M+H$^+$].

Compound 108.

3-Fluoro-N-[3-[4-(6-fluoro-1,2-benzoxazol-3-yl)piperidin-1-yl]propyl]benzenesulphonamide, hydrochloride The title compound was prepared starting from amine (IIa-6) and 3-fluorobenzenesulphonyl chloride. Yield: 63%, $^1$H-NMR (300 MHz, DMSO-d$_6$), hydrochloride: δ 10.40 (br. s, 1H), 8.15 (dd, 1H, J=8.7 Hz, J=5.4 Hz), 7.96 (t, 1H, J=5.9), 7.73-7.49 (m, 4H), 7.33 (td, 1H, J=9.2 Hz, J=2.3 Hz), 3.61-3.50 (m, 2H), 3.50-3.41 (m, 1H), 3.17-2.99 (m, 4H), 2.89-2.80 (m, 2H), 2.34-2.14 (m, 4H), 1.95-1.81 (m, 4H). MS: 436[M+H$^+$].

Compound 109.

3-Bromo-N-[4-[4-(6-fluoro-1,2-benzoxazol-3-yl)piperidin-1-yl]butyl]benzenesulphonamide The title compound was prepared starting from amine (IIa-5) and 3-bromobenzene-sulphonyl chloride. Yield: 72%. MS: 510[M+H$^+$].

Compound 110.

3-Bromo-N-[3-[4-(6-fluoro-1,2-benzoxazol-3-yl)piperidin-1-yl]propyl]benzenesulphonamide The title compound was prepared starting from amine (IIa-6) and 3-bromobenzene-sulphonyl chloride. Yield: 59%. MS: 497[M+H$^+$].

Compound 111.

N-[4-[4-(6-Fluoro-1,2-benzoxazol-3-yl)piperidin-1-yl]butyl]-4-phenylbenzenesulphonamide The title compound was prepared starting from amine (IIa-5) and 4-phenylbenzene-sulphonyl chloride. Yield: 80%. MS: 508[M+H$^+$].

Compound 112.

N-[3-[4-(6-Fluoro-1,2-benzoxazol-3-yl)piperidin-1-yl]propyl]-4-phenylbenzenesulphonamide The title compound was prepared starting from amine (IIa-6) and 4-phenylbenzene-sulphonyl chloride. Yield: 53%. MS: 494[M+H$^+$].

Compound 113.

N-[4-[4-(1H-Indol-4-yl)piperazin-1-yl]butyl]-3-chlorobenzenesulphonamide

The title compound was prepared starting from amine (IIa-8) and 3-chlorobenzene-sulphonyl chloride. Yield: 71%. $^1$H-NMR (300 MHz, CDCl$_3$): δ 8.23 (s, 1H), 7.84 (t, 1H, J=1.8 Hz), 7.74 (dt, 1H, J=1.3 and 7.9 Hz), 7.52-7.46 (m, 1H), 7.40 (m, 1H, J=7.7 Hz), 7.16-7.08 (m, 3H), 6.64 (dd, 1H, J=1.3 and 6.9 Hz), 6.52 (t, 1H, J=2.3 Hz), 3.36-3.28 (m, 4H), 3.04-2.96 (m, 2H), 2.76-2.68 (m, 4H), 2.50-2.46 (m, 2H), 1.66-1.60 (m, 4H). MS: 447[M+H$^+$].

Compound 165.

5-Chloro-3-methyl-N-[4-[4-(2-oxo-1,3-dihydrobenzimidazol-4-yl)piperazin-1-yl]butyl]-1-benzothiophene-2-sulfonamide The title compound was prepared starting from amine (IIa-16) and 5-chloro-3-methyl-1-benzothiophene-2-sulphonyl chloride. Yield: 55%. MS: 534[M+H$^+$].

Compound 173.

3-Chloro-N-[4-[4-(2-oxo-1,3-dihydrobenzimidazol-4-yl)piperazin-1-yl]butyl]benzenesulphonamide The title compound was prepared starting from amine (IIa-16) and 3-chlorobenzene-sulphonyl chloride. Yield: 61%. MS: 464[M+H$^+$].

Compound 174.

3-Chloro-N-[3-[4-(2-oxo-1,3-dihydrobenzimidazol-4-yl)piperazin-1-yl]propyl]benzenesulphonamide The title compound was prepared starting from amine (IIa-17) and 3-chlorobenzene-sulphonyl chloride. Yield: 53%. MS: 450[M+H$^+$].

Compound 175.

3-Fluoro-N-[4-[4-(2-oxo-1,3-dihydrobenzimidazol-4-yl)piperazin-1-yl]butyl]benzenesulphonamide The title compound was prepared starting from amine (IIa-16) and 3-fluorobenzenesulphonyl chloride. Yield: 71%. MS: 448[M+H$^+$].

Compound 176.

3-Fluoro-N-[3-[4-(2-oxo-1,3-dihydrobenzimidazol-4-yl)piperazin-1-yl]propyl]benzenesulphonamide The title compound was prepared starting from amine (IIa-17) and 3-fluorobenzenesulphonyl chloride. Yield: 62%. MS: 434[M+H$^+$].

Compound 195.

N-[4-[4-(1,2-Benzothiazol-3-yl)piperazin-1-yl]butyl]-5-chloro-thiophene-2-sulphonamide The title compound was prepared starting from amine (IIa-1) and 5-chloro-thiophene-2-sulphonyl chloride. Yield: 76%. MS: 471[M+H$^+$].

Compound 196.

N-[3-[4-(1,2-benzothiazol-3-yl)piperazin-1-yl]propyl]-5-chloro-thiophene-2-sulphonamide The title compound was prepared starting from amine (IIa-2) and 5-chloro-thiophene-2-sulphonyl chloride. Yield: 76%. MS: 457[M+H$^+$].

Compound 209.

3-Chloro-N-[4-[4-(3-oxo-4H-1,4-benzoxazin-8-yl)piperazin-1-yl]butyl]benzenesulphonamide The title compound was prepared starting from amine (IIa-18) and 3-chlorobenzene-sulphonyl chloride. Yield: 81%. $^1$H-NMR (300 MHz, CDCl$_3$): 8.39 (s, 1H), 7.38 (t, 1H, J=1.7 Hz), 7.72 (dt, 1H, J=1.3 and 7.7 Hz), 7.52-7.48 (m, 1H), 7.42 (t, 1H, J=7.7 Hz), 6.91 (t, 1H, J=7.7 Hz), 6.70 (dd, 1H, J=1.5 and 8.2 Hz), 6.52 (dd, 1H, J=1.3 and 7.9 Hz), 3.22-3.10 (m, 4H), 3.02-2.92 (m, 2H), 2.72-2.64 (m, 4H), 2.48-2.38 (m, 2H), 1.68-1.58 (m, 4H). MS: 479[M+H$^+$].

Compound 211.

3-Fluoro-N-[4-[4-(3-oxo-4H-1,4-benzoxazin-8-yl)piperazin-1-yl]butyl]benzenesulphonamide The title compound was prepared starting from amine (IIa-18) and 3-fluorobenzenesulphonyl chloride. Yield: 82%. $^1$H-NMR (300 MHz, CDCl$_3$): 8.40 (s, 1H), 7.66-7.62 (m, 1H), 7.58-7.52 (m, 1H), 7.50-7.42 (m, 1H), 7.28-7.20 (m, 1H), 6.91 (t, 1H, J=7.9 Hz), 6.67 (dd, 1H, J=8.2 and 1.2 Hz), 6.52 (dd, 1H, J=7.7 and 1.2 Hz), 4.60 (s, 2H), 3.22-3.12 (m, 4H), 3.02-2.94 (m, 2H), 2.74-2.64 (m, 4H), 2.48-2.40 (m, 2H), 1.68-1.58 (m, 4H). MS: 463[M+H$^+$].

Compound 225.

N-[4-[4-(1,2-Benzothiazol-3-yl)piperazin-1-yl]butyl]-4-fluorobenzenesulphonamide The title compound was prepared starting from amine (IIa-1) and 4-fluorobenzenesulphonyl chloride. Yield: 90%. MS: 449[M+H$^+$].

Compound 226.

N-[4-[4-(1,2-Benzothiazol-3-yl)piperazin-1-yl]butyl]-3,4-difluorobenzenesulphonamide The title compound was prepared starting from amine (IIa-1) and 3,4-difluorobenzene-sulphonyl chloride. Yield: 80%. MS: 467[M+H$^+$].

Compound 227.

N-[4-[4-(1,2-Benzothiazol-3-yl)piperazin-1-yl]butyl]-4-chlorobenzenesulphonamide The title compound was prepared starting from amine (IIa-1) and 4-chlorobenzene-sulphonyl chloride. Yield: 84%. MS: 465[M+H$^+$].

Compound 228.

N-[4-[4-(1,2-Benzothiazol-3-yl)piperazin-1-yl]butyl]-3,4-dichlorobenzenesulphonamide The title compound was prepared starting from amine (IIa-1) and 3,4-dichlorobenzenesulphonyl chloride. Yield: 82%. MS: 499[M+H$^+$].

Compound 229.

N-[4-[4-(1,2-Benzothiazol-3-yl)piperazin-1-yl]butyl]-4-bromobenzenesulphonamide The title compound was prepared starting from amine (IIa-1) and 4-bromobenzene-sulphonyl chloride. Yield: 81%. MS: 509[M+H$^+$].

Compound 230.

N-[4-[4-(1,2-Benzothiazol-3-yl)piperazin-1-yl]butyl]-3-bromobenzenesulphonamide The title compound was prepared starting from amine (IIa-1) and 3-bromobenzene-sulphonyl chloride. Yield: 77%. MS: 509[M+H$^+$].

Compound 231.

N-[4-[4-(1,2-Benzothiazol-3-yl)piperazin-1-yl]butyl]-3-hydroxybenzenesulphonamide The title compound was prepared starting from amine (IIa-1) and 3-hydroxybenzene-sulphonyl chloride. Yield: 41%. MS: 447[M+H$^+$].

Compound 232.

N-[4-[4-(1,2-Benzothiazol-3-yl)piperazin-1-yl]butyl]-3-methoxybenzenesulphonamide The title compound was prepared starting from amine (IIa-1) and 3-methoxybenzenesulphonyl chloride. Yield: 76%. MS: 461[M+H$^+$].

Compound 233.

N-[4-[4-(1,2-Benzothiazol-3-yl)piperazin-1-yl]butyl]-4-tert-butyl-benzenesulphonamide The title compound was prepared starting from amine (IIa-1) and 4-tert-butyl-benzenesulphonyl chloride. Yield: 65%. MS: 487[M+H$^+$].

Compound 234.

N-[4-[4-(1,2-Benzothiazol-3-yl)piperazin-1-yl]butyl]-4-(trifluoromethyl)benzenesulphonamide The title compound was prepared starting from amine (IIa-1) and 4-trifluoromethyl-benzenesulphonyl chloride. Yield: 82%. MS: 499[M+H$^+$].

Compound 235.

N-[4-[4-(1,2-Benzothiazol-3-yl)piperazin-1-yl]butyl]-3-(trifluoromethyl)benzenesulphonamide The title compound was prepared starting from amine (IIa- and 3-trifluoromethyl-benzenesulphonyl chloride. Yield: 79%. MS: 499[M+H$^+$].

Compound 236.

N-[4-[4-(1,2-Benzothiazol-3-yl)piperazin-1-yl]butyl]-4-(trifluoromethoxy)benzenesulphonamide The title compound was prepared starting from amine (IIa-1) and 4-trifluoromethoxy-benzenesulphonyl chloride. Yield: 71%. MS: 515[M+H$^+$].

Compound 237.

N-[4-[4-(1,2-Benzothiazol-3-yl)piperazin-1-yl]butyl]-4-phenylbenzenesulphonamide The title compound was prepared starting from amine (IIa-1) and 4-phenylbenzene-sulphonyl chloride. Yield: 94%. MS: 507[M+H$^+$].

Compound 238.

N-[4-[4-(1,2-Benzothiazol-3-yl)piperazin-1-yl]butyl]thiophene-2-sulphonamide

The title compound was prepared starting from amine (IIa-1) and thiophene-2-sulphonyl chloride. Yield: 88%, MS: 437 [M+H$^+$].

Compound 239.

N-[4-[4-(1,2-Benzothiazol-3-yl)piperazin-1-yl]butyl]benzothiophene-2-sulphonamide The title compound was prepared starting from amine (IIa-1) and benzothiophene-2-sulphonyl chloride. Yield: 71%. MS: 487[M+H$^+$].

Compound 240.

N-[4-[4-(1,2-Benzothiazol-3-yl)piperazin-1-yl]butyl]benzothiophene-3-sulphonamide The title compound was prepared starting from amine (IIa-1) and benzothiophene-3-sulphonyl chloride. Yield: 66%. $^1$H-NMR (300 MHz, DMSO-d$_6$): δ 8.43 (s, 1H), 8.19 (d, 1H, J=7.0 Hz), 8.09 (d, 1H, J=7.0 Hz), 8.02 (t, 2H, J=8.7 Hz), 7.92 (t, 1H, J=5.4 Hz), 7.57-7.39 (m, 4H), 3.36-3.31 (m, 4H), 2.88-2.81 (m, 2H), 2.42-2.36 (m, 4H), 2.14 (t, 2H, J=6.4 Hz), 1.34-1.27 (m, 4H). MS: 487[M+H$^+$].

Compound 241.

N-[4-[4-(1,2-Benzothiazol-3-yl)piperazin-1-yl]butyl]-6-chlorobenzothiophene-2-sulphonamide The title compound was prepared starting from amine (IIa-1) and 6-chlorobenzothiophene-2-sulphonyl chloride. Yield: 93%. MS: 521[M+H$^+$].

Compound 242.

N-[4-[4-(1,2-Benzothiazol-3-yl)piperazin-1-yl]butyl]-2,3-dihydrobenzofuran-5-sulphonamide The title compound was prepared starting from amine (IIa-1) and 2,3-dihydrobenzofuran-5-sulphonyl chloride. Yield: 78%. MS: 473[M+H$^+$].

Compound 243.

N-[4-[4-(1,2-Benzothiazol-3-yl)piperazin-1-yl]butyl]-1,3-benzothiazole-4-sulphonamide The title compound was prepared starting from amine (IIa-1) and 1,3-benzothiazole-4-sulphonyl chloride. Yield: 72%. MS: 488[M+H$^+$].

Compound 244.

N-[4-[4-(1,2-Benzothiazol-3-yl)piperazin-1-yl]butyl]-1H-indazole-6-sulphonamide

The title compound was prepared starting from amine (IIa-1) and 1H-indazole-6-sulphonyl chloride. Yield: 56%. MS: 471[M+H$^+$].

Compound 245.

N-[4-[4-(1,2-Benzothiazol-3-yl)piperazin-1-yl]butyl]-1,3-benzodioxole-5-sulphonamide The title compound was prepared starting from amine (IIa-1) and 1,3-benzodioxole-5-sulphonyl chloride. Yield: 80%. $^1$H-NMR (300 MHz, DMSO-d$_6$): δ 8.03 (dd, 2H, J=8.2 Hz, J=3.6 Hz), 7.57-7.39 (m, 3H), 7.31 (d, 1H, J=8.2 Hz), 7.23 (s, 1H), 7.06 (d, 1H, J=8.2 Hz), 6.56 (s, 2H), 3.40 (br.s, 4H), 2.77-2.71 (m, 2H), 2.53 (br. s, 4H), 2.28 (br. s, 2H), 1.39 (br. s, 4H). MS: 475[M+H$^+$].

Compound 246.

N-[4-[4-(1,2-Benzothiazol-3-yl)piperazin-1-yl]butyl]imidazo[1,2-a]pyridine-3-sulphonamide The title compound was prepared starting from amine (IIa-1) and imidazo[1,2-a]-pyridine-3-sulphonyl chloride. Yield: 60%. MS: 471[M+H$^+$].

Compound 247.

N-[4-[4-(1,2-Benzothiazol-3-yl)piperazin-1-yl]butyl]-1H-pyrrolo[2,3-b]pyridine-3-sulphonamide The title compound was prepared starting from amine (IIa-1) and 1H-pyrrolo-[2,3-b]-pyridine-3-sulphonyl chloride. Yield: 65%. MS: 471[M+H$^+$].

Compound 248.

N-[3-[4-(1,2-Benzothiazol-3-yl)piperazin-1-yl]propyl]-4-fluorobenzenesulphonamide The title compound was prepared starting from amine (IIa-2) and 4-fluorobenzenesulphonyl chloride. Yield: 75%. MS: 435[M+H$^+$].

Compound 249.

N-[3-[4-(1,2-Benzothiazol-3-yl)piperazin-1-yl]propyl]-3,4-difluorobenzenesulphonamide The title compound was prepared starting from amine (IIa-2) and 3,4-difluorobenzene-sulphonyl chloride. Yield: 89%. MS: 453[M+H$^+$].

Compound 250.

N-[3-[4(1,2-Benzothiazol-3-yl)piperazin-1-yl]propyl]-4-chlorobenzenesulphonamide The title compound was prepared starting from amine (IIa-2) and 4-chlorobenzene-sulphonyl chloride. Yield: 90%. MS: 452[M+H$^+$].

Compound 251.

N-[3-[4-(1,2-Benzothiazol-3-yl)piperazin-1-yl]propyl]-3,4-dichlorobenzenesulphonamide The title compound was prepared starting from amine (IIa-2) and 3,4-dichlorobenzenesulphonyl chloride. Yield: 87%. MS: 485[M+H$^+$].

Compound 252.

N-[3-[4-(1,2-Benzothiazol-3-yl)piperazin-1-yl]propyl]-4-bromobenzenesulphonamide The title compound was prepared starting from amine (IIa-2) and 4-bromobenzene-sulphonyl chloride. Yield: 92%. MS: 495[M+H$^+$].

Compound 253.

N-[3-[4-(1,2-Benzothiazol-3-yl)piperazin-1-yl]propyl]-3-bromobenzenesulphonamide The title compound was prepared starting from amine (IIa-2) and 3-bromobenzene-sulphonyl chloride. Yield: 88%. MS: 495[M+H$^+$].

Compound 254.

N-[3-[4-(1,2-Benzothiazol-3-yl)piperazin-1-yl]propyl]-3-hydroxybenzenesulphonamide The title compound was prepared starting from amine (IIa-2) and 3-hydroxybenzene-sulphonyl chloride. Yield: 45%. MS: 433[M+H$^+$].

Compound 255.

N-[3-[4-(1,2-Benzothiazol-3-yl)piperazin-1-yl]propyl]-3-methoxybenzenesulphonamide The title compound was prepared starting from amine (IIa-2) and 3-methoxybenzenesulphonyl chloride. Yield: 79%. MS: 447[M+H$^+$].

Compound 256.

N-[3-[4-(1,2-Benzothiazol-3-yl)piperazin-1-yl]propyl]-4-tert-butylbenzenesulphonamide The title compound was prepared starting from amine (IIa-2) and 4-tert-butyl-benzenesulphonyl chloride. Yield: 93%. MS: 473[M+H$^+$].

Compound 257.

N-[3-[4-(1,2-Benzothiazol-3-yl)piperazin-1-yl]propyl]-4-(trifluoromethyl)benzenesulphonamide The title compound was prepared starting from amine (IIa-2) and 4-(trifluoromethyl)-benzenesulphonyl chloride. Yield: 85%. MS: 485[M+H$^+$].

Compound 258.

N-[3-[4-(1,2-Benzothiazol-3-yl)piperazin-1-yl]propyl]-3-(fluoromethyl)benzenesulphonamide The title compound was prepared starting from amine (IIa-2) and 3-(trifluoromethyl)-benzenesulphonyl chloride. Yield: 90%. MS: 485[M+H$^+$].

Compound 259.

N-[3-[4-(1,2-Benzothiazol-3-yl)piperazin-1-yl]propyl]-4-(trifluoromethoxy)benzenesulphonamide The title compound was prepared starting from amine (IIa-2) and 4-(trifluoromethoxy)-benzenesulphonyl chloride. Yield: 76%. MS: 501[M+H$^+$].

Compound 260.

N-[3-[4-(1,2-Benzothiazol-3-yl)piperazin-1-yl]propyl]-4-phenylbenzenesulphonamide The title compound was prepared starting from amine (IIa-2) and 4-phenylbenzene-sulphonyl chloride. Yield: 93%. MS: 493[M+H$^+$].

Compound 261.

N-[3-[4-(1,2-Benzothiazol-3-yl)piperazin-1-yl]propyl]thiophene-2-sulphonamide

The title compound was prepared starting from amine (IIa-2) and thiophene-2-sulphonyl chloride. Yield: 86%. MS: 423 [M+H$^+$].

Compound 262.

N-[3-[4-(1,2-Benzothiazol-3-yl)piperazin-1-yl]propyl]benzothiophene-2-sulphonamide The title compound was prepared starting from amine (IIa-2) and benzothiophene-2-sulphonyl chloride. Yield: 73%. MS: 473[M+H$^+$].

Compound 263.

N-[3-[4-(1,2-Benzothiazol-3-yl)piperazin-1-yl]propyl]benzothiophene-3-sulphonamide The title compound was prepared starting from amine (IIa-2) and benzothiophene-3-sulphonyl chloride. Yield: 77%. MS: 473[M+H$^+$].

Compound 264.

N-[3-[4-(1,2-Benzothiazol-3-yl)piperazin-1-yl]propyl]-6-chlorobenzothiophene-2-sulphonamide The title compound was prepared starting from amine (IIa-2) and 6-chlorobenzothiophene-2-sulphonyl chloride. Yield: 86%. MS: 507[M+H$^+$].

Compound 265.

N-[3-[4-(1,2-Benzothiazol-3-yl)piperazin-1-yl]propyl]-2,3-dihydrobenzofuran-5-sulphonamide The title compound was prepared starting from amine (IIa-2) and 2,3-dihydrobenzofuran-5-sulphonyl chloride. Yield: 92%. MS: 459[M+H$^+$].

Compound 266.

N-[3-[4-(1,2-Benzothiazol-3-yl)piperazin-1-yl]propyl]-1,2-benzoxazole-5-sulphonamide The title compound was prepared starting from amine (IIa-2) and 1,2-benzoxazole-5-sulphonyl chloride. Yield: 75%. MS: 458[M+H$^+$].

Compound 267.

N-[3-[4-(1,2-Benzothiazol-3-yl)piperazin-1-yl]propyl]-1,3-benzothiazole-4-sulphonamide The title compound was prepared starting from amine (IIa-2) and 1,3-benzothiazole-4-sulphonyl chloride. Yield: 83%. MS: 474[M+H$^+$].

Compound 268.

N-[3-[4-(1,2-Benzothiazol-3-yl)piperazin-1-yl]propyl]-1H-indazole-6-sulphonamide The title compound was prepared starting from amine (IIa-2) and 1H-indazole-6-sulphonyl chloride. Yield: 57%. MS: 457[M+H$^+$].

Compound 269.

N-[3-[4-(1,2-Benzothiazol-3-yl)piperazin-1-yl]propyl]-1,3-benzodioxole-5-sulphonamide The title compound was prepared starting from amine (IIa-2) and 1,3-benzodioxole-5-sulphonyl chloride. Yield: 84%. MS: 461[M+H$^+$].

Compound 270.

N-[3-[4-(1,2-Benzothiazol-3-yl)piperazin-1-yl]propyl]-1H-pyrrolo[2,3-b]pyridine-3-sulphonamide The title compound was prepared starting from amine (IIa-2) and 1H-pyrrolo-[2,3-b]-pyridine-3-sulphonyl chloride. Yield: 68%. MS: 457[M+H$^+$].

Compound 271.

N-[4-[4-(1,2-Benzoxazol-3-yl)piperazin-1-yl]butyl]-4-fluorobenzenesulphonamide The title compound was prepared starting from amine (IIa-4) and 4-fluorobenzenesulphonyl chloride. Yield: 89%. $^1$H-NMR (300 MHz, DMSO-d$_6$): δ 7.86-7.81 (m, 2H), 7.64 (t, 1H, J=5.9 Hz), 7.48-7.35 (m, 3H), 7.26 (d, 1H, J=7.7 Hz), 7.13 (t, 1H, J=7.4 Hz), 6.99 (t, 1H, J=7.7 Hz), 3.56 (br. s, 4H), 2.79-2.72 (m, 2H), 2.41 (br. s, 4H), 2.23 (br. s, 2H), 1.37 (br. s, 4H). MS: 433[M+H$^+$].

Compound 272.

N-[4-[4-(1,2-Benzoxazol-3-yl)piperazin-1-yl]butyl]-3,4-difluorobenzenesulphonamide The title compound was prepared starting from amine (IIa-4) and 3,4-difluorobenzene-sulphonyl chloride. Yield: 84%. MS: 451[M+H$^+$].

Compound 273.

N-[4-[4-(1,2-Benzoxazol-3-yl)piperazin-1-yl]butyl]-4-chlorobenzenesulphonamide The title compound was prepared starting from amine (IIa-4) and 4-chlorobenzene-sulphonyl chloride. Yield: 93%. MS: 449[M+H$^+$].

Compound 274.

N-[4-[4-(1,2-Benzoxazol-3-yl)piperazin-1-yl]butyl]-4-bromobenzenesulphonamide The title compound was prepared starting from amine (IIa-4) and 4-bromobenzene-sulphonyl chloride. Yield: 91%. MS: 493[M+H$^+$].

Compound 275.

N-[4-[4-(1,2-Benzoxazol-3-yl)piperazin-1-yl]butyl]-3-bromobenzenesulphonamide The title compound was prepared starting from amine (IIa-4) and 3-bromobenzene-sulphonyl chloride. Yield: 71%. MS: 493[M+H$^+$].

Compound 276.

N-[4-[4-(1,2-Benzoxazol-3-yl)piperazin-1-yl]butyl]-3-chloro-4-fluorobenzenesulphonamide The title compound was prepared starting from amine (IIa-4) and 3-chloro-4-fluorobenzenesulphonyl chloride. Yield: 83%, MS: 467[M+H$^+$].

Compound 277.

N-[4-[4-(1,2-Benzoxazol-3-yl)piperazin-1-yl]butyl]-3-hydroxybenzenesulphonamide The title compound was prepared starting from amine (IIa-4) and 3-hydroxy-benzenesulphonyl chloride. Yield: 38%. MS: 431[M+H$^+$].

Compound 278.

N-[4-[4-(1,2-Benzoxazol-3-yl)piperazin-1-yl]butyl]-3-methoxybenzenesulphonamide The title compound was prepared starting from amine (IIa-4) and 3-methoxybenzenesulphonyl chloride. Yield: 89%. MS: 445[M+H$^+$].

Compound 279.

N-[4-[4-(1,2-Benzoxazol-3-yl)piperazin-1-yl]butyl]-4-tert-butylbenzenesulphonamide, hydrochloride The title compound was prepared starting from amine (IIa-4) and 4-tert-butyl-benzenesulphonyl chloride. Yield: 80%. MS: 471[M+H$^+$].

Compound 280.

N-[4-[4-(1,2-Benzoxazol-3-yl)piperazin-1-yl]butyl]-4-(trifluoromethyl)benzenesulphonamide The title compound was prepared starting from amine (IIa-4) and 4-(trifluoromethyl)-benzenesulphonyl chloride. Yield: 74%. MS: 483[M+H$^+$].

Compound 281.

N-[4-[4-(1,2-Benzoxazol-3-yl)piperazin-1-yl]butyl]-4-(trifluoromethoxy)benzenesulphonamide The title compound was prepared starting from amine (IIa-4) and 4-(trifluoromethoxy)-benzenesulphonyl chloride. Yield: 72%. $^1$H-NMR (300 MHz, DMSO-d$_6$): δ 7.93-7.88 (m, 2H), 7.76 (t, 1H, J=5.6 Hz), 7.58 (d, 2H, J=9.0 Hz), 7.37 (d, 1H, J=7.4 Hz), 7.26 (d, 1H, J=7.6 Hz), 7.13 (d, 1H, J=7.4 Hz), 7.00 (d, 1H, J=7.5 Hz), 3.54 (br. s, 4H), 2.82-237 (m, 2H), 2.40 (br. s, 4H), 2.22 (br. s, 2H), 1.37 (br. s, 4H). MS: 499 [M+H$^+$].

Compound 282.

N-[4-[4-(1,2-Benzoxazol-3-yl)piperazin-1-yl]butyl]-3-cyanobenzenesulphonamide The title compound was prepared starting from amine (IIa-4) and 3-cyanobenzene-sulphonyl chloride. Yield: 87%. MS: 440[M+H$^+$].

Compound 283.

N-{4-[4-(1,2-Benzoxazol-3-yl)piperazin-1-yl]butyl}-4-phenylbenzenesulphonamide The title compound was prepared starting from amine (IIa-4) and 4-phenylbenzene-sulphonyl chloride. Yield: 90%. MS: 491[M+H$^+$].

Compound 284.

N-[4-[4-(1,2-Benzoxazol-3-yl)piperazin-1-yl]butyl]thiophene-2-sulphonamide

The title compound was prepared starting from amine (IIa-4) and thiophene-2-sulphonyl chloride. Yield: 83%. MS: 421 [M+H$^+$].

Compound 285.

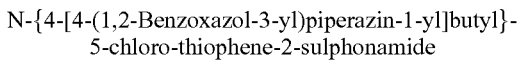

The title compound was prepared starting from amine (IIa-4) and 5-chloro-thiophene-2-sulphonyl chloride. Yield: 77%. MS: 455[M+H$^+$].

Compound 286.

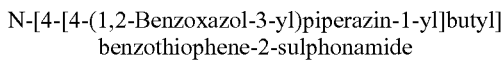

The title compound was prepared starting from amine (IIa-4) and benzothiophene-2-sulphonyl chloride. Yield: 79%. MS: 471[M+H$^+$].

Compound 287.

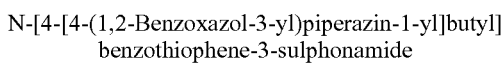

The title compound was prepared starting from amine (IIa-4) and benzothiophene-3-sulphonyl chloride. Yield: 75%. MS: 471[M+H.].

Compound 288.

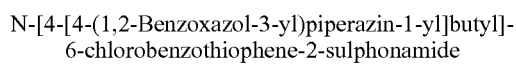

The title compound was prepared starting from amine (IIa-4) and 6-chlorobenzothiophene-2-sulphonyl chloride. Yield: 69%. MS: 505[M+H$^+$].

Compound 289.

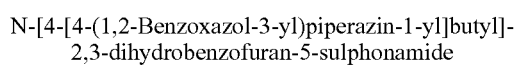

The title compound was prepared starting from amine (IIa-4) and 2,3-dihydrobenzofuran-5-sulphonyl chloride. Yield: 80%. MS: 457[M+H$^+$].

Compound 290.

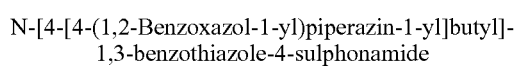

The title compound was prepared starting from amine (IIa-4) and 1,3-benzothiazole-4-sulphonyl chloride. Yield: 72%. MS: 472[M+H$^+$].

Compound 291.

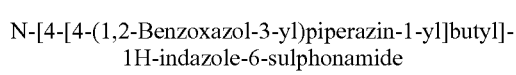

The title compound was prepared starting from amine (IIa-4) and 1H-indazole-6-sulphonyl chloride. Yield: 74%. MS: 455[M+H$^+$].

Compound 292.

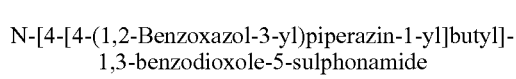

The title compound was prepared starting from amine (IIa-4) and 1,3-benzodioxole-5-sulphonyl chloride. Yield: 88%. MS: 459[M+H$^+$].

Compound 293.

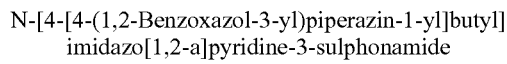

The title compound was prepared starting from amine (IIa-4) and imidazo[1,2-a]-pyridine-3-sulphonyl chloride. Yield: 64%. MS: 455[M+H$^+$].

Compound 294.

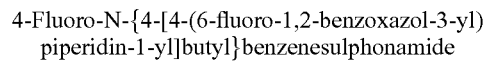

The title compound was prepared starting from amine (IIa-5) and 4-fluorobenzenesulphonyl chloride. Yield: 79%. MS: 450[M1-1-1].

Compound 295.

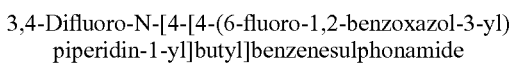

The title compound was prepared starting from amine (IIa-5) and 3,4-difluoro-benzenesulphonyl chloride. Yield: 70%. MS: 468[M+H$^+$].

Compound 296.

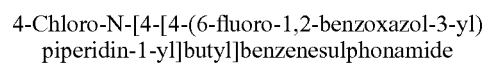

The title compound was prepared starting from amine (IIa-5) and 4-chlorobenzene-sulphonyl chloride. Yield: 71%. MS: 466[M+H$^+$].

Compound 297.

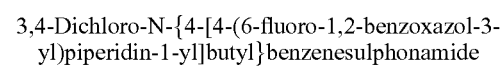

The title compound was prepared star from amine (IIa-5) and 3,4-dichlorobenzenesulphonyl chloride. Yield: 65%. MS: 500[M+H$^+$].

Compound 298.

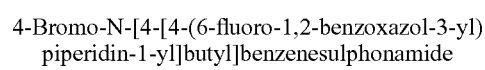

The title compound was prepared starting from amine (IIa-5) and 4-bromobenzene-sulphonyl chloride. Yield: 82%. MS: 510[M+H$^+$].

Compound 299.

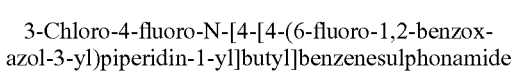

The title compound was prepared starting from amine (IIa-5) and 3-chloro-4-fluorobenzenesulphonyl chloride. Yield: 70%. MS: 484[M+H$^+$].

Compound 300.

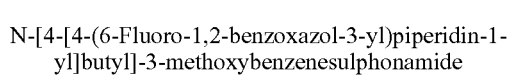

The title compound was prepared starting from amine (IIa-5) and 3-methoxybenzenesulphonyl chloride. Yield: 68%. MS: 462[M+H$^+$].

Compound 301.

4-tert-Butyl-N-[4-[4-(6-fluoro-1,2-benzoxazol-3-yl)piperidin-1-yl]butyl]benzenesulphonamide The title compound was prepared starting from amine (IIa-5) and 4-tert-butyl-benzenesulphonyl chloride. Yield: 69%. MS: 488[M+H$^+$].

Compound 302.

N-[4-[4-(6-Fluoro-1,2-benzoxazol-3-yl)piperidin-1-yl]butyl]-4-(trifluoromethyl)benzenesulphonamide The title compound was prepared starting from amine (IIa-5) and 4-fluoromethyl)-benzenesulphonyl chloride. Yield: 58%. MS: 500[M+H$^+$].

Compound 303.

N-[4-[4-(6-Fluoro-1,2-benzoxazol-3-yl)piperidin-1-yl]butyl]-3-(trifluoromethyl)-benzenesulphonamide The title compound was prepared starting from amine (IIa-5) and 3-(trifluoromethyl)-benzenesulphonyl chloride. Yield: 64%, MS: 500[M+H$^+$].

Compound 304.

N-[4-[4-(6-Fluoro-1,2-benzoxazol-3-yl)piperidin-1-yl]butyl]-4-(trifluoromethoxy benzenesulphonamide The title compound was prepared starting from amine (IIa-5) and 4-(trifluoromethoxy)-benzenesulphonyl chloride. Yield: 65%. MS: 516[M+H$^+$].

Compound 305.

4-Cyano-N-[4-[4-(6-fluoro-1,2-benzoxazol-3-yl)piperidin-1-yl]butyl]benzenesulphonamide The title compound was prepared starting from amine (IIa-5) and 4-cyanobenzene-sulphonyl chloride. Yield: 76%. MS: 457[M+H$^+$].

Compound 306.

3-Cyano-N-[4-[4-(6-fluoro-1,2-benzoxazol-3-yl)piperidin-1-yl]butyl]benzenesulphonamide The title compound was prepared starting from amine (IIa-5) and 3-cyanobenzene-sulphonyl chloride. Yield: 61%. MS: 457[M+H$^+$].

Compound 307.

N-[4-[4-(6-Fluoro-1,2-benzoxazol-3-yl)piperidin-1-yl]butyl]thiophene-3-sulphonamide The title compound was prepared starting from amine (IIa-5) and thiophene-3-sulphonyl chloride. Yield: 50%. MS: 438 [M+H$^+$].

Compound 308.

5-Chloro-N-[4-[4-(6-fluoro-1,2-benzoxazol-3-yl)piperidin-1-yl]butyl]thiophene-2-sulphonamide The title compound was prepared starting from amine (IIa-5) and 5-chloro-thiophene-2-sulphonyl chloride. Yield: 51%. MS: 472[M+H$^+$].

Compound 309.

N-[4-[4-(6-Fluoro-1,2-benzoxazol-3-yl)piperidin-1-yl]butyl]-2,5-dimethyl-thiophene-3-sulphonamide The title compound was prepared starting from amine (IIa-5) and 2,5-dimethyl-thiophene-3-sulphonyl chloride. Yield: 67%. MS: 466[M+H$^+$].

Compound 310.

N-[4-[4-(6-Fluoro-1,2-benzoxazol-3-yl)piperidin-1-yl]butyl]-1-methyl-indole-4-sulphonamide The title compound was prepared starting from amine (IIa-5) and 1-methyl-indole-4-sulphonyl chloride. Yield: 57%. MS: 485[M+H$^+$].

Compound 311.

N-[4-[4-(6-Fluoro-1,2-benzoxazol-3-yl)piperidin-1-yl]butyl]-1-methyl-indole-6-sulphonamide The title compound was prepared starting from amine (IIa-5) and 1-methyl-indole-6-sulphonyl chloride. Yield: 78%. MS: 485[M+H$^+$].

Compound 312.

N-[4-[4-(6-Fluoro-1,2-benzoxazol-3-yl)piperidin-1-yl]butyl]benzothiophene-2-sulphonamide The title compound was prepared starting from amine (IIa-5) and benzothiophene-2-sulphonyl chloride. Yield: 51%. MS: 488[M+H$^+$].

Compound 313.

N-[4-[4-(6-Fluoro-1,2-benzoxazol-3-yl)piperidin-1-yl]butyl]benzothiophene-3-sulphonamide The title compound was prepared starting from amine IIa-5) and benzothiophene-3-sulphonyl chloride. Yield: 62%. MS: 488[M+H$^+$].

Compound 314.

6-Chloro-N-[4-[4-(6-fluoro-1,2-benzoxazol-3-yl)piperidin-1-yl]butyl]benzothiophene-2-sulphonamide The title compound was prepared starting from amine (IIa-5) and 6-chlorobenzothiophene-2-sulphonyl chloride. Yield: 53%. MS: 522[M+H$^+$].

Compound 315.

5-Chloro-N-[4-[4-(6-fluoro-1,2-benzoxazol-3-yl)piperidin-1-yl]butyl]-3-methylbenzothiophene-2-sulphonamide The title compound was prepared starting from amine (IIa-5) and 5-chloro-3-methylbenzothiophene-2-sulphonyl chloride. Yield: 61%. MS: 536[M+H$^+$].

Compound 316.

N-[4-[4-(6-Fluoro-1,2-benzoxazol-3-yl)piperidin-1-yl]butyl]benzofuran-2-sulphonamide The title compound was prepared starting from amine (IIa-5) and benzofuran-2-sulphonyl chloride. Yield: 71%. MS: 472[M+H$^+$].

Compound 317.

N-[4-[4-(6-Fluoro-1,2-benzoxazol-3-yl)piperidin-1-yl]butyl]-2,3-dihydrobenzofuran-5-sulphonamide The title compound was prepared starting from amine (IIa-5) and 2,3-dihydrobenzofuran-5-sulphonyl chloride. Yield: 54%. MS: 474[M+H$^+$].

Compound 318.

N-[4-[4-(6-Fluoro-1,2-benzoxazol-3-yl)piperidin-1-yl]butyl]-1,3-benzothiazote-4-sulphonamide The title compound was prepared starting from amine (IIa-5) and 1,3-benzothiazole-4-sulphonyl chloride. Yield: 47%. MS: 489[M+H$^+$].

Compound 319.

N-[4-[4-(6-Fluoro-1,2-benzoxazol-3-yl)piperidin-1-yl]butyl]-1H-indazole-6-sulphonamide The title compound was prepared starting from amine (IIa-5) and 1H-indazole-6-sulphonyl chloride. Yield: 58%. MS: 472[M+H$^+$].

Compound 320.

N-[4-[4-(6-Fluoro-1,2-benzoxazol-3-yl)piperidin-1-yl]butyl]-1,3-benzodioxole-5-sulphonamide, hydrochloride The title compound was prepared starting from amine (IIa-5) and 1,3-benzodioxole-5-sulphonyl chloride. Yield: 65%. MS: 476[M+H$^+$].

Compound 321.

N-[4-[4-(6-Fluoro-1,2-benzoxazol-3-yl)piperidin-1-yl]butyl]-2,3-dihydro-1,4-benzodioxine-6-sulphonamide The title compound was prepared starting from amine (IIa-5) and 2,3-dihydro-1,4-benzodioxine-6-sulphonyl chloride. Yield: 78%. MS: 490[M+H$^+$].

Compound 322.

N-[4-[4-(6-Fluoro-1,2-benzoxazol-3-yl)piperidin-1-yl]butyl]imidazo[1,2-a]pyridine-3-sulphonamide The title compound was prepared starting from amine (IIa-5) and imidazo[1,2-a]-pyridine-3-sulphonyl chloride. Yield: 47%. MS: 472[M+H$^+$].

Compound 323.

N-[4-[4-(6-Fluoro-1,2-benzoxazol-3-yl)piperidin-1-yl]butyl]-1H-pyrrolo[2,3-b]pyridine-3-sulphonamide The title compound was prepared starting from amine (IIa-5) and 1H-pyrrolo-[2,3-b]-pyridine-3-sulphonyl chloride. Yield: 63%. MS: 472[M+H$^+$].

Compound 324.

N-[4-[4-(6-Fluoro-1,2-benzoxazol-3-yl)piperidin-1-yl]butyl]-2-oxo-indoline-5-sulphonamide The title compound was prepared starting from amine (IIa-5) and 2-oxo-indoline-5-sulphonyl chloride. Yield: 48%. $^1$H-NMR (300 MHz, DMSO-d$_6$): δ 7.98 (dd, 1H, J=8.7 Hz, J=5.4 Hz), 7.66 (dd, 1H, J=9.0 Hz, J=2.3 Hz), 7.59-7.53 (m, 2H), 7.29-7.17 (m, 2H), 3.35 (s, 2H), 3.18-3.09 (m, 1H), 2.95-2.88 (m, 2H), 2.74 (s, 2H), 2.27 (s, 2H), 2.12-1.95 (m, 6H), 1.86-1.75 (m, 2H), 1.42-1.34 (m, 4H). MS: 487[M+H$^+$].

Compound 325.

N-[4-[4-(6-Fluoro-1,2-benzoxazol-3-yl)piperidin-1-yl]butyl]thiophene-2-sulphonamide The title compound was prepared starting from amine (IIa-5) and thiophene-2-sulphonyl chloride. Yield: 70%. MS: 438 [M+H$^+$].

Compound 326.

4-Fluoro-N-[3-[4-(6-fluoro-1,2-benzoxazol-3-yl)piperidin-1-yl]propyl]benzenesulphonamide The title compound was prepared starting from amine (IIa-6) and 4-fluorobenzenesulphonyl chloride. Yield: 56%. MS: 436[M+H$^+$].

Compound 327.

3,4-Difluoro-N-[3-[4-(6-fluoro-1,2-benzoxazol-3-yl)piperidin-1-yl]propyl]benzenesulphonamide The title compound was prepared starting from amine (IIa-6) and 3,4-difluorobenzene-sulphonyl chloride. Yield: 69%. MS: 454[M+H$^+$].

Compound 328.

4-Chloro-N-[3-[4-(6-fluoro-1,2-benzoxazol-3-yl)piperidin-1-yl]propyl]benzenesulphonamide The title compound was prepared starting from amine (IIa-6) and 4-chlorobenzene-sulphonyl chloride. Yield: 56%. MS: 453[M+H$^+$].

Compound 329.

3,4-Dichloro-N-[3-[4-(6-fluoro-1,2-benzoxazol-3-yl)piperidin-1-yl]propyl]benzenesulphonamide The title compound was prepared starting from amine (IIa-6) and 3,4-dichlorobenzenesulphonyl chloride. Yield: 87%. MS: 486[M+H$^+$].

Compound 330.

4-Bromo-N-[3-[4-(6-fluoro-1,2-benzoxazol-3-yl)piperidin-1-yl]propyl]benzenesulphonamide The title compound was prepared starting from amine (IIa-6) and 4-bromobenzene-sulphonyl chloride. Yield: 48%. MS: 497[M+H$^+$].

Compound 331.

3-Chloro-4-fluoro-N-[3-[4-(6-fluoro-1,2-benzoxazol-3-yl)piperidin-1-yl]propyl]benzenesulphonamide The title compound was prepared starting from amine (IIa-6) and 3-chloro-4-fluorobenzenesulphonyl chloride. Yield: 83%. MS: 471[M+H$^+$].

Compound 332.

N-[3-[4-(6-Fluoro-1,2-benzoxazol-3-yl)piperidin-1-yl]propyl]-3-methoxybenzenesulphonamide The title compound was prepared starting from amine (IIa-6) and 3-methoxybenzenesulphonyl chloride. Yield: 81%. MS: 448[M+H$^+$].

Compound 333.

4-tert-Butyl-N-[3-[4-(6-fluoro-1,2-benzoxazol-3-yl)piperidin-1-yl]propyl]benzenesulphonamide The title compound was prepared starting from amine (IIa-6) and 4-tert-butyl-benzenesulphonyl chloride. Yield: 51%. MS: 474[M+H$^+$].

Compound 334.

N-[3-[4-(6-Fluoro-1,2-benzoxazol-3-yl)piperidin-1-yl]propyl]-4-(trifluoromethyl)-benzenesulphonamide The title compound was prepared starting from amine (IIa-6) and 4-(trifluoromethyl)-benzenesulphonyl chloride. Yield: 73%. MS: 486[M+H$^+$].

Compound 335.

N-[3-[4-(6-Fluoro-1,2-benzoxazol-3-yl)piperidin-1-yl]propyl]-3-(trifluoromethyl)-benzenesulphonamide The title compound was prepared starting from amine (IIa-6) and 3-(trifluoromethyl)-benzenesulphonyl chloride. Yield: 48%. MS: 486[M+H$^+$].

Compound 336.

N-[3-[4-(6-Fluoro-1,2-benzoxazol-3-yl)piperidin-1-yl]propyl]-4-(trifluoromethoxy)-benzenesulphonamide The title compound was prepared starting from amine (IIa-6) and 4-(trifluoromethoxy)-benzenesulphonyl chloride. Yield: 53%. MS: 502[M+H$^+$].

Compound 337.

4-Cyano-N-[3-[4-(6-fluoro-1,2-benzoxazol-3-yl)piperidin-1-yl]propyl]benzenesulphonamide The title compound was prepared starting from amine (IIa-6) and 4-cyanobenzene-sulphonyl chloride. Yield: 85%. MS: 443[M+H$^+$].

Compound 338.

3-cyano-N-[3-[4-(6-fluoro-1,2-benzoxazol-3-yl)piperidin-1-yl]propyl]benzenesulphonamide The title compound was prepared starting from amine (IIa-6) and 3-cyanobenzene-sulphonyl chloride. Yield: 84%. MS: 443[M+H$^+$].

Compound 339.

N-[3-[4-(6-Fluoro-1,2-benzoxazol-3-yl)piperidin-1-yl]propyl]thiophene-2-sulphonamide The title compound was prepared starting from amine (IIa-6) and thiophene-2-sulphonyl chloride. Yield: 68%, MS: 424 [M+H$^+$].

Compound 340.

N-[3-[4-(6-Fluoro-1,2-benzoxazol-3-yl)piperidin-1-yl]propyl]thiophene-3-sulphonamide The title compound was prepared starting from amine (IIa-6) and thiophene-3-sulphonyl chloride. Yield: 66%. MS: 424 [M+H$^+$].

Compound 341.

5-Chloro-N-[3-[4-(6-fluoro-1,2-benzoxazol-3-yl)piperidin-1-yl]propyl]thiophene-2-sulphonamide The title compound was prepared starting from amine (IIa-6) and 5-chloro-thiophene-2-sulphonyl chloride. Yield: 81%. MS: 459[M+H$^+$].

Compound 342.

N-[3-[4-(6-Fluoro-1,2-benzoxazol-3-yl)piperidin-1-yl]propyl]-2,5-dimethyl-thiophene-3-sulphonamide The title compound was prepared starting from amine (IIa-6) and 2,5-dimethyl-thiophene-3-sulphonyl chloride. Yield: 58%. MS: 452[M+H$^+$].

Compound 343.

N-[3-[4-(6-Fluoro-1,2-benzoxazol-3-yl)piperidin-1-yl]propyl]-1-methyl-indole-4-sulphonamide The title compound was prepared starting from amine (IIa-6) and 1-methyl-indole-4-sulphonyl chloride. Yield: 62%. MS: 471[M+H$^+$].

Compound 344.

N-[3-[4-(6-Fluoro-1,2-benzoxazol-3-yl)piperidin-1-yl]propyl]-1-methyl-indole-5-sulphonamide The title compound was prepared starting from amine (IIa-6) and 1-methyl-indole-5-sulphonyl chloride. Yield: 55%. MS: 471[M+H$^+$].

Compound 345.

N-[3-[4-(6-Fluoro-1,2-benzoxazol-3-yl)piperidin-1-yl]propyl]benzothiophene-2-sulphonamide The title compound was prepared starting from amine (IIa-6) and benzothiophene-2-sulphonyl chloride. Yield: 57%. MS: 474[M+H$^+$].

Compound 346.

N-[3-[4-(6-Fluoro-1,2-benzoxazol-3-yl)piperidin-1-yl]propyl]benzothiophene-3-sulphonamide The title compound was prepared starting from amine (IIa-6) and benzothiophene-3-sulphonyl chloride. Yield: 63%. MS: 474[M+H$^+$].

Compound 347.

6-Chloro-N-[3-[4-(6-fluoro-1,2-benzoxazol-3-yl)piperidin-1-yl]propyl]benzothiophene-2-sulphonamide The title compound was prepared starting from amine (IIa-6) and 6-chlorobenzothiophene-2-sulphonyl chloride. Yield: 66%. MS: 509[M+H$^+$].

Compound 348.

5-Chloro-N-[3-[4-(6-fluoro-1,2-benzoxazol-1-yl)piperidin-1-yl]propyl]-3-methylbenzothiophene-2-sulphonamide The title compound was prepared starting from amine (IIa-6) and 5-chloro-3-methylbenzothiophene-2-sulphonyl chloride. Yield: 88%. $^1$H-NMR (300 MHz, DMSO-d$_6$): δ 8.20 (br. s, 1H), 8.08-8.02 (m, 2H), 7.93 (dd, 1H, J=8.7 Hz, J=5.4 Hz), 7.68 (dd, 1H, J=92 Hz, J=2.1 Hz), 7.53 (dd, 1H, J=8.5 Hz, J=2.1 Hz), 7.25 (td, 1H, J=9.0 Hz, J=2.1 Hz), 3.10-3.00 (m, 1H), 2.96 (t, 2H, J=6.7 Hz), 2.77 (br. s, 2H), 2.61 (s, 3H), 2.28 (br. s, 2H), 2.02-1.86 (m, 4H), 1.76-1.64 (m, 2H), 1.60-1.50 (m, 2H). MS: 523[M+H$^+$].

Compound 349.

N-[3-[4-(6-Fluoro-1,2-benzoxazol-3-yl)piperidin-1-yl]propyl]benzofuran-2-sulphonamide The title compound was prepared starting from amine (IIa-6) and benzofuran-2-sulphonyl chloride. Yield: 48%. MS: 458[M+H$^+$].

Compound 350.

N-[3-[4-(6-Fluoro-1,2-benzoxazol-3-yl)piperidin-1-yl]propyl]-2,3-dihydrobenzofuran-5-sulphonamide The title compound was prepared starting from amine (IIa-6) and 2,3-dihydrobenzofuran-5-sulphonyl chloride. Yield: 29%. MS: 460[M+H$^+$].

Compound 351.

N-[3-[4-(6-Fluoro-1,2-benzoxazol-3-yl)piperidin-1-yl]propyl]-1,3-benzothiazole-4-sulphonamide The title compound was prepared starting from amine (IIa-6) and 1,3-benzothiazole-4-sulphonyl chloride. Yield: 57%. MS: 475[M+H$^+$].

Compound 352.

N-[3-[4-(6-Fluoro-1,2-benzoxazol-3-yl)piperidin-1-yl]propyl]-1H-indazole-6-sulphonamide The title compound was prepared starting from amine (IIa-6) and 1H-indazole-6-sulphonyl chloride. Yield: 80%. MS: 458[M+H$^+$].

Compound 353.

N-[3-[4-(6-Fluoro-1,2-benzoxazol-3-yl)piperidin-1-yl]propyl]-2-oxo-3H-1,3-benzoxazole-so 6-sulphonamide The title compound was prepared starting from amine (IIa-6) and 2-oxo-3H-1,3-benzoxazole-6-sulphonyl chloride. Yield: 57%, MS: 475[M+H$^+$].

Compound 354.

N-[3-[4-(6-Fluoro-1,2-benzoxazol-3-yl piperidin-1-yl]propyl]-1,3-benzodioxole-5-sulphonamide The title compound was prepared starting from amine (IIa-6) and 1,3-benzodioxole-5-sulphonyl chloride. Yield: 65%, MS: 462[M+H$^+$].

Compound 355.

N-[3-[4-(6-Fluoro-1,2-benzoxazol-3-yl)piperidin-1-yl]propyl]-2,3-dihydro-1,4-benzodioxine-6-sulphonamide The title compound was prepared starting from amine (IIa-6) and 2,3-dihydro-1,4-benzodioxine-6-sulphonyl chloride. Yield: 64%. MS: 476[M+H$^+$].

Compound 356.

N-[3-[4-(6-Fluoro-1,2-benzoxazol-3-yl)piperidin-1-yl]propyl]imidazo[1,2-a]pyridine-3-sulphonamide The title compound was prepared starting from amine (IIa-6) and imidazo[1,2-a]-pyridine-3-sulphonyl chloride. Yield: 62%. MS: 458[M+H$^+$].

Compound 357.

N-[3-[4-(6-Fluoro-1,2-benzoxazol-3-yl)piperidin-1-yl]propyl]-1H-pyrrolo[2,3-b]pyridine-2-sulphonamide The title compound was prepared starting from amine (IIa-6) and 1H-pyrrolo-[2,3-b]-pyridine-2-sulphonyl chloride. Yield: 64%. MS: 458[M+H$^+$].

Compound 358.

6-Chloro-N-[4-[4-(1H-indol-4-yl)piperazin-1-yl]butyl]naphthalene-2-sulphonamide The title compound was prepared starting from amine (IIa-8) and 6-chloro-naphthalene-2-sulphonyl chloride. Yield: 72%. $^1$H-NMR (300 MHz, CDCl$_3$): δ 8.39 (s, 1H), 8.20 (s, 1H), 7.88-7.82 (m, 3H), 7.78 (d, 1H, J=8.9 Hz), 7.49 (dd, 1H, J=2.0 and 8.7 Hz), 7.18-7.14 (m, 2H), 7.13-7.10 (m, 1H), 6.62 (dd, 1H, J=1.6 and 6.8 Hz), 6.51 (t, 1H, J=2.3 Hz), 3.35-3.30 (m, 4H), 3.09-3.00 (m, 2H), 2.75-2.70 (m, 4H), 2.49-2.42 (m, 2H), 1.65-1.60 (m, 4H). MS: 497[M+H$^+$].

Compound 359.

4-Fluoro-N-[4-[4-(1H-indol-4-yl)piperazin-1-yl]butyl]benzenesulphonamide

The title compound was prepared starting from amine (IIa-8) and 4-fluorobenzenesulphonyl chloride. Yield: 75%, $^1$H-NMR (300 MHz, CDCl$_3$): δ 8.22 (s, 1H), 7.90-7.82 (m, 2H), 7.18-7.00 (m, 5H), 6.62 (dd, 1H, J=1.2 and 7.1 Hz), 6.52 (t, 1H, J=2.3 Hz), 3.58-3.36 (m, 4H), 3.02-2.96 (m, 2H), 2.78-2.70 (m, 4H), 2.48-2.40 (m, 2H), 1.66-1.58 (m, 4H). MS: 431[M+H$^+$].

Compound 360.

N-[4-[4-(1H-Indol-4-yl)piperazin-1-yl]butyl]-4-(trifluoromethyl)benzenesulphonamide The title compound was prepared starting from amine (IIa-8) and 4-(trifluoromethyl)-benzenesulphonyl chloride. Yield: 60%. $^1$H-NMR (300 MHz, CDCl$_3$): δ 8.18 (s, 1H), 8.76 (d, 2H, J=7.9 Hz), 7.72 (d, 2H, J=8.2 Hz), 7.18-7.04 (m, 3H), 6.61 (dd, 1H, J=1.2 and 6.9 Hz), 6.52 (t, 1H, J=2.3 Hz), 3.36-3.18 (m, 4H), 3.08-2.96 (m, 2H), 2.78-2.70 (m, 4H), 2.48-2.40 (m, 2H), 1.68-1.60 (m, 4H). MS: 481[M+H$^+$].

Compound 361.

N-[4-[4-(1H-Indol-4-yl)piperazin-1-yl]butyl]-3-(trifluoromethyl)benzenesulphonamide The title compound was prepared starting from amine (IIa-8) and 3-(trifluoromethyl)-benzenesulphonyl chloride. Yield: 75%. $^1$H-NMR (300 MHz, CDCl$_3$): 8.45 (s, 1H), 8.15-8.00 (m, 2H), 7.82-7.78 (m, 2H), 7.50-7.46 (d, 1H, J=6.9 Hz), 7.31-7.20 (m, 2H), 6.62-6.58 (m, 1H), 6.52-6.46 (m, 1H), 3.62-3.42 (m, 4H), 3.48-3.40 (m, 2H), 3.38-3.30 (m, 2H), 3.02-2.88 (m, 1H), 2.75-2.60 (m, 2H), 2.50-2.40 (m, 1H), 2.22-2.14 (m, 2H), 1.68-1.54 (m, 2H). MS: 481[M+H$^+$].

Compound 362.

3-Cyano-N-[4-[4-(1H-indol-4-yl)piperazin-1-yl]butyl]benzenesulphonamide

The title compound was prepared starting from amine (IIa-8) and 3-cyanobenzene-sulphonyl chloride. Yield: 68%. $^1$H-NMR (300 MHz, CDCl$_3$): δ 8.32 (s, 1H), 8.12 (t, 1H, J=1.7 Hz), 8.06 (dt, 1H, J=1.0 and 7.9 Hz), 718 (dd, 1H, J=1.4 and 7.9 Hz), 7.18-7.06 (m, 3H), 6.62 (dd, 1H, J=1.3 and 6.9 Hz), 6.50 (t, 1H, J=2.3 Hz), 3.36-318 (m, 4H), 3.04-2.96 (m, 2H), 2.80-2.72 (m, 4H), 2.50-2.42 (m, 2H), 1.70-1.60 (m, 4H). MS: 438[M+H$^+$].

Compound 363.

6-Chloro-N-[4-[4-(1H-indol-4-yl)piperazin-1-yl]butyl]benzothiophene-2-sulphonamide The title compound was prepared starting from amine (IIa-8) and 6-chlorobenzothiophene-2-sulphonyl chloride. Yield: 68%. $^1$H-NMR 1300 MHz, CDCl$_3$): δ 8.26 (s, 1H), 7.80 (d, 1H, J=1.8 Hz), 7.76 (d, 1H, J=0.7 Hz), 7.70 (d, 1H, J=8.4 Hz), 7.38 (dd, 1H, J=1.6 and 8.7 Hz), 7.18-7.10 (m, 4H), 6.61 (dd, 1H, J=1.6 and 6.7 Hz), 6.51 (t, 1H, J=2.3 Hz), 3.40-3.32 (m, 4H), 312-3.08 (m, 2H), 2.80-2.72 (m, 4H), 2.50-2.42 (m, 2H), 1.70-1.16 (m, 4H). MS: 503[M+H$^+$].

Compound 364.

5-Fluoro-N-[4-[4-(1H-indol-4-yl)piperazin-1-yl]butyl]-3-methylbenzothiophene-2-sulphonamide The title compound was prepared starting from amine (IIa-8) and 5-fluoro-3-methylbenzothiophene-2-sulphonyl chloride. Yield: 75%. $^1$H-NMR (300 MHz, CDCl$_3$): δ 8.24 (s, 1H), 7.78-7.68 (m, 1H), 7.50-7.39 (m, 1H), 7.28-7.20 (m, 1H), 7.16-7.04 (m, 3H), 6.60-6.58 (m, 1H), 6.56-6.50 (m, 1H), 3.38-3.32 (m, 2H), 3.28-3.19 (m, 3H), 316-3.10 (m, 1H), 2.78-2.68 (m, 4H), 2.68 (s, 3H), 2.50-2.44 (m, 2H), 1.68-1.60 (m, 4H). MS: 501[M+H$^+$].

Compound 365.

N-[4-[4-(1H-Indol-4-yl)piperazin-1-yl]butyl]-1,3-benzodioxole-5-sulphonamide The title compound was prepared starting from amine (IIa-8) and 1,3-benzodioxole-5-sulphonyl chloride. Yield: 70%. MS: 378[M+H$^+$].

Compound 371.

N-[3-[4-(1,2-Benzoxazol-3-yl)piperazin-1-yl]propyl]naphthalene-1-sulphonamide The title compound was prepared starting from amine (IIa-13) and naphthalene-1-sulphonyl chloride. Yield: 87%. MS: 451[M+H$^+$].

Compound 372.

N-[3-[4-(1,2-Benzoxazol-3-yl)piperazin-1-yl]propyl]naphthalene-2-sulphonamide, hydrochloride The title compound was prepared starting from amine (IIa-13) and naphthalene-2-sulphonyl chloride. Yield: 80%. MS: 451[M+H$^+$].

Compound 373.

N-[3-[4-(1,2-Benzoxazol-3-yl)piperazin-1-yl]propyl]-4-fluorobenzenesulphonamide The title compound was prepared starting from amine (IIa-13) and 4-fluorobenzenesulphonyl chloride. Yield: 65%. MS: 419[M+H$^+$].

Compound 374.

N-[3-[4-(1,2-Benzoxazol-3-yl)piperazin-1-yl]propyl]-3,4-difluorobenzenesulphonamide The title compound was prepared starting from amine (IIa-13) and 3,4-difluorobenzene-sulphonyl chloride. Yield: 70%. MS: 437[M+H$^+$].

Compound 375.

N-[3-[4-(1,2-Benzoxazol-3-yl)piperazin-1-yl]propyl]-4-chlorobenzenesulphonamide The title compound was prepared starting from amine (IIa-13) and 4-chlorobenzene-sulphonyl chloride. Yield: 70%. MS: 435[M+H$^+$].

Compound 376.

N-[3-[4-(1,2-Benzoxazol-3-yl)piperazin-1-yl]propyl]-4-bromobenzenesulphonamide The title compound was prepared starting from amine (IIa-13) and 4-bromobenzene-sulphonyl chloride. Yield: 78%. MS: 479[M+H$^+$].

Compound 377.

N-[3-[4-(1,2-Benzoxazol-3-yl)piperazin-1-yl]propyl]-3-bromobenzenesulphonamide The title compound was prepared starting from amine (IIa-13) and 3-bromobenzene-sulphonyl chloride. Yield: 74%. MS: 479[M+H$^+$].

Compound 378.

N-[3-[4-(1,2-Benzoxazol-3-yl)piperazin-1-yl]propyl]-3-chloro-4-fluorobenzenesulphonamide The title compound was prepared starting from amine (IIa-13) and 3-chloro-4-fluorobenzenesulphonyl chloride. Yield: 60%. MS: 453[M+H$^+$].

Compound 379.

N-[3-[4-(1,2-Benzoxazol-3-yl)piperazin-1-yl]propyl]-4-tert-butyl-benzenesulphonamide The title compound was prepared starting from amine (IIa-13) and 4-tert-butyl-benzenesulphonyl chloride. Yield: 59%. MS: 457[M+H$^+$].

Compound 380.

N-[3-[4-(1,2-Benzoxazol-3-yl)piperazin-1-yl]propyl]-4-(trifluoromethyl)benzenesulphonamide The title compound was prepared starting from amine (IIa-13) and 4-(trifluoromethyl)-benzenesulphonyl chloride. Yield: 56%, MS: 469[M+H$^+$].

Compound 381.

N-[3-[4-(1,2-Benzoxazol-3-yl)piperazin-1-yl]propyl]-3-cyanobenzenesulphonamide The title compound was prepared starting from amine (IIa-13) and 3-cyanobenzene-sulphonyl chloride. Yield: 62%. MS: 426[M+H$^+$].

Compound 382.

N-[3-[4-(1,2-Benzoxazol-3-yl)piperazin-1-yl]propyl]-4-phenylbenzenesulphonamide The title compound was prepared starting from amine (IIa-13) and 4-phenylbenzene-sulphonyl chloride. Yield: 78%. MS: 477[M+H$^+$].

Compound 383.

N-[3-[4-(1,2-Benzoxazol-3-yl)piperazin-1-yl]propyl]-2,3-dihydrobenzofuran-5-sulphonamide The title compound was prepared starting from amine (IIa-13) and 2,3-dihydrobenzofuran-5-sulphonyl chloride. Yield: 67%, MS: 443[M+H$^+$].

Compound 384.

N-[3-[4-(1,2-Benzoxazol-3-yl)piperazin-1-yl]propyl]-1,3-benzothiazole-4-sulphonamide The title compound was prepared starting from amine (IIa-13) and 1,3-benzothiazole-4-sulphonyl chloride. Yield: 56%. MS: 458[M+H$^+$].

Compound 385.

N-[4-[4-(2,3-Dihydro-1,4-benzodioxin-5-yl)piperazin-1-yl]butyl]naphthalene-1-sulphonamide The title compound was prepared starting from amine (IIa-14) and naphthalene-1-sulphonyl chloride. Yield: 81%. MS: 482[M+H$^+$].

Compound 386.

N-[4-[4-(2,3-Dihydro-1,4-benzodioxin-5-yl)piperazin-1-yl]butyl]naphthalene-2-sulphonamide The title compound was prepared starting from amine (IIa-14) and naphthalene-2-sulphonyl chloride. Yield: 88%. MS: 482[M+H$^+$].

Compound 387.

6-Chloro-N-[4-[4-(2,3-dihydro-1,4-benzodioxin-5-yl)piperazin-1-yl]butyl]naphthalene-2-sulphonamide The title compound was prepared starting from amine (IIa-14) and 6-chloro-naphthalene-2-sulphonyl chloride. Yield: 74%. MS: 516[M+H$^+$].

Compound 388.

N-[4-[4-(2,3-Dihydro-1,4-benzodioxin-5-yl)piperazin-1-yl]butyl]-3-fluorobenzenesulphonamide The title compound was prepared starting from amine (IIa-14) and 3-fluorobenzenesulphonyl chloride. Yield: 70%. MS: 450[M+H$^+$].

Compound 389.

N-[4-[4-(2,3-Dihydro-1,4-benzodioxin-5-yl)piperazin-1-yl]butyl]-3,4-difluorobenzenesulphonamide The title compound was prepared starting from amine (IIa-14) and 3,4-difluorobenzene-sulphonyl chloride. Yield: 77%. MS: 468[M+H$^+$].

Compound 390.

3-Chloro-N-[4-[4-(2,3-dihydro-1,4-benzodioxin-5-yl)piperazin-1-yl]butyl]benzenesulphonamide The title compound was prepared starting from amine (IIa-14) and 3-chlorobenzene-sulphonyl chloride. Yield: 67%. MS: 466[M+H$^+$].

Compound 391.

3-Bromo-N-[4-[4-(2,3-dihydro-1,4-benzodioxin-5-yl)piperazin-1-yl]butyl]benzenesulphonamide The title compound was prepared starting from amine (IIa-14) and 3-bromobenzene-sulphonyl chloride. Yield: 73%. $^1$H-NMR (300 MHz, DMSO-d$_6$): δ 7.91 (s, 1H), 7.86-7.78 (m, 3H), 7.55 (t, 1H, J=8.0 Hz), 6.69 (t, 1H, J=8.0 Hz), 6.49-6.41 (m, 2H), 4.21-4.17 (m, 4H), 2.90 (br. s, 4H), 2.81-2.75 (m, 2H), 2.41 (br. s, 4H), 2.21 (br. s, 2H), 1.37 (br. s, 4H). MS: 510[M+H$^+$].

Compound 392.

3-Chloro-N-[4-[4-(2,3-dihydro-1,4-benzodioxin-5-yl)piperazin-1-yl]butyl]-4-fluorobenzenesulphonamide The title compound was prepared starting from amine (IIa-14) and 3-chloro-4-fluorobenzenesulphonyl chloride. Yield: 68%. MS: 484[M+H$^+$].

Compound 393.

N-[4-[4-(2,3-Dihydro-1,4-benzodioxin-5-yl)piperazin-1-yl]butyl]-3-hydroxybenzenesulphonamide The title compound was prepared starting from amine (IIa-14 and 3-hydroxybenzene-sulphonyl chloride. Yield: 45%. MS: 448[M+H$^+$].

Compound 394.

N-[4-[4-(2,3-Dihydro-1,4-benzodioxin-5-yl)piperazin-1-yl]butyl]-3-methoxybenzenesulphonamide The title compound was prepared starting from amine (IIa-14) and 3-methoxybenzenesulphonyl chloride. Yield: 70%. MS: 462[M+H$^+$].

Compound 395.

N-[4-[4-(2,3-Dihydro-1,4-benzodioxin-5-yl)piperazin-1-yl]butyl]-3-methylbenzenesulphonamide The title compound was prepared starting from amine (IIa-14) and 3-methylbenzene-sulphonyl chloride. Yield: 63%. MS: 446[M+H$^+$].

Compound 396.

N-[4-[4-(2,3-Dihydro-1,4-benzodioxin-5-yl)piperazin-1-yl]butyl]-4-phenylbenzene-so sulphonamide The title compound was prepared starting from amine (IIa-14) and 4-phenylbenzene-sulphonyl chloride. Yield: 76%. MS: 508[M+H$^+$].

Compound 397.

N-[4-[4-(2,3-Dihydro-1,4-benzodioxin-8-yl)piperazin-1-yl]butyl]thiophene-2-sulphonamide The title compound was prepared starting from amine (IIa-14) and thiophene-2-sulphonyl chloride. Yield: 73%. $^1$H-NMR (300 MHz, DMSO-d$_6$): δ 7.91 (d, 1H, J=5.1 Hz), 7.85 (t, 1H, J=5.7 Hz), 7.56 (d, 1H, J=3.9 Hz), 7.18-7.15 (m, 1H), 6.69 (t, 1H, J=8.2 Hz), 6.49-6.41 (m, 2H), 4.21-4.17 (m, 4H), 2.92 (br. s, 4H), 2.85-2.82 (m, 2H), 2.48 (br. s, 4H), 2.25 (br. s, 2H), 1.40 (br. s, 4H). MS: 438[M+H$^+$].

Compound 398.

5-Chloro-N-[4-[4-(2,3-dihydro-1,4-benzodioxin-5-yl)piperazin-1-yl]butyl]thiophene-2-sulphonamide The title compound was prepared starting from amine (IIa-14) and 5-chloro-thiophene-2-sulphonyl chloride. Yield: 64%. MS: 472[M+H$^+$].

Compound 399.

N-[4-[4-(2,3-Dihydro-1,4-benzodioxin-5-yl)piperazin-1-yl]butyl]benzothiophene-2-sulphonamide The title compound was prepared starting from amine (IIa-14) and benzothiophene-2-sulphonyl chloride. Yield: 66%. MS: 488[M+H$^+$].

Compound 400.

N-[4-[4-(2,3-Dihydro-1,4-benzodioxin-5-yl)piperazin-1-yl]butyl]benzothiophene-3-sulphonamide The title compound was prepared starting from amine (IIa-14) and benzothiophene-3-sulphonyl chloride. Yield: 68%. MS: 488[M+H$^+$].

Compound 401.

6-Chloro-N-[4-[4-(2,3-dihydro-1,4-benzodioxin-5-ylpiperazin-1-yl]butyl]benzothiophene-2-sulphonamide The title compound was prepared starting from amine (IIa-14) and 6-chlorobenzothiophene-2-sulphonyl chloride. Yield: 70%. MS: 522[M+H$^+$].

Compound 402.

N-[4-[4-(2,3-Dihydro-1,4-benzodioxin-5-yl)piperazin-1-yl]butyl]-1H-indazole-6-sulphonamide The title compound was prepared starting from amine (IIa-14) and 1H-indazole-6-sulphonyl chloride. Yield: 50%. MS: 472[M+H$^+$].

Compound 403.

N-[4-[4-(2,3-Dihydro-1,4-benzodioxin-5-yl)piperazin-1-yl]butyl]-2-oxo-3H-1,3-benzoxazole-6-sulphonamide The title compound was prepared starting from amine (IIa-14) and 2-oxo-3H-1,3-benzoxazole-6-sulphonyl chloride. Yield: 67%. MS: 489[M+H$^+$].

Compound 404.

N-[4-[4-(2,3-Dihydro-1,4-benzodioxin-5-yl)piperazin-1-yl]butyl]-1,3-benzodioxole-5-sulphonamide The title compound was prepared starting from amine (IIa-14) and 1,3-benzodioxole-5' sulphonyl chloride. Yield: 68%. MS: 476[M+H$^+$].

Compound 405.

N-[3-[4-(2,3-Dihydro-1,4-benzodioxin-5-yl)piperazin-1-yl]propyl]naphthalene-1-sulphonamide, hydrochloride The title compound was prepared starting from amine (IIa-15) and naphthalene-1-w sulphonyl chloride. Yield: 69%. MS: 468[M+H$^+$].

Compound 406.

N-[3-[4-(2,3-Dihydro-1,4-benzodioxin-5-yl)piperazin-1-yl]propyl]naphthalene-2-sulphonamide, hydrochloride The title compound was prepared starting from amine (IIa-15) and naphthalene-2-sulphonyl chloride. Yield: 69%. MS: 468[M+H$^+$].

Compound 407.

6-Chloro-N-[3-[4-(2,3-dihydro-1,4-benzodioxin-5-yl)piperazin-1-yl]propyl]naphthalene-2-sulphonamide, hydrochloride The title compound was prepared starting from amine (IIa15) and 6-chloro-naphthalene-2-sulphonyl chloride. Yield: 80%. MS: 502[M+H$^+$].

Compound 408.

N-[3-[4-(2,3-Dihydro-1,4-benzodioxin-5-yl)piperazin-1-yl]propyl]-4-fluorobenzenesulphonamide, hydrochloride The title compound was prepared starting from amine (IIa-15) and 4-fluorobenzenesulphonyl chloride. Yield: 68%. MS: 436[M+H$^+$].

Compound 409.

N-[3-[4-(2,3-Dihydro-1,4-benzodioxin-5-yl)piperazin-1-yl]propyl]-3-fluorobenzenesulphonamide, hydrochloride The title compound was prepared starting from amine (IIa-15) and 3-fluorobenzenesulphonyl chloride. Yield: 83%. MS: 436[M+H$^+$].

Compound 410.

N-[3-[4-(2,3-Dihydro-1,4-benzodioxin-5-yl)piperazin-1-yl]propyl]-3,4-difluorobenzenesulphonamide The title compound was prepared starting from amine (IIa-15) and 3,4-difluorobenzene-sulphonyl chloride. Yield: 62%. $^1$H-NMR (300 MHz, DMSO-d$_6$): δ 7.86-7.63 (m, 4H), 6.69 (t, 1H, J=8.2 Hz), 6.51-6.40 (m, 2H), 4.21-4.15 (m, 4H), 2.88 (br. s, 4H), 2.82-235 (m, 2H), 2.39 (br. s, 4H), 2.26 (br. s, 2H), 1.51-1.47 (m, 2H). MS: 454[M+H$^+$].

Compound 411.

3-Chloro-N-[3-[4-(2,3-dihydro-1,4-benzodioxin-5-yl)piperazin-1-yl]propyl]benzene-so sulphonamide The title compound was prepared starting from amine (IIa-15) and 3-chlorobenzene-sulphonyl chloride. Yield: 70%. MS: 452[M+H$^+$].

Compound 412.

4-Bromo-N-[3-[4-(2,3-dihydro-1,4-benzodioxin-5-yl)piperazin-1-yl]propyl]benzenesulphonamide, hydrochloride The title compound was prepared starting from amine (IIa-15) and 4-bromobenzene-sulphonyl chloride. Yield: 76%. MS: 496[M+H$^+$].

Compound 413.

3-Bromo-N-[3-[4-(2,3-dihydro-1,4-benzodioxin-5-yl)piperazin-1-yl]propyl]benzenesulphonamide The title compound was prepared starting from amine (IIa-15) and 3-bromobenzene-sulphonyl chloride. Yield: 70%. $^1$H-NMR (300 MHz, DMSO-d$_6$): δ 7.93-7.74 (m, 4H), 7.58-7.52 (m, 1H), 6.68 (t, 1H, J=8.2 Hz), 6.49-6.39 (m, 2H), 4.21-4.15 (m, 4H), 2.88 (br. s, 4H), 2.81-2.70 (m, 2H), 2.37 (br. s, 4H), 2.25 (br. s, 2H), 1.54-1.49 (m, 2H). MS: 496[M+H$^+$].

Compound 414.

N-[3-[4-(2,3-Dihydro-1,4-benzodioxin-8-yl)piperazin-1-yl]propyl]-3-methylbenzenesulphonamide The title compound was prepared starting from amine (IIa-15) and 3-methylbenzene-sulphonyl chloride. Yield: 78%. MS: 432[M+H$^+$].

Compound 415.

N-[3-[4-(2,3-Dihydro-1,4-benzodioxin-5-yl)piperazin-1-yl]propyl]-4-phenylbenzenesulphonamide, hydrochloride The title compound was prepared starting from amine (IIa-15) and 4-phenylbenzene-sulphonyl chloride. Yield: 70%. MS: 494[M+H$^+$].

Compound 416.

N-[3-[4-(2,3-Dihydro-1,4-benzodioxin-5-yl)piperazin-1-yl]propyl]benzothiophene-3-sulphonamide The title compound was prepared starting from amine (IIa-15) and benzothiophene-3-sulphonyl chloride. Yield: 46%. MS: 474[M+H$^+$].

Compound 417.

N-[3-[4-(2,3-Dihydro-1,4-benzodioxin-5-yl)piperazin-1-yl]propyl]-2,3-dihydrobenzofuran-5-sulphonamide, hydrochloride The title compound was prepared starting from amine (IIa-15) and 2,3-dihydrobenzofuran-5-sulphonyl chloride. Yield: 62%. MS: 460[M+H$^+$].

Compound 418.

N-[4-[4-(2-oxo-1,3-dihydrobenzimidazol-4-yl)piperazin-1-yl]butyl]naphthalene-1-sulphonamide The title compound was prepared starting from amine (IIa-16) and naphthalene-1-sulphonyl chloride. Yield: 52%. MS: 480[M+H$^+$].

Compound 419.

N-[4-[4-(2-oxo-1,3-dihydrobenzimidazol-4-yl)piperazin-1-yl]butyl]naphthalene-2-sulphonamide The title compound was prepared starting from amine (IIa-16) and naphthalene-2-sulphonyl chloride. Yield: 76%. MS: 480[M+H$^+$].

Compound 420.

4-Fluoro-N-[4-[4-(2-oxo-1,3-dihydrobenzimidazol-4-yl)piperazin-1-yl]butyl]benzenesulphonamide The title compound was prepared starting from amine (IIa-16) and 4-fluorobenzenesulphonyl chloride. Yield: 64%. MS: 448[M+H$^+$].

Compound 421.

4-Chloro-N-[4-[4-(2-oxo-1,3-dihydrobenzimidazol-4-yl)piperazin-1-yl]butyl]benzenesulphonamide The title compound was prepared starting from amine (IIa-16) and 4-chlorobenzene-sulphonyl chloride. Yield: 55%. MS: 464[M+H$^+$].

Compound 422.

3-Methyl-N-[4-[4-(2-oxo-1,3-dihydrobenzimidazol-4-yl)piperazin-1-yl]butyl]benzenesulphonamide The title compound was prepared starting from amine (IIa-16) and 3-methylbenzene-sulphonyl chloride. Yield: 71%. MS: 444[M+H$^+$].

Compound 423.

N-[3-[4-(2-Oxo-1,3-dihydrobenzimidazol-4-yl)piperazin-1-yl]propyl]naphthalene-1-sulphonamide The title compound was prepared starting from amine (IIa-17) and naphthalene-1-sulphonyl chloride. Yield: 56%. MS: 466[M+H$^+$].

Compound 424.

N-[3-[4-(2-oxo-1,3-dihydrobenzimidazol-4-yl)piperazin-1-yl]propyl]naphthalene-2-sulphonamide The title compound was prepared starting from amine (IIa-17) and naphthalene-2-sulphonyl chloride. Yield: 75%. MS: 466[M+H$^+$].

Compound 425.

4-chloro-N-[3-[4-(2-oxo-1,3-dihydrobenzimidazol-4-yl)piperazin-1-yl]propyl]-benzenesulphonamide The title compound was prepared starting from amine (IIa-17) and 4-chlorobenzene-sulphonyl chloride. Yield: 65%. MS: 449[M+H$^+$].

Compound 426.

3-Methyl-N-[3-[4-(2-oxo-1,3-dihydrobenzimidazol-4-yl)piperazin-1-yl]propyl]benzenesulphonamide The title compound was prepared starting from amine (IIa-17) and 3-methylbenzene-sulphonyl chloride. Yield: 57%. MS: 430[M+H$^+$].

Compound 427.

N-[4-[4-(3-oxo-4H-1,4-benzoxazin-8-yl)piperazin-1-yl]butyl]naphthalene-2-sulphonamide The title compound was prepared starting from amine (IIa-18) and naphthalene-2-sulphonyl chloride. Yield: 72%. $^1$H-NMR (300 MHz, CDCl$_3$): 8.40 (s, 1H), 8.39 (s, 1H), 7.96-7.70 (m, 4H), 7.64-7.54 (m, 2H), 6.91 (t, 1H, J=7.9 Hz), 6.66 (dd, 1H, J=8.2 and 1.2 Hz), 6.52 (dd, 1H, J=7.7 and 1.2 Hz), 4.60 (s, 2H), 3.20-3.12 (m, 4H), 3.08-2.98 (m, 2H), 2.70-2.60 (m, 4H), 2.42-2.38 (m, 2H), 1.62-1.54 (m, 4H). MS: 495[M+H$^+$].
Compound 428.

4-Fluoro-N-[4-[4-(3-oxo-4H-1,4-benzoxazin-8-yl)piperazin-1-yl]butyl]benzenesulphonamide The title compound was prepared starting from amine (IIa-18) and 4-fluorobenzenesulphonyl chloride. Yield: 80%. $^1$H-NMR (300 MHz, CDCl$_3$): 8.05 (s, 1H), 7.85-7.80 (m, 2H), 7.18-7.06 (m, 2H), 6.82 (t, 1H, J=7.9 Hz), 6.62 (dd, 1H, J=8.2 and 1.2 Hz), 6.45 (d, 1H, J=7.7 and 1.2 Hz), 4.60 (m, 2H), 3.20-3.16 (m, 4H), 3.00-2.88 (m, 2H), 2.75-2.60 (m, 4H), 2.47-2.40 (m, 2H), 1.65-1.58 (m, 4H). MS: 463[M+H$^+$].
Compound 429.

N-[4-[4-(3-oxo-4H-1,4-benzoxazin-8-yl)piperazin-1-yl]butyl]-4-(trifluoromethyl)benzenesulphonamide The title compound was prepared starting from amine (IIa-18) and 4-(trifluoromethyl)-benzenesulphonyl chloride. Yield: 76%. $^1$H-NMR (300 MHz, CDCl$_3$: 0.90 (d, 2H, J=8.2 Hz), 7.70 (d, 2H, J=8.2 Hz), 6.84 (t, 1H, J=7.9 Hz), 6.58 (dd, 1H, J=8.2 and 1.2 Hz), 6.50 (dd, 1H, J=7.7 and 1.2 Hz), 4.60 (s, 2H), 3.10-3.00 (m, 4H), 2.92-2.88 (m, 2H), 2.62-2.58 (m, 4H), 2.38-2.28 (m, 2H), 1.58-1.50 (m, 4H). MS: 513[M+H$^+$].
Compound 430.

N-[4-[4-(3-oxo-4H-1,4-benzoxazin-8-yl)piperazin-1-yl]butyl]-3-(trifluoromethylbenzenesulphonamide The title compound was prepared starting from amine (IIa-18) and 3-(trifluoromethyl)-benzenesulphonyl chloride. Yield: 65%. $^1$H-NMR (300 MHz, CDCl$_3$): 7.60-7.54 (m, 1H), 7.50-7.42 (m, 1H), 7.28-7.24 (m, 1H), 7.12-6.68 (m, 1H), 7.00-7.68 (m, 1H), 6.62 (d, 1H, J=6.6 Hz), 6.52 (d, 1H, J=3.0 Hz), 5.20 (s, 2H), 3.40-3.37 (m, 4H), 3.37-3.30 (m, 1H), 3.04-2.98 (m, 2H), 2.86-2.78 (m, 4H), 2.76-2.70 (m, 1H), 1.68-1.60 (m, 4H). MS: 513[M+H$^+$].
Compound 431.

5-Chloro-N-{4-[4-(3-oxo-4H-1,4-benzoxazin-8-yl)piperazin-1-yl]butyl}thiophene-2-sulphonamide The title compound was prepared starting from amine (IIa-18) and 5-chloro-thiophene-2-sulphonyl chloride. Yield: 85%. $^1$H-NMR (300 MHz, CDCl$_3$): 8.70 (s, 1H), 7.33 (d, 1H, J=3.8 Hz), 6.93-6.88 (m, 2H), 6.67 (dd, 1H, J=8.2 and 1.2 Hz), 6.52 (dd, 1H, J=7.7 and 1.2 Hz), 4.60 (s, 2H), 3.20-3.12 (m, 4H), 3.08-3.00 (m, 2H), 2.72-2.64 (m, 4H), 2.46-2.40 (m, 2H), 1.68-1.60 (m, 4H). MS: 485[M+H$^+$].
b) General Procedure for Compounds Wherein in Formula (IIa) ----- Represents Double Bond.

0.2 Mmol of amine (IIa) was dissolved in 5 ml of anhydrous N,N-dimethylformamide, and then 4 mmol of N,N-diisopropylethylamine was added. The mixture was purged with argon, and 0.24 mmol of appropriate arylsulphonyl chloride was subsequently added (IIb). After 30 minutes of stirring at room temperature the mixture was poured into is about 20 ml of ice water. The mixture was extracted with ethyl acetate or methylene chloride. Organic layer was washed with brine, dried over anhydrous sodium sulphate, and then concentrated under reduced pressure. Crude sulphonamides were usually purified by means of crystallization (from methanol), and some of them using column chromatography on silica gel with using methylene chloride/methanol 20:1 as eluent. Structure of prepared compounds was confirmed by MS data, and purity by HPLC analysis. For selected compounds structure identification was further confirmed by $^1$H-NMR analysis.

Following the general procedure described above and starting from appropriate compounds amine (IIa) and arylsulphonyl chloride (IIb), the following compounds were obtained.
Compound 34.

N-{4-[4-(5-Chloro-1H-indol-3-yl)-3,6-dihydropyridin-1(2H)-yl]butyl}naphthalene-1-sulphonamide The title compound was prepared starting from amine (IIa-9) and naphthalene-1-sulphonyl chloride. Yield: 42%. MS: 494[M+H$^+$].
Compound 35.

N-{4-[4-(5-Chloro-1H-indol-3-yl)-3,6-dihydropyridin-1(2H)-yl]butyl}naphthalene-2-sulphonamide The title compound was prepared starting from amine (IIa-9) and naphthalene-2-sulphonyl chloride. Yield: 40%. MS: 494[M+H$^+$].
Compound 36.

4-Fluoro-N-{4-[4-(5-chloro-1H-indol-3-yl)-3,6-dihydropyridin-1(2H)-yl]butyl}benzenesulphonamide The title compound was prepared starting from amine (IIa-9) and 4-fluorobenzenesulphonyl chloride. Yield: 42%. MS: 462[M+H$^+$].
Compound 37.

3-Fluoro-N-{4-[4-(5-chloro-1H-indol-3-yl)-3,6-dihydropyridin-1(2H)-yl]butyl}benzenesulphonamide The title compound was prepared starting from amine (IIa-9) and 3-fluorobenzenesulphonyl chloride. Yield: 60%. MS: 462[M+H$^+$].
Compound 38.

4-Chloro-N-{4-[4-(5-chloro-1H-indol-3-yl)-3,6-dihydropyridin-1(2H)-yl]butyl}benzenesulphonamide The title compound was prepared starting from amine (IIa-9) and 4-chlorobenzene-sulphonyl chloride. Yield: 55%. MS: 478[M+H$^+$].
Compound 39.

3-Chloro-N-{4-[4-(5-chloro-1H-indol-3-yl)-3,6-dihydropyridin-1(2H)-yl]butyl}benzenesulphonamide The title compound was prepared starting from amine (IIa-9) and 3-chlorobenzene-sulphonyl chloride. Yield: 30%. MS: 478[M+H$^+$].

Compound 40.

3-Methyl-N-{4-[4-(5-chloro-1H-indol-3-yl)-3,6-dihydropyridin-1(2H)-yl]butyl}benzenesulphonamide The title compound was prepared starting from amine (IIa-9) and 3-methylbenzene-sulphonyl chloride. Yield: 55%. MS: 458[M+H$^+$].

Compound 41.

3-Hydroxy-N-{4-[4-(5-chloro-1H-indol-3-yl)-3,6-dihydropyridin-1(2H)-yl]butyl}-benzenesulphonamide The title compound was prepared starting from amine (IIa-9) and 3-hydroxybenzene-sulphonyl chloride. Yield: 20%. MS: 460[M+H$^+$].

Compound 42.

4-Methoxy-N-{4-[4-(5-chloro-1H-indol-3-yl)-3,6-dihydropyridin-1(2H)-yl]butyl}benzenesulphonamide The title compound was prepared starting from amine (IIa-9) and 4-methoxybenzenesulphonyl chloride. Yield: 52%, MS: 474[M+H$^+$].

Compound 43.

N-{3-[4-(5-Chloro-1H-indol-3-yl)-3,6-dihydropyridin-1(2H)-yl]propyl}naphthalene-1-sulphonamide The title compound was prepared starting from amine (IIa-10 and naphthalene-1-sulphonyl chloride. Yield: 99%. MS: 480[M+H$^+$].

Compound 44.

N-{3-[4-(5-Chloro-1H-indol-3-yl)-3,6-dihydropyridin-1(2H)-yl]propyl}naphthalene-2-sulphonamide The title compound was prepared starting from amine (IIa-10) and naphthalene-2-sulphonyl chloride. Yield: 76%. MS: 480[M+H$^+$].

Compound 45.

4-Fluoro-N-{3-[4-(5-chloro-1H-indol-3-yl)-3,6-dihydropyridin-1(2H)-yl]propyl}benzenesulphonamide The title compound was prepared starting from amine (IIa-10) and 4-fluorobenzenesulphonyl chloride. Yield: 99%. MS: 448[M+H$^+$].

Compound 46.

3-Fluoro-N-{3-[4-(5-chloro-1H-indol-3-yl)-3,6-dihydropyridin-1(2H)-yl]propyl}benzenesulphonamide The title compound was prepared starting from amine (IIa-10) and 3-fluorobenzenesulphonyl chloride. Yield: 98%. MS: 448[M+H$^+$].

Compound 47.

4-Chloro-N-{3-[4-(5-chloro-1H-indol-3-yl)-3,6-dihydropyridin-1(2H)-yl]propyl}benzenesulphonamide The title compound was prepared starting from amine 0 and 4-chlorobenzene-sulphonyl chloride. Yield: 72%.

Compound 48.

3-Chloro-N-{3-[4-(5-chloro-1H-indol-3-yl)-3,6-dihydropyridin-1(2H)-yl]propyl}-s benzenesulphonamide The title compound was prepared starting from amine (IIa-10) and 3-chlorobenzene-sulphonyl chloride. Yield: 98%. MS: 464[M+H$^+$].

Compound 49.

3-Hydroxy-N-{3-[4-(5-chloro-1H-indol-3-yl)-3,6-dihydropyridin-1(2H)-yl]propyl}-benzenesulphonamide The title compound was prepared starting from amine (IIa-10) and 3-hydroxybenzene-sulphonyl chloride. Yield: 29%. MS: 446[M+H$^+$].

Compound 50.

N-{2-[4-(5-Chloro-1H-indol-3-yl)-3,6-dihydropyridin-1(2H)-yl]ethyl}naphthalene-1-sulphonamide The title compound was prepared starting from amine (IIa-11) and naphthalene-1-sulphonyl chloride. Yield: 99%. MS: 466[M+H$^+$].

Compound 51.

N-{2-[4-(5-Chloro-1H-indol-3-yl)-3,6-dihydropyridin-1(2H)-yl]ethyl}naphthalene-2-sulphonamide The title compound was prepared starting from amine (IIa-11) and naphthalene-2-sulphonyl chloride. Yield: 99%. MS: 466[M+H$^+$].

Compound 52.

N-{2-[4-(5-Chloro-1H-indol-3-yl)-3,6-dihydropyridin-1(2H)-yl]ethyl}-4-fluorobenzenesulphonamide The title compound was prepared starting from amine (IIa-11) and 4-fluorobenzenesulphonyl chloride. Yield: 98%. MS: 434[M+H$^+$].

Compound 53.

3-Fluoro-N-{2-[4-(5-chloro-1H-indol-3-yl)-3,6-dihydropyridin-1(2H)-yl]ethyl}benzenesulphonamide The title compound was prepared starting from amine (IIa-11) and 3-fluorobenzenesulphonyl chloride. Yield: 52%. MS: 434[M+H$^+$].

Compound 54.

4-Chloro-N-{2-[4-(5-chloro-1H-indol-3-yl)-3,6-dihydropyridin-1(2H)-yl]ethyl}benzenesulphonamide The title compound was prepared starting from amine (IIa-11) and 4-chlorobenzene-sulphonyl chloride. Yield: 98%. MS: 450[M+H$^+$].

Compound 55.

3-Chloro-N-{2-[4-(5-chloro-1H-indol-3-yl)-3,6-dihydropyridin-H)-yl]ethyl}benzenesulphonamide The title compound was prepared starting from amine (IIa-11) and 3-chlorobenzene-sulphonyl chloride. Yield: 89%. MS: 450[M+H$^+$].

Compound 56.

3-Methyl-N-{2-[4-(5-chloro-1H-indol-3-yl)-3,6-dihydropyridin-1(2H)-yl]ethyl}benzenesulphonamide The title compound was prepared starting from amine (IIa-11) and 3-methylbenzene-sulphonyl chloride. Yield: 48%. MS: 430[M+H$^+$].

Compound 57.

3-Hydroxy-N-{2-[4-(5-chloro-1H-indol-3-yl]-3,6-dihydropyridin-1(2H)-yl ethyl}-benzenesulphonamide The title compound was prepared starting from amine (IIa-11) and 3-hydroxybenzene-sulphonyl chloride. Yield: 12%. MS: 432[M+H$^+$].

Compound 58.

4-Chloro-N-{4-[4-(5-chloro-2-methyl-1H-indol-3-yl)-3,6-dihydropyridin-1(2H)-yl]butyl}benzenesulphonamide The title compound was prepared starting from amine (IIa-12) and 4-chlorobenzene-sulphonyl chloride. Yield: 10%. MS: 492[M+H$^+$].

Compound 137.

N-[4-[4-(5-Chloro-2-methyl-1H-indol-3-yl)-3,6-dihydro-2H-pyridin-1-yl]butyl]-3-chlorobenzene-sulphonamide The title compound was prepared starting from amine (IIa-12) and 3-chlorobenzene-sulphonyl chloride. Yield: 95%. MS: 492[M+H$^+$].

Compound 138.

N-[3-[4-(5-Chloro-2-methyl-1H-indol-3-yl)-3,6-dihydro-2H-pyridin-1-yl]propyl]-3-chlorobenzene-sulphonamide The title compound was prepared starting from amine (IIa-22) and 3-chlorobenzene-sulphonyl chloride. Yield: 89%. MS: 478[M+H$^+$].

Compound 139.

N-[4-[4-(5-Chloro-2-methyl-1H-indol-3-yl)-3,6-dihydro-2H-pyridin-1-yl]butyl]-3-fluorobenzene-sulphonamide The title compound was prepared starting from amine (IIa-12) and 3-fluorobenzenesulphonyl chloride. Yield: 86%. MS: 476[M+H$^+$].

Compound 140.

N-[3-[4-(5-Chloro-2-methyl-1H-indol-3-yl)-3,6-dihydro-2H-pyridin-1-yl]propyl]-3-fluorobenzene-sulphonamide The title compound was prepared starting from amine (IIa-22) and 3-fluorobenzenesulphonyl chloride. Yield: 85%. MS: 462[M+H$^+$].

Compound 141.

N-[4-[4-(5-Chloro-2-methyl-1H-indol-1-yl)-3,6-dihydro-2H-pyridin-1-yl]butyl]-4-tert-butyl-benzene-sulphonamide The title compound was prepared starting from amine (IIa-12) and 4-tert-butyl-benzenesulphonyl chloride. Yield: 67%. MS: 514[M+H$^+$].

Compound 366.

N-[4-[4-(5-Chloro-2-methyl-1H-indol-3-yl)-3,6-dihydro-2H-pyridin-1-yl]butyl]-naphthalene-1-sulphonamide The title compound was prepared starting from amine (IIa-12) and naphthalene-1-sulphonyl chloride. Yield: 60%. MS: 508[M+H$^+$].

Compound 367.

N-[4-[4-(5-Chloro-2-methyl-1H-indol-3-yl)-3,6-dihydro-2H-pyridin-1-yl]butyl]-naphthalene-2-sulphonamide The title compound was prepared starting from amine (IIa-12) and naphthalene-2-sulphonyl chloride. Yield: 82%, MS: 508[M+H$^+$].

Compound 368.

N-[4-[4-(5-Chloro-2-methyl-1H-indol-3-yl)-3,6-dihydro-2H-pyridin-1-yl]butyl]-4-fluorobenzene-sulphonamide The title compound was prepared starting from amine (IIa-12) and 4-fluorobenzenesulphonyl chloride. Yield: 93%. MS: 376[M+H$^+$].

Compound 369.

N-[4-[4-(5-Chloro-2-methyl-1H-indol-3-yl)-3,6-dihydro-2H-pyridin-1-yl]butyl]-3-hydroxybenzene-sulphonamide The title compound was prepared starting from amine (IIa-12) and 3-hydroxybenzene-sulphonyl chloride. Yield: 43%. MS: 474[M+H$^+$].

Compound 370.

N-[4-[4-(5-Chloro-2-methyl-1H-indol-3-yl)-3,6-dihydro-2H-pyridin-1-yl]butyl]-3-methylbenzene-sulphonamide The title compound was prepared starting from amine (IIa-12) and 3-methylbenzene-sulphonyl chloride. Yield: 84%. MS: 472[M+H$^+$].

Compound 432.

N-[4-[4-(5-Fluoro-1H-indol-3-yl)-3,6-dihydro-2H-pyridin-1-yl]butyl]naphthalene-2-sulphonamide The title compound was prepared starting from amine (IIa-19) and naphthalene-2-sulphonyl chloride. Yield: 65%. $^1$H-NMR (300 MHz, CDCl$_3$): 8.40 (s, 1H), 8.20 (s, 1H), 6.98 (t, 1H, J=3.4 Hz), 6.02 (5, 1H), 3.15-3.10 (m, 2H), 2.98-2.90 (m, 2H), 2.80-2.72 (m, 4H), 2.56-2.52 (m, 2H), 1.65-1.48 (m, 4H). MS: 478[M+H$^+$].

Compound 433.

3-Fluoro-N-[4-[4-(5-fluoro-1H-indol-3-yl)-3,6-dihydro-2H-pyridin-1-yl]butyl]benzenesulphonamide The title compound was prepared starting from amine (IIa-19) and 3-fluorobenzenesulphonyl chloride. Yield: 78%. $^1$H-NMR (300 MHz, CD$_3$OD): 8.01 (q, 1H, J=4.6 Hz), 7.88 (d, 1H, J=3.6 Hz), 7.78-7.62 (m, 2H), 7.58-7.48 (m, 2H), 7.38-7.32 (dt, 1H, J=8.9 and 2.5 Hz), 6.04-5.98 (m, 1H), 3.20-3.18 (m, 2H), 2.92 (t, 2H, J=6.4 Hz), 2.78 (t, 2H, J=6.1 Hz), 2.64-2.58 (m, 2H), 2.46 (t, 2H, J=6.9 Hz), 162-1.50 (m, 4H). MS: 446[M+H$^+$].

Compound 434.

N-[4-[4-(5-Fluoro-1H-indol-3-yl)-3,6-dihydro-2H-pyridin-1-yl]butyl]-3-hydroxybenzenesulphonamide The title compound was prepared starting from amine (IIa-19) and 3-hydroxybenzene-sulphonyl chloride. Yield: 67%. MS: 444[M+H$^+$].

Compound 435.

N-[4-[4-(5-Fluoro-1H-indol-3-yl)-3,6-dihydro-2H-pyridin-1-yl]butyl]-3-methylbenzenesulphonamide The title compound was prepared starting from amine (IIa-19) and 3-methylbenzene-sulphonyl chloride. Yield: 76%. $^1$H-NMR (300 MHz, CD$_3$OD): 7.54-7.46 (m, 3H), 7.30-7.18 (m, 4H), 6.90 (dt, 1H, J=8.9 and 2.5 Hz), 6.04-5.98 (m, 1H), 3.38-3.30 (m, 2H), 2.87 (t, 2H, J=5.9 Hz), 2.80-2.60 (m, 4H), 2.48 (t, 2H, J=6.6 Hz), 1.58-1.52 (m, 4H). MS: 442[M+H$^+$].

Compound 436.

3-Fluoro-N-[3-[4-(5-fluoro-1H-indol-3-yl)-3,6-dihydro-2H-pyridin-1-yl]propyl]benzenesulphonamide The title compound was prepared starting from amine (IIa-20) and 3-fluorobenzenesulphonyl chloride. Yield: 70%. $^1$H-NMR (300 MHz, CD$_3$OD): 7.54-7.46 (m, 3H), 7.30-7.18 (m, 4H), 6.90 (dt, 1H, J=8.9 and 2.5 Hz), 6.04-5.98 (m, 1H), 3.38-3.30 (m, 2H), 2.87 (t, 2H, J=5.9 Hz), 2.80-2.60 (m, 4H), 2.48 (t, 2H, J=6.6 Hz), 1.58-1.52 (m, 4H). MS: 432[M+H$^+$].

Compound 437.

N-[3-[4-(5-Fluoro-1H-indol-3-yl)-3,6-dihydro-2H-pyridin-1-yl]propyl]-3-hydroxybenzenesulphonamide The title compound was prepared starting from amine (IIa-20) and 3-hydroxybenzene-sulphonyl chloride. Yield: 62%. MS: 430[M+H$^+$].

Compound 438.

N-[2-[4-(5-Fluoro-1H-indol-3-yl)-3,6-dihydro-2H-pyridin-1-yl]ethyl]naphthalene-2-sulphonamide The title compound was prepared starting from amine (IIa-21) and naphthalene-2-sulphonyl chloride. Yield: 54%. MS: 450[M+H$^+$].

Compound 439.

3-Fluoro-N-[2-[4-(5-fluoro-1H-indol-3-yl)-3,6-dihydro-2H-pyridin-1-yl]ethyl]benzenesulphonamide The title compound was prepared starting from amine (IIa-21) and 3-fluorobenzenesulphonyl chloride. Yield: 70%. $^1$H-NMR (300 MHz, CDCl$_3$): 8.17 (s, 1H), 7.70-7.46 (m, 4H), 7.32-7.20 (m, 3H), 7.00-6.94 (m, 1H), 6.02-5.98 (m, 1H), 3.12 (t, 2H, J=5.3 Hz), 3.06-3.02 (m, 2H), 2.62-2.48 (m, 4H), 1.76-1.62 (m, 2H). MS: 418[M+H$^+$].

Compound 440.

N-[2-[4-(5-Fluoro-1H-indol-3-yl)-3,6-dihydro-2H-pyridin-1-yl]ethyl]-3-methylbenzenesulphonamide The title compound was prepared starting from amine (IIa-21) and 3-methylbenzene-sulphonyl chloride. Yield: 83%. $^1$H-NMR (300 MHz, CD$_3$OD): 7.71-7.62 (m, 2H), 7.48-7.40 (m, 3H), 7.32-7.28 (m, 2H), 6.86 (dt, 1H, J=8.9 and 2.5 Hz), 6.12-6.10 (m, 1H), 3.38 (s, 3H), 3.18-3.14 (m, 2H), 3.10-3.06 (m, 2H), 2.72-2.68 (m, 2H), 2.60-2.54 (m, 2H), 2.38-2.34 (m, 2H). MS: 414[M+H$^+$].

Compound 441.

N-[3-[4-(5-Chloro-2-methyl-1H-indol-3-yl)-3,6-dihydro-2H-pyridin-1-yl]propyl]-naphthalene-1-sulphonamide The title compound was prepared starting from amine (IIa-22) and naphthalene-1-sulphonyl chloride. Yield: 74%. MS: 494[M+H$^+$].

Compound 442.

N-[3-[4-(5-Chloro-2-methyl-1H-indol-3-yl)-3,6-dihydro-2H-pyridin-1-yl]propyl]-naphthalene-2-sulphonamide The title compound was prepared starting from amine (IIa-22) and naphthalene-2-sulphonyl chloride. Yield: 67%. MS: 494[M+H$^+$].

Compound 443.

N-[3-[4-(5-Chloro-2-methyl-1H-indol-3-yl)-3,6-dihydro-2H-pyridin-1-yl]propyl]-4-fluorobenzenesulphonamide The title compound was prepared starting from amine (IIa-22) and 4-fluorobenzenesulphonyl chloride. Yield: 50%. MS: 462[M+H$^+$].

Compound 444.

4-Chloro-N-[3-[4-(5-chloro-2-methyl-1H-indol-3-yl)-3,6-dihydro-2H-pyridin-1-yl]propyl]-benzenesulphonamide The title compound was prepared starting from amine (IIa-22) and 4-chlorobenzene-sulphonyl chloride. Yield: 69%. MS: 478[M+H$^+$].

Compound 445.

N-[3-[4-(5-Chloro-2-methyl-1H-indol-3-yl)-3,6-dihydro-2H-pyridin-1-yl]propyl]-3-hydroxybenzenesulphonamide The title compound was prepared starting from amine (IIa-22) and 3-hydroxybenzene-sulphonyl chloride. Yield: 40%, MS: 460[M+H$^+$].

Compound 446.

N-[3-[4-(5-Chloro-2-methyl-1H-indol-3-yl)-3,6-dihydro-2H-pyridin-1-yl]propyl]-3-methylbenzenesulphonamide The title compound was prepared starting from amine (IIa-22) and 3-methylbenzene-sulphonyl chloride. Yield: 82%, MS: 458[M+H$^+$].

Compound 447.

N-[2-[4-(5-Chloro-2-methyl-1H-indol-3-yl)-3,6-dihydro-2H-pyridin-1-yl]ethyl]-naphthalene-1-sulphonamide The title compound was prepared starting from amine (IIa-23) and naphthalene-1-sulphonyl chloride. Yield: 89%. MS: 480[M+H$^+$].

Compound 448.

N-[2-[4-(5-Chloro-2-methyl-1H-indol-3-yl)-3,6-dihydro-2H-pyridin-1-yl]ethyl]-naphthalene-2-sulphonamide The title compound was prepared starting from amine (IIa-23) and naphthalene-2-sulphonyl chloride. Yield: 61%. MS: 480[M+H$^+$].

Compound 449.

N-[2-[4-(5-Chloro-2-methyl-1H-indol-3-yl)-3,6-dihydro-2H-pyridin-1-yl]ethyl]-4-fluorobenzene-sulphonamide The title compound was prepared starting from amine (IIa-23) and 4-fluorobenzenesulphonyl chloride. Yield: 45%. MS: 448[M+H$^+$].

Compound 450.

N-[2-[4-(5-Chloro-2-methyl-1H-indol-3-yl)-3,6-dihydro-2H-pyridin-1-yl]ethyl]-3-fluorobenzene-sulphonamide The title compound was prepared starting from amine (IIa-23) and 3-fluorobenzenesulphonyl chloride. Yield: 56%. MS: 448[M+H$^+$].

Compound 451.

4-Chloro-N-[2-[4-(5-chloro-2-methyl-1H-indol-3-yl)-3,6-dihydro-2H-pyridin-1-yl]ethyl]-benzene-sulphonamide The title compound was prepared starting from amine (IIa-23) and 4-chlorobenzene-sulphonyl chloride. Yield: 88%. MS: 464[M+H$^+$].

Compound 452.

3-Chloro-N-[2-[4-(5-chloro-2-methyl-1H-indol-3-yl)-3,6-dihydro-2H-pyridin-1-yl]ethyl]-benzene-sulphonamide The title compound was prepared starting from amine (IIa-23) and 3-chlorobenzene-sulphonyl chloride. Yield: 63%, MS: 464[M+H$^+$].

Compound 453.

N-[2-[4-(5-Chloro-2-methyl-1H-indol-3-yl)-3,6-dihydro-2H-pyridin-1-yl]ethyl]-3-hydroxybenzene-sulphonamide The title compound was prepared starting from amine (IIa-23) and 3-hydroxybenzene-sulphonyl chloride. Yield: 46%. MS: 446[M+H$^+$].

Compound 454.

N-[2-[4-(5-Chloro-2-methyl-1H-indol-3-yl)-3,6-dihydro-2H-pyridin-1-yl]ethyl]-3-methylbenzene-sulphonamide The title compound was prepared starting from amine (IIa-23) and 3-methylbenzene-sulphonyl chloride. Yield: 51%. MS: 444[M+H$^+$].

Tests In Vitro

EXAMPLE 4

In Vitro Pharmacology: Binding Assays

The affinity of compounds of the present invention to dopaminergic, serotoninergic, adrenergic, muscarinic M3, histaminergic H1, sigma and serotonin transporter receptors was tested using the methods as described below, consisting in measuring their binding to these receptors using radioreceptors methods.

The specific ligand binding to the receptors is defined as the difference between the total binding and the nonspecific binding determined in the presence of an excess of unlabelled ligand.

The results are expressed as a percent of control specific binding ((measured specific binding/control specific binding)×100) and as a percent inhibition of control specific binding (100−((measured specific binding/control specific binding)×100)) obtained in the presence of the test compounds. The specific ligand binding to the receptor is defined as the difference between total and non-specific binding determined in the presence of an excess of unlabelled ligand. The compounds were tested at a concentration of 1×10$^{-6}$ M, and scintillation counting was the method of detection of ligand binding. Conditions and methodology (by reference to the literature) of in vitro tests are given in Table 1 and the tests results for representative compounds are given in Table 2 (dopaminergic receptor D2), in Table 3 (dopaminergic receptor D3), in Table 4 (serotoninergic receptors 5-HT1A and 5-HT2A), in Table 5 (serotoninergic receptors 5-HT6 and 5-HT7), in Table 6 (serotonine transporter (SERT) receptor), in Table 7 (sigma receptor σ), in Table 8 (adrenergic α1 receptor), in Table 9 (adrenergic α2C receptor), in Table 10 (histaminergic H1 receptor), in Table 11 (muscarinic M3 receptor) and in Table 12 (serotoninergic receptor 5-HT2C).

TABLE 1

| | | Conditions and methodology of in vitro tests for binding assays | | | | | |
|---|---|---|---|---|---|---|---|
| Assay | Origin | Radioligand | Concentration | Kd | Non Specific | Incubation | Ref. |
| α$_1$ (non-selective) | rat cerebral cortex | [$^3$H]prazosin | 0.25 nM | 0.09 nM | prazosin (0.5 μM) | 60 min 22° C. | 1 |
| α$_{2C}$ (h) | human recombinant (CHO cells) | [$^3$H]RX 821002 | 2 nM | 0.95 nM | (−)epinephrine (100 μM) | 60 min 22° C. | 2 |
| D$_{2S}$ (h) | human recombinant (HEK-293 cells) | [$^3$H]methyl-spiperone | 0.3 nM | 0.15 nM | (+)butaclamol (10 μM) | 60 min 22° C. | 3 |
| D$_3$ (h) | human recombinant (CHO cells) | [$^3$H]methyl-spiperone | 0.3 nM | 0.085 nM | (+)butactamol (10 μM) | 60 min 22° C. | 4 |

TABLE 1-continued

Conditions and methodology of in vitro tests for binding assays

| Assay | Origin | Radioligand | Concentration | Kd | Non Specific | Incubation | Ref. |
|---|---|---|---|---|---|---|---|
| $H_1$ (h) | human recombinant (HEK-293 cells) | [$^3$H]pyrilamine | 1 nM | 1.7 nM | pyrilamine (1 μM) | 60 min 22° C. | 5 |
| $M_3$ (h) | human recombinant (CHO cells) | [$^3$H]4-DAMP | 0.2 nM | 0.5 nM | atropine (1 μM) | 60 min 22° C. | 6 |
| $5\text{-}HT_{1A}$ (h) | human recombinant (HEK-293 cells) | [$^3$H]8-OH-DPAT | 0.3 nM | 0.5 nM | 8-OH-DPAT (10 μM) | 60 min 22° C. | 7 |
| $5\text{-}HT_{2A}$ (h) | human recombinant (HEK-293 cells) | [$^3$H]ketanserin | 0.5 nM | 0.6 nM | ketanserin (1 μM) | 60 min 22° C. | 8 |
| $5\text{-}HT_{2C}$ (h) | human recombinant (HEK-293 cells) | [$^3$H]mesulergine | 1 nM | 0.5 nM | RS 102221 (10 μM) | 120 min 37° C. | 9 |
| $5\text{-}HT_6$ (h) | human recombinant (CHO cells) | [$^3$H]LSD | 2 nM | 1.8 nM | serotonin (100 μM) | 120 min 37° C. | 10 |
| $5\text{-}HT_7$ (h) | human recombinant (CHO cells) | [$^3$H]LSD | 4 nM | 2.3 nM | serotonin (10 μM) | 120 min 22° C. | 11 |
| σ (non-selective) | rat cerebral cortex | [$^3$H]DTG | 8 nM | 29 nM | haloperidol (10 μM) | 120 min 22° C. | 12 |
| SERT (h) | human recombinant (CHO cells) | [$^3$H]imipramine | 2 nM | 1.7 nM | imipramine (10 μM) | 60 min 22° C. | 13 |

TABLE 2

Results of dopaminergic receptor D2 affinity test for representative compounds

| Cpd. | D2 [%] |
|---|---|
| 1 | 97 |
| 2 | 98 |
| 3 | 96 |
| 4 | 96 |
| 5 | 96 |
| 6 | 96 |
| 7 | 95 |
| 8 | 98 |
| 9 | 91 |
| 10 | 94 |
| 11 | 89 |
| 12 | 93 |
| 13 | 99 |
| 14 | 99 |
| 15 | 90 |
| 16 | 99 |
| 17 | 98 |
| 18 | 98 |
| 19 | 97 |
| 20 | 98 |
| 21 | 99 |
| 22 | 96 |
| 23 | 97 |
| 24 | 99 |
| 25 | 96 |
| 26 | 97 |
| 27 | 90 |
| 28 | 98 |
| 29 | 94 |
| 30 | 98 |
| 31 | 38 |
| 32 | 101 |
| 33 | 97 |
| 34 | 99 |
| 35 | 99 |
| 36 | 100 |
| 37 | 100 |
| 38 | 100 |
| 38 | 101 |
| 40 | 100 |
| 41 | 93 |
| 42 | 74 |
| 43 | 100 |
| 44 | 100 |
| 45 | 100 |
| 46 | 100 |
| 47 | 100 |
| 48 | 99 |
| 49 | 99 |
| 50 | 97 |
| 51 | 97 |
| 52 | 99 |
| 53 | 99 |
| 54 | 98 |
| 55 | 98 |
| 56 | 100 |
| 57 | 100 |
| 58 | 97 |
| 61 | 100 |
| 62 | 92 |
| 63 | 99 |
| 64 | 98 |
| 65 | 99 |
| 66 | 101 |
| 69 | 106 |
| 70 | 99 |
| 71 | 103 |
| 72 | 99 |
| 73 | 102 |
| 74 | 93 |
| 76 | 94 |
| 79 | 99 |
| 81 | 90 |
| 85 | 100 |
| 87 | 87 |
| 89 | 89 |
| 91 | 92 |
| 93 | 98 |
| 97 | 100 |
| 98 | 101 |
| 101 | 99 |
| 102 | 100 |
| 105 | 107 |
| 106 | 108 |
| 107 | 104 |
| 108 | 106 |
| 109 | 100 |
| 110 | 109 |
| 111 | 108 |
| 112 | 103 |
| 113 | 98 |
| 137 | 65 |
| 138 | 40 |
| 139 | 52 |
| 140 | 47 |
| 165 | 64 |

TABLE 2-continued

Results of dopaminergic receptor D2 affinity test for representative compounds

| Cpd. | D2 [%] |
|---|---|
| 174 | 91 |
| 176 | 89 |
| 195 | 99 |
| 196 | 98 |
| 209 | 82 |
| 211 | 81 |
| 225 | 77 |
| 226 | 87 |
| 227 | 104 |
| 228 | 103 |
| 229 | 101 |
| 230 | 105 |
| 231 | 99 |
| 232 | 92 |
| 233 | 83 |
| 234 | 85 |
| 235 | 103 |
| 236 | 99 |
| 237 | 62 |
| 238 | 87 |
| 239 | 102 |
| 240 | 101 |
| 241 | 100 |
| 242 | 105 |
| 243 | 100 |
| 244 | 105 |
| 245 | 97 |
| 246 | 98 |
| 247 | 104 |
| 248 | 99 |
| 249 | 98 |
| 250 | 97 |
| 251 | 97 |
| 252 | 97 |
| 253 | 99 |
| 254 | 87 |
| 255 | 98 |
| 256 | 97 |
| 257 | 99 |
| 258 | 95 |
| 259 | 93 |
| 260 | 99 |
| 261 | 97 |
| 262 | 98 |
| 263 | 98 |
| 264 | 87 |
| 267 | 100 |
| 268 | 98 |
| 269 | 99 |
| 270 | 74 |
| 273 | 88 |
| 274 | 96 |
| 276 | 95 |
| 282 | 97 |
| 283 | 99 |
| 288 | 103 |
| 289 | 99 |
| 291 | 99 |
| 293 | 85 |
| 294 | 105 |
| 295 | 95 |
| 296 | 105 |
| 297 | 93 |
| 298 | 99 |
| 299 | 87 |
| 300 | 96 |
| 301 | 96 |
| 302 | 90 |
| 303 | 108 |
| 304 | 94 |
| 305 | 88 |
| 306 | 106 |
| 307 | 88 |
| 308 | 96 |
| 309 | 84 |
| 310 | 96 |
| 311 | 105 |
| 312 | 99 |
| 313 | 101 |
| 314 | 99 |
| 315 | 99 |
| 316 | 98 |
| 317 | 105 |
| 318 | 67 |
| 319 | 109 |
| 320 | 100 |
| 321 | 98 |
| 322 | 96 |
| 323 | 105 |
| 324 | 105 |
| 325 | 96 |
| 326 | 109 |
| 327 | 89 |
| 328 | 108 |
| 329 | 109 |
| 330 | 108 |
| 331 | 100 |
| 332 | 83 |
| 333 | 92 |
| 334 | 75 |
| 335 | 105 |
| 336 | 97 |
| 337 | 59 |
| 338 | 98 |
| 339 | 96 |
| 340 | 101 |
| 341 | 98 |
| 342 | 106 |
| 343 | 101 |
| 344 | 107 |
| 345 | 109 |
| 346 | 100 |
| 347 | 103 |
| 348 | 104 |
| 349 | 93 |
| 350 | 102 |
| 351 | 101 |
| 352 | 100 |
| 353 | 91 |
| 354 | 83 |
| 355 | 99 |
| 356 | 98 |
| 357 | 99 |
| 358 | 96 |
| 359 | 96 |
| 360 | 99 |
| 361 | 99 |
| 362 | 101 |
| 363 | 99 |
| 364 | 100 |
| 365 | 99 |
| 366 | 54 |
| 367 | 49 |
| 368 | 41 |
| 369 | 67 |
| 370 | 58 |
| 385 | 75 |
| 386 | 70 |
| 387 | 90 |
| 388 | 50 |
| 389 | 50 |
| 390 | 61 |
| 391 | 76 |
| 392 | 57 |
| 393 | 46 |
| 394 | 72 |
| 395 | 61 |
| 396 | 68 |
| 398 | 73 |
| 399 | 79 |

TABLE 2-continued

Results of dopaminergic receptor D2 affinity test for representative compounds

| Cpd. | D2 [%] |
|---|---|
| 400 | 83 |
| 401 | 84 |
| 402 | 68 |
| 403 | 85 |
| 404 | 60 |
| 405 | 68 |
| 406 | 59 |
| 407 | 58 |
| 408 | 40 |
| 409 | 79 |
| 411 | 40 |
| 414 | 48 |
| 415 | 58 |
| 416 | 59 |
| 417 | 68 |
| 418 | 97 |
| 419 | 93 |
| 423 | 97 |
| 424 | 97 |
| 425 | 91 |
| 426 | 28 |
| 427 | 83 |
| 428 | 78 |
| 429 | 61 |
| 430 | 69 |
| 431 | 68 |
| 435 | 78 |
| 437 | 57 |
| 438 | 97 |
| 439 | 97 |
| 440 | 44 |
| 441 | 77 |
| 442 | 22 |
| 443 | 22 |
| 444 | 40 |
| 445 | 98 |
| 446 | 44 |
| 447 | 3 |
| 449 | 31 |
| 450 | 15 |
| 451 | 46 |
| 452 | 42 |
| 453 | 48 |
| 454 | −5 |

TABLE 3

Results of dopaminergic receptor D3 affinity test for representative compounds

| Compd. | D3 [%] |
|---|---|
| 1 | 96 |
| 2 | 100 |
| 3 | 98 |
| 4 | 98 |
| 5 | 98 |
| 6 | 97 |
| 7 | 97 |
| 8 | 97 |
| 9 | 90 |
| 10 | 97 |
| 11 | 91 |
| 12 | 92 |
| 13 | 92 |
| 14 | 97 |
| 15 | 88 |
| 16 | 99 |
| 17 | 93 |
| 18 | 98 |
| 19 | 90 |
| 20 | 96 |
| 21 | 97 |
| 22 | 96 |
| 23 | 93 |
| 24 | 98 |
| 25 | 94 |
| 26 | 98 |
| 27 | 96 |
| 28 | 99 |
| 29 | 98 |
| 30 | 98 |
| 31 | 96 |
| 33 | 101 |
| 34 | 100 |
| 35 | 101 |
| 36 | 100 |
| 37 | 101 |
| 38 | 100 |
| 38 | 101 |
| 40 | 100 |
| 41 | 100 |
| 42 | 101 |
| 43 | 99 |
| 44 | 98 |
| 45 | 100 |
| 46 | 100 |
| 47 | 101 |
| 48 | 97 |
| 49 | 99 |
| 50 | 95 |
| 51 | 87 |
| 52 | 99 |
| 53 | 99 |
| 54 | 98 |
| 55 | 96 |
| 56 | 99 |
| 57 | 98 |
| 58 | 100 |
| 61 | 96 |
| 62 | 63 |
| 63 | 103 |
| 64 | 98 |
| 65 | 74 |
| 66 | 101 |
| 69 | 77 |
| 70 | 101 |
| 71 | 91 |
| 72 | 95 |
| 73 | 94 |
| 74 | 92 |
| 76 | 71 |
| 79 | 96 |
| 81 | 97 |
| 85 | 77 |
| 87 | 77 |
| 89 | 95 |
| 91 | 70 |
| 93 | 86 |
| 97 | 100 |
| 98 | 104 |
| 101 | 92 |
| 102 | 103 |
| 105 | 88 |
| 106 | 97 |
| 107 | 97 |
| 108 | 98 |
| 109 | 99 |
| 110 | 97 |
| 111 | 93 |
| 112 | 98 |
| 113 | 99 |
| 137 | 92 |
| 138 | 57 |
| 139 | 92 |
| 140 | 73 |
| 165 | 89 |

TABLE 3-continued

Results of dopaminergic receptor D3 affinity test for representative compounds

| Compd. | D3 [%] |
|---|---|
| 173 | 98 |
| 174 | 96 |
| 175 | 87 |
| 176 | 95 |
| 195 | 89 |
| 196 | 97 |
| 209 | 103 |
| 211 | 102 |
| 225 | 76 |
| 226 | 90 |
| 227 | 90 |
| 228 | 92 |
| 229 | 95 |
| 230 | 87 |
| 231 | 97 |
| 232 | 89 |
| 233 | 76 |
| 234 | 91 |
| 235 | 87 |
| 236 | 85 |
| 237 | 85 |
| 238 | 85 |
| 239 | 102 |
| 240 | 99 |
| 241 | 97 |
| 242 | 89 |
| 243 | 93 |
| 244 | 91 |
| 245 | 97 |
| 246 | 86 |
| 247 | 83 |
| 248 | 100 |
| 249 | 100 |
| 250 | 85 |
| 251 | 97 |
| 252 | 98 |
| 253 | 99 |
| 254 | 98 |
| 255 | 82 |
| 256 | 96 |
| 257 | 100 |
| 258 | 97 |
| 259 | 85 |
| 260 | 98 |
| 261 | 98 |
| 262 | 98 |
| 263 | 98 |
| 264 | 65 |
| 267 | 99 |
| 268 | 98 |
| 269 | 100 |
| 270 | 82 |
| 273 | 85 |
| 274 | 91 |
| 276 | 69 |
| 282 | 87 |
| 283 | 101 |
| 288 | 102 |
| 289 | 79 |
| 291 | 85 |
| 293 | 65 |
| 294 | 95 |
| 295 | 98 |
| 296 | 100 |
| 297 | 100 |
| 298 | 98 |
| 299 | 98 |
| 300 | 96 |
| 301 | 96 |
| 302 | 99 |
| 303 | 97 |
| 304 | 87 |
| 305 | 103 |
| 306 | 99 |
| 307 | 95 |
| 308 | 95 |
| 309 | 90 |
| 310 | 97 |
| 311 | 101 |
| 312 | 97 |
| 313 | 99 |
| 314 | 100 |
| 315 | 97 |
| 316 | 95 |
| 317 | 97 |
| 318 | 95 |
| 319 | 90 |
| 320 | 99 |
| 321 | 98 |
| 322 | 93 |
| 323 | 96 |
| 324 | 103 |
| 325 | 95 |
| 326 | 99 |
| 327 | 97 |
| 328 | 99 |
| 329 | 99 |
| 330 | 99 |
| 331 | 100 |
| 332 | 96 |
| 333 | 89 |
| 334 | 96 |
| 335 | 93 |
| 336 | 96 |
| 337 | 79 |
| 338 | 100 |
| 339 | 100 |
| 340 | 101 |
| 341 | 98 |
| 342 | 99 |
| 343 | 96 |
| 344 | 101 |
| 345 | 100 |
| 346 | 93 |
| 347 | 103 |
| 348 | 102 |
| 349 | 100 |
| 350 | 95 |
| 351 | 103 |
| 352 | 97 |
| 353 | 97 |
| 354 | 88 |
| 355 | 97 |
| 356 | 96 |
| 357 | 94 |
| 358 | 99 |
| 359 | 100 |
| 360 | 100 |
| 361 | 98 |
| 362 | 102 |
| 363 | 101 |
| 364 | 100 |
| 365 | 100 |
| 366 | 81 |
| 367 | 87 |
| 368 | 94 |
| 369 | 97 |
| 370 | 91 |
| 385 | 89 |
| 386 | 88 |
| 387 | 93 |
| 388 | 83 |
| 389 | 85 |
| 390 | 81 |
| 391 | 85 |
| 392 | 93 |
| 393 | 92 |
| 394 | 86 |
| 395 | 87 |
| 396 | 86 |

TABLE 3-continued

Results of dopaminergic receptor D3 affinity test for representative compounds

| Compd. | D3 [%] |
|---|---|
| 398 | 90 |
| 399 | 92 |
| 400 | 88 |
| 401 | 95 |
| 402 | 89 |
| 403 | 99 |
| 404 | 92 |
| 405 | 62 |
| 406 | 54 |
| 407 | 84 |
| 408 | 70 |
| 409 | 85 |
| 411 | 52 |
| 414 | 81 |
| 415 | 76 |
| 416 | 56 |
| 417 | 67 |
| 418 | 99 |
| 419 | 97 |
| 420 | 97 |
| 421 | 94 |
| 422 | 98 |
| 423 | 98 |
| 424 | 98 |
| 425 | 104 |
| 426 | 94 |
| 427 | 104 |
| 428 | 104 |
| 429 | 104 |
| 430 | 101 |
| 431 | 103 |
| 434 | 98 |
| 435 | 95 |
| 436 | 96 |
| 437 | 100 |
| 438 | 98 |
| 439 | 95 |
| 440 | 92 |
| 441 | 72 |
| 442 | 53 |
| 443 | 71 |
| 444 | 74 |
| 445 | 97 |
| 446 | 66 |
| 447 | 17 |
| 449 | 34 |
| 450 | 39 |
| 451 | 30 |
| 452 | 14 |
| 453 | 56 |
| 454 | 58 |

TABLE 4

Results of serotoninergic receptors 5-HT1A and 5-HT2A affinity tests for representative compounds

| Compd. | 5-HT$_{1A}$ | 5-HT$_{2A}$ |
|---|---|---|
| 1 | 96 | 99 |
| 2 | 99 | 100 |
| 3 | 98 | 100 |
| 4 | 99 | 99 |
| 5 | 99 | 99 |
| 6 | 99 | 100 |
| 7 | 99 | 100 |
| 8 | 100 | 100 |
| 9 | 98 | 99 |
| 10 | 97 | 99 |
| 11 | 99 | 99 |
| 12 | 99 | 99 |
| 13 | 89 | 100 |
| 14 | 88 | 100 |
| 15 | 86 | 99 |
| 16 | 93 | 100 |
| 17 | 84 | 100 |
| 18 | 81 | 100 |
| 19 | 64 | 100 |
| 20 | 71 | 100 |
| 21 | 77 | 100 |
| 22 | 75 | 99 |
| 23 | 85 | 100 |
| 24 | 80 | 100 |
| 25 | 92 | 100 |
| 26 | 100 | 98 |
| 27 | 99 | 62 |
| 28 | 100 | 89 |
| 29 | 99 | 64 |
| 30 | 100 | 67 |
| 31 | 82 | 36 |
| 33 | 100 | 95 |
| 34 | 100 | 50 |
| 35 | 99 | 60 |
| 36 | 97 | 54 |
| 37 | 99 | 48 |
| 38 | 98 | 46 |
| 38 | 100 | 55 |
| 40 | 99 | 49 |
| 41 | 77 | 84 |
| 42 | 90 | 77 |
| 43 | 99 | 36 |
| 44 | 94 | 55 |
| 45 | 98 | 59 |
| 46 | 98 | 57 |
| 47 | 98 | 49 |
| 48 | 98 | 45 |
| 49 | 99 | 88 |
| 50 | 99 | 45 |
| 51 | 97 | 48 |
| 52 | 99 | 88 |
| 53 | 100 | 74 |
| 54 | 94 | 74 |
| 55 | 98 | 53 |
| 56 | 99 | 85 |
| 57 | 99 | 89 |
| 58 | 94 | 51 |
| 61 | 94 | 100 |
| 62 | 46 | 101 |
| 63 | 97 | 100 |
| 64 | 99 | 101 |
| 65 | 100 | 101 |
| 66 | 98 | 101 |
| 69 | 80 | 92 |
| 70 | 99 | 101 |
| 71 | 89 | 94 |
| 72 | 95 | 94 |
| 74 | 99 | 102 |
| 73 | 92 | 81 |
| 76 | 90 | 81 |
| 79 | 84 | 91 |
| 81 | 92 | 101 |
| 85 | 54 | 88 |
| 87 | 41 | 89 |
| 89 | 71 | 99 |
| 91 | 40 | 95 |
| 93 | 48 | 90 |
| 97 | 75 | 100 |
| 98 | 80 | 102 |
| 101 | 82 | 100 |
| 102 | 92 | 101 |
| 105 | 41 | 91 |
| 106 | 63 | 97 |
| 107 | 38 | 95 |
| 108 | 48 | 88 |
| 109 | 86 | 93 |
| 110 | 55 | 99 |
| 111 | 39 | 96 |

TABLE 4-continued

Results of serotoninergic receptors 5-HT1A and 5-HT2A affinity tests for representative compounds

| Compd. | 5-HT$_{1A}$ | 5-HT$_{2A}$ |
|---|---|---|
| 112 | 20 | 93 |
| 113 | 100 | 69 |
| 137 | 39 | 47 |
| 138 | 54 | 62 |
| 139 | 57 | 41 |
| 140 | 56 | 68 |
| 165 | 70 | 37 |
| 174 | 98 | −24 |
| 176 | 97 | 7 |
| 195 | 89 | 91 |
| 196 | 99 | 102 |
| 209 | 92 | 29 |
| 211 | 86 | 32 |
| 225 | 87 | 84 |
| 226 | 90 | 100 |
| 227 | 89 | 90 |
| 228 | 81 | 91 |
| 229 | 92 | 80 |
| 230 | 85 | 87 |
| 232 | 89 | 100 |
| 231 | 97 | 101 |
| 233 | 53 | 100 |
| 234 | 95 | 92 |
| 235 | 86 | 80 |
| 236 | 76 | 89 |
| 237 | 51 | 24 |
| 238 | 90 | 95 |
| 239 | 98 | 101 |
| 240 | 98 | 101 |
| 241 | 98 | 101 |
| 242 | 92 | 94 |
| 243 | 98 | 100 |
| 244 | 69 | 96 |
| 245 | 99 | 99 |
| 246 | 91 | 88 |
| 247 | 78 | 88 |
| 248 | 97 | 101 |
| 249 | 100 | 101 |
| 250 | 98 | 92 |
| 251 | 99 | 101 |
| 252 | 99 | 101 |
| 253 | 99 | 101 |
| 254 | 94 | 90 |
| 255 | 93 | 84 |
| 256 | 96 | 102 |
| 257 | 99 | 101 |
| 258 | 100 | 101 |
| 259 | 97 | 56 |
| 260 | 96 | 102 |
| 261 | 98 | 102 |
| 262 | 99 | 102 |
| 263 | 98 | 102 |
| 264 | 54 | 105 |
| 267 | 98 | 101 |
| 268 | 98 | 102 |
| 269 | 99 | 101 |
| 270 | 75 | 89 |
| 273 | 46 | 95 |
| 274 | 73 | 97 |
| 276 | 51 | 87 |
| 282 | 50 | 78 |
| 283 | 89 | 103 |
| 288 | 86 | 95 |
| 289 | 68 | 94 |
| 291 | 38 | 83 |
| 293 | 57 | 89 |
| 294 | 23 | 95 |
| 295 | 68 | 99 |
| 296 | 34 | 93 |
| 297 | 31 | 95 |
| 298 | 67 | 100 |
| 299 | 45 | 89 |
| 300 | 80 | 102 |
| 301 | 77 | 101 |
| 302 | 50 | 95 |
| 303 | 35 | 96 |
| 304 | 60 | 76 |
| 305 | 58 | 96 |
| 306 | 44 | 97 |
| 307 | 73 | 99 |
| 308 | 81 | 102 |
| 309 | 64 | 88 |
| 310 | 91 | 99 |
| 311 | 49 | 105 |
| 312 | 86 | 99 |
| 313 | 72 | 101 |
| 314 | 75 | 102 |
| 315 | 70 | 102 |
| 316 | 84 | 102 |
| 317 | 45 | 98 |
| 318 | 96 | 89 |
| 319 | 55 | 88 |
| 320 | 69 | 101 |
| 321 | 78 | 100 |
| 322 | 43 | 94 |
| 323 | 45 | 96 |
| 324 | 56 | 104 |
| 325 | 62 | 102 |
| 326 | 59 | 96 |
| 327 | 67 | 91 |
| 328 | 58 | 90 |
| 329 | 69 | 91 |
| 330 | 67 | 93 |
| 331 | 82 | 102 |
| 332 | 71 | 97 |
| 333 | 42 | 99 |
| 334 | 86 | 90 |
| 335 | 54 | 97 |
| 336 | 61 | 100 |
| 337 | 41 | 102 |
| 338 | 80 | 102 |
| 339 | 76 | 82 |
| 340 | 45 | 104 |
| 341 | 74 | 102 |
| 342 | 74 | 106 |
| 343 | 32 | 105 |
| 344 | 42 | 105 |
| 345 | 45 | 93 |
| 346 | 51 | 97 |
| 347 | 92 | 101 |
| 348 | 36 | 107 |
| 349 | 49 | 108 |
| 350 | 57 | 95 |
| 351 | 71 | 103 |
| 352 | 89 | 101 |
| 353 | 48 | 101 |
| 354 | 59 | 86 |
| 355 | 60 | 103 |
| 356 | 95 | 99 |
| 357 | 63 | 101 |
| 358 | 100 | 99 |
| 359 | 100 | 79 |
| 360 | 83 | 67 |
| 361 | 95 | 49 |
| 362 | 91 | 41 |
| 363 | 101 | 98 |
| 364 | 92 | 89 |
| 365 | 90 | 55 |
| 366 | 34 | 49 |
| 367 | 49 | 51 |
| 368 | −7 | 64 |
| 369 | 62 | 79 |
| 370 | 57 | 65 |
| 385 | 103 | 77 |
| 386 | 96 | 65 |
| 387 | 100 | 90 |
| 388 | 92 | 19 |
| 389 | 118 | 56 |
| 390 | 101 | 59 |
| 391 | 97 | 68 |

TABLE 4-continued

Results of serotoninergic receptors 5-HT1A and 5-HT2A affinity tests for representative compounds

| Compd. | 5-HT$_{1A}$ | 5-HT$_{2A}$ |
|---|---|---|
| 392 | 100 | 64 |
| 393 | 93 | 47 |
| 394 | 95 | 71 |
| 395 | 75 | 61 |
| 396 | 85 | 58 |
| 397 | 95 | 13 |
| 398 | 107 | 38 |
| 399 | 99 | 82 |
| 400 | 100 | 66 |
| 401 | 103 | 79 |
| 402 | 102 | 76 |
| 403 | 98 | 64 |
| 404 | 97 | 55 |
| 405 | 97 | 74 |
| 406 | 99 | 28 |
| 407 | 88 | 50 |
| 408 | 101 | −50 |
| 409 | 81 | 66 |
| 410 | 96 | 42 |
| 411 | 95 | 4 |
| 413 | 88 | 40 |
| 414 | 98 | 76 |
| 415 | 96 | 25 |
| 416 | 101 | 58 |
| 417 | 100 | −48 |
| 418 | 98 | 36 |
| 419 | 98 | 52 |
| 423 | 99 | 30 |
| 424 | 99 | 66 |
| 425 | 98 | 25 |
| 426 | 79 | 20 |
| 427 | 84 | 49 |
| 428 | 90 | 30 |
| 429 | 88 | 35 |
| 430 | 86 | 87 |
| 431 | 101 | 31 |
| 435 | 83 | 57 |
| 436 | 85 | 56 |
| 437 | 24 | 74 |
| 438 | 97 | 63 |
| 439 | 99 | 83 |
| 440 | 76 | 37 |
| 441 | 54 | 57 |
| 442 | 14 | 61 |
| 443 | 59 | 67 |
| 444 | 51 | 65 |
| 445 | 93 | 78 |
| 446 | 73 | 66 |
| 447 | 42 | 19 |
| 449 | 57 | 76 |

TABLE 5

Results of serotoninergic receptors 5-HT6 and 5-HT7 affinity tests for representative compounds

| Compd. | 5-HT6 | 5-HT7 |
|---|---|---|
| 1 | 95 | 96 |
| 2 | 97 | 97 |
| 3 | 83 | 97 |
| 4 | 87 | 97 |
| 5 | 84 | 98 |
| 6 | 88 | 98 |
| 7 | 98 | 97 |
| 8 | 91 | 97 |
| 9 | 22 | 98 |
| 10 | 37 | 99 |
| 11 | 54 | 99 |
| 12 | 80 | 89 |
| 13 | 96 | 100 |
| 14 | 99 | 99 |
| 15 | 71 | 100 |
| 16 | 94 | 99 |
| 17 | 99 | 99 |
| 18 | 100 | 98 |
| 19 | 69 | 100 |
| 20 | 85 | 101 |
| 21 | 93 | 99 |
| 22 | 99 | 99 |
| 23 | 69 | 96 |
| 24 | 76 | 95 |
| 25 | 71 | 98 |
| 26 | 51 | 98 |
| 27 | 34 | 92 |
| 28 | 98 | 92 |
| 29 | 37 | 91 |
| 30 | 5 | 96 |
| 31 | 18 | 87 |
| 32 | 23 | |
| 33 | 42 | 99 |
| 34 | 87 | 87 |
| 35 | 88 | 88 |
| 36 | 81 | 90 |
| 37 | 80 | 89 |
| 38 | 86 | 90 |
| 38 | 88 | 93 |
| 40 | 82 | 92 |
| 41 | 89 | 76 |
| 42 | 96 | 76 |
| 43 | 83 | 97 |
| 44 | 83 | 97 |
| 45 | 90 | 96 |
| 46 | 84 | 97 |
| 47 | 83 | 98 |
| 48 | 91 | 98 |
| 49 | 93 | 99 |
| 50 | 95 | 95 |
| 51 | 94 | 94 |
| 52 | 99 | 98 |
| 53 | 98 | 99 |
| 54 | 97 | 95 |
| 55 | 98 | 97 |
| 56 | 99 | 100 |
| 57 | 98 | 102 |
| 58 | 84 | 46 |
| 61 | 96 | 100 |
| 62 | 69 | 78 |
| 63 | 89 | 99 |
| 64 | 99 | 99 |
| 65 | 97 | 98 |
| 66 | 95 | 101 |
| 69 | 88 | 96 |
| 70 | 99 | 100 |
| 71 | 76 | 99 |
| 72 | 78 | 101 |
| 73 | 82 | 91 |
| 74 | 95 | 97 |
| 76 | 70 | 86 |
| 79 | 97 | 97 |
| 81 | 98 | 99 |
| 85 | 77 | 99 |
| 87 | 67 | 90 |
| 89 | 94 | 98 |
| 91 | 83 | 99 |
| 93 | 92 | 88 |
| 97 | 98 | 93 |
| 98 | 98 | 98 |
| 101 | 98 | 98 |
| 102 | 97 | 97 |
| 105 | 87 | 85 |
| 106 | 93 | 91 |
| 107 | 75 | 91 |
| 108 | 86 | 90 |
| 109 | 84 | 92 |
| 110 | 96 | 91 |
| 111 | 95 | 93 |

TABLE 5-continued

Results of serotoninergic receptors 5-HT6 and 5-HT7 affinity tests for representative compounds

| Compd. | 5-HT6 | 5-HT7 |
|---|---|---|
| 112 | 94 | 95 |
| 113 | 74 | 97 |
| 137 | 91 | 33 |
| 138 | 95 | 52 |
| 139 | 96 | 56 |
| 140 | 92 | 81 |
| 165 | −16 | 86 |
| 174 | 4 | 92 |
| 176 | 29 | 80 |
| 195 | 60 | 98 |
| 196 | 92 | 100 |
| 209 | 70 | 85 |
| 211 | 32 | 81 |
| 225 | 74 | 92 |
| 226 | 78 | 92 |
| 227 | 76 | 94 |
| 228 | 87 | 98 |
| 229 | 75 | 89 |
| 230 | 85 | 101 |
| 231 | 95 | 99 |
| 232 | 76 | 89 |
| 233 | 76 | 93 |
| 234 | 62 | 97 |
| 235 | 82 | 93 |
| 236 | 67 | 91 |
| 237 | 89 | 64 |
| 238 | 74 | 88 |
| 239 | 96 | 98 |
| 240 | 98 | 97 |
| 241 | 96 | 99 |
| 242 | 73 | 101 |
| 243 | 73 | 99 |
| 244 | 81 | 98 |
| 245 | 82 | 98 |
| 246 | 49 | 86 |
| 247 | 93 | 93 |
| 248 | 98 | 98 |
| 249 | 101 | 100 |
| 250 | 73 | 88 |
| 251 | 99 | 99 |
| 252 | 93 | 99 |
| 253 | 101 | 99 |
| 254 | 76 | 93 |
| 255 | 68 | 91 |
| 256 | 95 | 100 |
| 257 | 94 | 101 |
| 258 | 98 | 100 |
| 259 | 74 | 96 |
| 260 | 92 | 100 |
| 261 | 83 | 100 |
| 262 | 93 | 99 |
| 263 | 96 | 98 |
| 264 | 63 | 75 |
| 267 | 95 | 100 |
| 268 | 93 | 99 |
| 269 | 98 | 101 |
| 270 | 70 | 82 |
| 273 | 74 | 97 |
| 274 | 81 | 83 |
| 276 | 78 | 87 |
| 282 | 64 | 98 |
| 283 | 96 | 99 |
| 288 | 98 | 100 |
| 289 | 78 | 91 |
| 291 | 83 | 99 |
| 293 | 44 | 93 |
| 294 | 72 | 94 |
| 295 | 93 | 99 |
| 296 | 83 | 91 |
| 297 | 87 | 88 |
| 298 | 98 | 100 |
| 299 | 84 | 75 |
| 300 | 89 | 99 |
| 301 | 94 | 98 |
| 302 | 72 | 101 |
| 303 | 90 | 98 |
| 304 | 78 | 93 |
| 305 | 78 | 85 |
| 306 | 81 | 89 |
| 307 | 76 | 85 |
| 308 | 83 | 99 |
| 309 | 79 | 87 |
| 310 | 89 | 89 |
| 311 | 99 | 95 |
| 312 | 98 | 97 |
| 313 | 100 | 100 |
| 314 | 100 | 99 |
| 315 | 98 | 98 |
| 316 | 93 | 97 |
| 317 | 78 | 89 |
| 318 | 76 | 92 |
| 319 | 87 | 90 |
| 320 | 82 | 99 |
| 321 | 89 | 100 |
| 322 | 62 | 95 |
| 323 | 92 | 93 |
| 324 | 78 | 78 |
| 325 | 72 | 98 |
| 326 | 94 | 94 |
| 327 | 99 | 86 |
| 328 | 87 | 92 |
| 329 | 97 | 95 |
| 330 | 83 | 90 |
| 331 | 97 | 99 |
| 332 | 95 | 64 |
| 333 | 93 | 92 |
| 334 | 98 | 85 |
| 335 | 93 | 88 |
| 336 | 92 | 92 |
| 337 | 76 | 87 |
| 338 | 94 | 98 |
| 339 | 89 | 89 |
| 340 | 72 | 90 |
| 341 | 93 | 78 |
| 342 | 100 | 96 |
| 343 | 77 | 92 |
| 344 | 91 | 95 |
| 345 | 91 | 91 |
| 346 | 95 | 87 |
| 347 | 99 | 100 |
| 348 | 96 | 87 |
| 349 | 87 | 91 |
| 350 | 96 | 87 |
| 351 | 89 | 94 |
| 352 | 95 | 100 |
| 353 | 58 | 83 |
| 354 | 86 | 96 |
| 355 | 75 | 84 |
| 356 | 78 | 99 |
| 357 | 94 | 99 |
| 358 | 70 | 94 |
| 359 | 42 | 95 |
| 360 | 67 | 100 |
| 361 | 70 | 86 |
| 362 | 69 | 88 |
| 363 | 84 | 98 |
| 364 | 80 | 91 |
| 365 | 67 | 95 |
| 366 | 98 | 53 |
| 367 | 86 | 23 |
| 368 | 96 | 42 |
| 369 | 99 | 7 |
| 370 | 88 | 42 |
| 385 | 10 | 99 |
| 386 | 1 | 82 |
| 387 | 26 | 96 |
| 388 | −20 | 90 |
| 389 | 19 | 93 |
| 390 | 26 | 66 |
| 391 | 19 | 92 |

TABLE 5-continued

Results of serotoninergic receptors 5-HT6 and 5-HT7 affinity tests for representative compounds

| Compd. | 5-HT6 | 5-HT7 |
|---|---|---|
| 392 | 7 | 91 |
| 393 | 9 | 91 |
| 394 | 18 | 98 |
| 395 | −35 | 83 |
| 396 | 31 | 88 |
| 398 | 3 | 97 |
| 399 | 23 | 96 |
| 400 | 9 | 95 |
| 401 | 27 | 91 |
| 402 | 1 | 100 |
| 403 | −21 | 95 |
| 404 | 4 | 96 |
| 405 | 53 | 93 |
| 406 | 54 | 92 |
| 407 | 37 | 102 |
| 408 | 35 | 83 |
| 409 | −9 | 91 |
| 411 | 41 | 89 |
| 414 | −15 | 94 |
| 415 | 15 | 92 |
| 416 | 55 | 99 |
| 417 | 24 | 62 |
| 418 | 5 | 89 |
| 419 | 12 | 86 |
| 423 | 16 | 88 |
| 424 | 69 | 95 |
| 425 | 5 | 95 |
| 426 | −4 | 85 |
| 427 | 36 | 98 |
| 428 | 33 | 78 |
| 429 | −57 | 83 |
| 430 | 94 | 84 |
| 431 | 35 | 67 |
| 435 | 58 | 64 |
| 437 | 47 | 83 |
| 438 | 96 | 92 |
| 439 | 92 | 78 |
| 440 | 86 | 68 |
| 441 | 84 | 82 |
| 442 | 87 | 61 |
| 443 | 92 | 54 |
| 444 | 87 | 59 |
| 445 | 84 | 98 |
| 446 | 96 | 21 |
| 447 | 106 | 34 |
| 449 | 93 | 81 |
| 450 | 96 | 50 |
| 451 | 97 | 25 |
| 452 | 108 | 41 |
| 453 | 107 | 76 |
| 454 | 102 | 68 |

TABLE 6

Results of serotonine transporter (SERT) receptor affinity tests for representative compounds

| Compd. | SERT [%] |
|---|---|
| 1 | 49 |
| 2 | 69 |
| 3 | 57 |
| 4 | 26 |
| 5 | 84 |
| 6 | 95 |
| 7 | 88 |
| 8 | 63 |
| 9 | 29 |
| 10 | 50 |
| 11 | 1 |
| 12 | 7 |
| 13 | 7 |
| 14 | 3 |
| 15 | −3 |
| 16 | −3 |
| 17 | 44 |
| 18 | 39 |
| 19 | 8 |
| 20 | 85 |
| 21 | 46 |
| 22 | 44 |
| 23 | 68 |
| 24 | 53 |
| 25 | 20 |
| 26 | 14 |
| 27 | −3 |
| 28 | 53 |
| 29 | 12 |
| 30 | 14 |
| 31 | −2 |
| 33 | −4 |
| 34 | 101 |
| 35 | 99 |
| 36 | 101 |
| 37 | 101 |
| 38 | 101 |
| 38 | 101 |
| 40 | 101 |
| 41 | 94 |
| 42 | 96 |
| 43 | 100 |
| 44 | 100 |
| 45 | 98 |
| 46 | 102 |
| 47 | 101 |
| 48 | 101 |
| 49 | 101 |
| 50 | 98 |
| 51 | 100 |
| 52 | 100 |
| 53 | 99 |
| 54 | 99 |
| 55 | 98 |
| 56 | 99 |
| 57 | 100 |
| 58 | 78 |
| 61 | 55 |
| 62 | 15 |
| 63 | 53 |
| 64 | 80 |
| 65 | 57 |
| 66 | 93 |
| 69 | 6 |
| 70 | 82 |
| 71 | 41 |
| 72 | 44 |
| 73 | 37 |
| 74 | 79 |
| 76 | 15 |
| 79 | 3 |
| 81 | 28 |
| 85 | 2 |
| 87 | 2 |
| 89 | 2 |
| 91 | 2 |
| 93 | 0 |
| 97 | 61 |
| 98 | 54 |
| 101 | 47 |
| 102 | 38 |
| 105 | −11 |
| 106 | 2 |
| 107 | −12 |
| 108 | −9 |
| 109 | 15 |
| 110 | 8 |
| 111 | −14 |

TABLE 6-continued

Results of serotonine transporter (SERT) receptor affinity tests for representative compounds

| Compd. | SERT [%] |
|---|---|
| 112 | −17 |
| 113 | 28 |
| 137 | 38 |
| 138 | 25 |
| 139 | 17 |
| 140 | 14 |
| 165 | 4 |
| 174 | 11 |
| 176 | −3 |
| 195 | −3 |
| 196 | 75 |
| 209 | −1 |
| 211 | 33 |
| 225 | −4 |
| 226 | 4 |
| 227 | 2 |
| 228 | 16 |
| 229 | 9 |
| 230 | 13 |
| 231 | 59 |
| 232 | 13 |
| 233 | 5 |
| 234 | 32 |
| 235 | 0 |
| 236 | −15 |
| 237 | −7 |
| 238 | 13 |
| 239 | 64 |
| 240 | 46 |
| 241 | 50 |
| 242 | 12 |
| 243 | 63 |
| 244 | 19 |
| 245 | 38 |
| 246 | 31 |
| 247 | 14 |
| 248 | 80 |
| 249 | 77 |
| 250 | 23 |
| 251 | 87 |
| 252 | 94 |
| 253 | 79 |
| 254 | 9 |
| 255 | 29 |
| 256 | 93 |
| 257 | 93 |
| 258 | 80 |
| 259 | 16 |
| 260 | 90 |
| 261 | 60 |
| 262 | 87 |
| 263 | 87 |
| 264 | −18 |
| 267 | 91 |
| 268 | 86 |
| 269 | 96 |
| 270 | 12 |
| 273 | 22 |
| 274 | 30 |
| 276 | 3 |
| 282 | 12 |
| 283 | 24 |
| 288 | −14 |
| 289 | 9 |
| 291 | 8 |
| 293 | 3 |
| 294 | −14 |
| 295 | 16 |
| 296 | 49 |
| 297 | 23 |
| 298 | 35 |
| 299 | 14 |
| 300 | 30 |
| 301 | 45 |
| 302 | 19 |
| 303 | 9 |
| 304 | 4 |
| 305 | −18 |
| 306 | −10 |
| 307 | 3 |
| 308 | 28 |
| 309 | −5 |
| 310 | 57 |
| 311 | 34 |
| 312 | 35 |
| 313 | 23 |
| 314 | 50 |
| 315 | 68 |
| 316 | 47 |
| 317 | −17 |
| 318 | 45 |
| 319 | 8 |
| 320 | 13 |
| 321 | 61 |
| 322 | 16 |
| 323 | 41 |
| 324 | 37 |
| 325 | 20 |
| 326 | 19 |
| 327 | −1 |
| 328 | 7 |
| 329 | −2 |
| 330 | −2 |
| 331 | 31 |
| 332 | 18 |
| 333 | 5 |
| 334 | 30 |
| 335 | −25 |
| 336 | 41 |
| 337 | 35 |
| 338 | 21 |
| 339 | 3 |
| 340 | 9 |
| 341 | 8 |
| 342 | 26 |
| 343 | 4 |
| 344 | 31 |
| 345 | −10 |
| 346 | 17 |
| 347 | 33 |
| 348 | 6 |
| 349 | 0 |
| 350 | −5 |
| 351 | 31 |
| 352 | 56 |
| 353 | −1 |
| 354 | 6 |
| 355 | 45 |
| 356 | 11 |
| 357 | 41 |
| 358 | 40 |
| 359 | 33 |
| 360 | 8 |
| 361 | 6 |
| 362 | 37 |
| 363 | 32 |
| 364 | 35 |
| 365 | 25 |
| 366 | 8 |
| 367 | 4 |
| 368 | 14 |
| 369 | 29 |
| 370 | 30 |
| 385 | 6 |
| 386 | −5 |
| 387 | −14 |
| 388 | −28 |
| 389 | 44 |
| 390 | −15 |
| 391 | −28 |

TABLE 6-continued

Results of serotonine transporter (SERT) receptor affinity tests for representative compounds

| Compd. | SERT [%] |
|---|---|
| 392 | −11 |
| 393 | −7 |
| 394 | 12 |
| 395 | 69 |
| 396 | 16 |
| 398 | −7 |
| 399 | −22 |
| 400 | 30 |
| 401 | −8 |
| 402 | 16 |
| 403 | −9 |
| 404 | −9 |
| 405 | −5 |
| 406 | 10 |
| 407 | −2 |
| 408 | −18 |
| 409 | 2 |
| 411 | 12 |
| 414 | 18 |
| 415 | −5 |
| 416 | −4 |
| 417 | −11 |
| 418 | 5 |
| 419 | −21 |
| 423 | 25 |
| 424 | −3 |
| 425 | 10 |
| 426 | −18 |
| 427 | 13 |
| 428 | 23 |
| 429 | 22 |
| 430 | 19 |
| 431 | 12 |
| 435 | 81 |
| 437 | 105 |
| 438 | 97 |
| 439 | 93 |
| 440 | 70 |
| 441 | 1 |
| 442 | 4 |
| 443 | −9 |
| 444 | 44 |
| 445 | 68 |
| 446 | 20 |
| 447 | 23 |
| 449 | 21 |
| 450 | 54 |
| 451 | 32 |
| 452 | 18 |
| 453 | 23 |
| 454 | 14 |

TABLE 7

Results of sigma σ receptor affinity tests for representative compounds

| Compd. | σ [%] |
|---|---|
| 1 | 54 |
| 2 | 65 |
| 3 | 66 |
| 4 | 1 |
| 5 | 72 |
| 6 | 59 |
| 7 | 61 |
| 8 | 17 |
| 9 | 23 |
| 10 | 31 |
| 11 | 21 |
| 12 | 4 |
| 13 | 87 |
| 14 | 40 |
| 15 | 47 |
| 16 | 2 |
| 17 | 83 |
| 18 | 70 |
| 19 | 92 |
| 20 | 81 |
| 21 | 82 |
| 22 | 92 |
| 23 | 82 |
| 24 | 80 |
| 25 | 76 |
| 26 | 99 |
| 27 | 78 |
| 28 | 84 |
| 29 | 93 |
| 30 | 42 |
| 33 | 94 |
| 34 | 51 |
| 35 | 42 |
| 36 | 57 |
| 37 | 66 |
| 38 | 46 |
| 38 | 57 |
| 40 | 68 |
| 43 | 58 |
| 44 | 45 |
| 45 | 74 |
| 46 | 79 |
| 47 | 53 |
| 48 | 67 |
| 49 | 61 |
| 50 | 61 |
| 51 | 55 |
| 52 | 80 |
| 53 | 79 |
| 54 | 66 |
| 55 | 79 |
| 56 | 78 |
| 57 | 75 |
| 58 | 34 |
| 61 | 46 |
| 63 | 54 |
| 64 | 54 |
| 65 | 62 |
| 66 | 61 |
| 70 | 64 |
| 74 | 34 |
| 79 | 37 |
| 81 | 59 |
| 89 | −1 |
| 97 | 55 |
| 98 | 50 |
| 101 | 70 |
| 102 | 74 |
| 113 | 92 |
| 174 | −16 |
| 176 | −25 |
| 196 | 66 |
| 231 | 62 |
| 239 | 69 |
| 240 | 44 |
| 241 | 51 |
| 243 | 29 |
| 245 | 52 |
| 248 | 64 |
| 249 | 68 |
| 251 | 61 |
| 252 | 59 |
| 253 | 64 |
| 256 | 41 |
| 257 | 57 |
| 258 | 61 |
| 260 | 41 |
| 261 | 57 |

TABLE 7-continued

Results of sigma σ receptor affinity tests for representative compounds

| Compd. | σ [%] |
|---|---|
| 262 | 51 |
| 263 | 49 |
| 267 | 50 |
| 268 | 30 |
| 269 | 49 |
| 283 | 34 |
| 288 | 45 |
| 295 | 63 |
| 298 | 68 |
| 300 | 83 |
| 301 | 73 |
| 308 | 86 |
| 312 | 71 |
| 313 | 83 |
| 314 | 49 |
| 315 | 72 |
| 316 | 81 |
| 320 | 80 |
| 321 | 74 |
| 325 | 85 |
| 331 | 79 |
| 338 | 72 |
| 347 | 57 |
| 352 | 76 |
| 356 | 70 |
| 357 | 64 |
| 358 | 84 |
| 359 | 85 |
| 363 | 96 |
| 418 | 6 |
| 419 | −14 |
| 423 | 9 |
| 424 | −3 |
| 425 | −3 |
| 438 | 79 |
| 439 | 80 |
| 445 | 67 |

TABLE 8

Results of adrenergic α1 receptor affinity tests for representative compounds

| Compd. | α1 [%] |
|---|---|
| 1 | 99 |
| 2 | 97 |
| 3 | 100 |
| 4 | 96 |
| 5 | 98 |
| 6 | 95 |
| 7 | 98 |
| 8 | 94 |
| 9 | 74 |
| 10 | 79 |
| 11 | 85 |
| 12 | 67 |
| 13 | 102 |
| 14 | 102 |
| 15 | 102 |
| 16 | 101 |
| 17 | 100 |
| 18 | 101 |
| 19 | 99 |
| 20 | 99 |
| 21 | 97 |
| 22 | 100 |
| 23 | 97 |
| 24 | 97 |
| 25 | 98 |
| 26 | 98 |
| 27 | 96 |
| 28 | 92 |
| 29 | 99 |
| 30 | 96 |
| 31 | 101 |
| 33 | 100 |
| 34 | 81 |
| 35 | 70 |
| 36 | 84 |
| 37 | 82 |
| 38 | 77 |
| 38 | 84 |
| 40 | 86 |
| 41 | 87 |
| 42 | 77 |
| 43 | 70 |
| 44 | 54 |
| 45 | 84 |
| 46 | 78 |
| 47 | 68 |
| 48 | 71 |
| 49 | 84 |
| 50 | 50 |
| 51 | 40 |
| 52 | 57 |
| 53 | 61 |
| 54 | 43 |
| 55 | 46 |
| 56 | 61 |
| 57 | 65 |
| 58 | 76 |
| 61 | 94 |
| 62 | 61 |
| 63 | 99 |
| 64 | 93 |
| 65 | 95 |
| 66 | 93 |
| 69 | 94 |
| 70 | 96 |
| 71 | 99 |
| 72 | 93 |
| 73 | 98 |
| 74 | 94 |
| 76 | 95 |
| 79 | 88 |
| 81 | 96 |
| 85 | 98 |
| 87 | 98 |
| 89 | 98 |
| 91 | 99 |
| 93 | 97 |
| 97 | 98 |
| 98 | 97 |
| 101 | 99 |
| 102 | 99 |
| 105 | 96 |
| 106 | 101 |
| 107 | 100 |
| 108 | 100 |
| 109 | 101 |
| 110 | 103 |
| 111 | 100 |
| 112 | 99 |
| 113 | 99 |
| 137 | 10 |
| 138 | 8 |
| 139 | 20 |
| 140 | 17 |
| 165 | 47 |
| 173 | 89 |
| 174 | 86 |
| 175 | 82 |
| 176 | 77 |
| 195 | 96 |
| 196 | 93 |
| 209 | 90 |

TABLE 8-continued

Results of adrenergic α1 receptor affinity tests for representative compounds

| Compd. | α1 [%] |
|---|---|
| 211 | 80 |
| 225 | 94 |
| 226 | 94 |
| 227 | 92 |
| 228 | 92 |
| 229 | 96 |
| 230 | 98 |
| 231 | 96 |
| 232 | 94 |
| 233 | 94 |
| 234 | 91 |
| 235 | 95 |
| 236 | 92 |
| 237 | 87 |
| 238 | 103 |
| 239 | 99 |
| 240 | 96 |
| 241 | 93 |
| 242 | 98 |
| 243 | 97 |
| 244 | 98 |
| 245 | 96 |
| 246 | 99 |
| 247 | 98 |
| 248 | 91 |
| 249 | 99 |
| 250 | 95 |
| 251 | 95 |
| 252 | 27 |
| 253 | 97 |
| 254 | 96 |
| 255 | 92 |
| 256 | 87 |
| 257 | 94 |
| 258 | 97 |
| 259 | 88 |
| 260 | 91 |
| 261 | −90 |
| 262 | 95 |
| 263 | 90 |
| 264 | 53 |
| 267 | 97 |
| 268 | 90 |
| 269 | 97 |
| 270 | 88 |
| 273 | 101 |
| 274 | 99 |
| 276 | 95 |
| 282 | 102 |
| 283 | 92 |
| 288 | 94 |
| 289 | 100 |
| 291 | 99 |
| 293 | 98 |
| 294 | 101 |
| 295 | 96 |
| 296 | 101 |
| 297 | 100 |
| 298 | 103 |
| 299 | 98 |
| 300 | 96 |
| 301 | 96 |
| 302 | 100 |
| 303 | 97 |
| 304 | 101 |
| 305 | 99 |
| 306 | 99 |
| 307 | 105 |
| 308 | 91 |
| 309 | 103 |
| 310 | 107 |
| 311 | 107 |
| 312 | 100 |
| 313 | 100 |
| 314 | 100 |
| 315 | −13 |
| 316 | 90 |
| 317 | 99 |
| 318 | 98 |
| 319 | 94 |
| 320 | 98 |
| 321 | 98 |
| 322 | 103 |
| 323 | 103 |
| 324 | 103 |
| 325 | 95 |
| 326 | 101 |
| 327 | 109 |
| 328 | 101 |
| 329 | 102 |
| 330 | 102 |
| 331 | 101 |
| 332 | 107 |
| 333 | 106 |
| 334 | 105 |
| 335 | 101 |
| 336 | 107 |
| 337 | 93 |
| 338 | 99 |
| 339 | 108 |
| 340 | 110 |
| 341 | 108 |
| 342 | 103 |
| 343 | 86 |
| 344 | 106 |
| 345 | 102 |
| 346 | 103 |
| 347 | 99 |
| 348 | 90 |
| 349 | 98 |
| 350 | 102 |
| 351 | 97 |
| 352 | 99 |
| 353 | 103 |
| 354 | 103 |
| 355 | 105 |
| 356 | 101 |
| 357 | 99 |
| 358 | 88 |
| 359 | 97 |
| 360 | 93 |
| 361 | 98 |
| 362 | 96 |
| 363 | 92 |
| 364 | 87 |
| 365 | 100 |
| 366 | 8 |
| 367 | 9 |
| 368 | 34 |
| 369 | 50 |
| 370 | 38 |
| 385 | 96 |
| 386 | 96 |
| 387 | 86 |
| 388 | 91 |
| 389 | 93 |
| 390 | 73 |
| 391 | 90 |
| 392 | 99 |
| 393 | 91 |
| 394 | 92 |
| 395 | 92 |
| 396 | 84 |
| 397 | 92 |
| 398 | 97 |
| 399 | 99 |
| 400 | 94 |
| 401 | 90 |
| 402 | 94 |
| 403 | 98 |

TABLE 8-continued

Results of adrenergic α1 receptor affinity tests for representative compounds

| Compd. | α1 [%] |
|---|---|
| 404 | 93 |
| 405 | 82 |
| 406 | 77 |
| 407 | 72 |
| 408 | 70 |
| 409 | 81 |
| 410 | 84 |
| 411 | 87 |
| 413 | 90 |
| 414 | 88 |
| 415 | 78 |
| 416 | 81 |
| 417 | 73 |
| 418 | 98 |
| 419 | 86 |
| 420 | 82 |
| 421 | 88 |
| 422 | 86 |
| 423 | 91 |
| 424 | 93 |
| 425 | 93 |
| 426 | 67 |
| 427 | 86 |
| 428 | 72 |
| 429 | 78 |
| 430 | 46 |
| 431 | 88 |
| 435 | 48 |
| 437 | 52 |
| 438 | 44 |
| 439 | 27 |
| 440 | 14 |
| 441 | 16 |
| 442 | 1 |
| 443 | 41 |
| 444 | 26 |
| 445 | 50 |
| 446 | 29 |
| 447 | 1 |
| 449 | 12 |
| 450 | −1 |
| 451 | −4 |
| 452 | 14 |
| 453 | 23 |
| 454 | 7 |

TABLE 9

Results of adrenergic α2C receptor affinity tests for representative compounds

| Compd. | α2C [%] |
|---|---|
| 1 | 100 |
| 2 | 101 |
| 3 | 99 |
| 4 | 96 |
| 5 | 99 |
| 6 | 93 |
| 7 | 96 |
| 8 | 93 |
| 9 | 98 |
| 10 | 98 |
| 11 | 94 |
| 12 | 83 |
| 13 | 99 |
| 14 | 100 |
| 15 | 98 |
| 16 | 101 |
| 17 | 100 |
| 18 | 100 |
| 19 | 100 |
| 20 | 99 |
| 21 | 98 |
| 22 | 100 |
| 23 | 99 |
| 24 | 99 |
| 25 | 98 |
| 26 | 100 |
| 27 | 100 |
| 28 | 92 |
| 29 | 98 |
| 30 | 99 |
| 33 | 100 |
| 34 | 98 |
| 35 | 96 |
| 36 | 92 |
| 37 | 93 |
| 38 | 93 |
| 39 | 98 |
| 40 | 97 |
| 43 | 94 |
| 44 | 86 |
| 45 | 88 |
| 46 | 87 |
| 47 | 92 |
| 48 | 88 |
| 49 | 86 |
| 50 | 97 |
| 51 | 94 |
| 52 | 88 |
| 53 | 87 |
| 54 | 91 |
| 55 | 82 |
| 56 | 90 |
| 57 | 78 |
| 58 | 80 |
| 61 | 101 |
| 63 | 98 |
| 64 | 100 |
| 65 | 104 |
| 66 | 103 |
| 70 | 100 |
| 74 | 92 |
| 79 | 106 |
| 81 | 106 |
| 89 | 98 |
| 97 | 100 |
| 98 | 108 |
| 101 | 106 |
| 102 | 101 |
| 113 | 99 |
| 174 | 55 |
| 176 | 44 |
| 196 | 95 |
| 231 | 99 |
| 239 | 105 |
| 240 | 100 |
| 241 | 98 |
| 243 | 96 |
| 245 | 101 |
| 248 | 93 |
| 249 | 98 |
| 251 | 96 |
| 252 | 95 |
| 253 | 102 |
| 256 | 92 |
| 257 | 99 |
| 258 | 98 |
| 260 | 99 |
| 261 | 92 |
| 262 | 94 |
| 263 | 93 |
| 267 | 99 |
| 268 | 99 |
| 269 | 101 |
| 283 | 109 |

TABLE 9-continued

Results of adrenergic α2C receptor affinity
tests for representative compounds

| Compd. | α2C [%] |
|---|---|
| 288 | 109 |
| 295 | 97 |
| 298 | 98 |
| 300 | 94 |
| 301 | 98 |
| 308 | 96 |
| 312 | 92 |
| 313 | 100 |
| 314 | 108 |
| 315 | 93 |
| 316 | 94 |
| 320 | 101 |
| 321 | 100 |
| 325 | 93 |
| 331 | 104 |
| 338 | 104 |
| 347 | 110 |
| 352 | 100 |
| 356 | 96 |
| 357 | 94 |
| 358 | 101 |
| 359 | 99 |
| 363 | 101 |
| 418 | 94 |
| 419 | 93 |
| 423 | 69 |
| 424 | 67 |
| 425 | 59 |
| 438 | 94 |
| 439 | 68 |
| 445 | 69 |

TABLE 10

Results of histaminergic H1 receptor affinity
tests for representative compounds

| Compd. | H1 [%] |
|---|---|
| 1 | 91 |
| 2 | 94 |
| 3 | 94 |
| 4 | 100 |
| 5 | 92 |
| 6 | 93 |
| 7 | 93 |
| 8 | 97 |
| 9 | 77 |
| 10 | 81 |
| 11 | 74 |
| 12 | 79 |
| 13 | 84 |
| 14 | 88 |
| 15 | 84 |
| 16 | 97 |
| 17 | 80 |
| 18 | 79 |
| 19 | 79 |
| 20 | 78 |
| 21 | 90 |
| 22 | 88 |
| 23 | 67 |
| 24 | 56 |
| 25 | 62 |
| 26 | 52 |
| 27 | 27 |
| 28 | 57 |
| 29 | 74 |
| 30 | 40 |
| 33 | 56 |
| 34 | 67 |
| 35 | 51 |

TABLE 10-continued

Results of histaminergic H1 receptor affinity
tests for representative compounds

| Compd. | H1 [%] |
|---|---|
| 36 | 66 |
| 37 | 56 |
| 38 | 67 |
| 39 | 69 |
| 40 | 56 |
| 43 | 41 |
| 44 | 41 |
| 45 | 62 |
| 46 | 60 |
| 47 | 56 |
| 48 | 57 |
| 49 | 74 |
| 50 | 10 |
| 51 | 17 |
| 52 | 45 |
| 53 | 38 |
| 54 | 28 |
| 55 | 18 |
| 56 | 96 |
| 57 | 35 |
| 58 | 75 |
| 61 | 97 |
| 63 | 99 |
| 64 | 98 |
| 65 | 95 |
| 66 | 99 |
| 70 | 97 |
| 74 | 90 |
| 79 | 96 |
| 81 | 93 |
| 89 | 85 |
| 97 | 91 |
| 98 | 100 |
| 101 | 97 |
| 102 | 94 |
| 113 | 60 |
| 174 | 25 |
| 176 | 8 |
| 196 | 93 |
| 231 | 97 |
| 239 | 98 |
| 240 | 92 |
| 241 | 97 |
| 243 | 93 |
| 245 | 98 |
| 248 | 97 |
| 249 | 97 |
| 251 | −220 |
| 252 | −77 |
| 253 | 98 |
| 256 | 94 |
| 257 | 91 |
| 258 | 97 |
| 260 | 95 |
| 261 | 92 |
| 262 | 95 |
| 263 | 93 |
| 267 | 92 |
| 268 | 95 |
| 269 | 92 |
| 283 | 96 |
| 288 | 94 |
| 295 | 95 |
| 298 | 90 |
| 300 | 87 |
| 301 | 88 |
| 308 | 92 |
| 312 | 86 |
| 313 | 90 |
| 314 | 93 |
| 315 | 90 |
| 316 | 85 |
| 320 | 84 |
| 321 | 95 |
| 325 | 83 |

TABLE 10-continued

Results of histaminergic H1 receptor affinity tests for representative compounds

| Compd. | H1 [%] |
|---|---|
| 331 | 97 |
| 338 | 95 |
| 347 | 98 |
| 352 | 97 |
| 356 | 80 |
| 357 | 84 |
| 358 | 74 |
| 359 | 60 |
| 363 | 70 |
| 418 | 55 |
| 419 | 12 |
| 423 | 16 |
| 424 | 28 |
| 425 | 6 |
| 438 | 67 |
| 439 | 18 |
| 445 | 60 |

TABLE 11

Results of muscarinic M3 receptor affinity tests for representative compounds

| Compd. | M3 [%] |
|---|---|
| 1 | 13 |
| 2 | 17 |
| 3 | 13 |
| 4 | 3 |
| 5 | 7 |
| 6 | −1 |
| 7 | 13 |
| 8 | −11 |
| 9 | −2 |
| 10 | −2 |
| 11 | −6 |
| 12 | −9 |
| 13 | −1 |
| 14 | −6 |
| 15 | −9 |
| 16 | −1 |
| 17 | 7 |
| 18 | 6 |
| 19 | 9 |
| 20 | −9 |
| 21 | 2 |
| 22 | 12 |
| 23 | −2 |
| 24 | 10 |
| 25 | 6 |
| 26 | 17 |
| 27 | 46 |
| 28 | 50 |
| 29 | 25 |
| 30 | 66 |
| 33 | 5 |
| 34 | 9 |
| 35 | 4 |
| 36 | −3 |
| 37 | 11 |
| 38 | 9 |
| 39 | 11 |
| 40 | 10 |
| 43 | −7 |
| 44 | 11 |
| 45 | 9 |
| 46 | 8 |
| 47 | 3 |
| 48 | 8 |
| 49 | 10 |
| 50 | 10 |
| 51 | 1 |

TABLE 11-continued

Results of muscarinic M3 receptor affinity tests for representative compounds

| Compd. | M3 [%] |
|---|---|
| 52 | 5 |
| 53 | 8 |
| 54 | 8 |
| 55 | 8 |
| 56 | 3 |
| 57 | 10 |
| 58 | 11 |
| 61 | 5 |
| 63 | 11 |
| 64 | 7 |
| 65 | 8 |
| 66 | 10 |
| 70 | 25 |
| 74 | 17 |
| 79 | 12 |
| 81 | 6 |
| 89 | 22 |
| 97 | 16 |
| 98 | 16 |
| 101 | 14 |
| 102 | 18 |
| 113 | 29 |
| 174 | 15 |
| 176 | 6 |
| 196 | 18 |
| 231 | 11 |
| 239 | 9 |
| 240 | 15 |
| 241 | 4 |
| 243 | 10 |
| 245 | 25 |
| 248 | 13 |
| 249 | 9 |
| 251 | 8 |
| 252 | 16 |
| 253 | 24 |
| 256 | 15 |
| 257 | 12 |
| 258 | 15 |
| 260 | 11 |
| 261 | 15 |
| 262 | 19 |
| 263 | 7 |
| 267 | 13 |
| 268 | 14 |
| 269 | 20 |
| 283 | −4 |
| 288 | 3 |
| 295 | 19 |
| 298 | 19 |
| 300 | 18 |
| 301 | 18 |
| 308 | 30 |
| 312 | 19 |
| 313 | 25 |
| 314 | 13 |
| 315 | 24 |
| 316 | 28 |
| 320 | 24 |
| 321 | 14 |
| 325 | 26 |
| 331 | 10 |
| 338 | 1 |
| 347 | 12 |
| 352 | 12 |
| 356 | 2 |
| 357 | 25 |
| 358 | 17 |
| 359 | 63 |
| 363 | 15 |
| 418 | 4 |
| 419 | −8 |
| 423 | −1 |
| 424 | 7 |
| 425 | 2 |

TABLE 11-continued

Results of muscarinic M3 receptor affinity tests for representative compounds

| Compd. | M3 [%] |
|---|---|
| 438 | 15 |
| 439 | 16 |
| 445 | 27 |

TABLE 12

Results of serotoninergic 5-HT2C receptor affinity tests for representative compounds

| Cpd. | 5-HT2C [%] |
|---|---|
| 1 | 80 |
| 2 | 89 |
| 3 | 77 |
| 4 | 91 |
| 5 | 81 |
| 6 | 88 |
| 7 | 89 |
| 8 | 90 |
| 9 | 24 |
| 10 | 54 |
| 11 | 40 |
| 12 | 17 |
| 13 | 34 |
| 14 | 51 |
| 15 | 23 |
| 16 | 53 |
| 17 | 62 |
| 18 | 73 |
| 19 | 56 |
| 20 | 75 |
| 21 | 87 |
| 22 | 73 |
| 23 | 44 |
| 24 | 65 |
| 25 | 32 |
| 26 | 19 |
| 27 | −1 |
| 28 | 6 |
| 29 | 11 |
| 30 | 11 |
| 33 | 27 |
| 34 | 51 |
| 35 | 30 |
| 36 | 34 |
| 37 | 35 |
| 38 | 31 |
| 39 | 50 |
| 40 | 50 |
| 43 | 67 |
| 44 | 56 |
| 45 | 70 |
| 46 | 73 |
| 47 | 60 |
| 48 | 64 |
| 49 | 92 |
| 50 | 18 |
| 51 | 14 |
| 52 | 36 |
| 53 | 28 |
| 54 | 24 |
| 55 | 26 |
| 56 | 50 |
| 57 | 58 |
| 58 | 21 |
| 61 | 95 |
| 63 | 95 |
| 64 | v |
| 65 | 95 |
| 66 | 86 |
| 70 | 88 |
| 74 | 78 |

TABLE 12-continued

Results of serotoninergic 5-HT2C receptor affinity tests for representative compounds

| Cpd. | 5-HT2C [%] |
|---|---|
| 79 | 72 |
| 81 | 50 |
| 89 | 34 |
| 97 | 89 |
| 98 | 91 |
| 101 | 80 |
| 102 | 76 |
| 113 | 10 |
| 174 | 0 |
| 176 | 9 |
| 196 | 89 |
| 231 | 87 |
| 239 | 88 |
| 240 | 78 |
| 241 | 96 |
| 243 | 81 |
| 245 | 72 |
| 248 | 84 |
| 249 | 89 |
| 251 | 83 |
| 252 | 84 |
| 253 | 89 |
| 256 | 94 |
| 257 | 83 |
| 258 | 86 |
| 260 | 90 |
| 261 | 87 |
| 262 | 84 |
| 263 | 87 |
| 267 | 78 |
| 268 | 78 |
| 269 | 92 |
| 283 | 80 |
| 288 | 32 |
| 295 | 51 |
| 298 | 52 |
| 300 | 49 |
| 301 | 79 |
| 308 | 57 |
| 312 | 80 |
| 313 | 59 |
| 314 | 85 |
| 315 | 78 |
| 316 | 66 |
| 320 | 46 |
| 321 | 65 |
| 325 | 49 |
| 331 | 82 |
| 338 | 76 |
| 347 | 99 |
| 352 | 78 |
| 356 | 83 |
| 357 | 83 |
| 358 | 62 |
| 359 | 12 |
| 363 | 57 |
| 418 | 19 |
| 419 | 7 |
| 423 | 9 |
| 424 | 8 |
| 425 | 24 |
| 438 | 59 |
| 439 | 41 |
| 445 | 67 |

EXAMPLE 5

In Vitro Pharmacology

Cellular Functional Assays

The results are expressed as a percent of control specific agonist response ((measured specific response/control specific agonist response)×100) for agonist effect and as a percent inhibition of control specific agonist response (100−((measured specific response/control specific agonist response)×100)) for antagonist effect obtained in the presence of the test compounds. The compounds were tested at the concentration of $1×10^{-6}$ M.

Conditions and methodology (by reference to the literature) of cellular functional assays are given in Table 13 and the tests results for representative compounds are given in Table 14 (dopaminergic receptor D2), in Table 15 (dopaminergic receptor D3), in Table 16 (serotoninergic receptor 5-HT1A), in Table 17 (serotoninergic receptor 5-HT2A), in Table 18 (serotoninergic receptor 5-HT6), in Table 19 (serotoninergic receptor 5-HT7), in Table 20 (adrenergic α1 receptor), in Table 21 (adrenergic α2C receptor), in Table 22 (histaminergic H1 receptor) and in Table 23 (serotoninergic 5-HT2C receptor). In the Tables ag refers to agonism, and antag to antagonism),

TABLE 13

Conditions and methodology of in vitro tests for cellular functional assays

| Assay | Origin | Stimulus | Incubation | Reaction Product | Method of Detection | Ref. |
|---|---|---|---|---|---|---|
| $M_3$ (h) (agonist effect) | human recombinant (CHO cells) | none (1 μM acetylcholine for control) | 22° C. | intracellular $[Ca^{2+}]$ | Fluorimetry | 14 |
| $M_3$ (h) (antagonist effect) | human recombinant (CHO cells) | acetylcholine (10 nM) | 22° C. | intracellular $[Ca^{2+}]$ | Fluorimetry | 14 |
| 5-HT7 (h) (agonist effect) | human recombinant (CHO cells) | none (10 μM serotonin for control) | 45 min 37° C. | cAMP | HTRF | 15 |
| 5-HT7 (h) (antagonist effect) | human recombinant (CHO cells) | serotonin (300 nM) | 45 min 37° C. | cAMP | HTRF | 15 |
| 5-HT6 (h) (agonist effect) | human recombinant (CHO cells) | none (10 μM serotonin for control) | 45 min 37° C. | cAMP | HTRF | 16 |
| 5-HT6 (h) (antagonist effect) | human recombinant (CHO cells) | serotonin (100 nM) | 45 min 37° C. | cAMP | HTRF | 16 |
| D2S (h) (agonist effect) | human recombinant (HEK-293 cells) | none (3 μM dopamine for control) | 28° C. | impedance | cellular dielectric spectroscopy | 17 |
| D2S (h) (antagonist effect) | human recombinant (HEK-293 cells) | dopamine (30 nM) | 28° C. | impedance | cellular dielectric spectroscopy | 17 |
| 5-HT2C (h) (agonist effect) | human recombinant (HEK-293 cells) | none (1 μM serotonin for control) | 30 min 37° C. | IP1 | HTRF | 18 |
| 5-HT2C (h) (antagonist effect) | human recombinant (HEK-293 cells) | serotonin (10 nM) | 30 min 37° C. | IP1 | HTRF | 18 |
| H1 (h) (agonist effect) | human recombinant (HEK-293 cells) | none (10 μM histamine for control) | 22° C. | intracellular [Ca2+] | Fluorimetry | 19 |
| H1 (h) (antagonist effect) | human recombinant (HEK-293 cells) | histamine (300 nM) | 22° C. | intracellular [Ca2+] | Fluorimetry | 19 |
| $α_{1A}$ (h) (agonist effect) | human recombinant (CHO cells) | none (30 nM epinephrine for control) | 22° C. | intracellular [Ca2+] | Fluorimetry | 20 |
| $α_{1A}$ (h) (antagonist effect) | human recombinant (CHO cells) | epinephrine (3 nM) | 22° C. | intracellular [Ca2+] | Fluorimetry | 20 |
| 5-HT2A (h) (agonist effect) | human recombinant (HEK-293 cells) | none (100 nM serotonin for control) | 30 min 37° C. | IP1 | HTRF | 18 |
| 5-HT2A (h) (antagonist effect) | human recombinant (HEK-293 cells) | serotonin (100 nM) | 30 min 37° C. | IP1 | HTRF | 13 |
| D3 (h) (agonist effect) | human recombinant (CHO cells) | none (300 nM dopamine for control) | 10 min 37° C. | cAMP | HTRF | 21 |
| D3 (h) (antagonist effect) | human recombinant (CHO cells) | dopamine (10 nM) | 10 min 37° C. | cAMP | HTRF | 21 |
| 5-HT1A (h) (agonist effect) | human recombinant (CHO cells) | none (100 nM 8-OH-DPAT for control) | 15 min 22° C. | cAMP | HTRF | 22 |
| 5-HT1A (h) (antagonist effect) | human recombinant (CHO cells) | 8-OH-DPAT (10 nM) | 15 min 22° C. | cAMP | HTRF | 22 |
| $α_{2C}$ (h) (agonist effect) | human recombinant (CHO cells) | none (1 μM epinephrine for control) | 10 min 37° C. | cAMP | HTRF | 23 |
| $α_{2C}$ (h) (antagonist effect) | human recombinant (CHO cells) | epinephrine (100 nM) | 10 min 37° C. | cAMP | HTRF | 23 |

TABLE 14

Results of cellular functional assays for dopaminergic D2 receptor for representative compounds

| Cpd. | D2-ag [%] | D2-antag. [%] |
|---|---|---|
| 1 | −1 | 95 |
| 2 | 2 | 97 |
| 7 | 0 | 91 |
| 8 | 7 | 85 |
| 13 | 2 | 95 |
| 14 | 4 | 98 |
| 15 | 2 | 88 |
| 16 | 4 | 98 |
| 18 | −1 | 98 |
| 22 | 2 | 99 |
| 26 | 29 | 99 |
| 27 | 40 | 100 |
| 28 | 49 | 105 |
| 29 | 45 | 99 |
| 30 | 43 | 97 |
| 32 | 35 | 89 |
| 33 | 37 | 98 |
| 34 | 21 | 66 |
| 35 | 27 | 65 |
| 36 | 28 | 92 |
| 37 | 21 | 82 |
| 38 | 31 | 84 |
| 39 | 30 | 90 |
| 40 | 36 | 94 |
| 43 | 20 | 55 |
| 44 | 16 | 45 |
| 45 | 20 | 82 |
| 46 | 23 | 80 |
| 47 | 26 | 66 |
| 48 | 22 | 53 |
| 49 | 11 | 100 |
| 50 | 15 | 26 |
| 51 | 10 | 37 |
| 53 | 5 | 60 |
| 56 | 42 | 106 |
| 57 | 10 | 100 |
| 61 | 4 | 77 |
| 65 | 10 | 74 |
| 79 | 3 | 77 |
| 81 | 4 | 73 |
| 97 | 4 | 95 |
| 98 | 4 | 80 |
| 101 | 6 | 85 |
| 102 | 1 | 85 |
| 113 | 42 | 94 |
| 239 | 13 | 84 |
| 240 | 3 | 83 |
| 241 | 6 | 82 |
| 288 | 5 | 79 |
| 298 | 12 | 84 |
| 312 | 4 | 90 |
| 313 | −5 | 85 |
| 314 | 9 | 86 |
| 331 | 4 | 87 |
| 338 | 3 | 88 |
| 352 | 12 | 88 |
| 358 | 30 | 84 |
| 359 | 39 | 96 |
| 363 | 50 | 94 |
| 423 | 41 | 96 |
| 424 | 44 | 97 |
| 452 | 24 | 53 |

TABLE 15

Results of cellular functional assays for dopaminergic D3 receptor for representative compounds

| Compd. | D3-ag [%] | D3-antag. [%] |
|---|---|---|
| 1 | −17 | 49 |
| 2 | −15 | 81 |
| 7 | −21 | 66 |
| 8 | −24 | 73 |
| 14 | −15 | 92 |
| 18 | −27 | 114 |
| 22 | −25 | 81 |
| 26 | 64 | −8 |
| 28 | 59 | −2 |
| 30 | 52 | 35 |
| 33 | 60 | −1 |
| 36 | 29 | 53 |
| 40 | 33 | 59 |
| 45 | 18 | |
| 46 | 18 | 48 |
| 48 | 14 | 54 |
| 49 | −3 | 71 |
| 53 | 5 | 48 |
| 56 | 34 | 45 |
| 57 | 24 | 41 |
| 61 | 4 | 45 |
| 79 | −9 | 77 |
| 81 | −10 | 76 |
| 89 | −18 | 69 |
| 97 | −23 | 87 |
| 98 | −10 | 109 |
| 101 | −18 | 112 |
| 102 | 4 | 83 |
| 113 | 39 | 30 |
| 239 | 6 | 84 |
| 240 | 8 | 72 |
| 241 | 7 | 78 |
| 283 | −10 | 58 |
| 288 | 0 | 72 |
| 298 | −8 | 99 |
| 312 | 10 | 97 |
| 313 | 8 | 81 |
| 314 | −30 | 110 |
| 331 | −15 | 114 |
| 338 | −10 | 109 |
| 352 | −18 | 113 |
| 358 | 47 | 35 |
| 359 | 25 | 79 |
| 363 | 65 | −3 |
| 423 | 70 | 22 |
| 424 | 70 | 18 |

TABLE 16

Results of cellular functional assays for serotoninergic 5-HT1A receptor for representative compounds

| Compd. | 5-HT1A -ag [%] | 5-HT1A -antag. [%] |
|---|---|---|
| 2 | 47 | 18 |
| 7 | 59 | 51 |
| 8 | 14 | 81 |
| 16 | −14 | 91 |
| 22 | 0 | 99 |
| 26 | 67 | 22 |
| 27 | 56 | 48 |
| 28 | 63 | 27 |
| 29 | 71 | 26 |
| 30 | 22 | 86 |
| 33 | 63 | 24 |
| 34 | 97 | −31 |
| 35 | 102 | −37 |
| 36 | 99 | −33 |
| 37 | 92 | −28 |
| 38 | 94 | −33 |

TABLE 16-continued

Results of cellular functional assays for serotoninergic 5-HT1A receptor for representative compounds

| Compd. | 5-HT1A -ag [%] | 5-HT1A -antag. [%] |
|---|---|---|
| 39 | 86 | −25 |
| 40 | 102 | −37 |
| 43 | 87 | −27 |
| 44 | 90 | −29 |
| 45 | 99 | −27 |
| 46 | 92 | −20 |
| 47 | 90 | −31 |
| 48 | 90 | −24 |
| 49 | 82 | 7 |
| 50 | 98 | −34 |
| 51 | 86 | −27 |
| 53 | 90 | −6 |
| 56 | 92 | −6 |
| 57 | 92 | −8 |
| 61 | 75 | 20 |
| 65 | 9 | 35 |
| 81 | 5 | 22 |
| 97 | 13 | 38 |
| 102 | 1 | 35 |
| 113 | 32 | 92 |
| 239 | 7 | 58 |
| 240 | 9 | 50 |
| 241 | 5 | 42 |
| 358 | 22 | 70 |
| 359 | 22 | 94 |
| 363 | 78 | 27 |
| 423 | 35 | 73 |
| 424 | 23 | 75 |
| 452 | 30 | 7 |

TABLE 17

Results of cellular functional assays for serotoninergic 5-HT2A receptor for representative compounds

| Compd. | 5-HT2A -ag [%] | 5-HT2A -antag. [%] |
|---|---|---|
| 1 | 0 | 99 |
| 2 | 2 | 102 |
| 7 | 0 | 100 |
| 8 | −2 | 99 |
| 13 | 2 | 100 |
| 14 | 1 | 100 |
| 15 | −1 | 100 |
| 16 | −1 | 98 |
| 18 | −1 | 102 |
| 22 | −1 | 102 |
| 26 | −1 | 77 |
| 33 | −1 | 41 |
| 61 | 0 | 97 |
| 65 | −2 | 98 |
| 79 | −2 | 97 |
| 81 | −1 | 95 |
| 89 | −2 | 94 |
| 97 | −3 | 102 |
| 98 | −2 | 97 |
| 101 | −1 | 100 |
| 102 | −2 | 99 |
| 239 | −2 | 94 |
| 240 | −3 | 93 |
| 241 | −2 | 99 |
| 283 | 0 | 99 |
| 288 | −2 | 97 |
| 298 | −1 | 99 |
| 312 | −2 | 98 |
| 313 | −3 | 98 |
| 314 | −2 | 99 |
| 331 | −1 | 98 |
| 338 | −1 | 100 |
| 352 | −1 | 100 |

TABLE 17-continued

Results of cellular functional assays for serotoninergic 5-HT2A receptor for representative compounds

| Compd. | 5-HT2A -ag [%] | 5-HT2A -antag. [%] |
|---|---|---|
| 358 | −1 | 57 |
| 363 | −1 | 62 |

TABLE 18

Results of cellular functional assays for serotoninergic 5-HT6 receptor for representative compounds

| Cpd. | 5-HT6 -ag [%] | 5-HT6 -antag. [%] |
|---|---|---|
| 1 | 1 | 39 |
| 2 | 2 | 28 |
| 3 |  | 22 |
| 4 | −1 | 37 |
| 5 |  | 18 |
| 6 |  | 26 |
| 7 | 1 | 65 |
| 8 | −1 | 64 |
| 9 | 0 | −4 |
| 10 | 1 | −16 |
| 11 | −1 | −10 |
| 12 | −1 | −2 |
| 13 | 1 | 56 |
| 14 | 1 | 69 |
| 15 | 2 | 21 |
| 16 | 0 | 50 |
| 17 | 2 | 69 |
| 18 | 1 | 87 |
| 19 | −1 | 23 |
| 20 | −2 | 23 |
| 21 | −2 | 39 |
| 22 | 1 | 82 |
| 23 | 0 | 1 |
| 24 | 2 | 9 |
| 25 | 0 | 6 |
| 28 | 0 | 53 |
| 36 | 1 | 7 |
| 49 | 2 | 71 |
| 53 | 1 | 87 |
| 56 | 2 | 92 |
| 57 | 3 | 86 |
| 61 | −2 | 72 |
| 65 | −1 | 81 |
| 79 | 1 | 76 |
| 81 | 1 | 88 |
| 89 | 0 | 83 |
| 97 | −2 | 95 |
| 98 | −2 | 79 |
| 101 | −2 | 103 |
| 102 | −1 | 82 |
| 239 | 0 | 70 |
| 240 | −2 | 71 |
| 241 | 0 | 69 |
| 283 | 0 | 64 |
| 288 | 0 | 74 |
| 298 | 0 | 89 |
| 312 | −1 | 76 |
| 313 | −3 | 91 |
| 314 | 0 | 91 |
| 331 | −1 | 98 |
| 338 | 0 | 88 |
| 352 | −2 | 75 |

TABLE 19

Results of cellular functional assays for serotoninergic 5-HT7 receptor for representative compounds

| Cpd. | 5-HT7-ag [%] | 5-HT7-antag. [%] |
|---|---|---|
| 1 | −1 | 97 |
| 2 | −1 | 80 |
| 3 | −2 | 93 |
| 4 | −1 | 81 |
| 5 | −1 | 85 |
| 6 | 0 | 66 |
| 7 | −1 | 98 |
| 8 | −1 | 82 |
| 9 | 0 | 48 |
| 10 | 0 | 85 |
| 11 | 0 | 85 |
| 12 | −1 | 68 |
| 13 | 1 | 95 |
| 14 | −1 | 85 |
| 15 | 0 | 96 |
| 16 | −1 | 80 |
| 17 | | 95 |
| 18 | −1 | 89 |
| 19 | −1 | 99 |
| 20 | −1 | 101 |
| 21 | 0 | 98 |
| 22 | −1 | 100 |
| 23 | 0 | 88 |
| 24 | 0 | 99 |
| 25 | −1 | 97 |
| 26 | 14 | 13 |
| 27 | 5 | 8 |
| 28 | 4 | 23 |
| 29 | 5 | 9 |
| 30 | 5 | 73 |
| 33 | 19 | 20 |
| 36 | 0 | 16 |
| 40 | −1 | 30 |
| 49 | −1 | 85 |
| 53 | 1 | 25 |
| 56 | 1 | 36 |
| 57 | 1 | 91 |
| 61 | −1 | 78 |
| 65 | −2 | 91 |
| 79 | −2 | 97 |
| 81 | −2 | 98 |
| 89 | −2 | 91 |
| 97 | −2 | 100 |
| 98 | −2 | 92 |
| 101 | −2 | 101 |
| 102 | −2 | 94 |
| 113 | 9 | 45 |
| 239 | −2 | 81 |
| 240 | −2 | 98 |
| 241 | −2 | 83 |
| 283 | −2 | 93 |
| 288 | −2 | 92 |
| 298 | −3 | 98 |
| 312 | −2 | 97 |
| 313 | −2 | 100 |
| 314 | −3 | 95 |
| 331 | −2 | 102 |
| 338 | −3 | 100 |
| 352 | −2 | 102 |
| 358 | 10 | 28 |
| 359 | 8 | 43 |
| 363 | 6 | 24 |
| 424 | 18 | 43 |

TABLE 20

Results of cellular functional assays for adrenergic α1A receptor for representative compounds

| Compd. | α1A-ag [%] | α1A-antag. [%] |
|---|---|---|
| 1 | 0 | 100 |
| 2 | 0 | 100 |
| 7 | 0 | 100 |
| 8 | 0 | 100 |
| 13 | 0 | 100 |
| 14 | 0 | 100 |
| 16 | 0 | 100 |
| 18 | 0 | 99 |
| 22 | 0 | 100 |
| 26 | 0 | 100 |
| 27 | 1 | 100 |
| 30 | 0 | 97 |
| 33 | 0 | 100 |
| 61 | 0 | 100 |
| 65 | 0 | 98 |
| 81 | 1 | 100 |
| 89 | −1 | 100 |
| 97 | 0 | 99 |
| 98 | 0 | 99 |
| 101 | 0 | 100 |
| 102 | 0 | 100 |
| 113 | 1 | 100 |
| 239 | −1 | 100 |
| 240 | 0 | 100 |
| 241 | 0 | 95 |
| 283 | 0 | 100 |
| 288 | 0 | 97 |
| 298 | 1 | 100 |
| 312 | 0 | 100 |
| 313 | 0 | 100 |
| 314 | 1 | 100 |
| 331 | 1 | 100 |
| 338 | 2 | 100 |
| 352 | 1 | 100 |
| 359 | 1 | 100 |
| 363 | 0 | 100 |
| 423 | 16 | 70 |
| 424 | 39 | 76 |

TABLE 21

Results of cellular functional assays for adrenergic α2C receptor for representative compounds

| Compd. | α2C-ag [%] | α2C-antag. [%] |
|---|---|---|
| 1 | −9 | 7 |
| 2 | −8 | 30 |
| 7 | −6 | 2 |
| 8 | −16 | 1 |
| 13 | −7 | 18 |
| 14 | −3 | 12 |
| 16 | −7 | 9 |
| 18 | −10 | 28 |
| 22 | −8 | 12 |
| 26 | 25 | 53 |
| 27 | 3 | 31 |
| 28 | 4 | 27 |
| 30 | 18 | 35 |
| 33 | −1 | 6 |
| 36 | −2 | 4 |
| 40 | −9 | 9 |
| 56 | 20 | 4 |
| 61 | 1 | 18 |
| 65 | 8 | 20 |
| 79 | 7 | 22 |
| 81 | 9 | 20 |
| 89 | −10 | 7 |
| 97 | −4 | 36 |
| 98 | −1 | 16 |

TABLE 21-continued

Results of cellular functional assays for adrenergic
α2C receptor for representative compounds

| Compd. | α2C -ag [%] | α2C -antag. [%] |
|---|---|---|
| 101 | 1 | 46 |
| 102 | −7 | 14 |
| 113 | 13 | 53 |
| 239 | 3 | 33 |
| 240 | 13 | 35 |
| 241 | −1 | 14 |
| 283 | 2 | 25 |
| 288 | 1 | 13 |
| 298 | −4 | 19 |
| 312 | 61 | 39 |
| 313 | −11 | 46 |
| 314 | −2 | 30 |
| 331 | −14 | 7 |
| 338 | −3 | 9 |
| 352 | −16 | 16 |
| 358 | 28 | 48 |
| 359 | 13 | 38 |
| 363 | 17 | 42 |

TABLE 22

Results of cellular functional assays for histaminergic
H1 receptor for representative compounds

| Cpd. | H1 -ag [%] | H1 -antag. [%] |
|---|---|---|
| 1 | 0 | 51 |
| 2 | −1 | 48 |
| 7 | 1 | 70 |
| 8 | 1 | 98 |
| 56 | 0 | 68 |
| 61 | 1 | 76 |
| 65 | 0 | 60 |
| 79 | 0 | 57 |
| 81 | 1 | 38 |
| 97 | 3 | 57 |
| 98 | −1 | 78 |
| 101 | 33 | 94 |
| 102 | 0 | 48 |
| 239 | 0 | 54 |
| 240 | 0 | 69 |
| 241 | 1 | 47 |
| 283 | 0 | 41 |
| 288 | 0 | 57 |
| 298 | 30 | 90 |
| 313 | 4 | 47 |
| 314 | 5 | 50 |
| 331 | 2 | 85 |
| 338 | 1 | 51 |
| 352 | 1 | 60 |

TABLE 23

Results of cellular functional assays for serotoninergic
5-HT2C receptor for representative compounds

| Cpd. | 5-HT2C -ag [%] | 5-HT2C -antag. [%] |
|---|---|---|
| 65 | 0 | 18 |
| 98 | −5 | 35 |
| 241 | −4 | 52 |

EXAMPLE 6

Ability to block hERG potassium channels was determined using the electrophysiological method and cloned hERG potassium channels (KCNH2 gene, expressed in CHO cells) as biological material. The effects were evaluated using IonWorks™ Quattro system (MDS-AT).

hERG Test Procedures hERG current was elicited using a pulse pattern with fixed amplitudes (conditioning prepulse: −80 mV for 25 ms; test pulse: +40 mV for 80 ms) from a holding potential of 0 mV. hERG current was measured as a difference between the peak current at 1 ms after the test step to +40 mV and the steady-state current at the end of the step to +40 mV.

Data Analysis

Data acquisition and analyses was performed using the IonWorks Quattro™ system operation software (version 2.0.2; Molecular Devices Corporation, Union City, Calif.). Data were corrected for leak current.

The hERG block was calculated as: % Block=(1−I TA/IControl)×100%, where IControl and ITA were the currents elicited by the test pulse in control and in the presence of a test compound, respectively. Results are presented in Table 24.

TABLE 24

Results of hERG potassium channels affinity
tests for representative compounds

| Cpd. | hERG [%] |
|---|---|
| 1 | 16 |
| 2 | 14 |
| 3 | 17 |
| 5 | 17 |
| 6 | 13 |
| 7 | 14 |
| 14 | −1.4 |
| 17 | 24 |
| 18 | 30 |
| 22 | 52 |
| 30 | −3 |
| 31 | 2 |
| 36 | 2.4 |
| 50 | 6 |
| 53 | 12 |
| 55 | 8 |
| 56 | 9 |
| 57 | 0 |
| 61 | 12 |
| 97 | 1 |
| 101 | 14 |
| 113 | 16 |
| 331 | 32 |
| 338 | 40.5 |
| 358 | 0 |
| 359 | 9 |
| 360 | 5 |
| 363 | 0 |
| 445 | 2 |

EXAMPLE 7

Guinea-Pig Ileum Test

Ileum was prepared from male guinea-pigs with 300-350 g of body weight, fasted for 24 h before experiment with free access to drinking water. Terminal ileum was dissected and placed into a Krebs solution (NaCl 120 mM, KCl 5.6 mM, $MgCl_2$ 2.2 mM, $CaCl_2$ 2.4 mM, NaHCO, 19 mM, glucose 10 mM) and 2 cm-tong fragments were cut. Each segment of the gut was placed in 30 ml chamber filled with the Krebs solution at 37 C, pH 7.4, with constant oxygenation ($O_2/CO_2$, 19:1), fixed by the lower end to a glass rod and by the upper end to the force-displacement transducer FDT 10-A (Biopac Systems. COMMAT, Ltd., Turkey). The preparation was allowed to stabilize in organ baths for 60 min under a resting tension of 0.5 g, washing every 15 min with fresh Krebs solution. AU responses were recorded using software Biopac Systems Inc MP-35 Data Acquisition, Turkey.

Stock solutions of test and reference compounds were prepared in concentration $10^{-3}$ M. About 1 mg of each tested compound was weighed and dissolved in appropriate volume of dimethylsulfoxide, ethanol or water or in a mixture of them (depending on the solubility). In next step, stock solutions were diluted 10× in water.

The equilibration period a cumulative concentration-response curve was constructed in each tissue for respective agonist-carbachol ($3\times10^{-9}$-$3\times10^{-6}$ M) or histamine ($10^{-8}$-$10^{-5}$ M) by the method of van Rossum (Ref. 24). Following the first agonist curve, tissues were incubated with one of the concentrations of tested compounds for 15 min and the next cumulative concentration curve to agonist was obtained. Only one concentration of the antagonist was tested in each piece of tissue. Experiments were repeated three to eight times.

After the equilibration period a cumulative concentration-response curve was constructed in each tissue for histamine ($10^{-8}$-$10^{-5}$ M) by the method of van Rossum. Following the first histamine curve, tissues were incubated with one of the concentrations of tested compounds for 15 min and the next cumulative concentration curve to histamine was obtained. Only one concentration of the antagonist was tested in each piece of tissue. Experiments were repeated three to seven times.

Concentration-response curves were analysed using GraphPad Prism 4.0 (GraphPad Software Inc., San Diego, Calif., USA). Contractile responses to carbachol (in the presence or absence of tested compounds) are expressed as a percentage of maximal carbachol effect (Emax=100%), reached in the concentration-response curves obtained before incubation with the tested compounds. The data are expressed as the mean±SEM of at least four separate experiments. The affinity was estimated with the equation pKB=log(concentration ratio−1)−log(molar antagonist concentration), where the concentration ratio is the ratio of equieffective agonist concentrations in the absence and in the presence of the antagonist.

TABLE 25

Results of Guinea-pig ileum test for representative compounds

| Compound | M ant *(pKb) | H ant** (pKb) |
|---|---|---|
| 1 | 5.102 | 6.303 |
| 2 | 5.54 | 6.34 |
| 3 | 4.74 | 6.83 |

* antagonistic activity towards muscarinic receptor
** antagonistic activity towards histaminergic receptor Results of in vitro tests as described in Examples 4-7 show that compounds of the invention display high affinity for dopamine and serotonin receptors, especially D2, D3, 5-HT1A, 5-HT2A, 5-HT6 and 5-HT7 subtypes, adrenergic alpha2C and alpha1A as well as sigma receptors and serotonin transporter. Most of the tested compounds possess antagonistic profile for all of the receptors they have affinity for, with some of them showing partially agonistic properties for D2 and/or D3 receptors as well as fully or partially agonistic activity towards 5-HT1A receptors. This confirms their potential usefulness in the treatment of diseases connected with disturbances in dopaminergic, serotoninergic and noradrenergic transmission, e.g. psychoses, depression as well as anxiety disorders etc. It should be stressed that some of the compounds possess parallel (simultaneous) affinity for D2,5-HT6 and 5-HT7 receptors, displaying efficient antagonistic properties for all of them, which particularly differentiates them from the compounds currently used for treatment of abovementioned diseases. Such a pharmacological profile suggests possible efficacy in the treatment of psychoses as well as precognitive and antidepressant activity. In the same time compounds of the invention possess weak affinity for potassium hERG channel and muscarine receptors as well as moderate affinity for H1 and 5-HT2C receptors, what may potentially contribute to reduced side effects such as, arrhythmia, vegetative disorders, weight gain and metabolic disorders, which are frequently caused by many of the currently used drugs for treatment of the abovementioned diseases.

Tests In Vivo

EXAMPLE 8

Activity testing in mice

Male CD-1 mice weighing 20-22 g derived from accredited animal facility localized at Medical College of Jagiellonian University, male C57BL/6J mice weighing 20-21 g and male Swiss Albino mice weighing 21-22 g derived from the licensed dealer (Staniszewska; Ilkowice, Poland) were group-housed for 3-4 day period in polycarbonate Makrolon type 3 cages (dimensions 26.5×15×42 cm) in an environmentally controlled, experimental room (ambient temperature 22-20C; relative humidity 50-60%; 12:12 light:dark cycle, lights on at 8:00), in groups of 15. Male Wistar rats weighing 205-225 g upon arrival from accredited animal facility Charles River (Sulzfeld, Germany) were group-housed for 6 day period in polycarbonate Makrolon type 3 cages (dimensions 26.5×15×42 cm) in an environmentally controlled room (ambient temperature 20-22° C.; relative humidity 50-60%; 12:12 light:dark cycle, lights on at 8:00), in groups of 4. Standard laboratory food (LSM-B) and filtered water were freely available. Standard laboratory food (Ssniff M-Z) and filtered water were freely available. On the day before experiments the equipment produces "white noise" was turned on for 30 minutes and mice or rats were weighted exact to 1 g. Animals were assigned randomly to treatment groups. All the experiments were performed by two observers unaware of the treatment applied between 9:00 and 14:00 on separate groups of animals. All animals were used only once and were killed immediately after the experiment. All the experimental procedures were approved by the IV Local Bioethics Commission in Warszawa.

d-Amphetamine-Induced Locomotor Hyperactivity

The locomotor activity was recorded with an Opto M3 multi-channel activity monitor (MultiDevice Software v.1.3, Columbus Instruments). The mice were individually placed in plastic cages (22×12×13 cm) for 30 minutes habituation period, and then the crossings of each channel (ambulation) were counted during 1 h with data recording every 5 minutes. The cages were cleaned up with 70% ethanol after each mouse. Drugs were administered to 10 mice per treatment group, d-Amphetamine was administered 30 minutes before the test. Compound 22 was given 30 minutes before the experiment, and other compounds were given 60 minutes before the experiment.

TABLE 26

Results of d-amphetamine-induced locomotor hyperactivity test

| Compound | MED* [mg/kg] |
|---|---|
| 2 | 5 |
| 7 | 2 |
| 18 | 2.5 |
| 22 | 2.5 |
| 97 | 2.5 |

*minimum effective dose [mg of compound/kg of body weight]

MK-801-Induced Locomotor Hyperactivity

The locomotor activity was recorded according to method described above. Instead of d-Amphetamine, MK-801 was administered 15 min before the test. Compound 22 was given 30 minutes before the experiment.

TABLE 27

Results of MK-801-induced locomotor hyperactivity test

| Compound | MED* [mg/kg] |
|---|---|
| 22 | 1.25 |

Tail Suspension Test in C57BL/6J Mice

The testing procedure was based on a method of Steru et al. (The tail suspension test: a new method for screening antidepressants in mice, Psychopharmacology 85, 367-370, 1985). An automated device (Kinder Scientific) was used. Mice were suspended by the tail with tape to an aluminum hook connected to a strain gauge. Mice were positioned such that the base of their tail was aligned with the bottom of the hook. This positioning was found to decrease the propensity for mice to climb their tail during the test. A strain gauge connected to computer software detected any movements by the mouse in order to record the number of times (events) each subject enters into an escape behavior (struggling episodes), the duration of the event, and the average strength of each event during a 6-min test session. The total duration of immobility was calculated as the time the force of the mouse's movements was below a preset threshold. An optimum threshold was determined by comparing manually scored videotapes with automated scores. The following settings were used in all experiments: threshold 0.20 Newtons, off delay 30 msec. Drugs were administered to 7-8 mice per treatment group. Compound 22 was given 30 minutes, while Compound 36 was given 60 minutes before the experiment.

TABLE 28

Results of tail suspension test in C57BL/6J mice

| Compound | MED [mg/kg] |
|---|---|
| 22 | 0.156 |
| 36 | 0.312 |

Four-Plate Test in Swiss Mice

The four-plate test (BIOSEB, France) was performed in a cage (25×18×16 cm) floored by four identical rectangular metal plates (8×11 cm) separated from one another by a gap of 4 mm. The top of the cage was covered by a transparent Perspex lid that prevented escape behaviour. The plates were connected to a device that can generated electric shocks. Following a 15-s habituation period, the animal's motivation to explore a novel environment was suppressed by an electric foot shock (0.8 mA, 0.5 s) every time it moved from one plate to another during a 1-minute test session (Aron et al., Evaluation of a rapid technique for detecting minor tranquilizers, Neuropharmacology 10, 459-469, 1971). This action is referred to as a 'punished crossing', and was followed by a 3 s shock interval, during which the animal could move across plates without receiving a shock. Drugs were administered to 8-10 mice per treatment group. Compound 22 was given 30 minutes, while Compound 36 was given 60 minutes before the experiment.

TABLE 29

Results of four-plate test in mice

| Compound | MED [mg/kg] |
|---|---|
| 22 | 0.312 |
| 36 | 0.312 |

EXAMPLE 9

Activity Testing in Rats

Drug-naive male Wistar rats (Charles River, Sulzfeld, Germany) weighing 250-400 g were used in all experiments. Rats were housed two per standard plastic cage and kept in a room with constant environmental conditions (21.22° C., relative humidity 60%, a 12:12 light-dark cycle with lights on at 7:00 a.m.). Animals were supplied by the breeder two weeks before the onset of behavioral procedures. During this time, the subjects were weighed and handled several times. Tap water and standard lab chow (Labofeed H, WPIK, Kcynia, Poland) was available ad libitum.

Test Compounds

Compounds 22 and 36 were prepared as a suspension in 1% aqueous solution of Tween 80, whereas d-amphetamine and MK-801 were dissolved in distilled water immediately before administration. An injection volume of 10 ml/kg (mice) or 2 ml/kg (rats) was used throughout and all compounds were administered intraperitoneally (i.p.), except d-amphetamine that was given subcutaneously (s.c.).

Statistical Analysis

All the data are expressed as the mean±SEM. The statistical significance of effects was evaluated using separate one-way analysis of variance (ANOVA) with comparison between individual groups by Dunnett's test (when only one drug was given) or by the Tukey's test when two drugs were used; $p<0.05$, $p<0.01$ and $p<0.001$ were considered statistically significant. $ED_{50}$ values were calculated using Graph Pad Prism 5 Software.

Apomorphine-Induced Stereotyped Behaviour

All tests were carried out in a sound-attenuated experimental room between 9:00 a.m. and 3:00 p.m. Within 24 h prior to testing, rats were habituated to glass observation cages (25× 25×40 cm, W×H×L) with wood chip bedding on the floor for 20 min. On the day of testing, stereotyped behaviour was observed 20 to 25 min. after apomorphine injection (s.c.) as described by Bristow et al. (L-745,870, a subtype selective dopamine D4 receptor antagonist, does not exhibit a neuroleptic-like profile in rodent behavioral tests. J Pharmacol Exp Ther. 1997; 283:1256-63) and Feldman et al. (Mixed D2/5-HT2 antagonism differentially affects apomorphine- and amphetamine-induced stereotyped behavior. Pharmacol Biochem Behav. 1997:58:565-72). Rats were injected with apomorphine (0.6 mg/kg) and placed in the observation cages. Views of other rats in the experiment were prohibited. Twenty minutes later, the time spent licking/biting and sniffing downward was recorded by a trained observer for 5 minutes (300 s). Rats were pre-injected i.p. with a test drug 60 min. before the start of the 5-min. test session (the observation period).

The duration of stereotyped sniffing and licking/biting was analyzed with the aid of the Kruskal-Wallis analysis of variance (ANOVA). The Mann-Whitney U test was used for individual post hoc comparisons. P values lower than 0.05 were considered significant.

MK-801-Induced Stereotyped Behaviour

All tests were carried out in a sound-attenuated experimental room between 9:00 a.m. and 3:00 p.m. Within 24 h prior to testing, rats were habituated to glass observation cages (25× 25×40 cm, W×H×L) with wood chip bedding on the floor for 20 min. On the day of testing, stereotyped behaviour was observed 15 min. after MK-801 administration. Rats were injected with MK-801 (0.6 mg/kg, i.p.) and placed in the observation cages. Views of other rats in the experiment were prohibited. Fifteen minutes later, the time spent circling/head waving was recorded by a trained observer for 5 min. (300 s). Rats were pre-injected with a test drug 60 min. before the start of the observation period.

The duration of stereotyped circling as analyzed with the aid of the Kruskal-Wallis analysis of variance (ANOVA). The Mann-Whitney U test was used for individual post hoc comparisons. P values lower than 0.05 were considered significant.

2,5-Dimethoxy-4-iodoamphetamine (DOI)-induced Head Twitches

All tests were carried out in a sound-attenuated experimental room between 9:00 a.m. and 3:00 p.m. as described above for spontaneous head twitches. DOI-induced head twitches were scored as described by Millan et al. (S18327 (1-[2-[4-(6-fluoro-1,2-benzisoxazol-3-yl)piperid-1-yl]ethyl]3-phenyl imidazolin-2-one), a novel, potential antipsychotic displaying marked antagonist properties at alpha(1)- and alpha(2)-adrenergic receptors: II. Functional profile and a multiparametric comparison with haloperidol, clozapine, and 11 other antipsychotic agents. J Pharmacol Exp Ther 2000292:54-66). Rats were pre-injected i.p. with a test drug 60 min. before the start of the test session. Fifty five minutes later, rats were injected with DOI (2.5 mg/kg, i.p.) and placed in glass observation cages (25×25×40 cm, W×H×L) with wood chip bedding on the floor. Five minutes later, head twitches were counted for 5 minutes. (300 s) by a trained observer.

Total numbers of head twitches (n/5 min.) were analyzed by means of the Kruskal-Wallis analysis of variance (ANOVA). The Mann-Whitney U test was used for individual post hoc comparisons. P values lower than 0.05 were considered significant but values tower than 0.1 are also reported.

Conditioned Avoidance Response (CAR)

The effects of a test drug on conditioned response in rats were evaluated using active avoidance responding test. The apparatus consisted of six identical shuttle boxes (PACS-30, Columbus Instruments, USA). Each stainless steel box was 22.8 cm wide, 48.3 cm long and 27.6 cm high and was divided into two equal-sized compartments, separated by a sliding door end equipped with an overhead lights audio generator. An infrared-type beam assembly was used for detecting subject transfers. Each chamber floor was composed of stainless steel grid wired for presentation of a scrambled electric food shock (0.5 mA).

Rats trained to avoid the foot shock were placed in the experimental chambers for a 3 min. habituation period followed by 50 CAR trials presented on a 15-s variable interval (VI) schedule. Each trial consisted of a 10 s warning tone and stimulus light (conditioned stimulus) followed by 10 s electric shock (0.5 mA). If during the initial 10 s of the trial an animal crossed through the sliding door, the tone and light were terminated, no shock was applied, and the response was considered as "an avoidance response". If the animal crossed through the sliding door after a foot shock was initiated, the response was considered as "an escape response". If the animal did not cross the sliding door the response was considered as "none". If a response was made during an intertrial interval, it was punished with 0.5 s shock (0.5 mA). The PACS-30 software (Columbus) controlled the sessions and counted the number of trials in which a rat avoided the shock, escaped or did not respond. A stable demonstration of >80% of correct avoidance responses after 14-18 training sessions was a criterion for inclusion in subsequent drug tests. On test days, a tested drug was administered i.p. 60 minutes before the start of the test session. Each drug was tested at 3-4 different doses in the same group of eight animals. A 7-day wash-out period was introduced between the subsequent tests. Two CAR sessions were conducted during the wash-out in order to maintain stable conditioned responding. The number of CAR trials during the test and wash-out sessions was reduced to 30.

Avoidances, escapes, and "none" responses were analyzed with the aid of a one-way analysis of variance (ANOVA). The Newman-Keuls test was used for individual post hoc comparisons.

Passive Avoidance Procedure

Potentially impairing effects of test substance on learning and memory function in rats were evaluated using a step-through passive avoidance (PA) test. The apparatus consisted of 6 identical shuttle boxes divided into lighted and dark compartments (220×240×270 mm) and equipped with grid floors (PACS-30, Columbus Instruments, USA). The two compartments were separated by a sliding door.

In the training session (acquisition), animals were placed in the lighted compartment and allowed to explore it freely for 10 s. The sliding door was then opened, and the step-through latency for a rat to enter the dark compartment was measured. As soon as the rat entered the dark compartment, the door was closed. Three seconds later, an inescapable foot-shock (0.5 mA for 3 s) was delivered through the grid floor with a constant current shock generator. All animals entered the dark compartment within 300 s (a cut-off) and received a foot-shock.

Rats were pre-injected a test drug 60 minutes before the start of the training session.

The test (expression) session was performed 24 h after the training session. The same procedure was used (see above) but no foot-shock was delivered. A step-through latency for animals to enter the dark compartment was measured with a cut-off of 300 s.

Weights and step-trough latencies were analyzed with the aid of a one-way analysis of variance (ANOVA). The Newman-Keuls test was used for individual post hoc comparisons.

Prepulse Inhibition (PPI) Procedure

The PPI apparatus consisted of eight startle chambers (SR-LAB, San Diego Instruments, San Diego, Calif., USA). Each chamber consisted of a Plexiglas cylinder (8.9 cm diameter× 20 cm long) resting on a Plexiglas frame in a sound attenuated, ventilated enclosure. Background noise and acoustic stimuli were presented via a loudspeaker mounted 24 cm above the animal. Startle responses, reflecting the motion of animals in the cylinder following the acoustic stimulus, were detected by a piezoelectric transducer mounted below the frame. The administration of stimuli and response recording were controlled by the SR-LAB software. Test sessions started with a 5-minutes acclimatization period. Throughout the whole session, the chamber light was on, and the background white noise was set at 70 dB. The test session included 3 initial startling stimuli (intensity: 120 dB, duration: 40 ms) to accustom the rat to the experimental procedure. The initial stimuli were followed by 60 trials (6×10 trials) presented in a random order:

10 background trials (B) which involved a presentation of a sham stimulus (intensity: 70 dB, duration: 40 ms),
two types (2×10) of prepulse trials (PP) which included only a prepulse stimuli (84 dB or 90 dB, 20 ms),
10 pulse trials (P) which included only a pulse startling stimulus (120 dB, 40 ms).
two types (2×10) of prepulse-and-pulse trials (PP-P) which involved a prepulse (84 dB or 90 dB, 20 ms) followed 100 ms later by a 120-dB pulse stimulus (P).

The average inter-trial interval was 22.5 s (range: 15-30 s). This interval was randomized by the SR-LAB software. Startle responses were measured for 100 ms after the onset of the last trial stimulus. For each type of stimulation, startle amplitudes were averaged across the 10 trials. The magnitude of PPI was calculated as a percent inhibition of the startle amplitude in the pulse trial (treated as 100%) according to the formula: [(startle amplitude in P trials−startle amplitude in PP-P trials)/startle amplitude in P trials]×100%. Startle responses to the 3 initial stimuli were excluded from the statistical analyses.

Effects of Tested Compounds on PPI and on Amphetamine-Induced PPI Deficits

Rats were pre-injected with the test drug (60 min.). Each compound was tested in two separate experiments performed over two consecutive days (Experiments 1-2) in separate groups of drug-naive rats. Fifteen minutes before the start of the PPI session, rats were injected with saline (Experiment 1) or amphetamine (Experiment 2).

In Experiment 1, each reference compound, or its vehicle, was given in combination with physiological saline (0.9% NaCl). The purpose of this experiment was to assess effects of the reference drug on basic startle responses and PPI. Results of Experiment 1 determined a range of drug doses tested in Experiment 2. In Experiment 2, the reference drug, or its vehicle, was administered in combination with amphetamine (6 mg/kg, i.p.). The purpose of Experiment 2 was to assess drug's effects on amphetamine-induced PPI deficits.

Startle responses (in manufacturer's arbitrary units), and magnitudes of PPI (%) were analyzed with the aid of a one-way analysis of variance (ANOVA). The Newman-Keuls test was used for individual post hoc comparisons.

Forced Swimming Test (the Porsolt's Test)

The animals were individually subjected to two experimental trials during which they were forced to swim in a cylinder (40 cm high, 18 cm in diameter) filled with warm water (25° C.) to a height of 15 cm. A video camera was mounted 50 cm above the cylinder. The first (habituation) and second (test) trial lasted 15 and 5 minutes, respectively. There was a 24-h interval between the trials. The total duration of immobility was measured during the second trial by a trained observer located in a separate room.

Weights and time of immobility were analyzed with the aid of a one-way analysis of variance (ANOVA). The Newman-Keuls test was used for individual post hoc comparisons.

Elevated Plus Maze Test in Rats

The testing procedure was based on a method described by Pellow and File (1986). Plus-maze apparatus (an automated device produced by Kinder Scientific) made of durable, high density, non porous black plastic, elevated to a height of 50 cm, consisted of two open arms (50×10 cm) and two closed arms (50×10 cm, and 30 cm high walls), arranged so that the two arms of each type were opposite each other. Floor of the plus-maze was made of infrared transparent material what means that there are no visible sensors. The plus-maze was placed in a darkened room, and the center of the apparatus was illuminated with a 25 W electric bulb hanging 100 cm above. Plus-maze apparatus was connected to PC software by control chassis. Each rat was gently placed in the center of the plus-maze, facing one of the closed arms, immediately after a 5-min adaptation period in a plastic black box (60×60×35 cm). During a 5-minutes test period, automated Motor Monitor System recorded the number of entries into the closed and open arms, the time spent in and the distance (cm) covered by a rat in either type of the arms. After each trial the maze was wiped clean. All compounds were administered to 5-8 rats per treatment group. Compounds 22 and 36 were administered 60 minutes before the experiment.

Conflict Drinking Test (Vogel Test) in Rats

Anxiety Monitoring System "Vogel test" produced by TSE Systems was used. It was consisted of a polycarbonate cage (dimensions 26.5×15×42 cm), equipped with a grid floor made from stainless steel bars and a drinking bottle containing tap water. Experimental chambers (two) were connected to PC software by control chassis and a device that generates electric shocks. On the first day of the experiment, the rats were adapted to the test chamber for 10 min. After the adaptation period, the animals were deprived of water for 24 h and were then placed in the test chamber for another 10-min adaptation period during which they had free access to the drinking bottle. Afterwards, they were allowed a 30-min free-drinking session in their home cage. After another 24-h water deprivation period, the rats were placed again in the test chamber. Recording data started immediately after the first lick and every 20 licks rats were punished with an electric shock (0.5 mA, lasting 1 s). The impulses were released via the spout of the drinking bottle. If a rat was drinking when an impulse was released, it received a shock. The number of licks and the number of shocks received throughout a 5-min experimental session was recorded automatically. Compounds 22 and 36 were administered to 10 rats per treatment group, 60 min before the experiment.

TABLE 30

Results of tests in rats

| Test | Compound MED [mg/kg] | |
| --- | --- | --- |
| | 22 | 36 |
| Apomorphine-induced stereotyped behaviour (pharmacological dopamine-related psychosis model) | 10 | — |
| MK-801-induced stereotyped behaviour (pharmacological glutamate-related psychosis model) | 3 | — |
| DOI-induced head twitches (pharmacological serotonin-related psychosis model) | 1 * | — |
| Active-avoidance response (model of positive symptoms of schizophrenia) | 3 | — |
| Passive-avoidance (model of memory disturbance) | >30 | — |
| Prepulse inhibition disruption caused by amphetamine administration (model of sensorimotor gating deficits involved in schizophrenia pathomechanism; dopaminergic psychotomimetic) | 30 | — |
| Porsolt forced swimm test (test indicative of potential antidepressant activity) | 0.3 | 1 * |
| Vogel test in rats (test indicative of potential anxiolytic activity) | 3 | 1 * |

TABLE 30-continued

Results of tests in rats

| Test | Compound MED [mg/kg] | |
|---|---|---|
| | 22 | 36 |
| Elevated plus-maze (test indicative of potential anxiolytic activity) | 0.3 * | — |

* lower doses not tested

Results of behavioral tests described in Example 8 confirm potential activity of the compounds of invention in therapy of psychotic symptoms.

Data for the representative compound 22 in Examples 8 and 9 show its wide antipsychotic activity in all applied rodent models. It is noteworthy that the compound was active in models utilizing psychotomimetic substances affecting either dopaminergic (d-amphetamine, apomorphine), serotoninergic (DOI) or glutamatergic transmission (MK-801) as well as in specific conditioning procedure (active avoidance response). Compound 22 was active in procedures indicative of efficacy in either positive symptoms of schizophrenia, such as: d-amphetamine and MK-801 induced hyperlocomotion, stereotyped behavior induced by apomorphine and DOI, active avoidance response, as well as in procedure assessing ability to treat attention deficits and information filtering (dimensions of cognitive deficits), underlying the pathomechanism of schizophrenia —reversal of deficits in prepulse inhibition in rats. Moreover compound 22 was active in well established models for detecting substances with potential antidepressant activity, i.e. tail suspension test in mice and forced swim test (Porsolt) in rats as well as potential anxiolytic activity, i.e. four plates test in mice, elevated plus maze and conflict drinking test (Vogel) in rats. Such a wide pharmacological activity, beyond the purely antipsychotic effects is a particularly desirable feature of modern antipsychotic drug, considering complexity of clinical conditions associated with schizophrenia, including depression and anxiety.

Data for compound 36 show its wide antidepressant and anxiolytic activity in all applied models in mice and rats (tail suspension test in mice and forced swim test (Porsolt) in rats, four plates test in mice and conflict drinking test (Vogel) in rats). This confirms its potential efficacy in treatment of depression and anxiety, as well as its potential use as add on therapy for currently used antipsychotics in treatment of negative symptoms of schizophrenia. ps References 1. Greengrass, P. and Bremner, R. (1979), *Eur. J. Pharmacol.,* 55: 323-326.
2. Devedjian et al. (1994), *Eur. J. Pharmacol.,* 252: 43-49
3. Grandy et al. (1989), *Proc. Natl. Acad. Sci. U.S.A.,* 86: 9762-9766.
4. Mackenzie et al. (1994), *Eur. J. Pharmacol.,* 266: 79-85.
5. Smit et al (1996), *Brit. J. Pharmacol.,* 117: 1071-1080.
6. Peratta et al. (1987), *Embo. J.,* 6: 3923-3929.
7. Mulheron et al. (1994), *J. Biol. Chem.,* 269: 12954-12962.
8. Bonhaus et al. (1995), *Brit. J. Pharmacol.,* 115: 622-628.
9. Stam at al. (1994), *Eur. J. Pharmacol.,* 269: 339-348.
10. Monsma et al. (1993), *Mol. Pharmacol.,* 43: 320-327.
11. Shen et al. (1993), *J. Biol. Chem.,* 268: 18200-18204.
12. Shirayama et al. (1993), *Eur. J. Pharmacol.,* 237: 117-126.
13. Tatsumi et al. (1999), *Eur. J. Pharmacol.,* 368: 277-283.
14. Sur, C et al. (2003) Proc. Natl. Acad. Sci. U.S.A., 100: 13674-13679;
15. Adham at al. (1998), J. Pharmacol. Exp. Ther., 287: 508-514;
16. Kohen et al. (1996), J. Neurochem., 66: 47-56;
17. Payne et al. (2002), J. Neurochem., 82: 1106-1117;
18. Porter et al. (1999), Brit. J. Pharmacol., 128: 13-20;
19. Miller, T. R et al. (1999) J. Biomol. Screen., 4: 249-258;
20. Vicentic et al. (2002), J. Pharmacol. Exp. Ther., 302: 58-65;
21. Missale et al. (1998), Physiol. Rev., 78: 189-225;
22. Newman-Tancredi et al. (2001), Brit. J. Pharmacol., 132: 518-524;
23. Regan, J. W et al. (1988) Biochem., 85: 6301-6305;
24. Van Rossum J. M. (1963) Arch. Int. Pharmacodyn., 1963, 143, 299-330.

The invention claimed is:
1. A compound of the general formula (I)

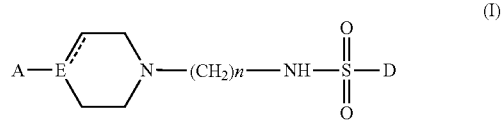

or a pharmaceutically acceptable salt thereof,
wherein
E represents C;
<u>-----</u> represents a double bond;
n represents an integer from 2 to 6, inclusive;
A is linked to E through one of its carbon atoms and is represented by the general formula (A2):

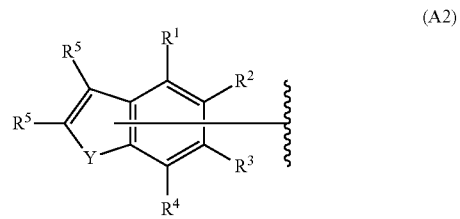

wherein
$R^5$ represents hydrogen, halogen or $C_1$-$C_4$-alkyl;
Y represents NH, O or S;
each of $R^1$, $R^2$, $R^3$ and $R^4$ independently represents hydrogen or halgen;
D represents a group selected from;
unsubstituents phenyl or phenyl substituted with one or more substituents independently selected from the group consisting of branched $C_1$-$C_4$-alkyl, straight $C_1$-$C_4$-alkyl in ortho or meta position with respect to sulphonamide group, $C_1$-$C_3$-alkyloxy, halogeno-$C_1$-$C_3$-alkyl, halogeno-$C_1$-$C_3$-alkyloxy, halogen atom, —CN, —OH, and phenyl;
unsubstituted naphthyl or naphthyl substituted with one or more substituents independently selected from the group consisting of $C_1$-$C_4$-alkyl, $C_1$-$C_3$-alkyloxy, halogeno-$C_1$-$C_3$-alkyl, halogen atom, —CN, —OH, and phenyl;
5-membered aromatic heterocyclic group having 1 to 3 heteroatoms independently selected from the group consisting of N, O, and S, the 5-membered aromatic heterocyclic group being unsubstituted or substituted with one or more sustituents independently selected from the group consisting of $C_1$-$C_4$-alkyl, $C_1$-$C_3$-alkyloxy, halogeno-$C_1$-$C_3$-alkyl, halogen atom, —CN —OH, and phenyl, bicyclic group consisting of benzene or pyridine ring fused with a 5-membered aromatic or non-aromatic heterocyclic ring having 1 to 3 hetaroatoms independently selected from the group consisting of N, O, and S, which bicyclic group is unsubstituted or substituted with one or more substituents independently selected ,from the group consisting of $C_1$-$C_4$-alkyl, $C_1$-$C_3$-alkyloxy, halogeno-$C_1$-$C_3$alkyl, halogen atom, =O, —CN, —OH, and phenyl;

bicyclic group consisting of benzene or pyridine ring fused with 6-membered non-aromatic heterocyclic ring having from 1 to 3 heteroatoms independenly selected from the group consisting of N, O, and S, which bicyclic group is unsubstituted or substituted with one or more substituents independently selected from the group consistng of $C_1$-$C_4$-alkyl, $C_1$-$C_3$-alkyloxy, halogeno-$C_1$-$C_3$-alkyl, halogen atom, =O, —CN, —OH, and phenyl.

2. The compound or salt according or claim 1, wherein D represents unsubstituted phenyl or phenyl substituted with one or more substituents independently selected from the group consisting of branched $C_1$-$C_4$-alkyl, straight $C_1$-$C_4$-alkyl in ortho or meta position with respect to sulphonamide group; $C_1$-$C_3$-alkyloxy, halogeno-$C_1$-$C_3$-alkyl, halogeno-$C_1$-$C_3$-alkyloxy, halogen atom, —CN, —OH, and phenyl.

3. The compound or salt according to claim 1, wherein D represents unsubstituted naphthyl or naphthyl substituted with one or more substituents independently selected from the group consisting of $C_1$-$C_4$-alkyl, $C_1$-$C_3$-alkyloxy, halogeno-$C_1$-$C_3$-alkyl, halogen atom, —CN, —OH, and phenyl.

4. The compound according to claim 1, wherein D represents 5-membered aromatic heterocyclic group having 1 to 3 heteroatoms independently selected from the group consisting of N, O, and S, and wherein D is unsubstituted or substituted with one or more substituents independently selected from the group consisting of $C_1$-$C_4$-alkyl, $C_1$-$C_3$-alkyloxy, halogeno-$C_1$-$C_3$-alkyl, halogen atom, —CN, —OH, and phenyl.

5. The compounds or salt according to claim 4, wherein D represents thienyl.

6. The compound or salt according to claim 1, wherein D represents benzene ring fused with 5-membered aromatic heterocyclic ring having 1to 3 heteroatoms independently selected from the group consisting of N, O, and S, and wherein D is unsubstituted or substituted with one or more substituents independently selected from the group consisting of $C_1$-$C_4$-alkyl, $C_1$-$C_3$-alkyloxy, halogeno-$C_1$-$C_3$-alkyl, halogen atom, —CN, —OH, and phenyl.

7. The compound or salt according to claim 6, wherein D is selected from the group consisting of 1-benzothiophen-3-yl, 1-benzothiophen-2-yl, 1-benzofuran-2-yl, 1-benzofuran-3-yl, 1H-benzimidazol-2-yl, 1H-indol-2-yl, 1H-indol-5-yl, 1 H-indol-6-yl, 1H-indazol-7-yl, 1H-indazol-6-yl, 1,2-benzoxazol-5-yl, 1,3-benzoxazol-4-yl, 1,3-benzothiazol-4-yl, and 1,3-benzothiazol-5-yl.

8. of the compound or salt according to claim 1, wherein D represents bicyclic group consisting of benzene ring fused with 5-membered non-aromatic heterocyclic ring having from 1 to 3 heteroatoms independently selected from the group consisting of N, O, and S, and wherein D is unsubstituted or substituted with one or more substituents independently selected from the group consisting of $C_1$-$C_4$-alkyl, $C_1$-$C_3$-alkyloxy, halogeno-$C_1$-$C_3$-alkyl, halogen atom, =O, —CN, —OH, and phenyl.

9. The compound or salt according to claim 8, wherein D is selected from the group consisting of 2,3-dihydro-1-benzofuran-5-yl, 2-oxo-2,3-dihydro-1,3-benzooxazol-6yl, 2-oxo-1,3-dihydro-2H-indol-5-yl, and 1,3-benzodioxol-5-yl.

10. The compound or salt according to claim 1, wherein D represents bicyclic group consisting of pyridine ring fused with 5-membered aromatic heterocyclic ring having from 1 to 3 heteroatoms independently selected from the group consisting of N, O, and S, and wherein D is unsubstituted or substituted with one or more substituents independently selected from the group consisting of $C_1$-$C_4$-alkyl, $C_1$-$C_3$-alkyloxy, halogeno-$C_1$-$C_3$-alkyl, halogen atom, —CN, —OH, and phenyl.

11. The compound or salt according to claim 10, wherein D is selected from the group consisting of imidazo[1,2-a]-pyridin-3-yl, and 1H-pyrrolo[2,3-b]-pyridin-3-yl.

12. The compound or salt according to claim 1, wherein n is 2.

13. The compound or salt according to claim 1, wherein n is 3.

14. The compound or salt according to claim 1, wherein n is 4.

15. The compound or salt according to claim 1, wherein A is linked to E through carbon atom of a heterocyclic ring.

16. The compound according to claim 1 selected from the group consisting of the following compounds:

N-{4-[4-(5-chloro-1H-indol-3-yl)-3,6-dihydropyridin-1(2H)-yl]butyl}naphthalene-1-sulphonamide, N-{4-[4-(5-chloro-1H-indol-3-yl)-3,6-dihydropyridin-1(2H)-yl]butyl}naphthalene-2-sulphonamide, 4-fluoro-N-{4-[4-(5-chloro-1H-indol-3-yl)-3,6-dihydro-pyridin-1(2H)-yl]butyl)benzene-sulphonamide, 3-fluoro-N-{4-[4-(5-chloro-1H-indol-3-yl)-3,6-dihydro-pyridin-1(2H)-yl]butyl}benzene-sulphonamide, 4-chloro-N-{4[4-(5-chloro-1H-indol-3-yl)-3,6-dihydro-pyridin-1(2H)-yl]butyl}benzene-sulphonamide, 3-chloro-N-{4[4-(5-chloro-1H-indol-3-yl)-3,6-dihydro-pyridin-1(2H)-yl]butyl}benzene-sulphonamide, 3-methyl-N-{4[4-(5-chloro-1H-indol-3-yl)-3,6dihydro-pyridin-1(2H)-yl]butyl}benzene-sulphonamide, 3-hydroxy-N-{4-[4(5-chloro-1H-indol-3-yl)-3,6-dihydro-pyridin-1(2H)-yl]butyl}benzene-sulphonamide, 4-methoxy-N-}4-[4-(5-chloro-1H-indol-3-yl)-3,6-dihydropyridin-1(2H)-yl]butyl}benzene-sulphonamide, N-{3-[4-(5-chloro-1H-indol-3yl)-3,6-dihydropyridin-1(2H)-yl]propyl}naphthalene-1-sulphonamide, N-{3-[4-(5-chloro-1H-indol-3yl)-3,6-dihydropyridin-1(2H)-yl]propyl}naphthalene-2-sulphonamide, 4-fluoro-N-{3-[4-(5-chloro-1H-indol-3-yl)-3,6-dihydro-pyridin-1(2H)-yl]propyl}benzene-sulphonamide, 3-fluoro-N-{3-[4-(5-chloro-1H-indol-3-yl)-3,6-dihydro-pyridin-1(2H)-yl]propyl}benzene-sulphonamide, 4-chloro-N-{3-[4-(5-chloro-1H-indol-3-yl)-3,6-dihydro-pyridin-1(2H)-yl]propyl}-benzenesulphonamide, 3-chloro-N-{3-[4-(5-chloro-1H-indol-3-yl)-3,6-dihydro-pyridin-1(2H)-yl]propyl}benzene-sulponamide, 3-hydroxy-N-}3-[4-(5-chloro-1H-indol-3-yl)-3,6-dihydropyridin-1(2H)-yl]propyl}benzene-sulphonamide, N-{2-[4-(5-chloro-1H-indol-3-yl)-3,6-dihydropyridin-1(2H)-yl]ethyl}naphthalene-1-sulphonamide, N-{2-[4-(5-chloro-1H-indol-3-yl)-3,6-dihydropyridin-1(2H)-yl]ethyl}naphthalene-2-sulphonamide, N-{2-[4-(5-chloro-1H-indol-3-yl)-3,6-dihydropyridin-1(2H)-yl]ethyl}-4-fluorobenzene-sulphonamide, 3-fluoro-N-{2-[4-(5-chloro-1H-indol-3-yl)-3,6-dihydro-pyridin-1(2H)-yl]ethyl}benzene-sulphonamide, 4-chloro-N-{2-[4-(5-chloro-1H-indol-3-yl)-3,6-dihydropyridin-1(2H)-yl]ethyl}benzene-sulphonamide,
3-chloro-N-{2-[4-(5-chloro-1H-indol-3-yl)-3,6-dihydropyridin-1(2H)-yl]ethyl}benzene-sulphonamide,
3-methyl-N-{2-[4-(5-chloro-1H-indol-3-yl)-3,6-dihydropyridin-1(2H)-yl]ethyl}benzene-sulphonamide,
3-hydroxy-N-{2-[4-(5-chloro-1H-indol-3-yl)-3,6-dihydropyridin-1(2H)-yl]ethyl}benzene-sulphonamide,
4-choloro-N-{4-[4-(5-chloro-2-methyl-1H-indol-3-yl)-3,6-dihydropyridin-1(2H)-yl]-butyl}-benzenesulphonamide,
N-[4-[4-(5-chloro-2-,methyl-1H-indol-3-yl)-3,6-dihydro-2H-pyridin-1-yl]butyl]-3-chloro-benzenesulphonamide,
N-[3-[4-(5-chloro-2-methyl-1H-indol-3-yl)-3,6-dihydro-2H-pyridin-1-yl]propyl]-3-chloro-benzenesulphonamide,
N-[4-[4-(5-chloro-2-methyl-1H-indol-3-yl)-3,6-dihydro-2H-pyridin-1-yl]butyl]-3-fluoro-benzenesulphonamide,
N-[3-[4-(5-chloro-2-methyl-1H-indol-3-yl)-3,6-dihydro-2H-pyridin-1-yl]propyl]-3-fluoro-benezenesulphonamide,
N-[4-[4-(5-chloro-2-methyl-1H-indol-3-yl)-3,6-dihydro-2H-pyridin-1-yl]butyl]-4-tert-butyl-benzenesulphonamide,
N-[4-[4-(5-chloro-2-methyl-1H-indol-3-yl)-3,6-dihydro-2H-pyridin-1-yl]butyl]-naphthalene-1-sulphonamide,
N-[4-[4-(5-chloro-2-methyl-1H-indol-3-yl)-3,6-dihydro-2H-pyridin-1-yl]butyl]-naphthalene-2-sulphonamide,
N-[4-[4-(5-chloro-2-methyl-1H-indol-3-yl)-3,6-dihydro-2H-pyridin-1-yl]butyl]-4-fluoro-benzenesulphonamide,
N-[4-[4-(5-chloro-2-methyl-1H-indol-3-yl)-3,6-dihydro-2H-pyridin-1-yl]butyl]-3-hydroxy-benzenesulphonamide,
N-[4-[4-(5-chloro-2-methyl-1H-indol-3-yl)-3,6-dihydro-2H-pyridin-1-yl]butyl]-3-methyl-benzenesulphonamide,
N-[4-[4-(5-fluoro-1H-indol-3-yl)-3,6-dihydro-2H-pyridin-1-yl]butyl]naphthalene-2-sulphonamide,
3-fluoro-N-[3-[4-(5-fluoro-1H-indol-3-yl)-3,6-dihydro-2H-pyridin-1-yl]propyl]benzene-sulphonamide,
N-[4-[4(5-fluoro-1H-indol-3-yl)-3,6-dihydro-2H-pyridin-1-yl]butyl]-3-hydroxybenzene-sulphonamide,
N-[4-[4(5-fluoro-1H-indol-3-yl)-3,6-dihydro-2H-pyridin-1-yl]butyl]-3-methylbenzenesulphonamide,
3-fluoro-N-[3-[4-(5-fluoro-1H-indol-3-yl)-3,6-dihydro-2H-pyridin-1-yl]propyl]benzene-sulphonamide,
N-[3-[4-(5-fluoro-1H-indol-3-yl)-3,6-dihydro-2H-pyridin-1-yl]propyl]-3-hydroxybenzene-sulphonamide,
N-[2-[4-(5-fluoro-1H-indol-3-yl)-3,6-dihydro-2H-pyridin-1-yl]ethyl]naphthalene-2-sulphonamide,
3-fluoro-N-[2-[4-(5-fluoro-1H-indol-3-yl)-3,6-dihydro-2H-pyridin-1-yl]ethyl]benzene-sulphonamide,
N-[2-[4-(5-fluoro-1H-indol-3-yl)-3,6-dihydro-2H-pyridin-1-yl]ethyl]-3-methylbenzene-sulphonamide,
N-[3-[4-(5-chloro-2-methyl-1H-indol-3-yl)-3,6-dihydro-2H-pyridin-1-yl]propyl]-naphthalene-1-sulphonamide,
N-[3-[4-(5-chloro-2-methyl-1H-indol-3-yl)-3,6-dihydro-2H-pyridin-1-yl]propyl]-naphthalene-2-sulphonamide,
N-[3-[4-(5-chloro-2-methyl-1H-indol-3-yl)-3,6-dihydro-2H-pyridin-1-yl]propyl]-4-fluoro-benzenesulphonamide,
4-chloro-N-[3-[4-(5-chloro-2-methyl-1H-indol-3-yl)-3,6-dihydro-2H-pyridin-1-yl]propyl]-benzenesulphonamide,
N-[3-[4-(5-chloro-2-methyl-1H-indol-3-yl)-3,6-dihydro-2H-pyridin-1-yl]propyl]-3-hydroxy-benzenesulphonamide,
N-[3-[4-(5-chloro-2-methyl-1H-indol-3-yl)-3,6-dihydro-2H-pyridin-1-yl]propyl]-3-methyl-benzenesulphonamide,
N-[2-[4-(5-chloro-2-methyl-1H-indol-3-yl)-3,6-dihydro-2H-pyridin-1-yl]ethyl]naphthalene-1-sulphonamide,
N-[2-[4-(5-chloro-2-methyl-1H-indol-3-yl)-3,6-dihydro-2H-pyridin-1-yl]ethyl]-naphthalene-1-sulphonamide,
N-[2-[4-(5-chloro-2-methyl-1H-indol-3-yl)-3,6-dihydro-2H-pyridin-1-yl]ethyl]-4-fluoro-benzenesulphonamide,
N-[2-[4-(5-chloro-2-methyl-1H-indol-3-yl)-3,6-dihydro-2H-pyridin-1-yl]ethyl]-3-fluoro-benzenesulphonamide,
4-chloro-N-[2-[4-(5-chloro-2-methyl-1H-indol-3-yl)-3,6-dihydro-2H-pyridin-1-yl]ethyl]-benzenesulphonamide,
3-chloro-N-[2-[4-(5-chloro-2-methyl-1H-indol-3-yl)-3,6-dihydro-2H-pyridin-1-yl]ethyl]-benzenesulphonamide,
N-[2-[4-(5-chloro-2-methyl-1H-indol-3-yl)-3,6-dihydro-2H--pyridin-1-yl]ethyl]-3-hydroxy-benzenesulphonamide, and
N-[2-[4-(5-chloro-2-methyl-1H-indol-3-yl)-3,6-2H-pyridin-1-yl]ethyl]-3-methyl-benzenesulphonamide,
or a pharmaceutically acceptable salt thereof.

17. A pharmaceutical composition comprising a compound of formula (I) as defined in claim 1 as an active ingredient in combination with pharmaceutically acceptable carrier(s) and/or excipient(s).

18. A method of treatment of disorders of the central nervous system related to serotoninergic and dopaminergic transmission in a mammal, comprising administration to the mammal of the pharmaceutically effective amount of a compound of formula (I) according to claim 1 or a pharmaceutical composition comprising the compound, wherein the disorder of the central nervous system is schizophrenia, schizoaffective disorders, schizophreniform disorders, delusional syndromes and other psychotic conditions related and not related to taking psychoactive substances, affective disorder, bipolar disorder, mania, depression, anxiety disorders of various aetiology, stress reactions, conciousness disorders, coma, delirium of alcoholic or other aetiology, aggression, psychomotor agitation and other conduct disorders, sleep disorders of various aetiology, withdrawal syndomes of various aetiology, addiction, pain syndromes of various aetiology, intoxication with psychoactive substances, cerebral circulatory disorders of various aetiology, psychosomatic disorders of various artiology, conversion disorders, dissociative disorders, urination disorders, autism and other developmental disorders, including nocturia, stuttering, tics, cognitive disorders of various types, including Alzheimer's disease, psychopatological symptoms, or neurological disorders in the course of other diseases of the central and peripheral nervous systems.

19. The method of claim 18, wherein said disorder is schizophrenia.

* * * * *